(12) United States Patent
Schneider et al.

(10) Patent No.: US 12,168,666 B2
(45) Date of Patent: *Dec. 17, 2024

(54) MORPHIC FORMS OF TRILACICLIB AND METHODS OF MANUFACTURE THEREOF

(71) Applicant: G1 Therapeutics, Inc., Research Triangle Park, NC (US)

(72) Inventors: Stephen Schneider, Raleigh, NC (US); Alexander Smith, Apex, NC (US); Hannah S. White, Chapel Hill, NC (US); Jay Copeland Strum, Hillsborough, NC (US); Jaroslaw Mazurek, Amsterdam (NL)

(73) Assignee: G1 Therapeutics, Inc., Research Triangle Park, NC (US)

( * ) Notice: Subject to any disclaimer, the term of this patent is extended or adjusted under 35 U.S.C. 154(b) by 676 days.

This patent is subject to a terminal disclaimer.

(21) Appl. No.: 17/236,687

(22) Filed: Apr. 21, 2021

(65) Prior Publication Data

US 2021/0387993 A1 Dec. 16, 2021

Related U.S. Application Data

(63) Continuation of application No. 17/097,854, filed on Nov. 13, 2020, now Pat. No. 10,988,479.
(Continued)

(51) Int. Cl.
*C07D 487/20* (2006.01)
*A61K 9/00* (2006.01)
(Continued)

(52) U.S. Cl.
CPC .......... *C07D 487/20* (2013.01); *A61K 9/0019* (2013.01); *A61K 9/08* (2013.01);
(Continued)

(58) Field of Classification Search
CPC ........................... C07D 487/20; A61K 9/0019
(Continued)

(56) References Cited

U.S. PATENT DOCUMENTS

| 5,591,855 A | 1/1997 | Hudkins et al. |
| 5,628,984 A | 5/1997 | Boucher |

(Continued)

FOREIGN PATENT DOCUMENTS

| CA | 2656290 A1 | 1/2008 |
| WO | WO 1998/033798 A2 | 8/1998 |

(Continued)

OTHER PUBLICATIONS

An, H. X. et al., "Gene amplification and overexpression of CDK4 in sporadic breast carcinomas is associated with high tumor cell proliferation", American Journal of Pathology, 1999; 154: 113-118.
(Continued)

*Primary Examiner* — Jeffrey S Lundgren
*Assistant Examiner* — Heather Dahlin
(74) *Attorney, Agent, or Firm* — Knowles Intellectual Property Strategies, LLC

(57) ABSTRACT

An advantageous isolated morphic form of trilaciclib which is 2'-((5-(4-methylpiperazin-1-yl)pyridin-2-yl)amino)-7',8'-dihydro-6'H-spiro[cyclohexane-1,9'-pyrazino[1',2':1,5]pyrrolo[2,3-d]pyrimidin]-6'-one, for example in the form of a di-hydrochloride salt or a dihydrochloride, dihydrate.

27 Claims, 53 Drawing Sheets

Related U.S. Application Data

(60) Provisional application No. 63/039,372, filed on Jun. 15, 2020.

(51) Int. Cl.
*A61K 9/08* (2006.01)
*A61K 9/19* (2006.01)
*A61K 47/02* (2006.01)
*A61K 47/12* (2006.01)
*A61K 47/26* (2006.01)

(52) U.S. Cl.
CPC ................ *A61K 9/19* (2013.01); *A61K 47/02* (2013.01); *A61K 47/12* (2013.01); *A61K 47/26* (2013.01); *C07B 2200/13* (2013.01)

(58) Field of Classification Search
USPC ........................................................ 514/250
See application file for complete search history.

(56) References Cited

U.S. PATENT DOCUMENTS

| | | |
|---|---|---|
| 6,291,504 B1 | 9/2001 | Nugiel et al. |
| 6,369,086 B1 | 4/2002 | Davis et al. |
| 6,610,684 B2 | 8/2003 | Zaharevitz et al. |
| 6,667,346 B2 | 12/2003 | Reddy et al. |
| 6,936,612 B2 | 8/2005 | Barvian et al. |
| 6,962,993 B2 | 11/2005 | Blumenkopf et al. |
| 6,982,277 B2 | 1/2006 | Gudkov et al. |
| 7,208,489 B2 | 4/2007 | Barvain et al. |
| 7,345,171 B2 | 3/2008 | Beylin et al. |
| 7,482,354 B2 | 1/2009 | Traquandi et al. |
| 7,855,211 B2 | 12/2010 | Coates et al. |
| 7,977,347 B2 | 7/2011 | Qian et al. |
| 8,598,186 B2 | 12/2013 | Tavares et al. |
| 9,683,048 B2 | 6/2017 | Freeman et al. |
| 10,988,479 B1 * | 4/2021 | Schneider et al. ..... A61K 47/26 |
| 2002/0042412 A1 | 4/2002 | Zaharevitz et al. |
| 2003/0069430 A1 | 4/2003 | Davis et al. |
| 2003/0073668 A1 | 4/2003 | Booth et al. |
| 2003/0224522 A1 | 12/2003 | de Jong et al. |
| 2003/0229026 A1 | 12/2003 | Al-Awar et al. |
| 2004/0006074 A1 | 1/2004 | Kelley et al. |
| 2004/0048915 A1 | 3/2004 | Engler et al. |
| 2004/0236084 A1 | 11/2004 | Biwersi et al. |
| 2005/0222163 A1 | 10/2005 | Eck et al. |
| 2005/0267073 A1 | 12/2005 | Dairi et al. |
| 2007/0027147 A1 | 2/2007 | Hayama et al. |
| 2007/0179118 A1 | 8/2007 | Barvian et al. |
| 2007/0207143 A1 | 9/2007 | Dang et al. |
| 2007/0212736 A1 | 9/2007 | Chen-Kiang et al. |
| 2007/0270362 A1 | 11/2007 | Harlan et al. |
| 2008/0085890 A1 | 4/2008 | Tsou et al. |
| 2008/0161355 A1 | 7/2008 | Curry et al. |
| 2008/0182853 A1 | 7/2008 | Kruman et al. |
| 2011/0009353 A1 | 1/2011 | Chen-Kiang et al. |
| 2011/0224221 A1 | 9/2011 | Sharpless et al. |
| 2011/0224227 A1 | 9/2011 | Sharpless et al. |
| 2011/0312909 A1 | 12/2011 | Ciomei et al. |
| 2012/0100100 A1 | 4/2012 | Sharpless et al. |
| 2013/0289031 A1 | 10/2013 | Arigon et al. |
| 2014/0037622 A1 | 2/2014 | Boshoff et al. |
| 2014/0080838 A1 | 3/2014 | Wendel et al. |
| 2014/0107114 A1 | 4/2014 | Kim et al. |
| 2014/0271460 A1 | 9/2014 | Strum et al. |
| 2014/0274896 A1 | 9/2014 | Strum et al. |
| 2015/0210769 A1 | 7/2015 | Freeman et al. |
| 2015/0297606 A1 | 10/2015 | Strum et al. |
| 2015/0297607 A1 | 10/2015 | Strum et al. |
| 2015/0297608 A1 | 10/2015 | Strum et al. |
| 2016/0045509 A1 | 2/2016 | Strum et al. |
| 2016/0185870 A1 | 6/2016 | Van Eenennaam |
| 2016/0220569 A1 | 8/2016 | Strum et al. |
| 2016/0310499 A1 | 10/2016 | Strum et al. |
| 2016/0332989 A1 | 11/2016 | Wu et al. |
| 2017/0119774 A1 | 5/2017 | Strum et al. |
| 2017/0209574 A1 | 7/2017 | Cao et al. |
| 2017/0246171 A1 | 8/2017 | Strum et al. |
| 2017/0296659 A1 | 10/2017 | Lebwohl et al. |
| 2019/0135820 A1 | 5/2019 | Smith et al. |

FOREIGN PATENT DOCUMENTS

| | | |
|---|---|---|
| WO | WO 1999/015500 A1 | 4/1999 |
| WO | WO 2001/012188 A1 | 2/2001 |
| WO | WO 2002/044174 A2 | 6/2002 |
| WO | WO 2003/062236 A1 | 7/2003 |
| WO | WO 2005/005426 A1 | 1/2005 |
| WO | WO 2005/040166 A1 | 5/2005 |
| WO | WO 2005/052147 A2 | 6/2005 |
| WO | WO 2005/094830 A1 | 10/2005 |
| WO | WO 2005/105213 A1 | 11/2005 |
| WO | WO 2006/074985 A1 | 7/2006 |
| WO | WO 2006/127587 A1 | 11/2006 |
| WO | WO 2007/025090 A2 | 3/2007 |
| WO | WO 2007/048847 A2 | 5/2007 |
| WO | WO 2007/065820 A1 | 6/2007 |
| WO | WO 2007/124252 A2 | 11/2007 |
| WO | WO 2008/005538 A2 | 1/2008 |
| WO | WO 2008/079933 A2 | 7/2008 |
| WO | WO 2009/003003 A2 | 12/2008 |
| WO | WO 2009/061345 A2 | 5/2009 |
| WO | WO 2009/085185 A1 | 7/2009 |
| WO | WO 2010/012777 A1 | 2/2010 |
| WO | WO 2010/020675 A1 | 2/2010 |
| WO | WO 2010/039997 A2 | 4/2010 |
| WO | WO 2010/051127 A2 | 5/2010 |
| WO | WO 2010/132725 A2 | 11/2010 |
| WO | WO 2011/101409 A1 | 8/2011 |
| WO | WO 2011/101417 A1 | 8/2011 |
| WO | WO 2011/103485 A1 | 8/2011 |
| WO | WO 2012/061156 A1 | 5/2012 |
| WO | WO 2012/068381 A2 | 5/2012 |
| WO | WO 2012/129344 A1 | 9/2012 |
| WO | WO 2013/006532 A1 | 1/2013 |
| WO | WO 2013/014448 A1 | 1/2013 |
| WO | WO 2013/148748 A1 | 10/2013 |
| WO | WO 2013/163239 A1 | 10/2013 |
| WO | WO 2014/085318 A1 | 6/2014 |
| WO | WO 2014/144326 A1 | 9/2014 |
| WO | WO 2014/144596 A2 | 9/2014 |
| WO | WO 2014/144740 A2 | 9/2014 |
| WO | WO 2014/144847 A2 | 9/2014 |
| WO | WO 2014/168975 A1 | 10/2014 |
| WO | WO 2015/061407 A1 | 4/2015 |
| WO | WO 2015/084892 A1 | 6/2015 |
| WO | WO 2015/161283 A1 | 10/2015 |
| WO | WO 2015/161285 A1 | 10/2015 |
| WO | WO 2015/161287 A1 | 10/2015 |
| WO | WO 2015/161288 A1 | 10/2015 |
| WO | WO 2016/040848 A1 | 3/2016 |
| WO | WO 2016/040858 A1 | 3/2016 |
| WO | WO 2016/040892 A1 | 3/2016 |
| WO | WO 2016/100561 A2 | 6/2016 |
| WO | WO 2016/126889 A1 | 8/2016 |
| WO | WO 2017/222958 A1 | 12/2017 |
| WO | WO 2018/089518 A1 | 5/2018 |
| WO | WO 2018/091999 A1 | 5/2018 |
| WO | WO 2018/099952 A1 | 6/2018 |
| WO | WO 2018/106729 A1 | 6/2018 |
| WO | WO 2018/156812 A1 | 8/2018 |
| WO | WO 2018/183479 A1 | 10/2018 |
| WO | WO 2019/108589 A1 | 6/2019 |
| WO | WO 2020/041770 A1 | 2/2020 |

OTHER PUBLICATIONS

Anderson, M. S. and J. A. Bluestone, "The NOD mouse: a model of immune dysregulation", Annu Rev Immunol, 2005; 23: 447-485.

Barginear, M. F. and D. R. Budman, "Trastuzumab-DM1: A review of the novel immuno-conjugate for HER2-overexpressing breast cancer", The Open Breast Cancer Journal, 2009; 1: 25-30.

(56) References Cited

OTHER PUBLICATIONS

Baughn, L. B. et al., "A novel orally active small molecule potently induces G1 arrest in primary myeloma cells and prevents tumor growth by specific inhibition of cyclin-dependent kinase 4/6", Cancer Res., Aug. 1, 2006; 66(15): 7661-7667.

Bisi et al., Preclinical development of G1T38: A novel, potent and selective inhibitor of cyclin dependent kinases 4/6 for use as an oral antineoplastic in patients with CDK4/6 sensitive tumors, Oncotarget. Mar. 15, 2017: doi:10.18632/oncotarget.16216.

Bisi, J.E. et al. "Preclinical Characterization of G1T28: A Novel CDK4/6 Inhibitor for Reduction of Chemotherapy-Induced Myelosuppression", Molecular Cancer Therapeutics, 2016, 15(5), 783-793, XP055457141.

Blachly et al., "Emerging Drug Profile: Cyclin-dependent kinase inhibitors", Leuk. Lymphoma, 2013, 54(10), 2133-2143.

Blagosklonny, M. V. and A. B. Pardee "Exploiting cancer cell cycling for selective protection of normal cells" Cancer Res, Jun. 1, 2001; 61(11): 4301-4305.

Bose et al., "Cyclin-dependent kinase inhibitor therapy for hematologic malignancies", Expert Opin. Investig. Drugs, 2013, 22(6), 723-738.

Boss et al., "Safety, tolerability, pharmacokinetics and pharmacodynamics of the oral cyclin-dependent kinase inhibitor AZD5438 when administered at intermittent and continuous dosing schedules in patient with advanced solid tumors", Annals of Oncology, 2010, 21, 884-894.

Brookes et al., "INK4a-deficient human diploid fibroblasts are resistant to RAS-induced senescence", EMBO J., Jun. 17, 2002; 21(12): 2936-2945.

Bucher, N. and C. D. Britten, "G2 checkpoint abrogation and checkpoint kinase-1 targeting in the treatment of cancer", Br J Cancer, Feb. 12, 2008; 98(3): 523-528.

Burdelya et al., "An agonist of toll-like receptor 5 has radioprotective activity in mouse and primate models", Science, Apr. 11, 2008; 320(5873): 226-230.

Chari, R. V. "Targeted cancer therapy: conferring specificity to cytotoxic drugs" Accounts of Chemical Research, 2008; 41(1): 98-107.

Chen, X. et al. "Protection of normal proliferating cells against chemotherapy by staurosporine-mediated, selective, and reversible G1 arrest" J Natl Cancer Inst., Dec. 20, 2000; 92(24): 1999-2008.

Chin et al. "Cooperative effects of INK4a and ras in melanoma susceptibility in vivo" Genes & Development, 1997; 11: 2822-2834.

Choi et al., "Signaling through cyclin D-dependent kinase", Oncogene, 2014, 33, 1890-1903.

Choi et al., "The requirement for cyclin D function in tumor maintenance", Cancer Cell, 2012 22(4), 438-451.

Chou, A. et al., "Tailored first-line and second-line CDK4-targeting treatment combinations in mouse models of pancreatic cancer", Gut, 2017; 0:1-14. Published online Oct. 28, 2017 doi: 10.1136.gutjnl-2017-315144.

Chu et al., "Discovery of [4-Amino-2-(1-methanesulfonylpiperidin-4-ylamino)pyrimidin-5-y1](2,3-difluoro-6-methoxyphenyl)methanone (R547), a potent and selective cyclindependent kinase inhibitor with significant in vivo antitumor activity", J Med Chem, Nov. 2, 2006; 49(22): 6549-6560.

Curtin et al., "Distinct Sets of Genetic Alterations in Melanoma", N Engl J Med 2005; 353: 2135-2147.

Daniel et al., "Trilaciclib decreases myelosuppression in extensive-stage small cell lung cancer (ES-SCLC) patients receiving first-line chemotherapy plus atezolizumab," ESMO 2019 Congress Poster Abstract #1742PD).

Daniotti et al., "BRAF alterations are associated with complex mutational profiles in malignant melanoma", Oncogene, 2004; 23: 5968-5977.

Davis, S. T. et al., "Prevention of chemotherapy-induced alopecia in rats by CDK inhibitors", Science, Jan. 5, 2001; 291(5501): 134-137.

Davis, S.T. et al. "Retraction" Science, Dec. 20, 2002; 298(5602): 2327.

Davis, T. A. et al., "Genistein induces radioprotection by hematopoietic stem cell quiescence", Int J Radiat Biol, Sep. 2008, 84(9): 713-726.

Decker et al., "Expression of Cyclin E in resting and activated B-chronic lymphocytic leukemia cells: cyclin E/cdk2 as potential therapeutic target", British Journal of Hematology, Jan. 13, 2004, 125, 141-148.

Deep, G. et al., "New Combination Therapies with Cell Cycle Agents" Current Opinion in Investigational Drugs, 2008; 9: 591-605.

Deng et al., "New Strategies in the Treatment of Mantle Cell Lymphoma" Clinical Cancer Research, 2012; 18(13): 3499-3508.

Deng et al., CDK4/6 Inhibition Augments Antitumor Immunity by Enhancing T-cell Activation, Cancer Discovery Feb. 2018. Published online Nov. 3, 2017; doi: 10.1158/2159-8290.CD-17-0915.

Dickson, M. A. and G. K. Schwartz "Development of cell-cycle inhibitors for cancer therapy" Curr Oncol, Mar. 2009; 16(2): 36-43.

Dickson, Mark, et al. "Phase II Trial of the CDK4 Inhibitor PD0332991 in Patients with Advanced CDK4-Amplified Well-Differentiated or Dedifferentiated Liposarcoma." J Clin Oncol. Jun. 1, 2013; 31(16): 2024-2028.

Diehl, J. A. "Cycling to Cancer with Cyclin D1" Cancer Biology and Therapy, 2002; 1(3): 226-231.

Disis, ML., "Mechanism of Action of Immunotherapy", Seminars in Oncology, vol. 41 (5), Suppl. 5, pp. S3-S13, 2014; p. S8, col. 1, paragraph 4.

El-Diery, W. S. "Meeting report: The international conference on tumor progression and therapeutic resistance", Cancer Res, Jun. 1, 2005; 65(11): 4475-4484.

Engler et al. "Novel, potent and selective cyclin D1/CDK4 inhibitors: indolo[6,7-a]pyrrolo[3,4-c]carbazoles", Bioorg Med Chem Lett, Jul. 21, 2003; 13(14): 2261-2267.

Finn et al., "PD 0332991, a selective cyclin D kinase 4/6 inhibitor, preferentially inhibits proliferation of luminal estrogen receptor-positive human breast cancer cell lines in vitro", Breast Cancer Research, Oct. 29, 2009; 11(5): R77.

Finn et al., Abstract S1-6: "Results of a randomized phase 2 study of PD 0332991, a cyclin-dependent kinase (CDK) 4/6 inhibitor, in combination with letrozole vs letrozole alone for first-line treatment of ER+/HER2-advanced breast cancer (BC)", Cancer Res, 2012; 72(24 Suppl): Abstract nr S1-6.

Firer, M. A. and G. J. Gellerman, "Targeted drug delivery for cancer therapy: the other side of antibodies", J. Hematol. Oncol., 2012; 5: 70. [retrieved from http://www.jhoonline.org/content/5/1/70 on Jul. 16, 2014].

Fry, D. W. et al., "Specific inhibition of cyclin-dependent kinase 4/6 by PD 0332991 and associated antitumor activity in human tumor xenografts", Mol Cancer Ther., Nov. 2004; 3(11): 1427-1438.

Giacinti et al., "RB and cell cycle progression", Oncogene, 2006, 25, 5220-5227.

Goel, S. et al., "CDK4/6 Inhibition Triggers Anti-Tumour Immunity", Nature. Aug. 24, 2017; 548 (7668): 471-475. doi: 10.1038/nature23465. Epub Aug. 16, 2017.

Gojo et al., "Phase II study of the cyclin-dependent kinase (CDK) inhibitor Dinaciclib (SCH 727965) in patients with advanced acute leukemia", Blood, 2010, 116(21), 3287.

Goldberg et al. "Pyrazinoindolone inhibitors of MAPKAP-K2" Bioogranic & Medicinal Chemistry Letters, Dec. 23, 2007, 18, 938-941.

Gthx Corp Presentation, "Next Generation Cancer Therapies", Presented Jan. 2020.

Guillard et al., "Synthesis and biological evaluations of new pyrrolo[2,3-b]pyrimidine as SDI analogs" Heterocycles, 2008, vol. 75(5), pp. 1163-1189.

Guo et al. "Staurosporine modulates radiosensitivity and radiation-induced apoptosis in U937 cells" Int J Radiat Biol., Feb. 2006; 82(2): 97-109.

Hallahan, D. E. et al. "Inhibition of protein kinases sensitizes human tumor cells to ionizing radiation" Radiat Res., Mar. 1992; 129(3): 345-350.

Hamilton et al., "Synergism of Cyclin-Dependent Kinase Inhibitors with Camptothecin Derivatives in Small Cell Lung Cancer Cell Lines", Molecules, 2014, 19(2): 2077-2088.

(56) References Cited

OTHER PUBLICATIONS

Hamilton et al., Synergistic Anticancer Activity of Topotecan-Cyclin-Dependent Kinase Inhibitor Combinations against Drug-Resistant Small Cell Lung Cancer (SCLC) Cell Lines, Journal of Cancer Therapy, 2013, 4: 47-53.
Hara, E. et al. "Regulation of p16$^{CDKN2}$ expression and its implications for cell immortalization and senescence" Mol Cell Biol, Mar. 1996; 16(3): 859-867.
He et al., "Transient CDK4/6 inhibition protects hematopoietic stem cells from chemotherapy-induced exhaustion", Science Translational Medicine, 2017, 9, 13986.
Herodin, F. et al. "Short-term injection of antiapoptotic cytokine combinations soon after lethal gamma-irradiation promotes survival" Blood, Apr. 1, 2003; 101(7): 2609-2616.
Hershman, D et al. "Acute myeloid leukemia or myelodysplastic syndrome following use of granulocyte colony-stimulating factors during breast cancer adjuvant chemotherapy" J Natl Cancer Inst, Feb. 7, 2007; 99(3): 196-205.
Hibbs, M. L. et al. "Multiple defects in the immune system of Lyn-deficient mice, culminating in autoimmune disease" Cell, Oct. 20, 1995; 83(2): 301-311.
Hirose, Y. et al. "Abrogation of the Chk1-mediated G(2) checkpoint pathway potentiates temozolomide-induced toxicity in a p53-independent manner in human glioblastoma cells" Cancer Res, Aug. 1, 2001; 61(15): 5843-5849.
Honma, T. et al. "A novel approach for the development of selective Cdk4 inhibitors: library design based on locations of Cdk4 specific amino acid residues" J Med Chem, Dec. 20, 2001; 44(26): 4628-4640.
Honma, T. et al. "Structure-based generation of a new class of potent Cdk4 inhibitors: new de novo design strategy and library design" J Med Chem, Dec. 20, 2001; 44(26): 4615-4627.
Humphreys, B.D. et al. "Intrinsic epithelial cells repair the kidney after injury" Cell Stem Cell, 2008; 2: 284-291.
Humphreys, B.D. et al. "Repair of injured proximal tubule does not involve specialized progenitors" Proc Natl Acad Sci USA, 2011; 108: 9226-9231.
Ikuta, M. et al. "Crystallographic approach to identification of cyclin-dependent kinase 4 (CDK4)-specific inhibitors by using CDK4 mimic CDK2 protein" J Biol Chem, Jul. 20, 2001; 276(29): 27548-27554.
Johnson et al., "Cyclin-dependent kinases (cdks) and the DNA damage response: rationale for cdk inhibitor-chemotherapy combinations as an anticancer strategy for solid tumors", Expert Opin Ther Targets. Nov. 2010; 14(11): 1199-1212.
Johnson, D. G. and C. L. Walker, "Cyclins and Cell Cycle Checkpoints", Annual Review of Pharmacology and Toxicology, Apr. 1999; 39: 295-312.
Johnson, N. and G. Shapiro, "Cyclin-dependent kinase 4/6 inhibition in cancer therapy", Cell Cycle, Nov. 1, 2012; 11(21): 3913-3918.
Johnson, S.M., et al., "Mitigation of hematologic radiation toxicity in mice through pharmacological quiescence induced by CDK4/6 inhibition", J Clin Invest, Jul. 2010; 120(7): 2528-2536.
Karaman, M. W. et al. "A quantitative analysis of kinase inhibitor selectivity" Nat Biotechnol., Jan. 2008; 26(1): 127-132.
Khuri, F. R. "Weighing the hazards of erythropoiesis stimulation in patients with cancer" N Engl J Med, Jun. 14, 2007; 356(24): 2445-2448.
Kiel et al. "SLAM Family Receptors Distinguish Hematopoietic Stem and Progenitor Cells and Reveal Endothelial Niches for Stem Cells" Cell, 2005; 121: 1109-1121.
Knockaert et al. "Pharmacological inhibitors of cyclin-dependent kinases" Trends Pharmacol Sci, Sep. 2002; 23(9): 417-425.
Konecny, Gottfried E., et al., "Expression of p16 and Retinoblastoma Determines Response to CDK4/6 Inhibition in Ovarian Cancer", Clinical Cancer Research, 2011, vol. 17, No. 6, p. 1591-1602.
Kubinyi. "3D QSAR in Drug Design: Ligand-Protein Interactions and Molecular Similarity", Springer, 1998, vol. 2-3, (800 pages). p. 243-44.
Kubo, et al. "The p16 status of tumor cell lines identifies small molecule inhibitors specific for cyclin-dependent kinase 4" Clin Cancer Res, 1999; 5: 4279-4286.
Landis, M.W. et al. Cyclin D1-dependent kinase activity in murine development and mammary tumorigenesis. Cancer Cell, 2006; 9: 13-22.
Laredo, J. et al. "Effect of the protein kinase C inhibitor staurosporine on chemosensitivity to daunorubicin of normal and leukemic fresh myeloid cells" Blood, Jul. 1, 1994; 84(1): 229-237.
Le Deley et al. "Anthracyclines, Mitoxantrone, Radiotherapy, and Granulocyte Colony-Stimulating Factor: Risk Factors for Leukemia and Myelodysplastic Syndrome After Breast Cancer" J Clin Oncol, 2007; 25: 292-300.
Malumbres, M. and M. Barbacid "Cell cycle, CDKs and cancer: a changing paradigm" Nature Reviews Cancer, Mar. 2009; 9(3): 153-166.
Malumbres, M. and M. Barbacid "Mammalian cyclin-dependent kinases" Trends Biochem. Sci., Nov. 2005; 30(11): 630-641.
Matsui, K. et al., "Phase II trial of carboplatin plus oral etoposide for elderly patients with small-cell lung cancer", British Journal of Cancer 77(11), pp. 1961-1965, 1998; abstract.
McClendon et al., "CDK4/6 inhibition antagonizes the cytotoxic response to anthracycline therapy", Cell Cycle, 2012, 11(14), 2747-2755.
McInnes Campbell, "Progress in the evaluation of CDK inhibitors as anti-tumor agents", Drug Discovery Today, 2008, 13, (19/20), 875-881.
Menu, E. et al. "A novel therapeutic combination using PD 0332991 and bortezomib: study in the 5T33MM myeloma model" Cancer Res, Jul. 15, 2008; 68(14): 5519-5523.
Michaud, Karine et al. "Pharmacologic inhibition of cdk4/6 arrests the growth of glioblastoma multiforme intracranial xenografts" Cancer Res, Apr. 15, 2011; 70: 3228-3238.
Mino, R Caira., "Crystalline Polymorphism of Organic Compounds", Topics in Current Chemistry, Springer, berlin, DE, 1998, 198, 163-208; ISSN: 0340-1022; DOI: 10.1007/3-540-69178-2_5.
Mita et al., "Randomized Phase II trial of the cyclin-dependent kinase inhibitors Dinaciclib (MK-7965) versus Capecitabine in patients with advanced breast cancer", Clinical Breast Cancer, 2014, 14(3), 169-176.
Morgan, D.O. "Cyclin-dependent Kinases: Engines, Clocks, and Microprocessors" Annual Review of Cell and Developmental Biology, 1997; 13: 261-291.
NCT02079636—A Study of Abemaciclib (LY2835219) in Combination with Another Anticancer Drug in Participants with Lung Cancer (NSCLC); Mar. 6, 2014.
NCT02693535—TAPUR: Testing the Use of Food and Drug Administration (FDA) Approved Drugs That Target a Specific Abnormality in a Tumor Gene in People with Advanced Stage Cancer (TAPUR); Feb. 26, 2016.
NCT02779751—A Study of Abemaciclib (LY2835219) in Participants with Non-Small Cell Lung Cancer or Breast Cancer; May 20, 2016.
NCT03041311—Carboplatin, Etoposide, and Atezolizumab with or without Trilaciclib; Jul. 26, 2019.
NCT03294694—Ribociclib + PDR001 in Breast Cancer and Ovarian Cancer; Sep. 27, 2017.
O'dwyer, et al. "A phase I dose escalation trial of a daily oral CDK 4/6 inhibitor PD-0332991" J Clin Oncol, 2007; 25(18S): 3550. [Abstract].
Ojeda, F. et al. "Role of protein kinase-C in thymocyte apoptosis induced by irradiation" Int J Radiat Biol., May 1992; 61(5): 663-667.
Ottensmeier, et al., "A Novel Phase II Trial of Ipilimumab, Carboplatin and Etoposide (ICE) for the First Line Treatment of Extensive Stage Small Cell Lung Cancer (SCLC)", Annals of Oncology 25 (Supplement 4): iv511-iv516, 2014.
Parsam et al., "A comprehensive, sensitive and economical approach for the detection of mutations in the RB1 gene in retinoblastoma", Journal of Genetics, Dec. 2009; 88(4): 517-527.
Rader et al., "Dual CDK4/CDK6 inhibition induces cell cycle arrest and senescence in neuroblastoma", Clinical Cancer Res., 2013, 19(22), 6173-6182.

(56) References Cited

OTHER PUBLICATIONS

Ramsey, M. R. et al. "Expression of p16Ink4a compensates for p18Ink4c loss in cyclin-dependent kinase 4/6-dependent tumors and tissues" Cancer Res, May 15, 20075; 67(10): 4732-4741.

Reck et al., Phase III Randomized Trial of Ipilimumab Plus Etoposide and Platinum Versus Placebo Plus Etoposide and Platinum in Extensive-Stage Small-Cell Lung Cancer. J Clin Oncol., 2016, 34:3740-3748.

Reddy, H. K. et al. "Cyclin-dependent kinase 4 expression is essential for neu-induced breast tumorigenesis" Cancer Research, 2005; 65: 10174-10178.

Roberts et al. "Multiple Roles of Cyclin-Dependent Kinase 4/6 Inhibitors in Cancer Therapy" JNCI, 2012; 104(6):476-487.

Rocha Lima et al., Abstract CT151:"G1T28, a cyclin dependent kinase 4/6 inhibitor, in combination with etoposide and carboplatin for extensive stage small cell lung cancer (ES-SCLC): preliminary results", Cancer Research, 2016, 76(14), CT151, XP002799585; & 107th Annual Meeting of the American Association of Cancer Research (AACR), New Orleans, LA Apr. 16-20, 2016.

Ruas et al. "CDK4 and CDK6 Delay Senescence by Kinase-Dependent and p16INK4a-Independent Mechanisms" Molecular and Cellular Biology, Jun. 2007; 27(12): 4273-4282.

Samady, L. et al. "Activation of CDK4 gene expression in human breast cancer cells by the Brn-3b POU family transcription factor" Cancer Biology & Therapy, 2004; 3: 317-323.

Sanchez-Martinez, C. et al. "Aryl[a]pyrrolo[3,4-c]carbazoles as selective cyclin D1-CDK 4 inhibitors" Bioorg Med Chem Lett, Nov. 3, 2003; 13(21): 3835-3839.

Sanchez-Martinez, C. et al. "Studies on cyclin-dependent kinase inhibitors: indolo-[2,3-a]pyrrolo[3,4-c]carbazoles versus bis-indolylmaleimides" Bioorg Med Chem Lett, Nov. 3, 2003; 13(21): 3841-3846.

Sawai, Catherine M., et al., "Therapeutic Targeting of the Cyclin D3:CDK4/6 Complex in T Cell Leukemia," Cancer Cell, Oct. 16, 2012, vol. 22, pp. 452-465.

Schmidt, M. and Z. Fan, "Protection against chemotherapy-induced cytotoxicity by cyclin-dependent kinase inhibitors (CKI) in CKI-responsive cells" Oncogene, Sep. 27, 2001; 20(43): 6164-6171.

Schwartz, G.K. et al., "Phase I study of PD 0332991, a cyclin-dependent kinase inhibitor, administered in 3-week cycles (Schedule 2/1)" Br J Cancer, Jun. 7, 2011; 104(12): 1862-1868.

Seed, T. M., "Radiation protectants: current status and future prospects" Health Phys, Nov. 2005; 89(5): 531-545.

Sharma, P.S. et al. "Inhibitors of cyclin dependent kinases: useful targets for cancer treatment" Curr. Cancer Drug Targets, Feb. 2008; 8(1): 53-75.

Sharpless et al. "Both products of the mouse Ink4a/Arf locus suppress melanoma formation in vivo" Oncogene, Aug. 7, 2003; 22(32): 5055-5059.

Sherr, C. J., "Cancer Cell Cycles" Science, Dec. 6, 1996; 274(5293): 1672-1677.

Shields et al. "Lack of Extracellular Signal-Regulated Kinase Mitogen-Activated Protein Kinase Signaling Shows a New Type of Melanoma" Cancer Res, 2007; 67: 1502-1512.

Shimamura, T. et al. "Identification of potent 5-pyrimidinyl-2-aminothiazole CDK4, 6 inhibitors with significant selectivity over CDK1, 2, 5, 7, and 9" Bioorg Med Chem Lett., Jul. 15, 2006; 16(14): 3751-3754.

Sielecki et al."Quinazolines as cyclin dependent kinase inhibitors", Bioogranic & Medicinal Chemistry Letters, May 7, 2001, 11, 1157-1160.

Soni, R. et al. "Selective in vivo and in vitro effects of a small molecule inhibitor of cyclin-dependent kinase 4" J Natl Cancer Inst, Mar. 21, 2001; 93(6): 436-446.

Sorrentino Jessica et al., Abstract 941: "G1T28-1, a novel CDK 4/6 inhibitor, protects murine hematopoietic stem and progenitor cells from cytotoxic chemotherapy", Cancer Research, 2015, 75(15), 941, XP002799586; & 106th Annual Meeting of the American Association for Cancer Research (AACR), Philadelphia, PA, Apr. 18-22, 2015.

Sorrentino Jessica et al., Abstract 5628: "Trilaciclib (G1T28), a CDK 4/6 inhibitor, enhances the efficacy of combination therapy and immune checkpoint inhibitor treatment in preclinical models", Cancer Research, 2017, 77(13), Supplement 1, XP002799587.

Stice, James P. et al., "CDK4/6 Therapeutic Intervention and viable alternative to taxane in CRPC", Molecular Cancer Research, 2017, 15(6), 660-669, XP55457140.

Stone, S. et al. "Reversible, p16-mediated cell cycle arrest as protection from chemotherapy" Cancer Research, Jul. 15, 1996; 56(14): 3199-3202.

Tan et al., "Trilaciclib plus chemotherapy versus chemotherapy alone in patients with metastatic triple-negative breast cancer: a multicenter, randomized, open-label, phase 2 trial", Lancet Oncol., 2019, 20, 1587-1601.

Tao Z et al., "Coadministration of trametinib and palbociclib radiosensitizers KRAS-Mutant non-small cell lung cancers in vitro and in vivo", Cancer Therapy, 2016, 22(1), 122-133.

Teicher, B. A. and R. V. Chari "Antibody conjugate therapeutics: challenges and potential" Clinical Cancer Research, 2011; 17(20): 6389-6397.

Tong et al., "Phase I and pharmacologic study of SNS-032, a potent and selective CDK2, 7 and 9 inhibitors in patients with advanced chronic lymphocytic leukemia and multiple myeloma", Journal of Clinical Oncology, 2010, 28(18), 3015-3022.

Toogood, P. L. et al. "Discovery of a potent and selective inhibitor of cyclin-dependent kinase 4/6" J Med Chem, Apr. 7, 2005; 48(7): 2388-2406.

Tsou, H. R. et al. "4-(Phenylaminomethylene)isoquinoline-1,3(2H,4H)-diones as potent and selective inhibitors of the cyclin-dependent kinase 4 (CDK4)" J Med Chem, Jun. 26, 2008; 51(12): 3507-3525.

Tsou, H. R. et al. "Discovery of 4-(benzylaminomethylene)isoquinoline-1,3-(2H,4H)-diones and 4-[(pyridylmethyl)aminomethylene]isoquinoline-1,3-(2H,4H)-diones as potent and selective inhibitors of the cyclin-dependent kinase 4" J Med Chem, Apr. 23, 2009; 52(8): 2289-2310.

Tu, S. et al. "New potential inhibitors of cyclin-dependent kinase 4: design and synthesis of pyrido[2,3-d]pyrimidine derivatives under microwave irradiation" Bioorg Med Chem Lett, Jul. 1, 2006; 16(13): 3578-3581.

Uckun, F. M. et al. "In vivo radioprotective effects of recombinant human granulocyte colony-stimulating factor in lethally irradiated mice" Blood, Feb. 1, 1990; 75(3): 638-645.

Vanderwel, S.N. et al. "Pyrido[2,3-d]pyrimidin-7-ones as specific inhibitors of cyclin-dependent kinase 4" J Med Chem., Apr. 7, 2005; 48(7): 2371-2387.

Walker et al. "Virtually 100% of melanoma cell lines harbor alterations at the DNA level within CDKN2A, CDKN2B, or one of their downstream targets" Genes Chromosomes & Cancer, 1998; 22: 157-163.

Wang et al. "Loss of p21 increases sensitivity to ionizing radiation and delays the onset of lymphoma in atm-deficient mice" Proc Natl Acad Sci, USA, 1997; 94: 14590-14595.

Wang, R. H. et al. "Protein kinase inhibitor staurosporine enhances cytotoxicity of antitumor drugs to cancer cells" Yao Xue Xue Bao, 1996; 31(6): 411-415. [Abstract].

Weiss et al., "Myelopreservation with the CDK4/6 inhibitor trilaciclib in patients with small-cell lung cancer receiving first-line chemotherapy: a phase Ib/randomized phase II trial," Annals of Oncology, 2019, 30:1613-1621.

Wermuth, The Practice of Medicinal Chemistry, 2d ed. (2003), 768 pages. Chs. 9-10.

Wilson et al., "Hematopoietic Stem Cells Reversibly Switch from Dormancy to Self-Renewal during Homeostasis and Repair", Cell, 2008; 135: 1118-1129.

Yu, Q. et al., "Requirement for CDK4 kinase function in breast cancer", Cancer Cell, 2006; 9: 23-32.

Zhang, et al., "Cyclin D-CDK4 kinase destabilizes PD-L1 via Cul3$^{SPOP}$ to control cancer immune surveillance", Nature, 2018, 553(7686), 91-95; Jan. 4, 2018.

Zhu, G. et al., "Synthesis, structure-activity relationship, and biological studies of indolocarbazoles as potent cyclin D1-CDK4 inhibitors", J Med Chem., May 22, 2003; 46(11): 2027-2030.

(56) References Cited

OTHER PUBLICATIONS

Zhu, G. et al., "Synthesis of quinolinyl/isoquinolinyl[a]pyrrolo [3,4-c] carbazoles as cyclin D1/CDK4 inhibitors", Bioorg Med Chem Lett, Apr. 7, 2003; 13(7): 1231-1235.
US, U.S. Pat. No. 8,598,186, B2, U.S. Appl. No. 13/869,520, Tavares et al., Dec. 3, 2013.
US, U.S. Pat. No. 8,598,197, B2, U.S. Appl. No. 13/869,576, Tavares et al., Dec. 3, 2013.
US, U.S. Pat. No. 8,691,830, B2, U.S. Appl. No. 13/869,594, Tavares et al., Apr. 8, 2014.
US, U.S. Pat. No. 8,822,683, B2, U.S. Appl. No. 14/162,637, Tavares et al., Sep. 2, 2014.
US, U.S. Pat. No. 8,829,012, B2, U.S. Appl. No. 14/162,649, Tavares et al., Sep. 9, 2014.
US, U.S. Pat. No. 9,102,682, B2, U.S. Appl. No. 14/452,296, Tavares et al., Aug. 11, 2015.
US, U.S. Pat. No. 9,260,442, B2, U.S. Appl. No. 14/498,796, Tavares, Jan. 27, 2016.
US, U.S. Pat. No. 9,464,092, B2, U.S. Appl. No. 14/212,911, Strum et al., Oct. 11, 2016.
US, U.S. Pat. No. 9,481,691, B2, U.S. Appl. No. 14/712,630, Tavares et al., Nov. 1, 2016.
US, U.S. Pat. No. 9,487,530, B2, U.S. Appl. No. 14/212,430, Strum et al., Nov. 8, 2016.
US, U.S. Pat. No. 9,499,564, B2, U.S. Appl. No. 14/712,582, Tavares et al., Nov. 22, 2016.
US, U.S. Pat. No. 9,527,857, B2, U.S. Appl. No. 14/214,048, Strum et al., Dec. 27, 2016.
US, U.S. Pat. No. 9,717,735, B2, U.S. Appl. No. 14/690,180, Strum et al., Aug. 1, 2017.
US, U.S. Pat. No. 9,745,316, B2, U.S. Appl. No. 14/982,443, Tavares, Aug. 29, 2017.
US, U.S. Pat. No. 9,856,268, B2, U.S. Appl. No. 15/348,862, Tavares, Jan. 2, 2018.
US, U.S. Pat. No. 9,931,345, B2, U.S. Appl. No. 15/288,878, Strum et al., Apr. 3, 2018.
US, U.S. Pat. No. 9,957,276, B2, U.S. Appl. No. 15/348,770, Tavares et al., May 1, 2018.
US, U.S. Pat. No. 10,076,523, B2, U.S. Appl. No. 15/387,083, Strum et al., Sep. 18, 2018.
US, U.S. Pat. No. 10/085,992, B2, U.S. Appl. No. 15/342,990, Strum et al., Oct. 2, 2018.
US, U.S. Pat. No. 10/189,849, B2, U.S. Appl. No. 15/918,834, Tavares et al., Jan. 29, 2019.
US, U.S. Pat. No. 10,189,850, B2, U.S. Appl. No. 15/918,852, Tavares et al., Jan. 29, 2019.
US, U.S. Pat. No. 10,189,851, B2, U.S. Appl. No. 15/918,877, Tavares et al., Jan. 29, 2019.
US, U.S. Pat. No. 10,231,969, B2, U.S. Appl. No. 15/457,699, Strum, et al., Mar. 19, 2019.
US, U.S. Pat. No. 10,376,519, B2, U.S. Appl. No. 15/665,071, Strum, et al., Aug. 13, 2019.
US, U.S. Pat. No. 10,413,547, B2, U.S. Appl. No. 16/142,574, Strum, et al., Sep. 17, 2019.
US, U.S. Pat. No. 10,434,104, B2, U.S. Appl. No. 16/112,362, Strum, et al., Oct. 8, 2019.
US, U.S. Pat. No. 10,464,940, B2, U.S. Appl. No. 15/860,483, Tavares et al., Nov. 5, 2019.
US, U.S. Pat. No. 10,618,905, B2, U.S. Appl. No. 16/230,412, Strum, et al., Apr. 14, 2020.
US, U.S. Pat. No. 10/660,896, B2, U.S. Appl. No. 15/943,278, Strum, et al., May 26, 2020.
US, U.S. Pat. No. 10,654,831, B2, U.S. Appl. No. 16/230,388, Strum, et al., May 19, 2020.
US, U.S. Pat. No. 10,696,682, B2, U.S. Appl. No. 16/226,430, Tavares, et al., Jun. 30, 2020.
US, U.S. Pat. No. 10,709,711, B2, U.S. Appl. No. 16/228,308, Strum et al., Jul. 14, 2020.
US, U.S. Pat. No. 10,829,490, B2, U.S. Appl. No. 16/230,396, Strum et al., Nov. 10, 2020.
US, U.S. Pat. No. 10,865,210, B2, U.S. Appl. No. 16/230,381, Smith et al., Dec. 15, 2020.
US, U.S. Pat. No. 10,925,878, B2, U.S. Appl. No. 16/178,419, Smith et al., Feb. 23, 2021.
US, U.S. Pat. No. 10,927,120, B2, U.S. Appl. No. 16/721,631, Smith et al., Feb. 23, 2021.
US, U.S. Pat. No. 10,966,984, B2, U.S. Appl. No. 16/112,360, Strum et al., Apr. 6, 2021.
US, U.S. Pat. No. 10,988,479, B2, U.S. Appl. No. 17/097,854, Schneider, Apr. 27, 2021.
US, U.S. Pat. No. 11,040,042, B2, U.S. Appl. No. 16/886,309, Strum et al., Jun. 22, 2021.
US, U.S. Pat. No. 11,090,306, B2, U.S. Appl. No. 16/572,418, Strum, et al., Aug. 17, 2021.
US, 2019/0151311, A1, U.S. Appl. No. 16/254,364, Strum, et al., May 23, 2019.
US, 2019/0167691, A1, U.S. Appl. No. 16/268,317, Strum, et al., Jun. 6, 2019.
US, 2019/0321370, A1, U.S. Appl. No. 16/432,244, Sorrentino, et al., Oct. 24, 2019.
US, 2019/0321332, A1, U.S. Appl. No. 16/460,502, Strum et al., Oct. 24, 2019.
US, 2019/0374545, A1, U.S. Appl. No. 16/547,342, Sorrentino, et al., Dec. 12, 2019.
US, 2020/0123168, A1, U.S. Appl. No. 16/721,631, Smith et al., Apr. 23, 2020.
US, 2020/0239486, A1, U.S. Appl. No. 16/847,426, Strum, et al., Jul. 30, 2020.
US, 2020/0283406, A1, U.S. Appl. No. 16/877,249, Strum, et al., Sep. 10, 2020.
US, 2020/0331925, A1, U.S. Appl. No. 16/918,985, Strum, et al., Oct. 22, 2020.
US, 2020/0345743, A1, U.S. Appl. No. 16/926,035, Strum, et al., Nov. 5, 2020.
US, 2020/0405721, A1, U.S. Appl. No. 16/924,033, Beelen et al., Dec. 31, 2020.
US, 2021/0030758, A1, U.S. Appl. No. 17/067,549, Strum, et al., Feb. 4, 2021.
US, 2021/0047328, A1, U.S. Appl. No. 17/088,298, Strum, et al., Feb. 18, 2021.
US, 2021/0077498, A1, U.S. Appl. No. 17/102,311, Strum, et al., Mar. 18, 2021.
US, 2021/0122755, A1, U.S. Appl. No. 17/121,392, Smith et al., Apr. 29, 2021.
US, 2021/0213022, A1, U.S. Appl. No. 17/181,638, Strum, et al., Jul. 15, 2021.
US, 2021/0179567, A1, U.S. Appl. No. 17/184,354, Schneider et al., Jun. 17, 2021.
US, 2021/0267986, A1, U.S. Appl. No. 17/315,011, Sorrentino et al., Sep. 2, 2021.
US, 2021/0299130, A1, U.S. Appl. No. 17/222,873, Strum, et al., Sep. 30, 2021.
US, 2021/0395259, A1, U.S. Appl. No. 17/153,516, Tavares et al., Dec. 23, 2021.
US, U.S. Appl. No. 17/683,146, Smith et al., filed Feb. 28, 2022.
US, U.S. Appl. No. 17/403,577, Strum et al., filed Aug. 16, 2021.
US, U.S. Appl. No. 17/554,940, Roberts et al., filed Dec. 17, 2021.
US, U.S. Pat. No. 11,261,193, B2, U.S. Appl. No. 16/721,631, Smith et al., Mar. 1, 2022.
US, U.S. Pat. No. 11,357,779, B2, U.S. Appl. No. 16/924,033, Beelen et al., Jun. 14, 2022.
US, U.S. Pat. No. 11,364,222, B2, U.S. Appl. No. 16/460,502, Strum et al., Jun. 21, 2022.
US, U.S. Pat. No. 11,395,821, B2, U.S. Appl. No. 16/547,342, Sorrentino et al., Jun. 26, 2022.
US, U.S. Pat. No. 11,446,295, B2, U.S. Appl. No. 16/254,364, Strum et al., Sep. 20, 2022.
US, U.S. Pat. No. 11,529,352, B2, U.S. Appl. No. 16/432,244, Sorrentino et al., Dec. 20, 2022.
US, U.S. Pat. No. 11,629,150, B2, U.S. Appl. No. 17/121,392, Smith et al., Apr. 18, 2023.
US, U.S. Pat. No. 11,654,148, B2, U.S. Appl. No. 17/181,638, Strum et al., May 23, 2023.

(56) References Cited

OTHER PUBLICATIONS

US, U.S. Pat. No. 11,708,337, B2, U.S. Appl. No. 17/184,354, Schneider et al., Jul. 25, 2023.
US, U.S. Pat. No. 11,717,523, B2, U.S. Appl. No. 17/222,873, Strum et al., Aug. 8, 2023.
US, 2022/0175780, A1, U.S. Appl. No. 17/403,577, Strum et al., Jun. 9, 2022.
US, 2022/0175787, A1, U.S. Appl. No. 17/544,940, Roberts et al., Jun. 9, 2022.
US, 2022/0241275 A1, U.S. Appl. No. 17/718,052, Strum et al., Aug. 4, 2022.
US, 2023/0043305, A1, U.S. Appl. No. 17/683,146, Smith et al., Feb. 9, 2023.
US, 2023/0146638, A1, U.S. Appl. No. 17/854,755, Sorrentino et al., May 11, 2023.
US, 2023/0149406, A1, U.S. Appl. No. 17/839,215, Beelen et al., May 18, 2023.
US, 2023/0241059, A1, U.S. Appl. No. 17/898,196, Strum et al., Aug. 3, 2023.
US, 2023/0248733, A1, U.S. Appl. No. 17/890,130, Strum et al., Aug. 10, 2023.
US, 2023/0302001, A1, U.S. Appl. No. 18/072,963, Sorrentino et al., Sep. 28, 2023.
US, 2023/0364098, A1, U.S. Appl. No. 18/117,983, Strum et al., Nov. 16, 2023.
US, 2023/0381189, A1, U.S. Appl. No. 18/231,091, Strum et al., Nov. 30, 2023.
US, 2024/0109906, A1, U.S. Appl. No. 18/120,806, Tavares et al., Apr. 4, 2024.
US, 2024/0139196, A1, U.S. Appl. No. 18/394,512, Beelen et al., May 2, 2024.
US, U.S. Appl. No. 18/225,537, Schneider et al., filed Jul. 24, 2023.
Braun, D. E. and Griesser, U. J. "Stoichiometric and Nonstoichiometric Hydrates of Brucine". Cryst. Growth Des.; 16, 6111-6121, Aug. 26, 2016.
EU Clinical Trials Register, pp. 1-5, Feb. 28, 2020.
Kiang et al. "Structural studies of a non-stoichiometric channel hydrate using high resolution X-ray powder diffraction, solid-state nuclear magnetic resonance, and moisture sorption methods". J. Pharm. Sci.; 103:2809-2818, Jan. 27, 2014.
Zhao, Guisen et al."Basis for Design and Development of Drugs", Shandong University Press, pp. 93-94, Nov. 30, 2015.

\* cited by examiner

MORPHIC FORMS OF TRILACICLIB AND METHODS OF MANUFACTURE THEREOF

CROSS-REFERENCE TO RELATED APPLICATIONS

This application is a continuation of U.S. patent application Ser. No. 17/097,854, filed Nov. 13, 2020, which claims priority to U.S. Provisional Application 63/039,372, filed Jun. 15, 2020. The entirety of each of these applications is incorporated herein by reference.

FIELD OF THE INVENTION

This invention provides advantageous isolated morphic forms of trilaciclib which is 2'-((5-(4-methylpiperazin-1-yl)pyridin-2-yl)amino)-7',8'-dihydro-6'H-spiro[cyclohexane-1,9'-pyrazino[1',2':1,5]pyrrolo[2,3-d]pyrimidin]-6'-one, for example in the form of a free base, a di-hydrochloride salt, or a dihydrochloride, dihydrate.

BACKGROUND

U.S. Pat. Nos. 8,598,186; 8,598,197; 9,957,276 10,189,849; and 10,189,850 and corresponding WO 2012/061156 assigned to G1 Therapeutics, Inc. describe a class of N-(heteroaryl)-pyrrolo[3,2-d]pyrimidin-2-amine cyclin dependent kinase inhibitors including 2'-((5-(4-methylpiperazin-1-yl)pyridin-2-yl)amino)-7',8'-dihydro-6'H-spiro [cyclohexane-1,9'-pyrazino[1',2':1,5]pyrrolo[2,3-d]pyrimidin]-6'-one (Compound 1) with the formula

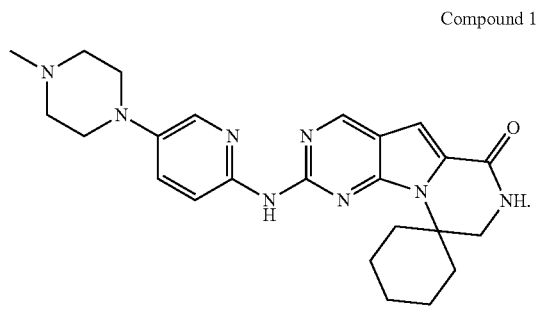 [SMILES: CN1CCN(c2ccc(Nc3ncc4cc5n(c4n3)C3(CCCCC3)CNC5=O)nc2)CC1]

Compound 1

Synthetic procedures to make Compound 1 are described in US 2019/135820 and WO 2020/041770 both of which are assigned to G1 Therapeutics, Inc.

Compound 1 is referred to as "G1T28" or "trilaciclib." It transiently arrests normal cells to prevent chemotherapy-induced myelosuppression and improve anti-tumor efficacy. It can be used, for example, in patients with small cell lung cancer (SCLC) receiving topotecan chemotherapy, as well as in combination with etoposide and carboplatin in SCLC. It is also useful, for example, in combination with carboplatin, etoposide, and atezolizumab (a PD-L1 inhibitor) in small cell lung cancer (SCLC). Based on myelopreservation data in patients with SCLC trilaciclib has been granted Breakthrough Therapy Designation (BTD) from the U.S. Food and Drug Administration (FDA) (see, e.g., Weiss et al., "Myelopreservation with the CDK4/6 inhibitor trilaciclib in patients with small-cell lung cancer receiving first-line chemotherapy: a phase Ib/randomized phase II trial," Annals of Oncology 30:1613-1621 (2019); Daniel et al., "Trilaciclib decreases myelosuppression in extensive-stage small cell lung cancer (ES-SCLC) patients receiving first-line chemotherapy plus atezolizumab," ESMO 2019 Congress Poster Abstract #1742PD). Compound 1 is also in human clinical trials for treatment of triple-negative breast cancer in combination with the standard of care for neoadjuvant treatment of breast cancer.

SUMMARY

It has been discovered that Compound 1 (2'-((5-(4-methylpiperazin-1-yl)pyridin-2-yl)amino)-7',8'-dihydro-6'H-spiro[cyclohexane-1,9'-pyrazino[1',2':1,5]pyrrolo[2,3-d]pyrimidin]-6'-one) as a dihydrochloride can be prepared in a highly purified, advantageous morphic form.

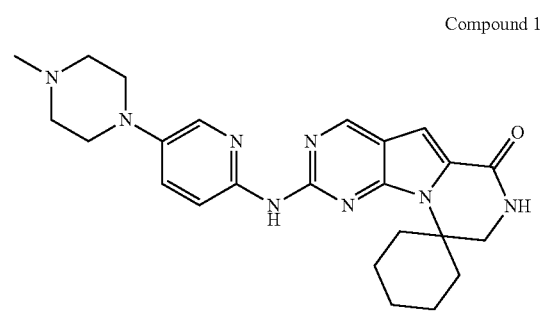 [SMILES: CN1CCN(c2ccc(Nc3ncc4cc5n(c4n3)C3(CCCCC3)CNC5=O)nc2)CC1]

Compound 1

This highly purified, advantageous morphic form has been denoted "Pattern 1." Pattern 1 is a highly crystalline form of Compound 1 as a dihydrochloride. Pattern 1 exhibits superior stability when compared to other morphic forms. For example, in competitive slurry experiments (see Example 10) Pattern 1 is the predominantly formed morphic structure of Compound 1 as a dihydrochloride. Pattern 1 also has advantageous properties in the manufacture of Compound 1 as a dihydrochloride. For example, Pattern 1 can be made on large scale via crystallization of Compound 1 in a heated HCl solution. Pattern 1 can also be formed from other morphic or amorphous forms of Compound 1 via recrystallization.

Compound 1 Pattern 1 can be in the form of a dihydrochloride, dihydrate. Pattern 1 typically, initially, forms a dihydrochloride, dihydrate and even after being dried will eventually revert to a dihydrochloride, dihydrate when exposed to air. Regardless of water content Pattern 1 can maintain its representative XRPD peaks as described in more detail below. For example, if the morphic form of Compound 1 is prepared as described herein to form Pattern 1 and then dried, the representative XRPD peaks will remain the same before and after drying.

Trilaciclib is used in certain embodiments as a myelopreservation agent to protect healthy cells, notably hematopoietic cells, during chemotherapy. It is intended to be administered by intravenous injection for fast access to the blood stream just prior to administration of chemotherapy, typically also by IV injection. However, a problem is evident that trilaciclib is not very soluble in water, and also practically insoluble in DMSO. Further, it becomes less soluble as the pH increases. Blood typically has a pH of 7.35-7.45, which is mildly basic. Phosphate buffered saline typically has a pH of 7.2-7.4. Trilaciclib is not very soluble at this pH, and thus multiple problems can occur. Most importantly, a significant amount of trilaciclib is required to achieve a therapeutic effect. A typical dose is 240 mg/m$^2$ and can be estimated to be about a 300 mg dose for a normal adult. Because of the lack of solubility in water, it would take a dilute solution in a lot of fluid to provide this dosage of free base trilaciclib, which would have to be given over a long period of time, in contradiction to how it should be delivered. The trilaciclib IV is typically administered over about 30 minutes (20-60 minutes), which means that the drug has to be concentrated, not dilute, in the IV fluid. Also, when the free base trilaciclib is injected into blood, there is a real possibility of at least some of it falling out of solution because of the fact that blood is mildly basic. This can cause problems at the site of injection caused by drug deposition and a loss of activity.

It has been discovered that an IV solution of trilaciclib for injection to cancer patients to preserve healthy cells or for an antineoplastic can be accomplished by administering it as a dihydrochloride or a dihydrochloride, dihydrate. This enables the intended therapeutic effect because it can be delivered quickly in a concentrated form directly to the blood stream. In a principal embodiment, the IV solution is prepared from a lyophilized powder of the dihydrochloride, dihydrate crystalline Pattern 1.

In certain embodiments Compound 1 Pattern 1 is a dihydrochloride, dihydrate morphic form. In certain embodiments the invention provides the composition of Compound 1 as a dihydrochloride, dihydrate. In certain embodiments the invention provides the composition of Compound 1 Pattern 1 as a dihydrochloride, dihydrate. In certain embodiments Compound 1 Pattern 1 as a dihydrochloride, dihydrate can be treated for any condition that is responsive to trilaciclib, including for myelopreservation or as an antineoplastic agent.

Other morphic forms of Compound 1 as a dihydrochloride have also been identified. Pattern 2, and Pattern 3 are also highly crystalline forms of Compound 1 as a dihydrochloride. Pattern 4 is a crystalline solvate of Compound 1 as a dihydrochloride with acetonitrile. Pattern 5 is a crystalline form of Compound 1 as a dihydrochloride. Pattern 6 is a metastable form of Compound 1 as a dihydrochloride. Pattern 11 is a crystalline form of Compound 1 as a dihydrochloride, hemi-hydrate.

Morphic forms of Compound 1 as a free base have also been identified. Pattern 8 and Pattern 10 are crystalline forms of Compound 1 as a free base. Pattern 9 is a crystalline form of Compound 1 as a free base which may be either a solvate or hydrate.

In certain embodiments Pattern 1 is the most stable morphic form of Compound 1 as a dihydrochloride and formed by competitive slurry experiments with either Pattern 2 or Pattern 3.

In one aspect of the present invention, isolated Compound 1 Pattern 1 is used in the manufacture of a lyophilized form that is then formulated with a suitable solvent such as phosphate buffered saline for administration to a patient, for example, by intravenous delivery. In another embodiment it can be formulated into a parenteral dosage form. This dosage form can be used, for example, in subcutaneous administration.

In another aspect of the present invention I Compound 1 Pattern 1 in the form of a dihydrochloride, dihydrate in a formulation is provided. In certain embodiments the formulation comprises about 300 to 400 mg, about 350-400 mg or more particularly about 373 mg of Compound 1 Pattern 1 dihydrochloride, dihydrate. In a specific embodiment the pharmaceutically acceptable formulation includes about 373 mg of Compound 1 Pattern 1 dihydrochloride, dihydrate (equivalent to about 300 mg of trilaciclib free base), about 50-100 mg, about 60-80 mg, or more particularly about 76 mg of citric acid monohydrate, about 280-320 mg, for example 300 mg, of mannitol which may be provided as a lyophilized form for later reconstitution.

Trilaciclib is typically administered to the patient in an intravenous formulation. However, the solid forms of trilaciclib can be important because they may be used to achieve desired manufacturing purity and/or performance, and may also be important to solid state shelf life prior to formulation, or in a solid dosage form for therapeutic delivery.

Given the therapeutic importance of trilaciclib to medical therapy for patients suffering from a proliferative disorder such as a tumor or cancer, it is beneficial to provide this advantageous solid form of the compound that contributes to the success or performance of the compound during manufacture, storage, formulation, and/or administration.

Figure 8:
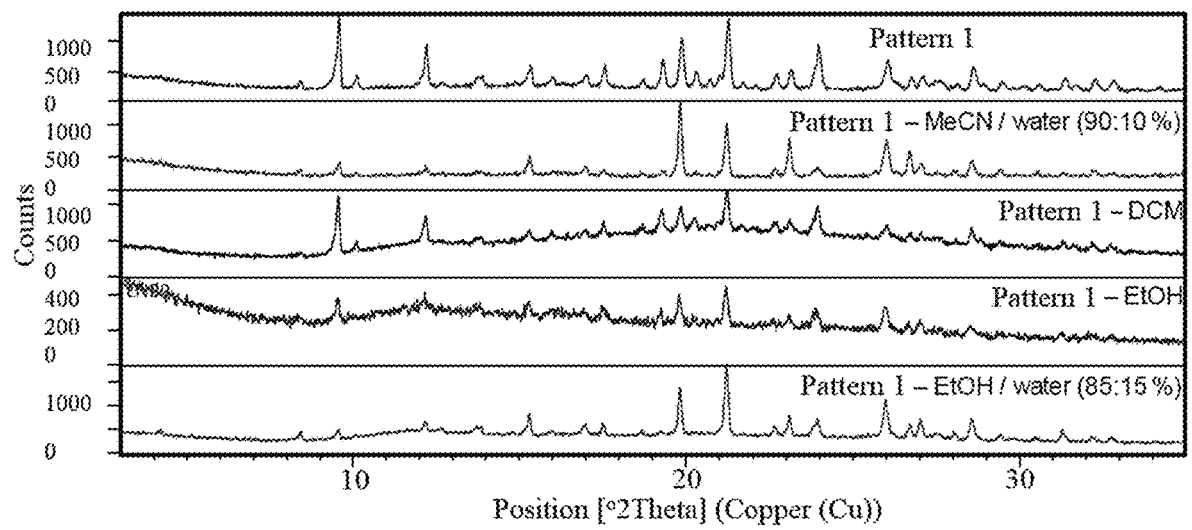

FIG. 8 is a comparison of XRPD diffractograms of Pattern 1 before solvent solubility studies and the Pattern 1 material that results from various solvent solubility studies. The diffractograms were obtained as described in Example 1 and the studies were conducted as described in Example 13. The x-axis is 2Theta measured in degrees and the y-axis is intensity measured in counts.

Figure 9:
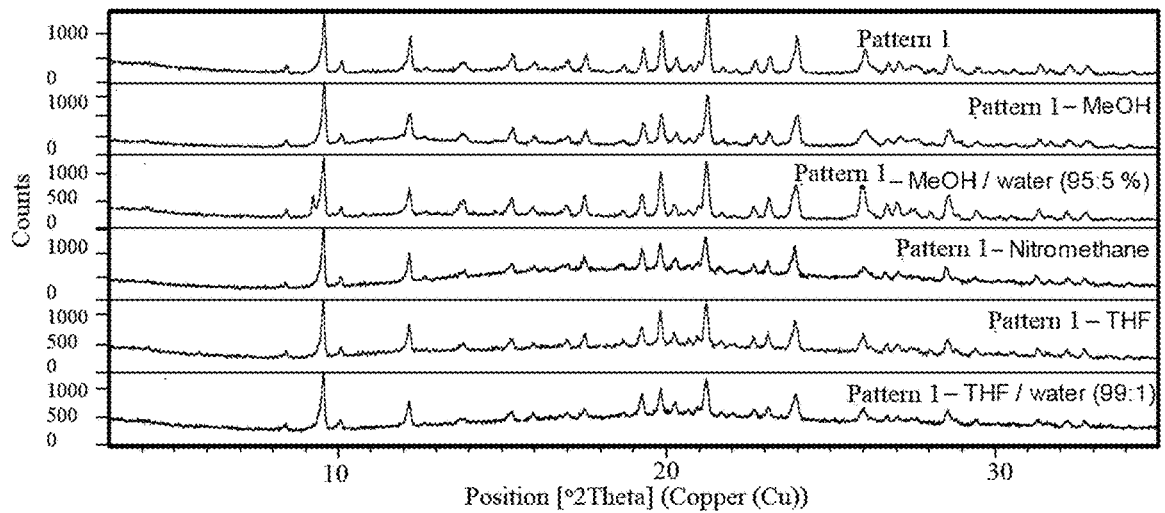

FIG. 9 is a comparison of XRPD diffractograms of Pattern 1 before solvent solubility studies and the Pattern 1 material that results from various solvent solubility studies. The diffractograms were obtained as described in Example 1 and the studies were conducted as described in Example 13. The x-axis is 2Theta measured in degrees and the y-axis is intensity measured in counts.

Figure 10:
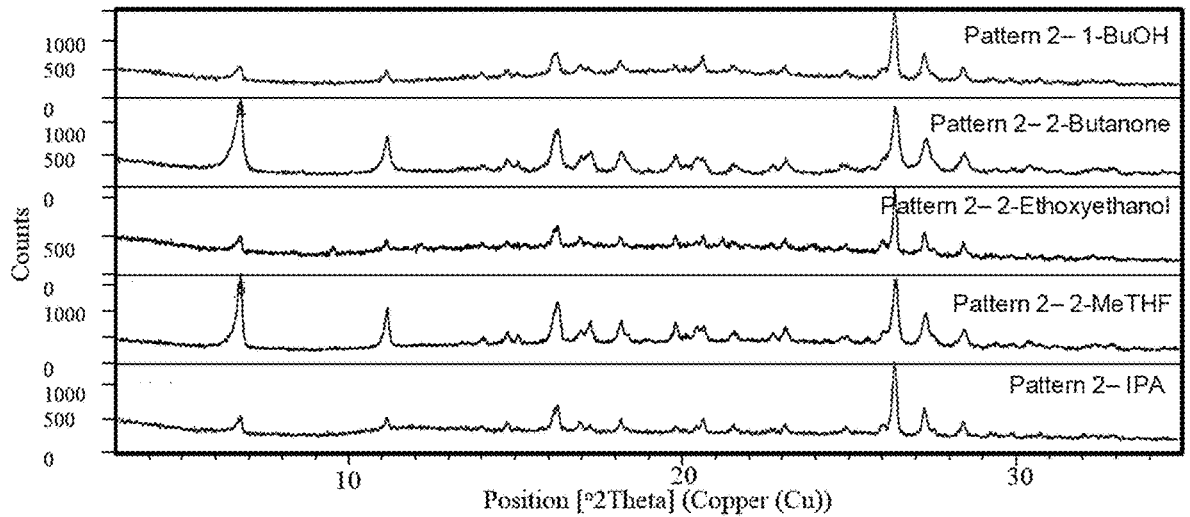

FIG. 10 is a comparison of XRPD diffractograms of Pattern 2 resulting from various solvent solubility studies. The diffractograms were obtained as described in Example 1 and the studies were conducted as described in Example 13. The x-axis is 2Theta measured in degrees and the y-axis is intensity measured in counts.

Figure 11:
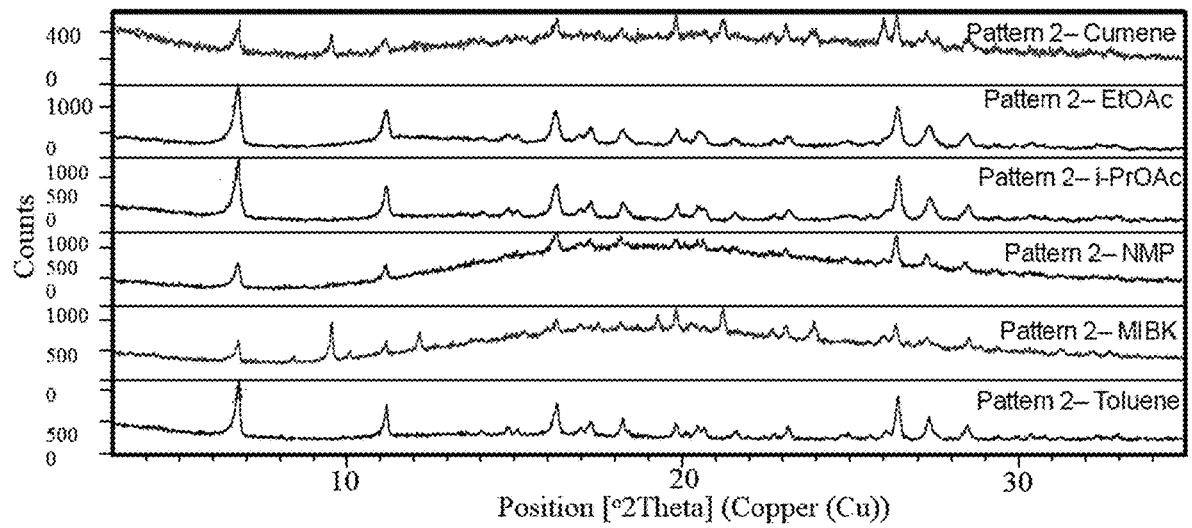

FIG. 11 is a comparison of XRPD diffractograms of Pattern 2 resulting from various solvent solubility studies. The diffractograms were obtained as described in Example 1 and the studies were conducted as described in Example 13. The x-axis is 2Theta measured in degrees and the y-axis is intensity measured in counts.

Figure 12:
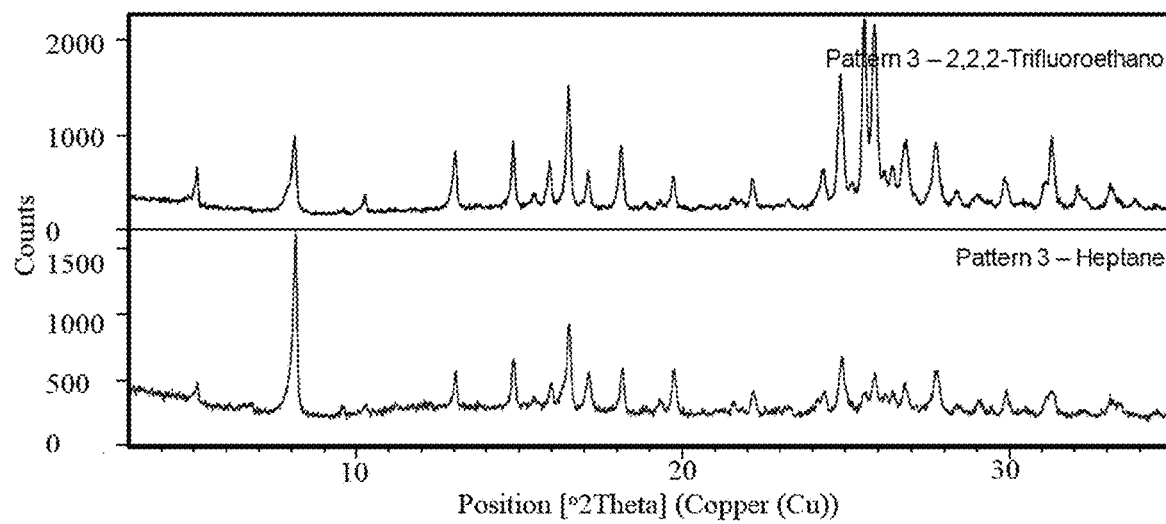

FIG. 12 is a comparison of XRPD diffractograms of Pattern 3 resulting from various solvent solubility studies. The diffractograms were obtained as described in Example 1 and the studies were conducted as described in Example 13. The x-axis is 2Theta measured in degrees and the y-axis is intensity measured in counts.

Figure 13:
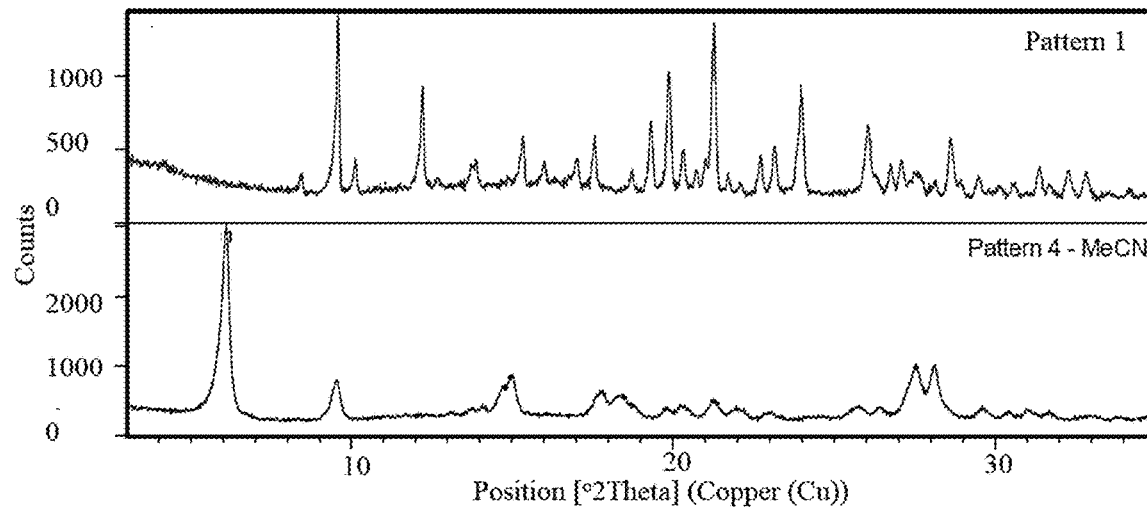

FIG. 13 is a comparison of XRPD diffractograms of Pattern 1 and Pattern 4 which resulted from the solubility study in MeCN. The diffractograms were obtained as described in Example 1 and Example 4 and the studies were conducted as described in Example 13. The x-axis is 2Theta measured in degrees and the y-axis is intensity measured in counts.

Figure 14:
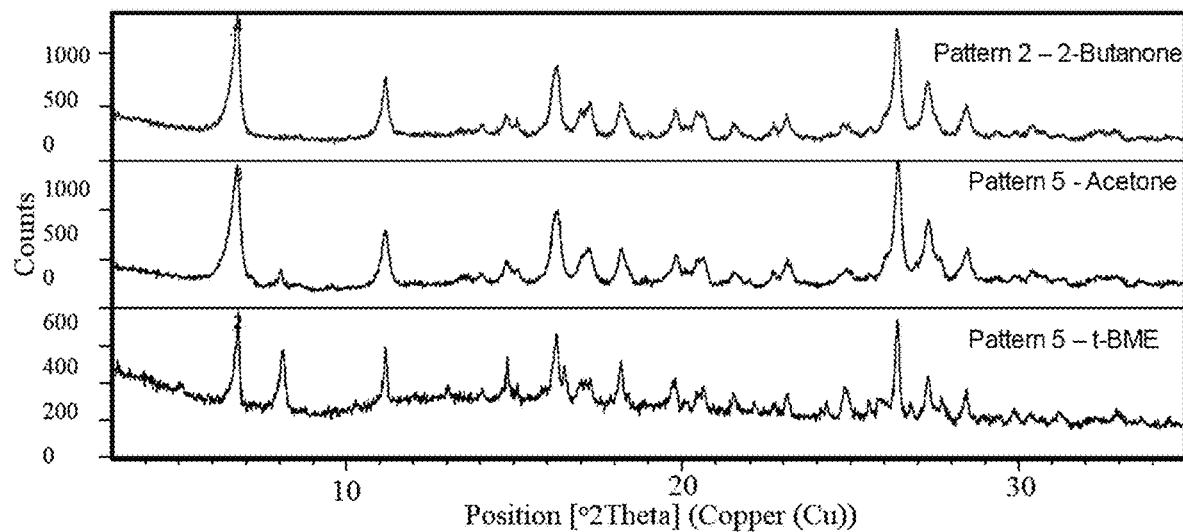

FIG. 14 is a comparison of XRPD diffractograms Pattern 2 and Pattern 5 which resulted from various solvent systems. The diffractograms were obtained as described in Example 1 and the studies were conducted as described in Example 13. The x-axis is 2Theta measured in degrees and the y-axis is intensity measured in counts.

Figure 15:
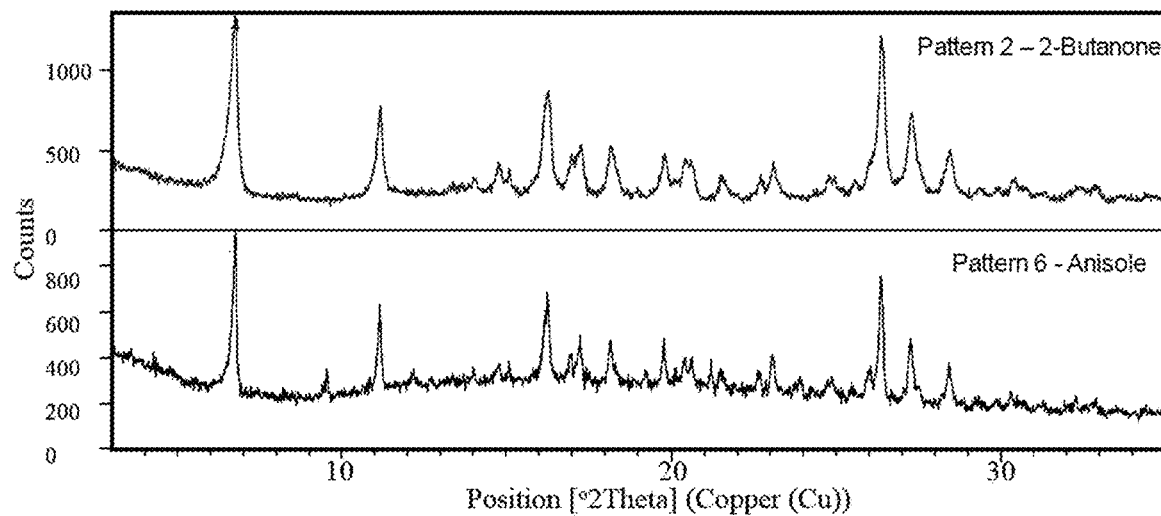

FIG. 15 is a comparison of XRPD diffractograms Pattern 2 and Pattern 6 which resulted from various solvent systems. The diffractograms were obtained as described in Example 1 and the studies were conducted as described in Example 13. The x-axis is 2Theta measured in degrees and the y-axis is intensity measured in counts.

Figure 16:
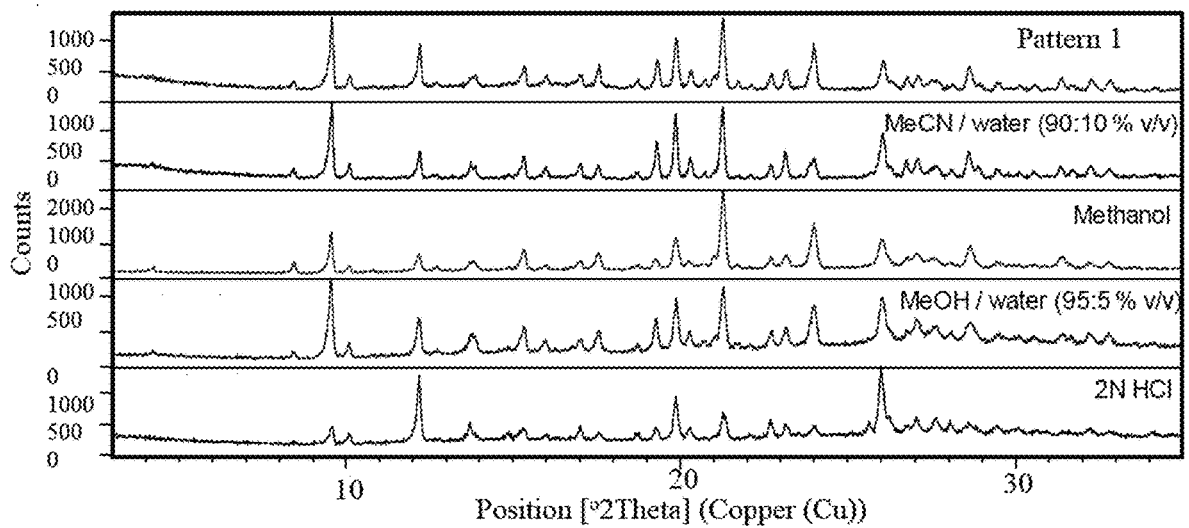

FIG. 16 is a comparison of XRPD diffractograms of Pattern 1 before and after maturation experiments in various solvents systems. The diffractograms were obtained as described in Example 1 and the studies were conducted as described in Example 21. The x-axis is 2Theta measured in degrees and the y-axis is intensity measured in counts.

Figure 17:
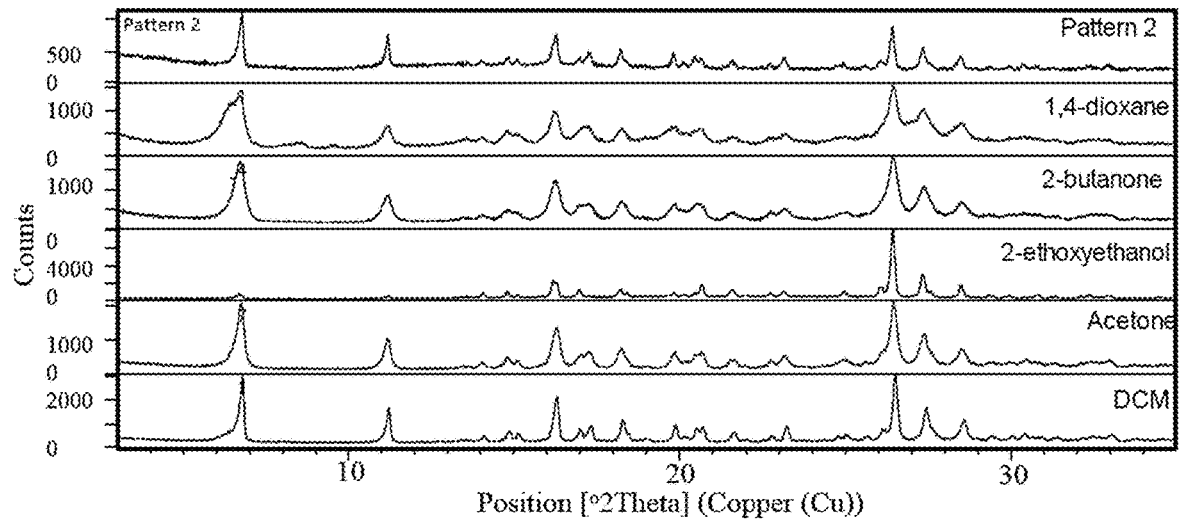

FIG. 17 is a comparison of XRPD diffractograms of Pattern 2 before and after maturation experiments in various solvents systems. The diffractograms were obtained as described in Example 1 and the studies were conducted as described in Example 21. The x-axis is 2Theta measured in degrees and the y-axis is intensity measured in counts.

Figure 18:
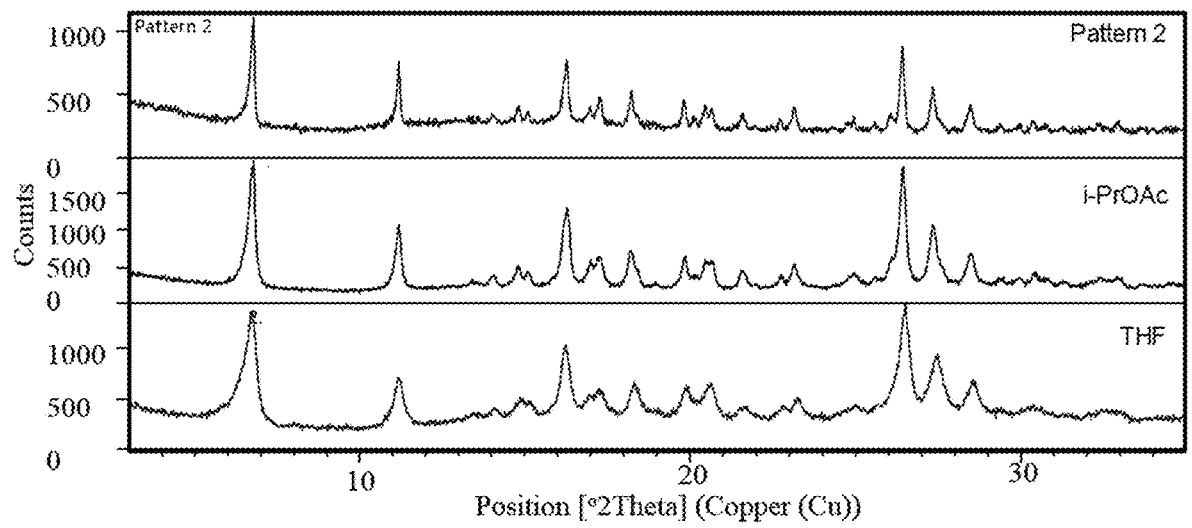

FIG. 18 is a comparison of XRPD diffractograms of Pattern 2 before and after maturation experiments in various solvents systems. The diffractograms were obtained as described in Example 1 and the studies were conducted as described in Example 21. The x-axis is 2Theta measured in degrees and the y-axis is intensity measured in counts.

Figure 19:
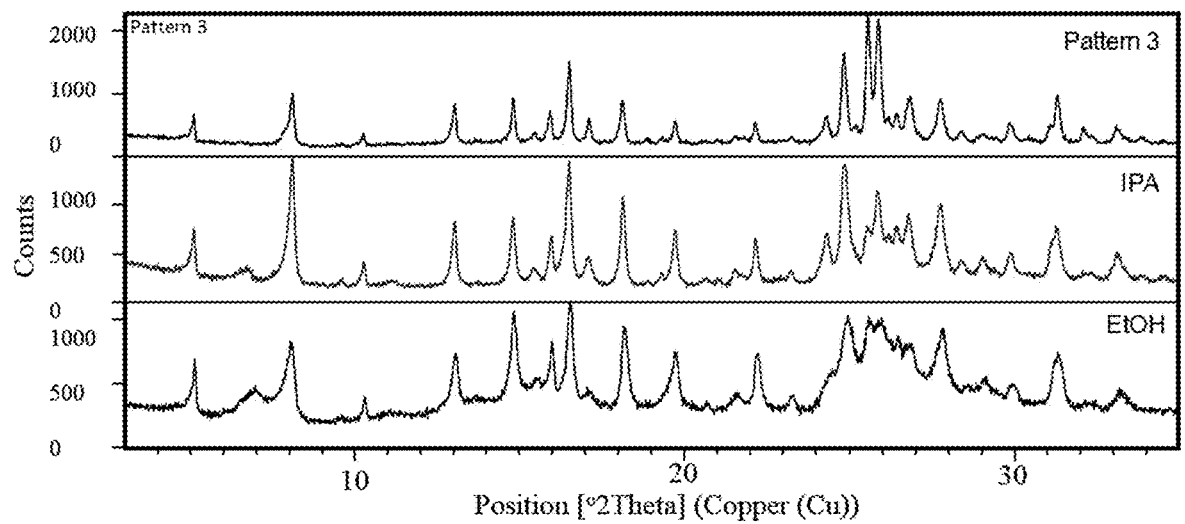

FIG. 19 is a comparison of XRPD diffractograms of Pattern 3 before and after a maturation experiments in isopropyl alcohol and ethanol. The diffractograms were obtained as described in Example 1 and the studies were conducted as described in Example 21. The x-axis is 2Theta measured in degrees and the y-axis is intensity measured in counts.

Figure 20:
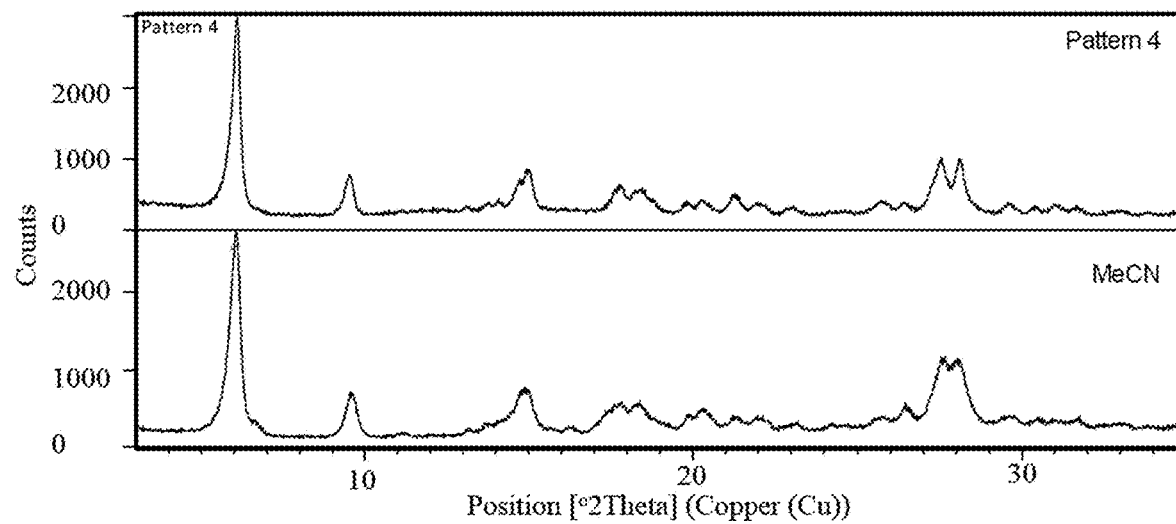

FIG. 20 is a comparison of XRPD diffractograms of Pattern 4 before and after a maturation experiment in acetonitrile. The diffractograms were obtained as described in Example 4 and the studies were conducted as described in Example 21. The x-axis is 2Theta measured in degrees and the y-axis is intensity measured in counts.

Figure 21:
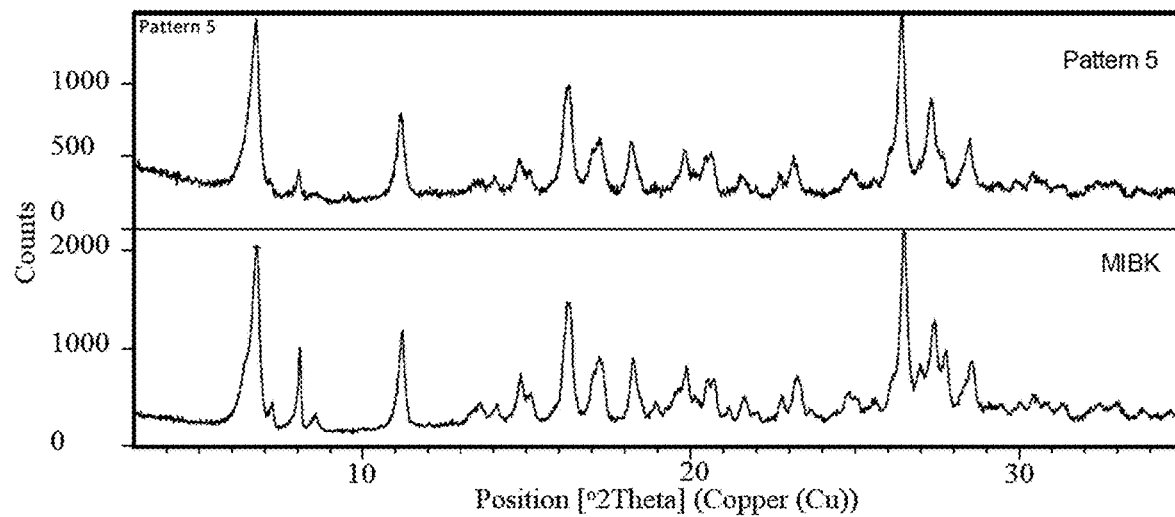

FIG. 21 is a comparison of XRPD diffractograms of Pattern 5 before and after a maturation experiment in methyl isobutyl ketone. The diffractograms were obtained as described in Example 1 and the studies were conducted as described in Example 21. The x-axis is 2Theta measured in degrees and the y-axis is intensity measured in counts.

Figure 22:
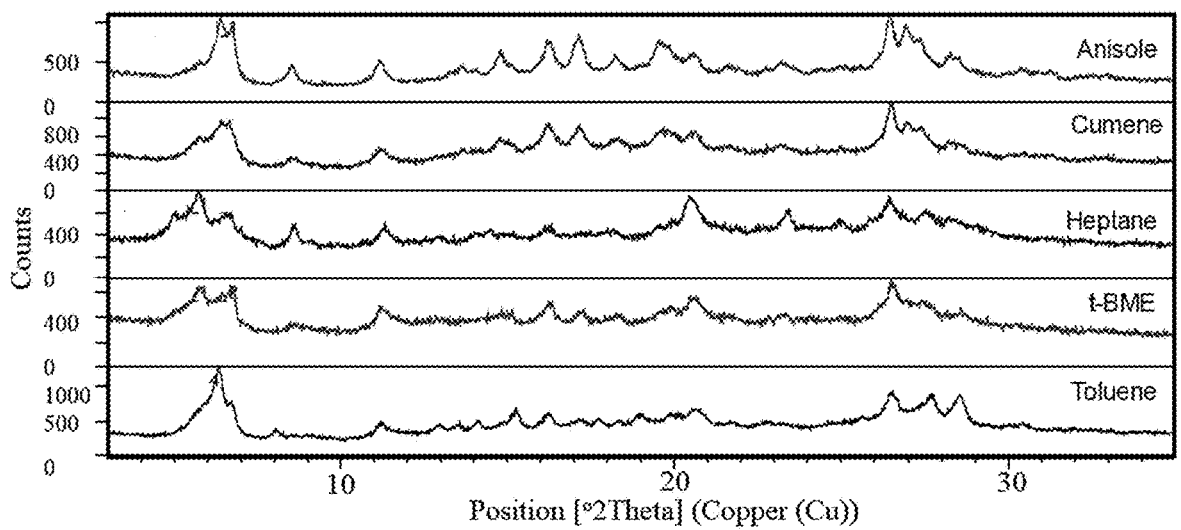

FIG. 22 is a comparison of XRPD diffractograms resulting from maturation experiments in various solvent systems. The diffractograms were obtained as described in Example 1 and the studies were conducted as described in Example 21. The x-axis is 2Theta measured in degrees and the y-axis is intensity measured in counts.

Figure 23:
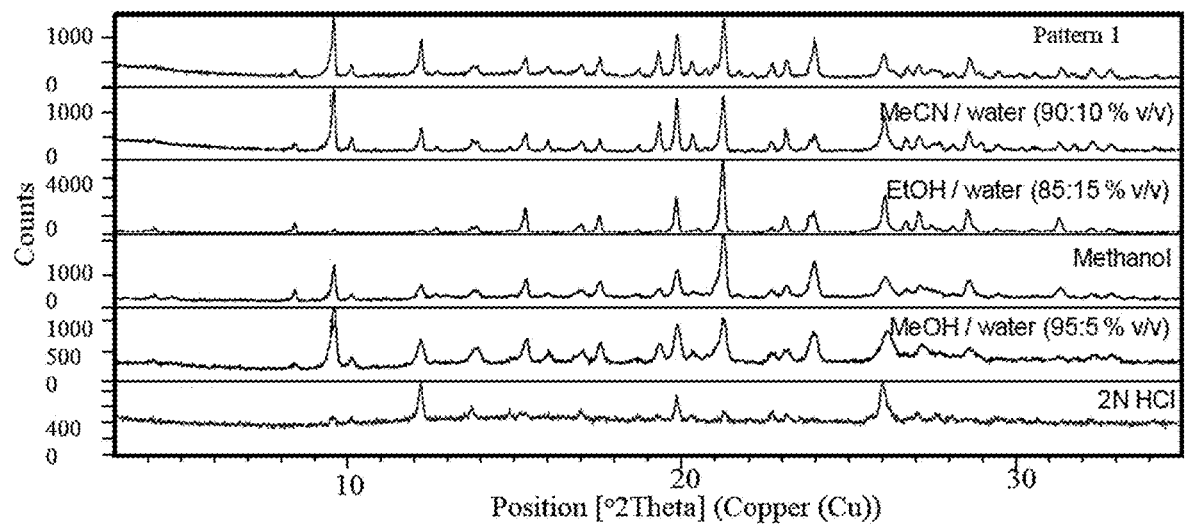

FIG. 23 is a comparison of XRPD Pattern 1 diffractogram and diffractograms resulting from maturation experiments in various solvent systems after drying. The diffractograms were obtained as described in Example 1 and the studies were conducted as described in Example 21. The x-axis is 2Theta measured in degrees and the y-axis is intensity measured in counts.

Figure 24:
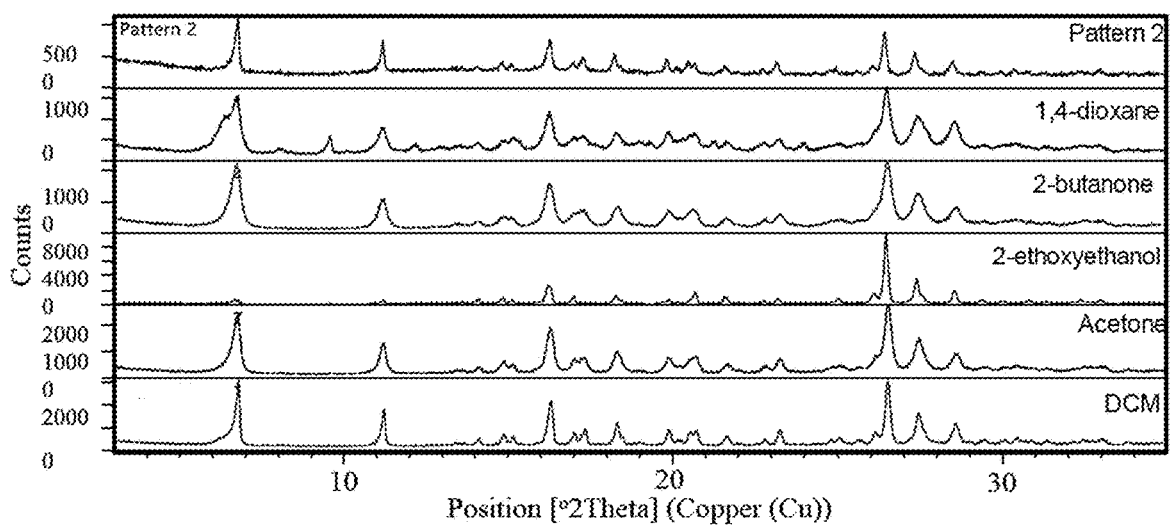

FIG. 24 is a comparison of XRPD Pattern 1 diffractogram and diffractograms resulting from maturation experiments in various solvent systems after drying. The diffractograms were obtained as described in Example 1 and the studies were conducted as described in Example 21. The x-axis is 2Theta measured in degrees and the y-axis is intensity measured in counts.

Figure 25:
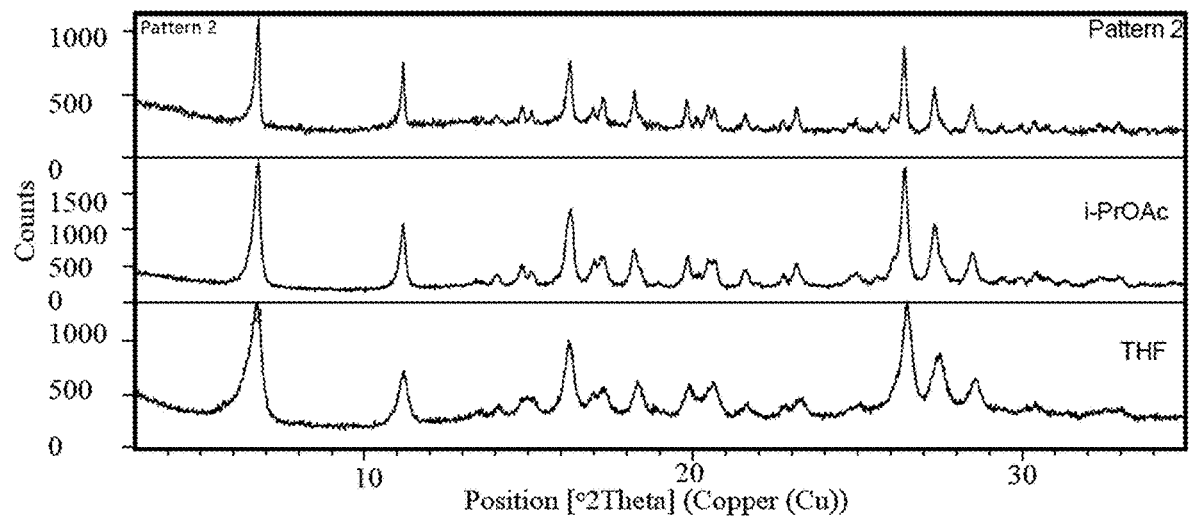

FIG. 25 is a comparison of XRPD Pattern 2 diffractogram and diffractograms resulting from maturation experiments in various solvent systems after drying. The diffractograms were obtained as described in Example 1 and the studies were conducted as described in Example 21. The x-axis is 2Theta measured in degrees and the y-axis is intensity measured in counts.

Figure 26:
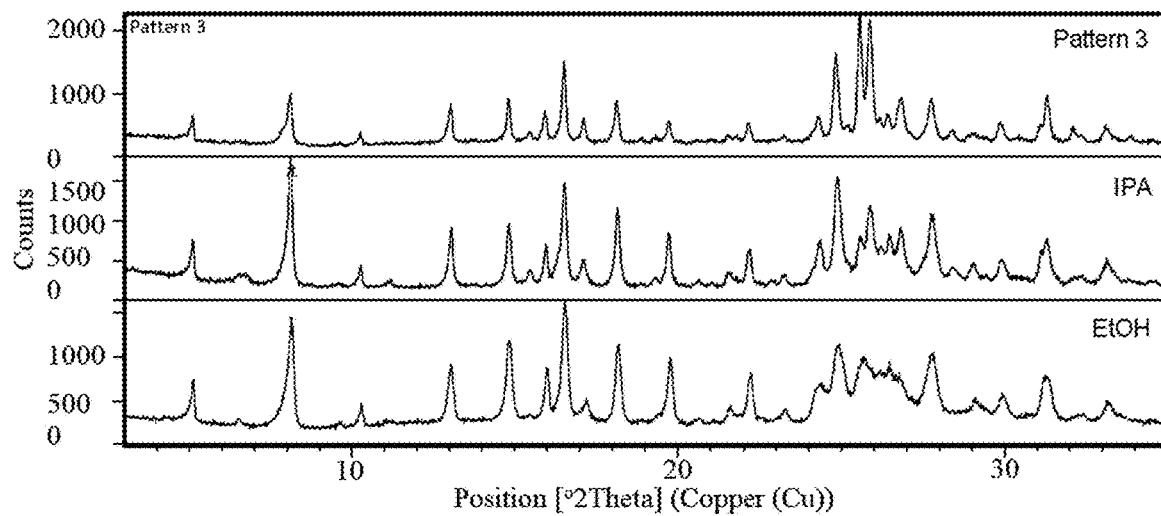

FIG. 26 is a comparison of XRPD Pattern 3 diffractogram and diffractograms resulting from maturation experiments in various solvent systems after drying. The diffractograms were obtained as described in Example 1 and the studies were conducted as described in Example 21. The x-axis is 2Theta measured in degrees and the y-axis is intensity measured in counts.

Figure 27:
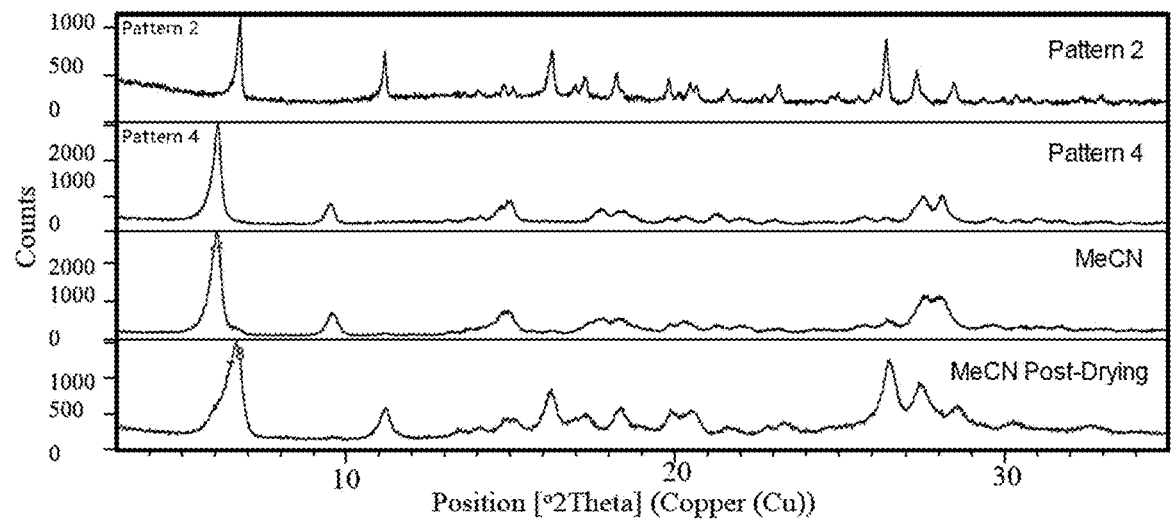

FIG. 27 is a comparison of XRPD Pattern 3 diffractogram, Pattern 4 diffractogram and diffractograms resulting from maturation experiments in various solvent systems after drying. The diffractograms were obtained as described in Example 1 and Example 4 and the studies were conducted as described in Example 21. The x-axis is 2Theta measured in degrees and the y-axis is intensity measured in counts.

Figure 28:
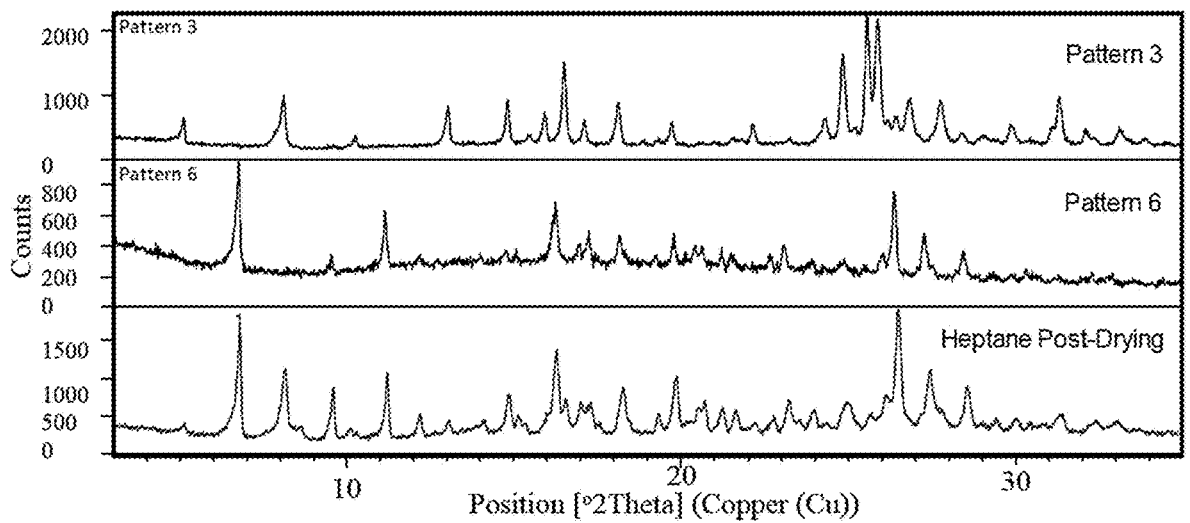

FIG. 28 is a comparison of XRPD Pattern 3 diffractogram, Pattern 6 diffractogram and the diffractogram resulting from maturation in heptane after drying. The diffractograms were obtained as described in Example 1 and the studies were conducted as described in Example 21. The x-axis is 2Theta measured in degrees and the y-axis is intensity measured in counts.

Figure 29:
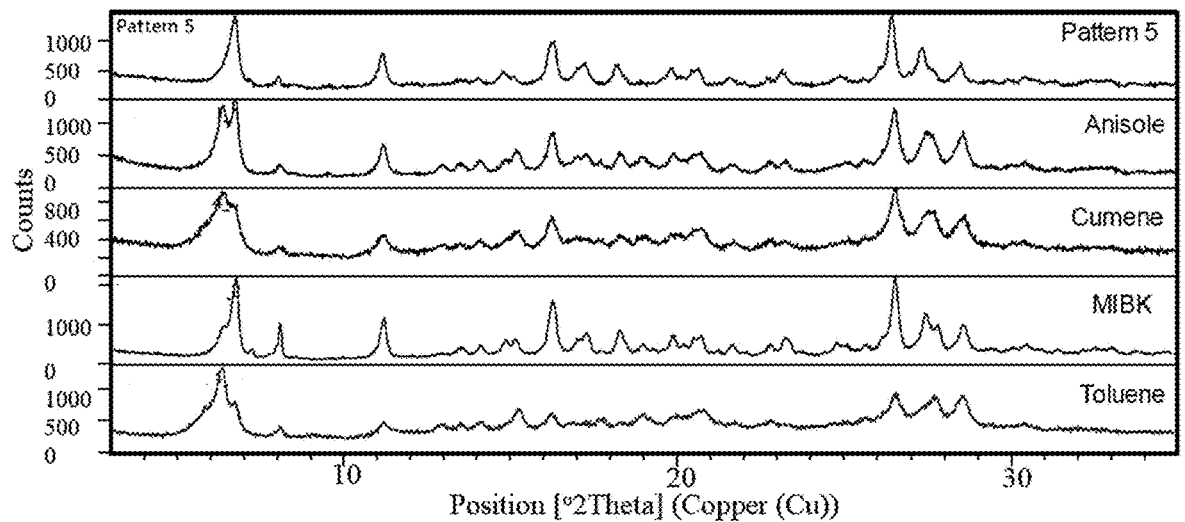

FIG. 29 is a comparison of XRPD Pattern 5 and diffractograms resulting from maturation in various solvents after drying. The diffractograms were obtained as described in Example 1 and the studies were conducted as described in Example 21. The x-axis is 2Theta measured in degrees and the y-axis is intensity measured in counts.

Figure 30:
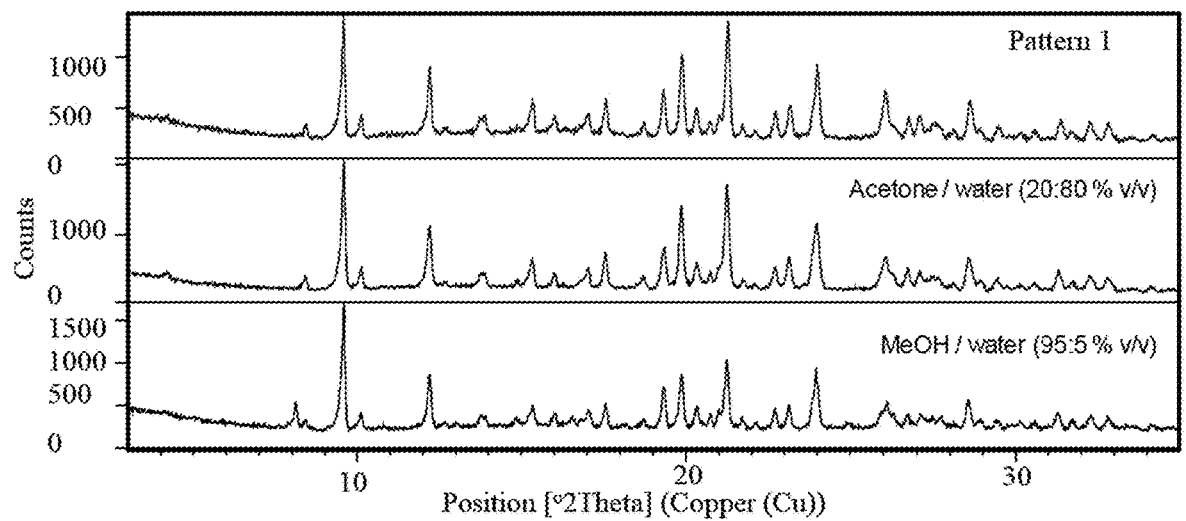

FIG. 30 is a comparison of XRPD diffractogram of Pattern 1 and solids that were left after evaporation experiments. The diffractograms were obtained as described in Example 1. The solids were obtained as described in Example 13. Samples were left uncapped and placed in a cupboard to allow evaporation. The x-axis is 2Theta measured in degrees and the y-axis is intensity measured in counts.

Figure 31:
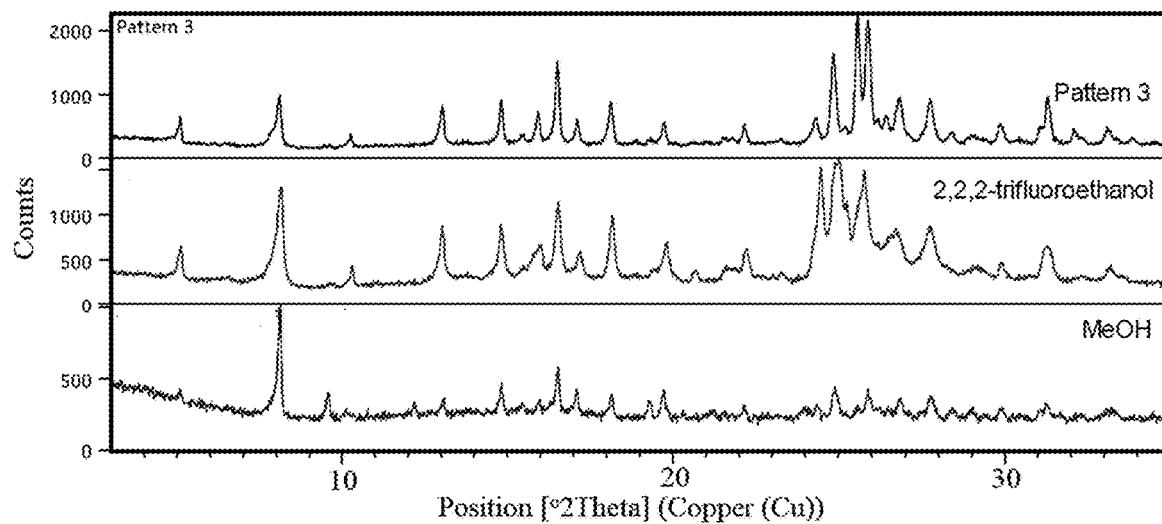

FIG. 31 is a comparison of XRPD diffractogram of Pattern 3 and solids that were left after evaporation experiments. The diffractograms were obtained as described in Example 1. The solids were obtained as described in Example 13. Samples were left uncapped and placed in a cupboard to allow evaporation. The x-axis is 2Theta measured in degrees and the y-axis is intensity measured in counts.

Figure 32:
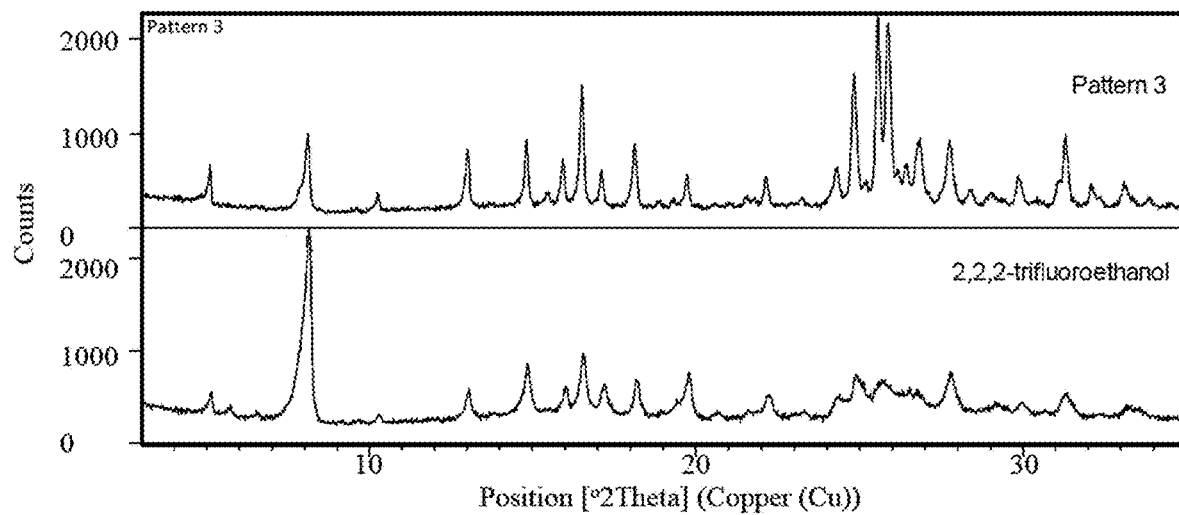

FIG. 32 is a comparison of XRPD diffractogram of Pattern 3 and the solid that resulted from the addition of methyl tert-butyl ether (t-BME) to 2,2,2-trifluoroethanol. The diffractograms were obtained as described in Example 1. The solids were obtained as described in Example 13. The x-axis is 2Theta measured in degrees and the y-axis is intensity measured in counts.

Figure 33:
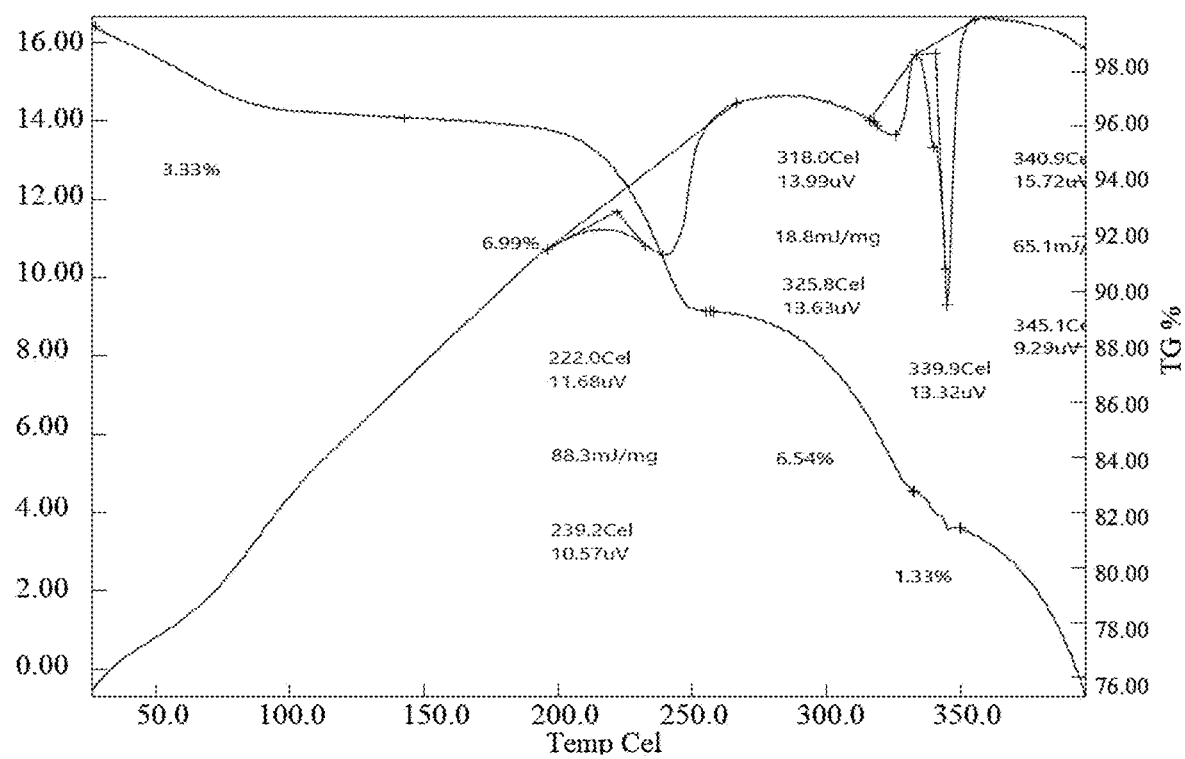

FIG. 33 is a thermogravimetric/differential thermal (TG/DTA) thermogram of Pattern 2 small scale material. The TG/DTA thermogram of Pattern 2 was obtained as described in Example 6. The initial mass loss of ca. 3% from the onset of heating related to the loss of surface moisture. Two mass losses of ca. 7% were observed from ca. 222° C. peaking at 239° C., 318° C. peaking at 340° C., and 345° C. peaking at 325° C. The x-axis in Temp (° C.) and the y-axis is TG (%).

Figure 34:
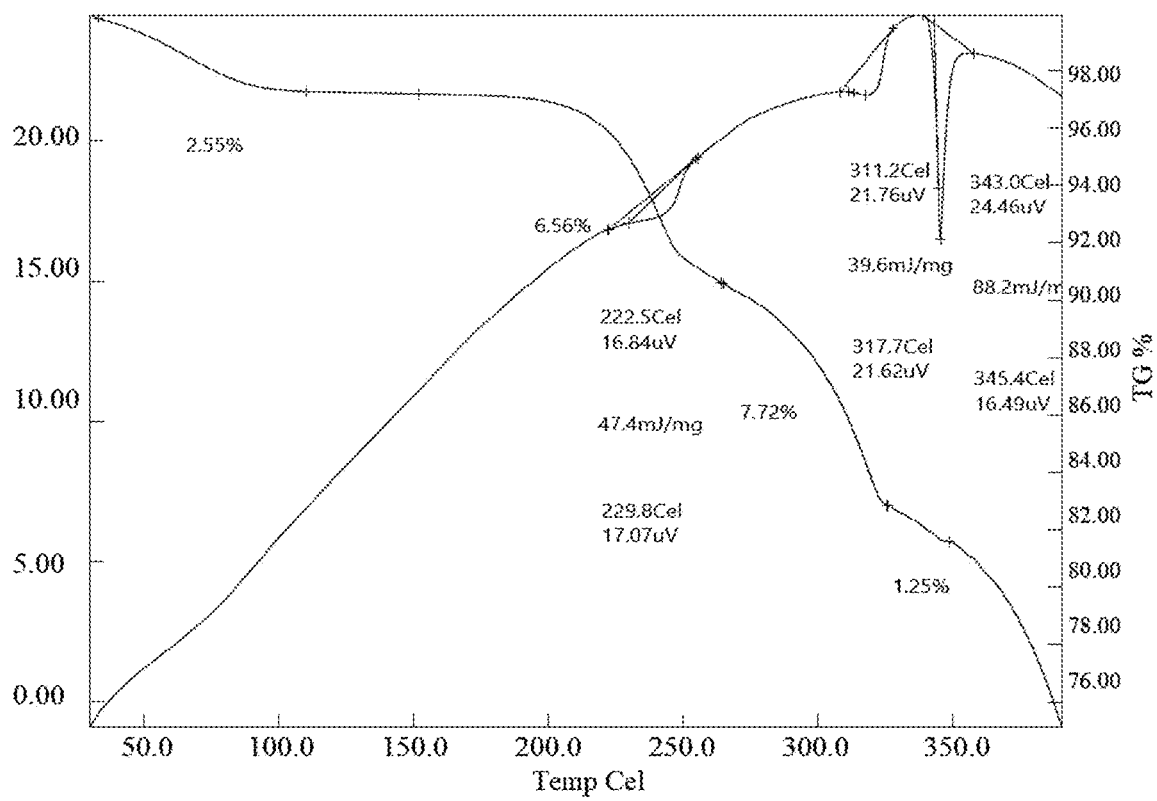

FIG. 34 is a thermogravimetric/differential thermal (TG/DTA) thermogram of Pattern 3 small scale material. The TG/DTA thermogram of Pattern 3 was obtained as described in Example 6. The initial mass loss of ca. 2.6% from the onset of heating related to the loss of surface moisture. Two mass losses of ca. 6.6% were observed from ca. 222° C. peaking at 229° C., 311° C. peaking at 317° C., and 343° C. peaking at 345° C. The x-axis in Temp (° C.) and the y-axis is TG (%).

Figure 35:
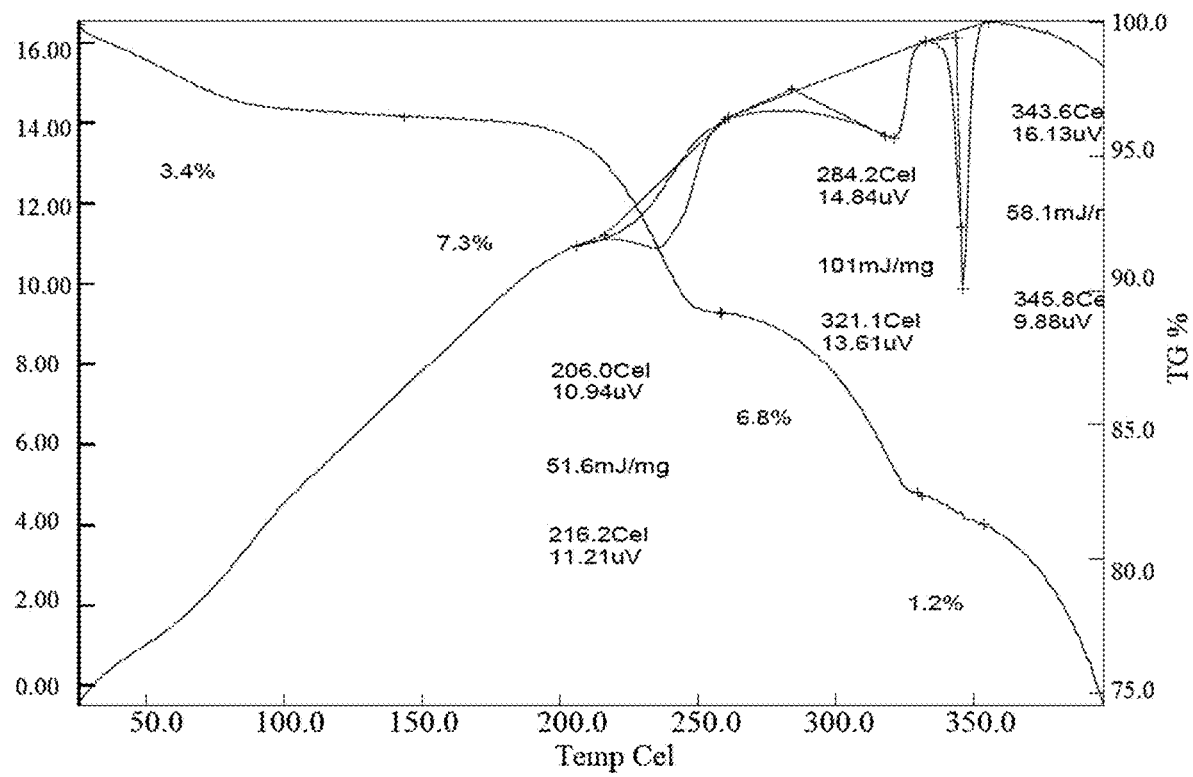

FIG. 35 is a thermogravimetric/differential thermal (TG/DTA) thermogram of Pattern 5 small scale material. The TG/DTA thermogram of Pattern 5 was obtained as described in Example 6. The initial mass loss of ca. 3.4% from the onset of heating related to the loss of surface moisture. Three mass losses of ca. 7.3% were observed from ca. 206° C. peaking at 216° C., 284° C. peaking at 321° C. and 343° C. peaking at 345° C. The x-axis in Temp (° C.) and the y-axis is TG (%).

Figure 36:
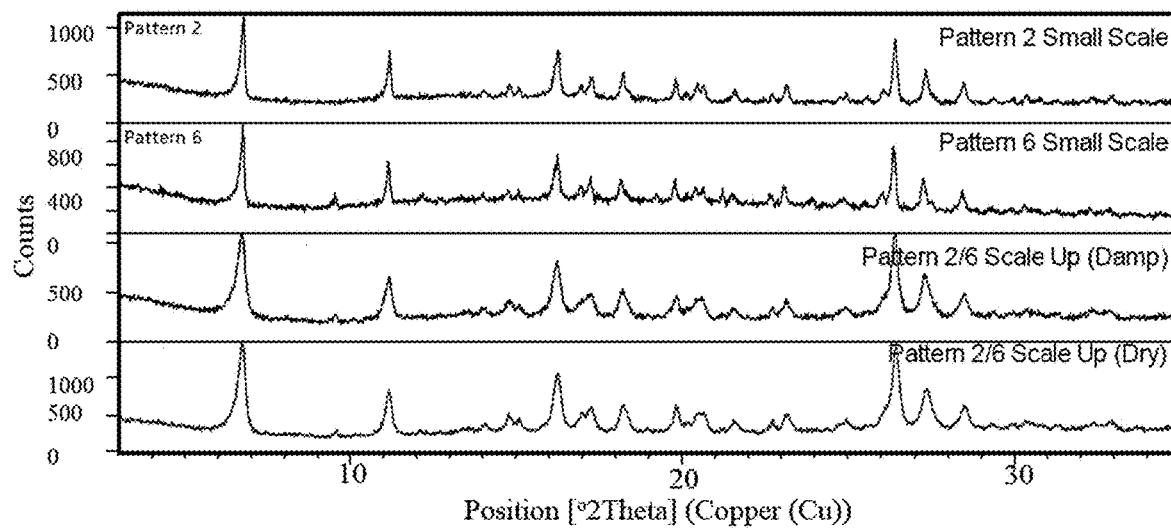

FIG. 36 is a comparison of XRPD patterns for small scale and scale-up materials of Pattern 2 and Pattern 6. When the Pattern 2 synthesis was scaled it produced a mixture of Pattern 6 and Pattern 2 as shown in the XRPD diffractograms. The diffractograms were obtained as described Example 1. The x-axis is 2Theta measured in degrees and the y-axis is intensity measured in counts.

Figure 37:
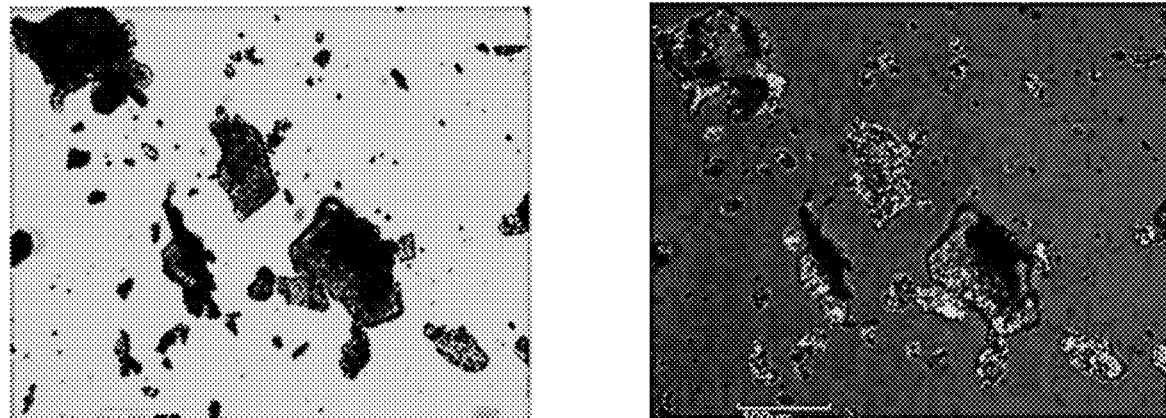

FIG. 37 is a PLM image of the mixture of Pattern 2 and Pattern 6 that resulted from the scaleup attempt. The PLM imaging of Pattern 2/6 mixture was obtained as described in Example 5. Pattern 2/6 scale-up material appeared highly crystalline under PLM imaging with the non-polarized material shown on the left, and the polarized material shown on the right.

Figure 38:
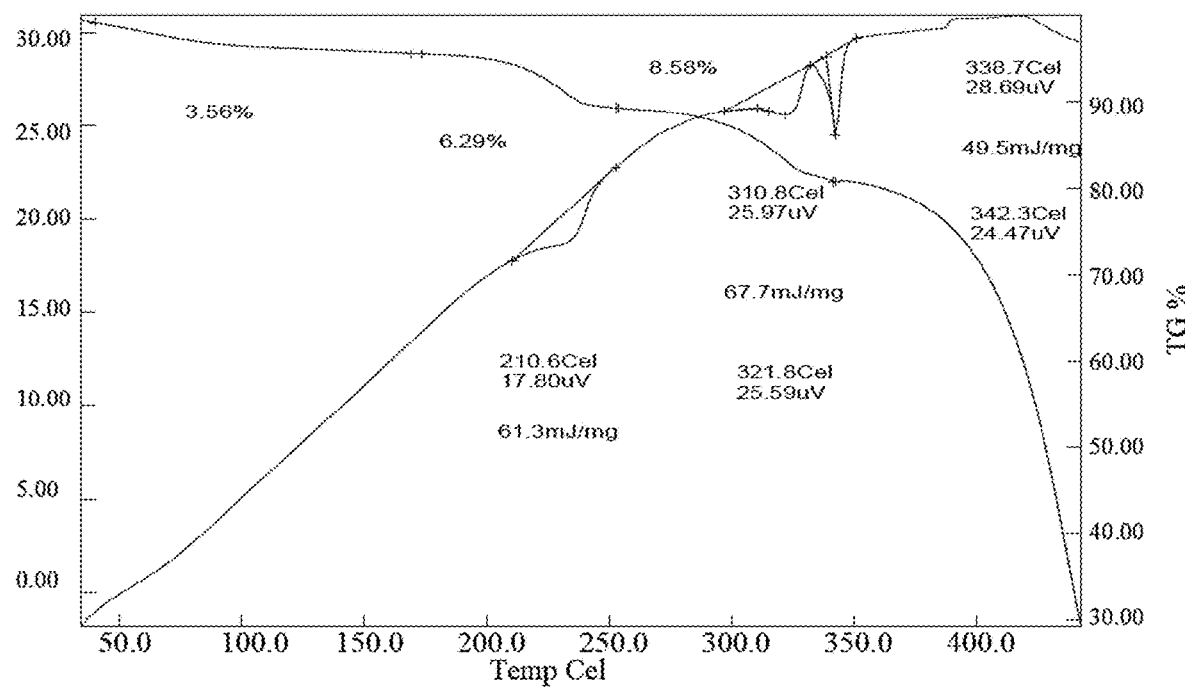

FIG. 38 is a thermogravimetric/differential thermal (TG/DTA) thermogram of the mixture of Pattern 2 and Pattern 6 that resulted from the scaleup attempt. The initial mass loss of ca. 3.6% from the onset of heating related to the loss of surface moisture. Two mass losses of ca. 6.3% were observed from ca. 211° C. and 310° C. peaking at 321° C. The x-axis in Temp (° C.) and the y-axis is TG (%).

Figure 39:
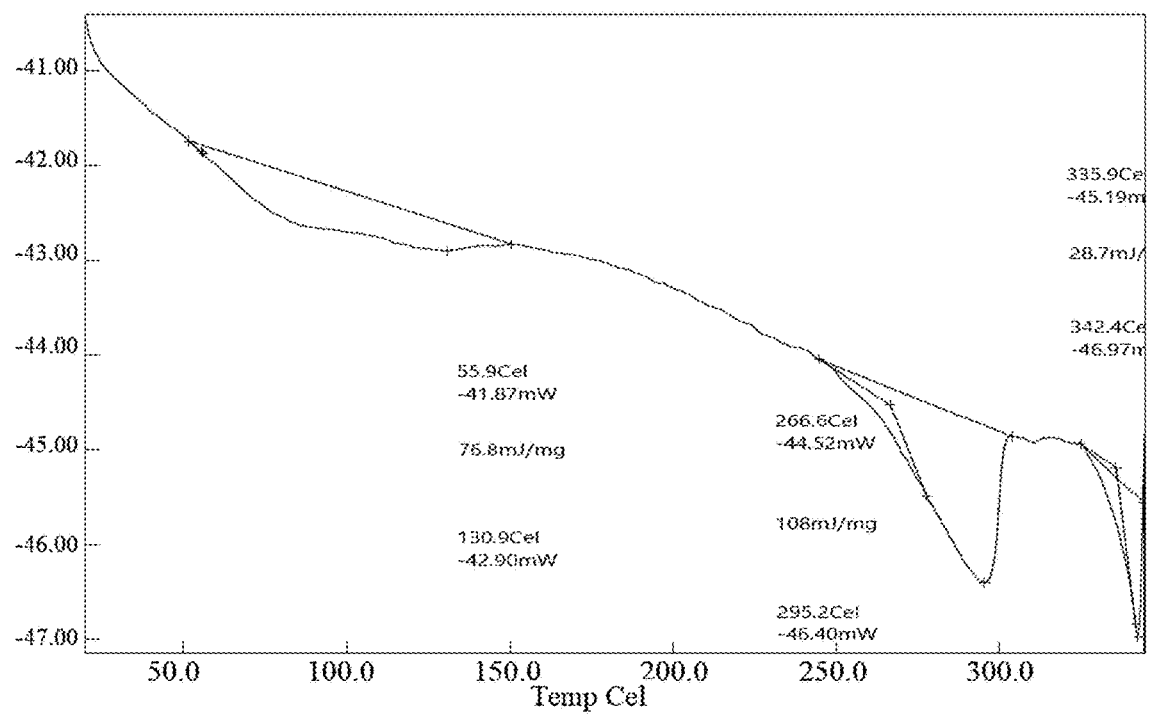

FIG. 39 is a differential scanning calorimetry (DSC) thermogram of the mixture of Pattern 2 and Pattern 6 that resulted from the scaleup attempt. The DSC thermogram of Pattern 2/6 mixture was obtained as described in Example 7. DSC analysis showed 2 broad endotherms ca. 55.9° C. peaking at 131° C. and 267° C. peaking at 295° C. A sharp melting endotherm was observed from an onset of 336° C.

Figure 40:
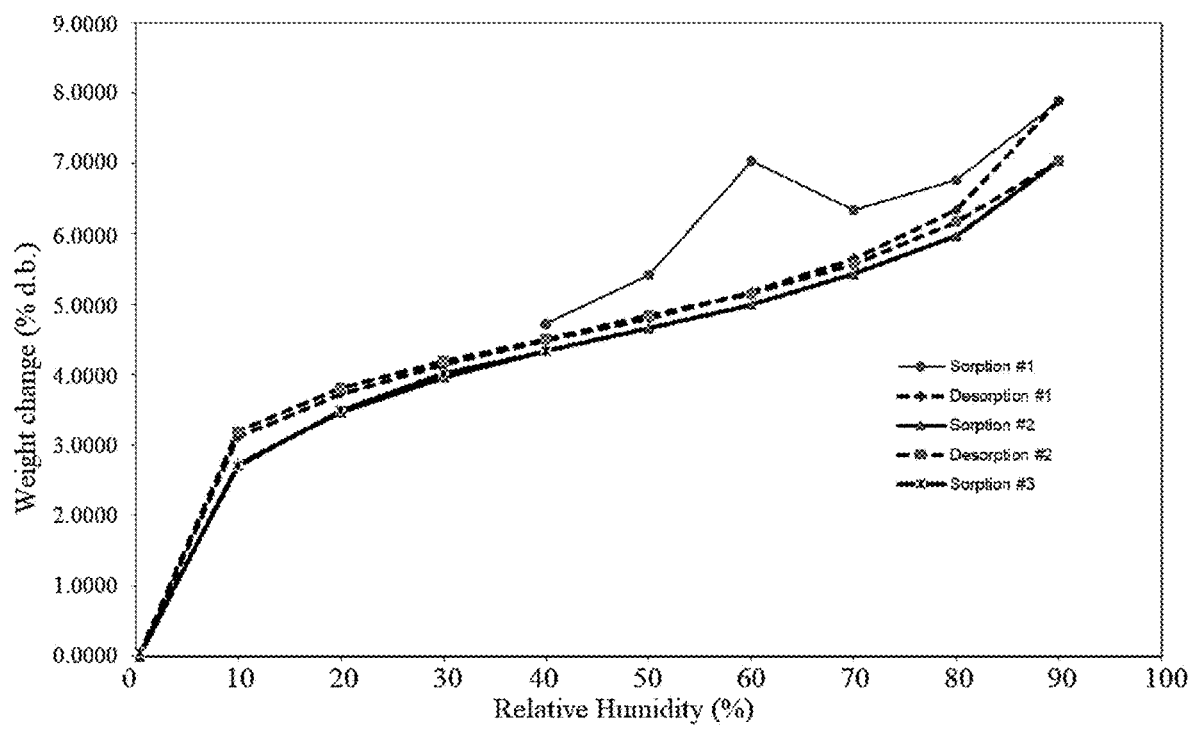

FIG. 40 is a gravimetric vapor sorption (GVS) isotherm plot of the mixture of Pattern 2 and Pattern 6 that resulted from the scaleup attempt. The GVS isotherm plot of Pattern 2/6 mixture was obtained as described in Example 2. The mixture of pattern 2 and pattern 6 adsorbed 4.00% wt % at 40% RH (relative humidity) and 7.00% wt % at 90% RH. The x-axis is relative humidity measured as a percent and the y-axis is weight of water of the material measured as a percent.

Figure 41:
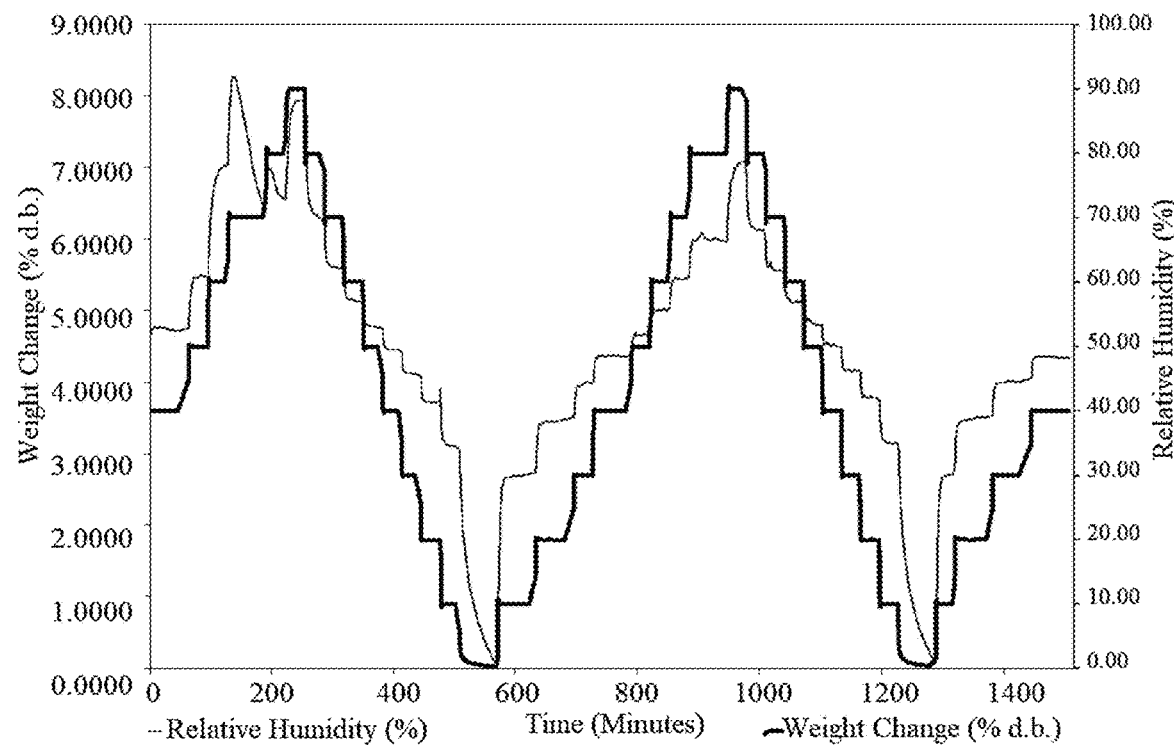

FIG. 41 is a gravimetric vapor sorption (GVS) kinetic plot of the mixture of Pattern 2 and Pattern 6 that resulted from the scaleup attempt. The GVS isotherm plot of Pattern 2/6 mixture was obtained as described in Example 2. The sample was subjected to a ramping profile from 40-90% relative humidity (RH) at 10% increments, maintaining the sample at each step until a stable weight had been achieved (dm/dt 0.004%, minimum step length 550 minutes, maximum step length 900 minutes) at 25° C. After completion of the sorption cycle, the sample was dried using the same procedure to 0% RH and then a second sorption cycle back to 40% RH. Two cycles were performed. The material appeared hygroscopic by DVS with a mass increase of 8% between 0% and 90% RH. During the desorption cycles the material dehydrates.

Figure 42:
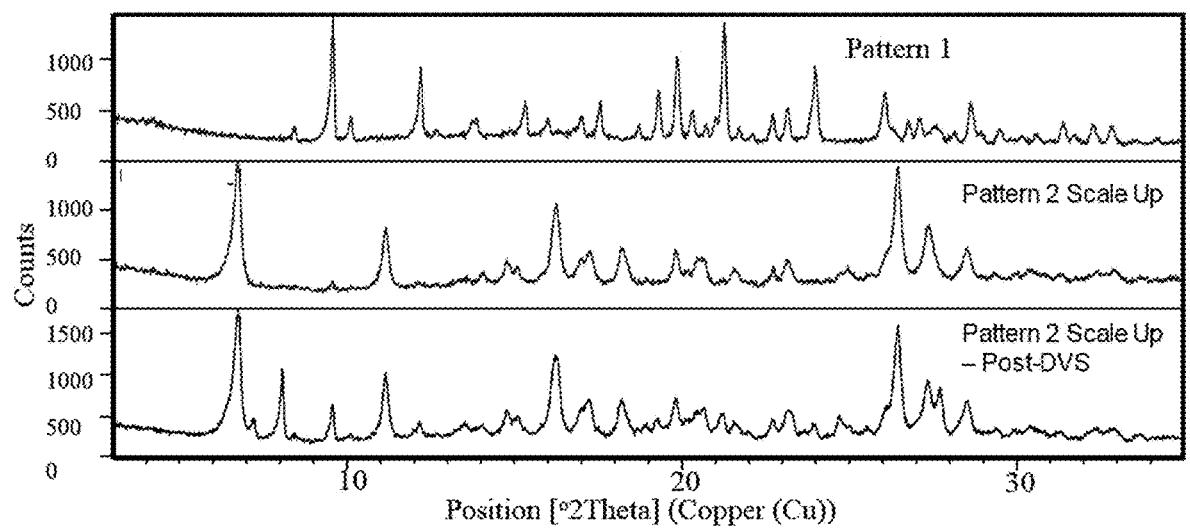

FIG. 42 is a comparison of XRPD diffractograms of Pattern 1, Pattern 2 scale up and Pattern 2 scale up post-DVS. The diffractograms were obtained as described in Example 1. The x-axis is 2Theta measured in degrees and the y-axis is intensity measured in counts.

Figure 43:
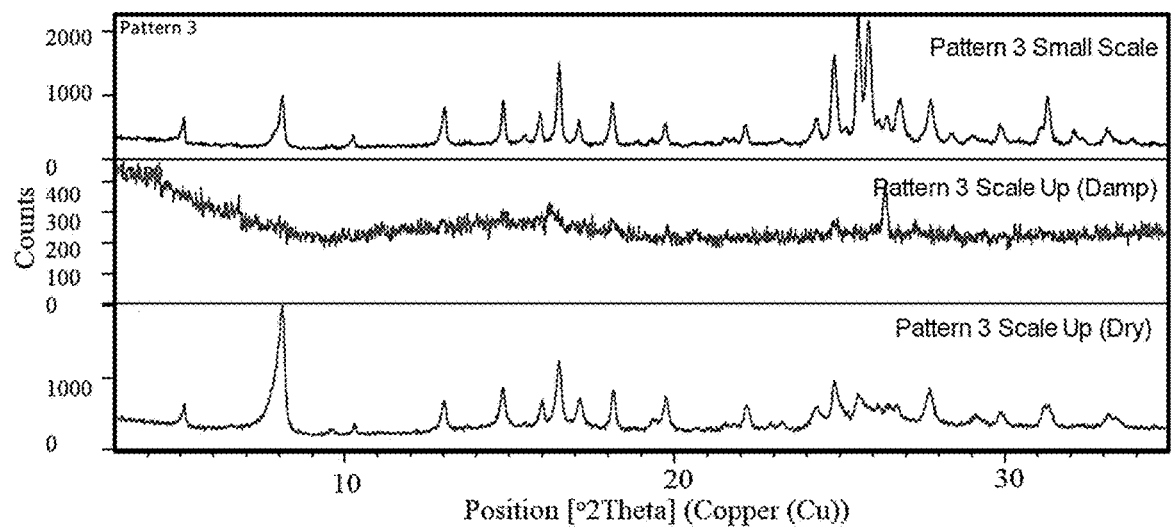

FIG. 43 is a comparison of XRPD diffractograms of Pattern 3 small scale and Pattern 3 scaled in dry and damp form. The diffractogram were obtained as described in Example 1. The x-axis is 2Theta measured in degrees and the y-axis is intensity measured in counts.

Figure 44:
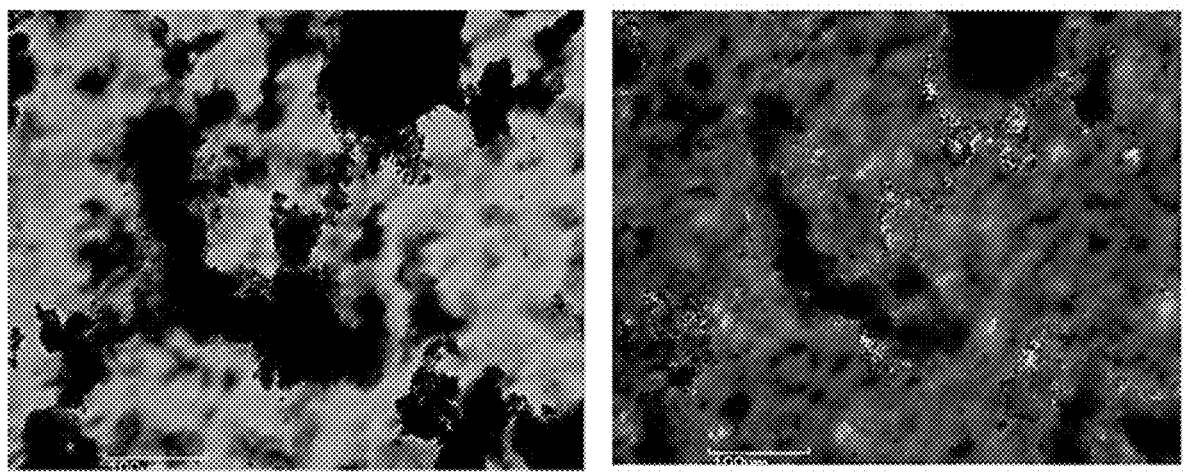

FIG. 44 is a PLM image of the Pattern 3 scale-up material. Pattern 3 scale-up material appeared highly crystalline under PLM imaging as described in Example 5. The non-polarized material shown on the left, and the polarized material shown on the right.

Figure 45:
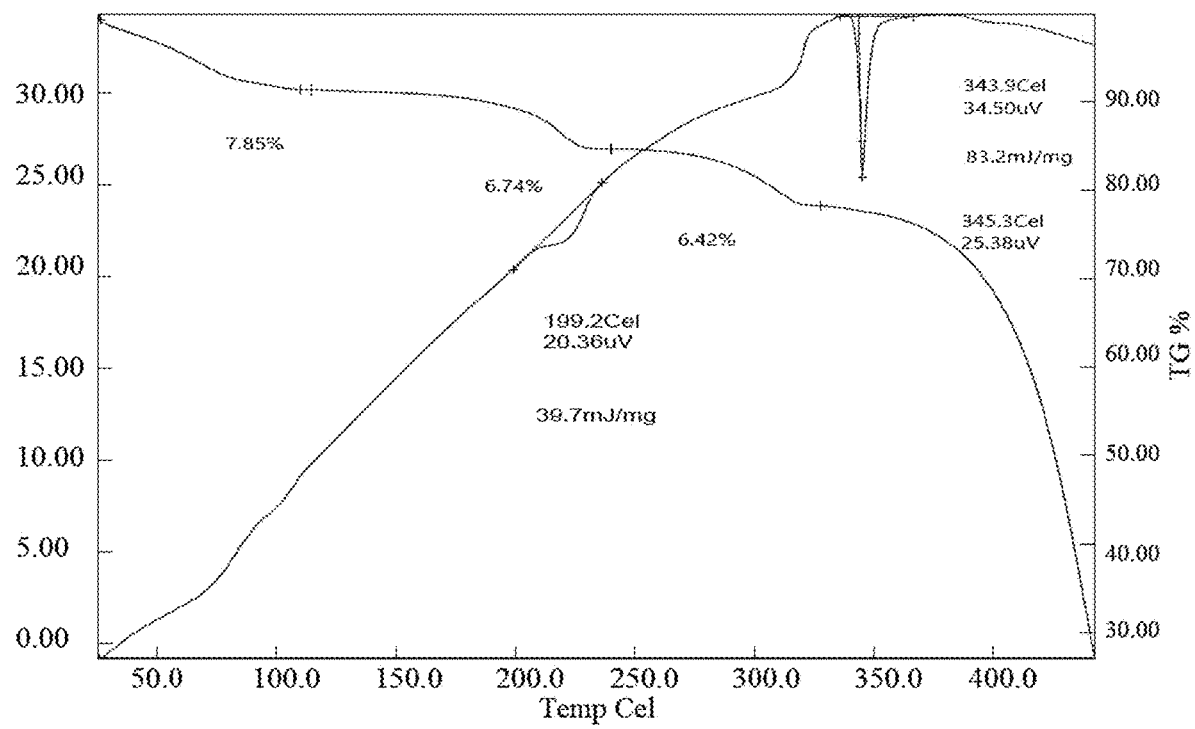

FIG. 45 is a TG/DTA thermogram of the Pattern 3 scale up material. The TG/DTA thermogram of Pattern 3 scale-up was obtained as described in Example 6. The TG/DTA shows two peaks at 199° C. and 345° C. The initial mass loss of ca. 8% from the onset of heating related to the loss of surface moisture. Two mass losses of ca. 7% were observed from ca. 199° C. and 343° C. peaking at 345° C. The x-axis in Temp (° C.) and the y-axis is TG (%).

Figure 46:
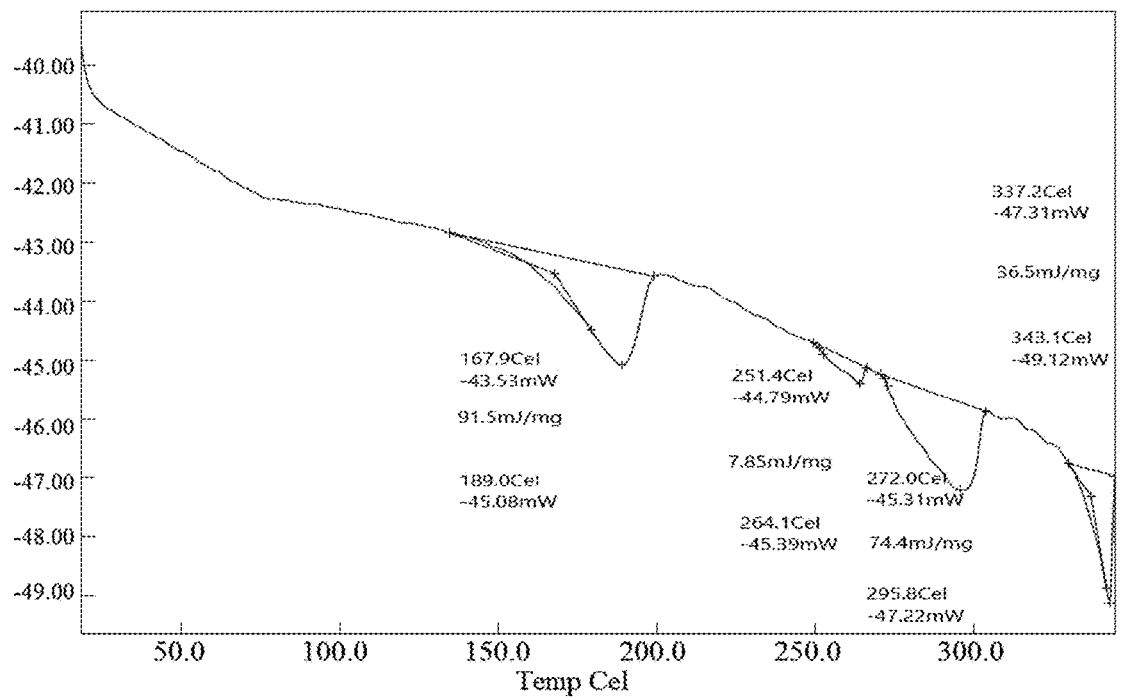

FIG. 46 is a differential scanning calorimetry (DSC) thermogram of the Pattern 3 scale-up material. The DSC thermogram of Pattern 3 was obtained as described in Example 7. DSC analysis showed 3 broad endotherms ca. 168° C. peaking at 189° C., 251° C. peaking at 264° C. and 272° C. peaking at 296° C. A sharp melting endotherm was observed from an onset of 337° C. peaking at 343° C.

Figure 47:
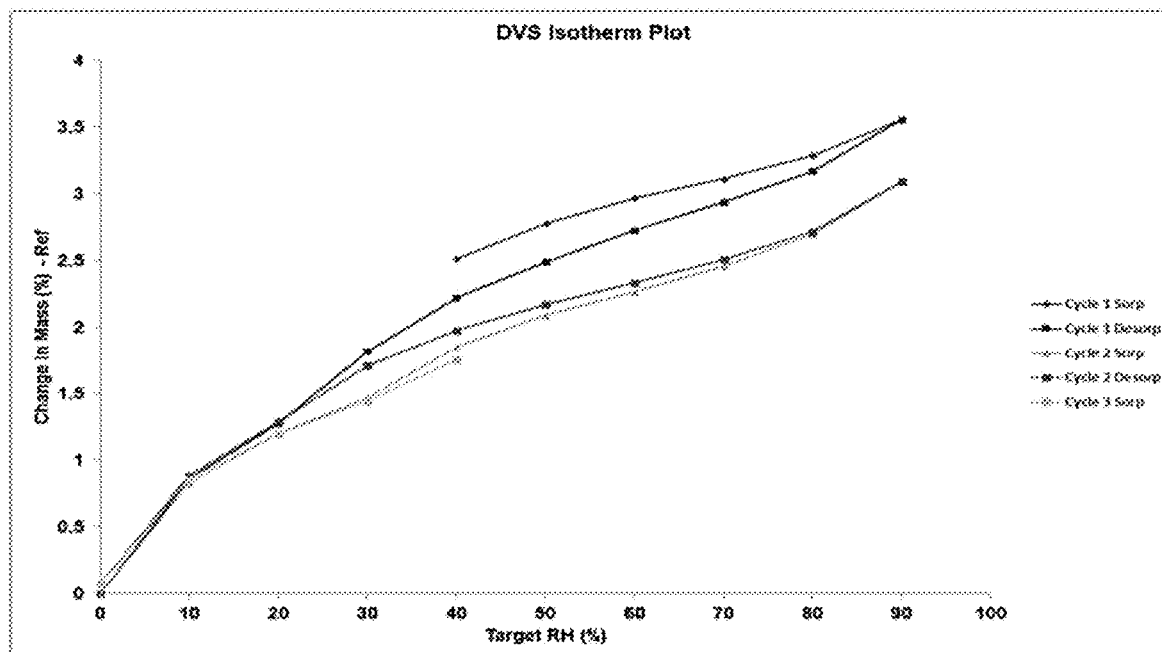

FIG. 47 is a DVS isotherm plot of the Pattern 3 scale-up material. The DVS isotherm plot of Pattern 3 was obtained as described in Example 3. The material appeared hygroscopic by DVS with a mass increase of 4% between 0% and 90% RH. During the desorption cycles the material dehydrates.

Figure 48:
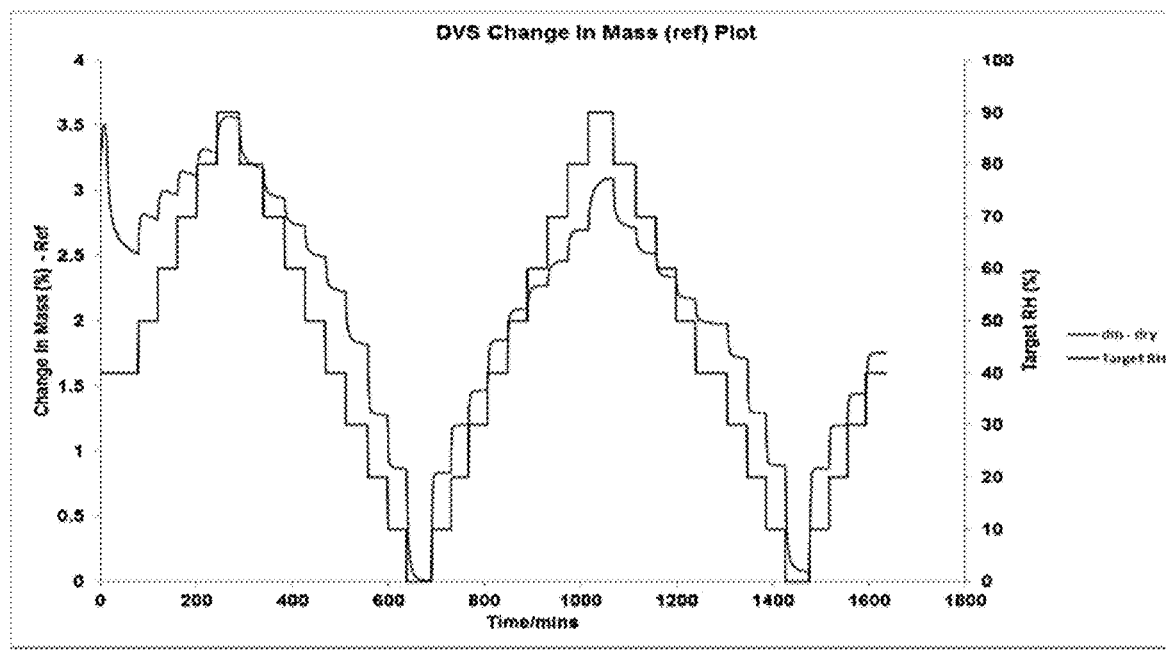

FIG. 48 is a DVS kinetic plot of the Pattern 3 scale-up material. The DVS kinetic plot of Pattern 3 was obtained as described in Example 3. The sample was subjected to a ramping profile from 40-90% relative humidity (RH) at 10% increments, maintaining the sample at each step until a stable weight had been achieved (change in mass 0.004%, minimum step length 650 minutes, maximum step length 1050 minutes) at 25° C. After completion of the sorption cycle, the sample was dried using the same procedure to 0% RH and then a second sorption cycle back to 40% RH. Two cycles were performed. The material appeared hygroscopic by DVS with a mass increase of 4% between 0% and 90% RH. During the desorption cycles the material dehydrates.

Figure 49:
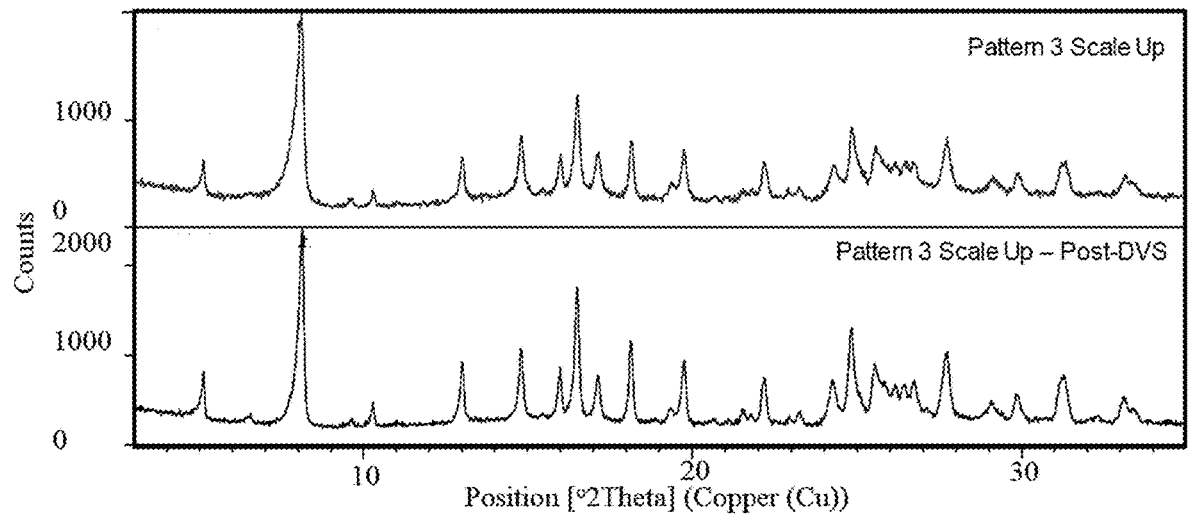

FIG. 49 is a comparison of XRPD diffractograms of the Pattern 3 scale-up material before and after DVS. The diffractograms were obtained as described in Example 1. The x-axis is 2Theta measured in degrees and the y-axis is intensity measured in counts.

Figure 50:
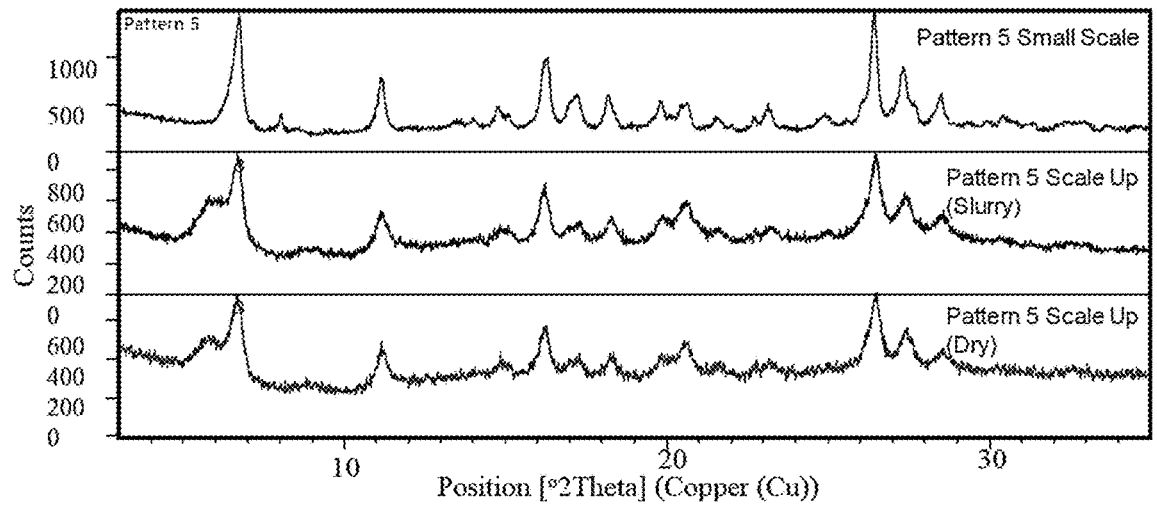

FIG. 50 is a comparison of the XRPD diffractograms of Pattern 5 from small scale and scale up experiments. The diffractogram were obtained as described in Example 1. The x-axis is 2Theta measured in degrees and the y-axis is intensity measured in counts.

Figure 51:
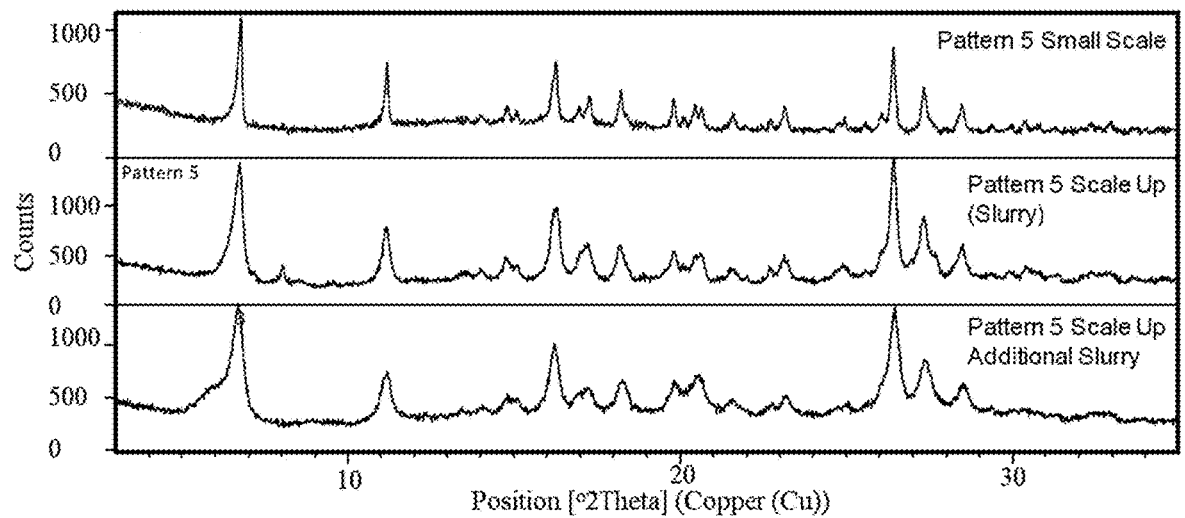

FIG. 51 is a comparison of the XRPD diffractograms of Pattern 5 from small scale and scale up experiments after repeating the process. The diffractogram were obtained as described in Example 1. The x-axis is 2Theta measured in degrees and the y-axis is intensity measured in counts.

Figure 52:
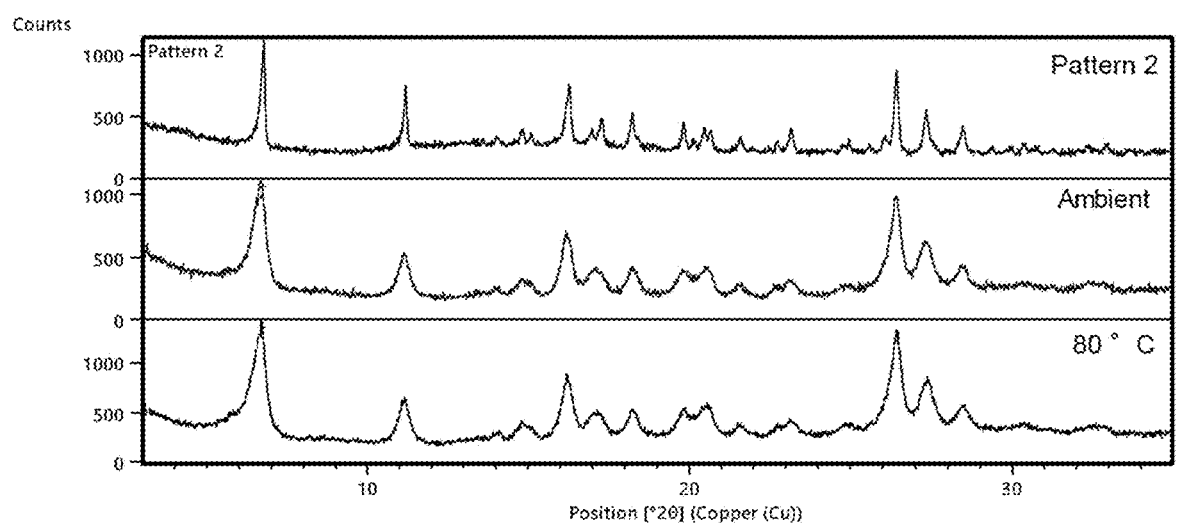

FIG. 52 is a comparison of XRPD diffractograms of Pattern 2 in various weeklong stability studies. The diffractograms were obtained as described in Example 1. The stability study compares Pattern 2, and Pattern 2 after 1 week at ambient temperature and at 80° C., respectively. The x-axis is 2Theta measured in degrees and the y-axis is intensity measured in counts. Repeat Scale Up.

Figure 53:
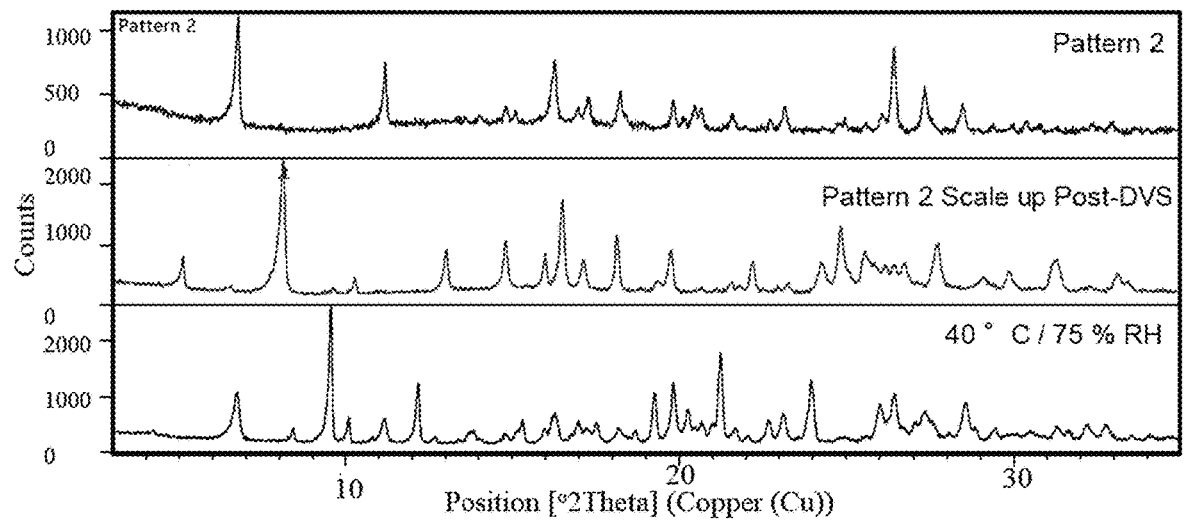

FIG. 53 is a comparison of XRPD diffractograms of Pattern 2 in various weeklong stability studies. The diffractograms were obtained as described in Example 1. The stability study compares Pattern 2, Pattern 2 scale-up and Pattern 2 at 40° C. The x-axis is 2Theta measured in degrees and the y-axis is intensity measured in counts. Repeat Scale Up.

Figure 54:
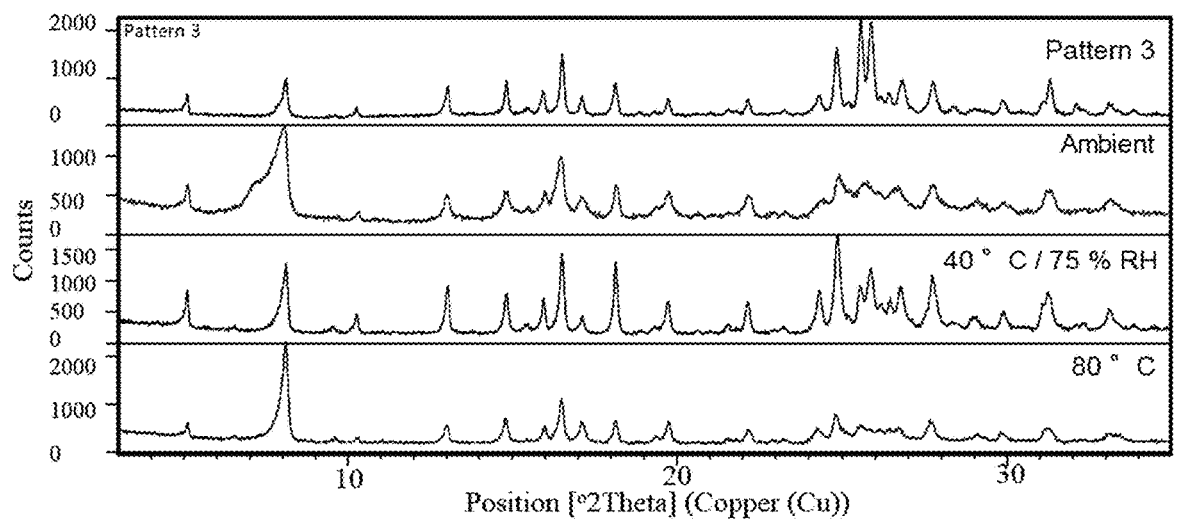

FIG. 54 is a comparison of XRPD diffractograms of Pattern 3 in various weeklong stability studies. The diffractograms were obtained as described in Example 1. The stability study compares Pattern 3, and Pattern 3 after 1 week at ambient temperature, 40° C. and at 80° C., respectively. The x-axis is 2Theta measured in degrees and the y-axis is intensity measured in counts.

Figure 55:
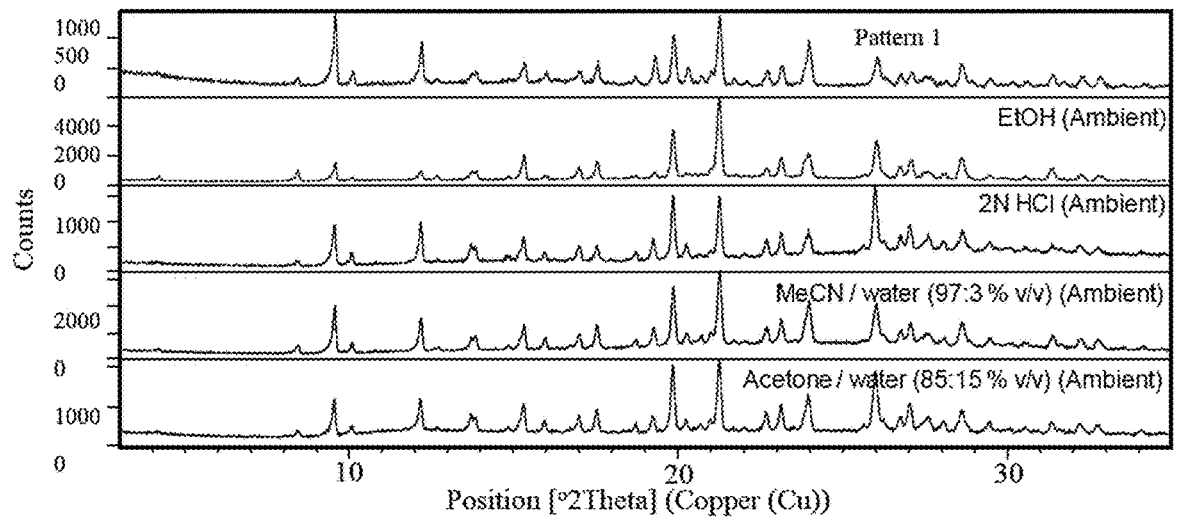

FIG. 55 is a comparison of XRPD diffractograms resulting from competitive slurry experiments of Pattern 1 mixed with Pattern 2 and Pattern 3. The diffractograms were obtained as described in Example 1 after the procedure form Example 11 was pursued. The x-axis is 2Theta measured in degrees and the y-axis is intensity measured in counts.

Figure 56:
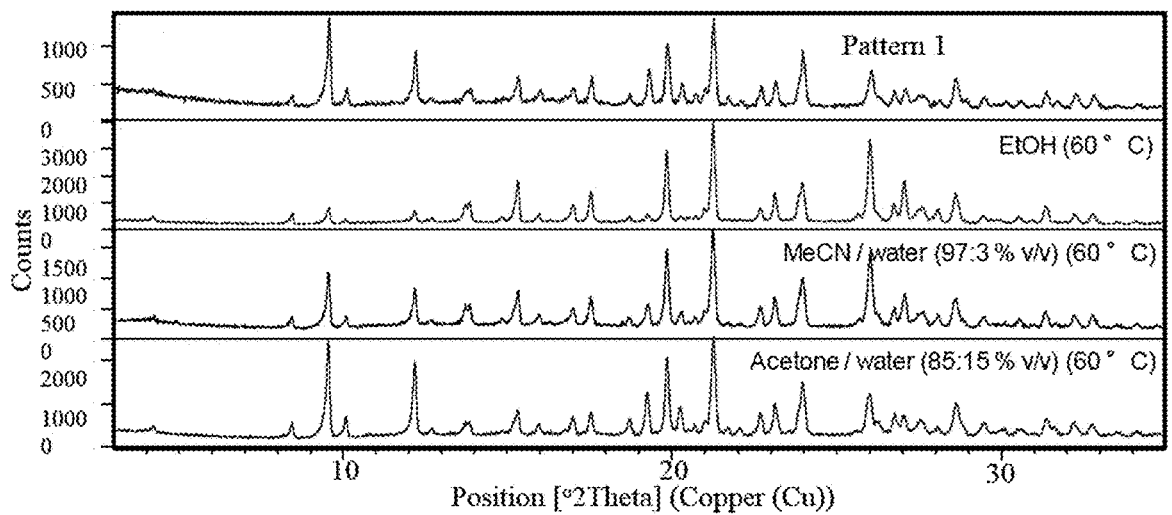

FIG. 56 is a comparison of XRPD diffractograms resulting from competitive slurry experiments of Pattern 1 mixed with Pattern 2 and Pattern 3. The diffractograms were obtained as described in Example 1 after the procedure form Example 11 was pursued. The x-axis is 2Theta measured in degrees and the y-axis is intensity measured in counts.

Figure 57:
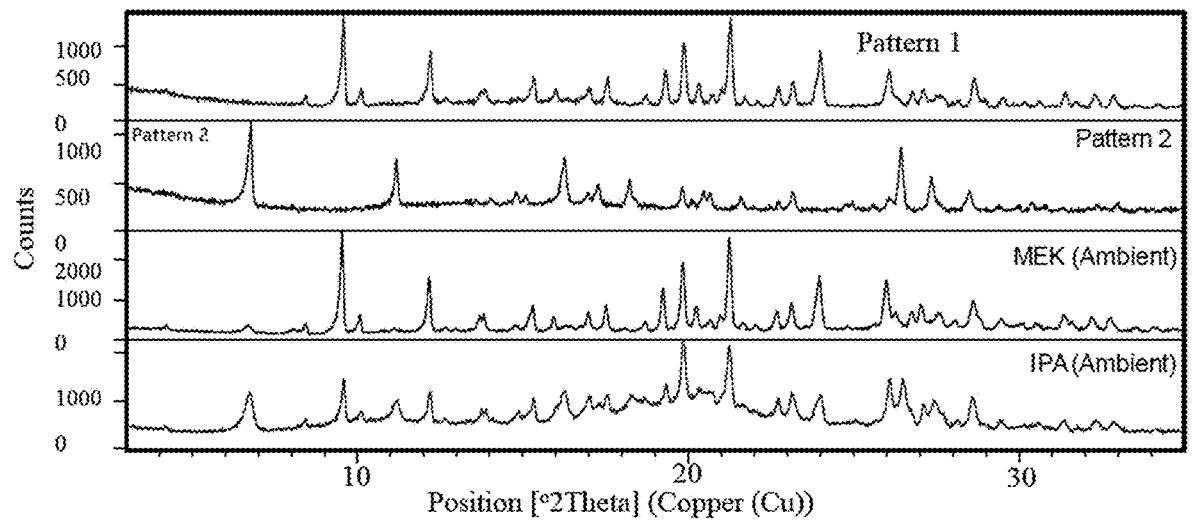

FIG. 57 is a comparison of XRPD diffractograms resulting from competitive slurry experiments of Pattern 1 mixed with Pattern 2 and Pattern 3. The diffractograms were obtained as described in Example 1 after the procedure form Example 11 was pursued. The x-axis is 2Theta measured in degrees and the y-axis is intensity measured in counts.

Figure 58:
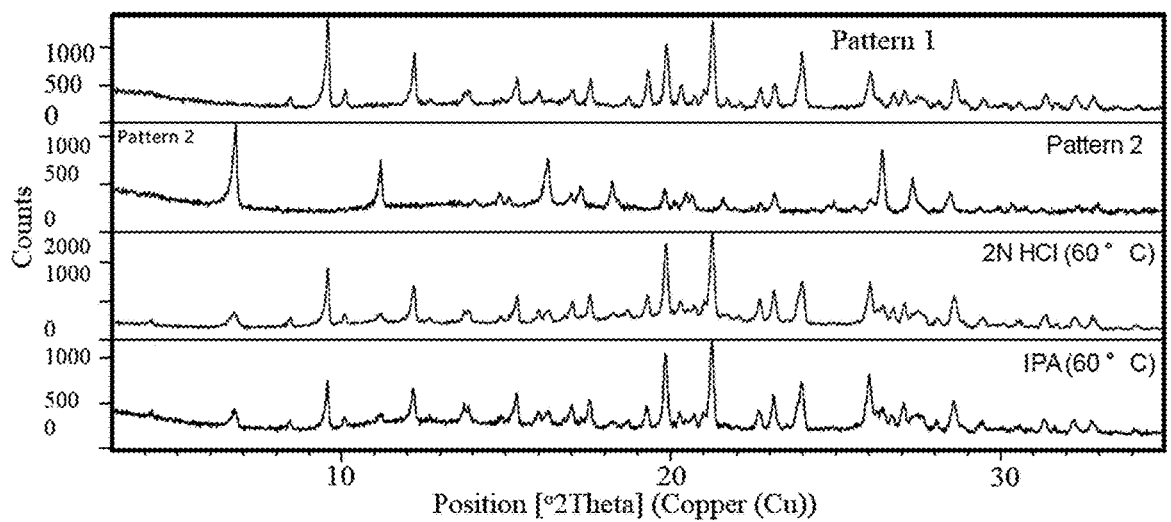

FIG. 58 is a comparison of XRPD diffractograms resulting from competitive slurry experiments of Pattern 1 mixed with Pattern 2 and Pattern 3. The diffractograms were obtained as described in Example 1 after the procedure form Example 11 was pursued. The x-axis is 2Theta measured in degrees and the y-axis is intensity measured in counts.

Figure 59:
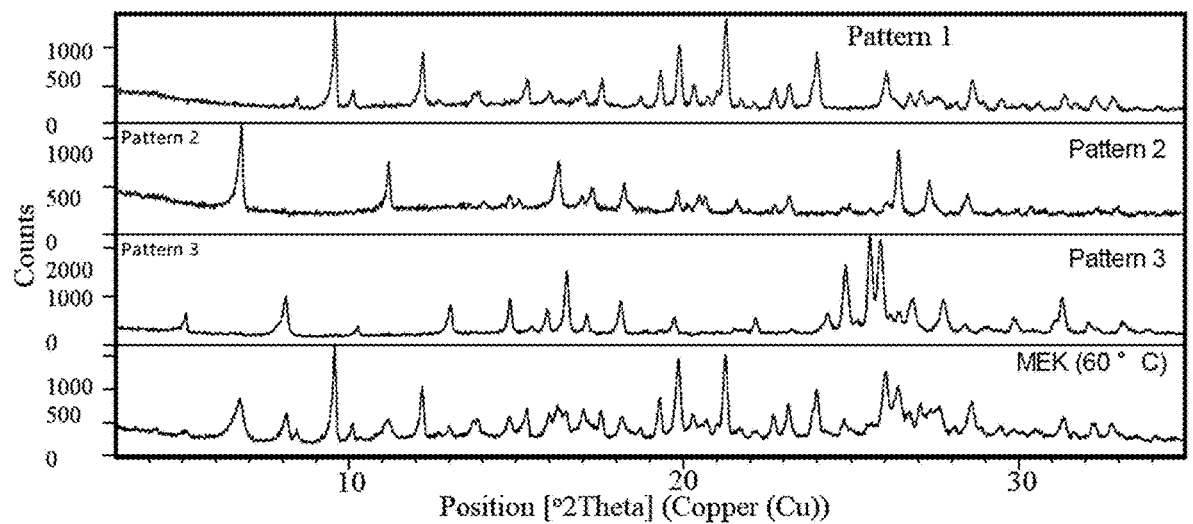

FIG. 59 is a comparison of XRPD diffractograms resulting from competitive slurry experiments of Pattern 1 mixed with Pattern 2 and Pattern 3. The diffractograms were obtained as described in Example 1 after the procedure form Example 11 was pursued. The x-axis is 2Theta measured in degrees and the y-axis is intensity measured in counts.

Figure 60:
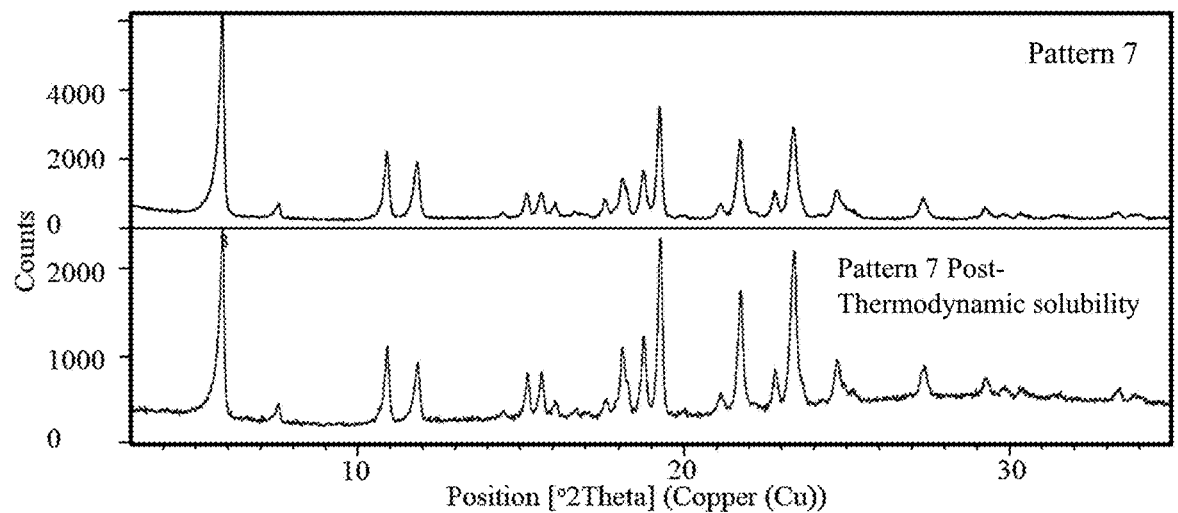

FIG. 60 is a comparison of XRPD diffractograms of Pattern 7 prior to and after thermodynamic solubility experiments. The thermodynamic solubility experiment is described in Example 22. The diffractograms were obtained using the procedure from Example 1. The x-axis is 2Theta measured in degrees and the y-axis is intensity measured in counts.

Figure 61:
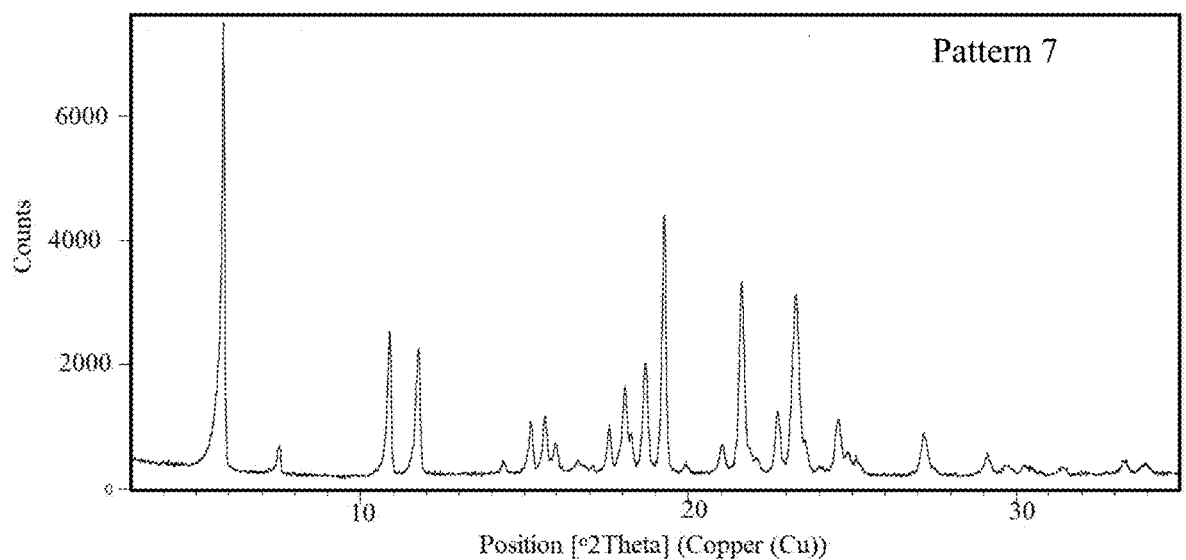

FIG. 61 is an XRPD diffractogram of Pattern 7. The diffractogram of Pattern 7 was obtained as described in Example 1. The x-axis is 2Theta measured in degrees and the y-axis is intensity measured in counts.

Figure 62:
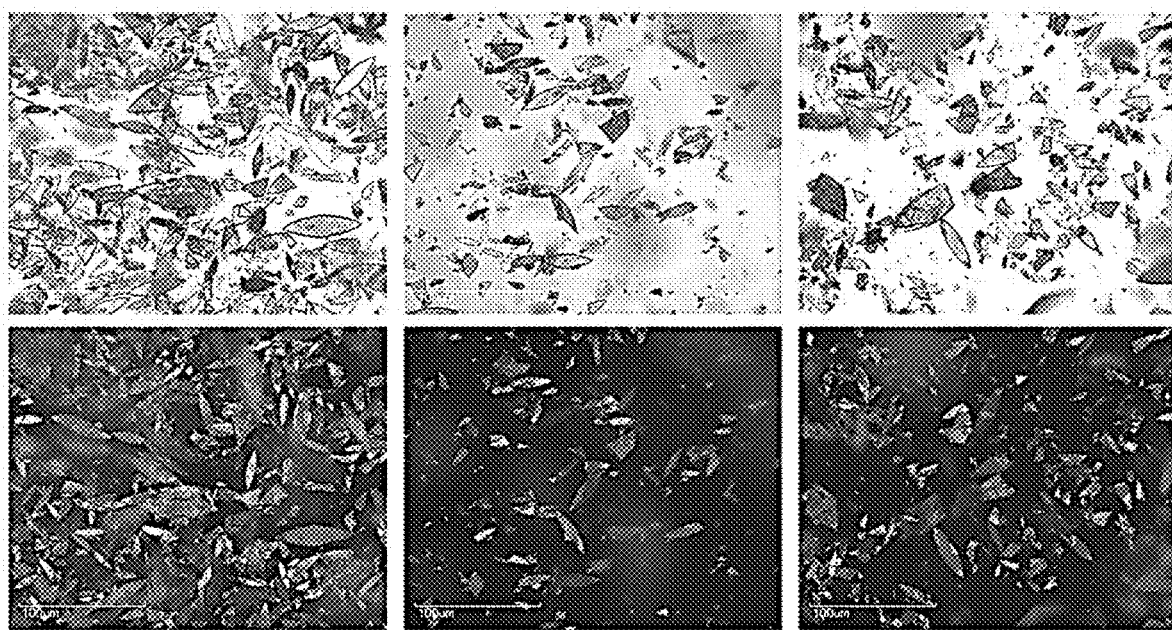

FIG. 62 is a PLM image of Pattern 7 at 200× Magnification. The PLM image of Pattern 7 was obtained as described in Example 5. The birefringent sample under polarized light is shown on the bottom and the Non-Polarized Light of the sample is shown on the top.

Figure 63:
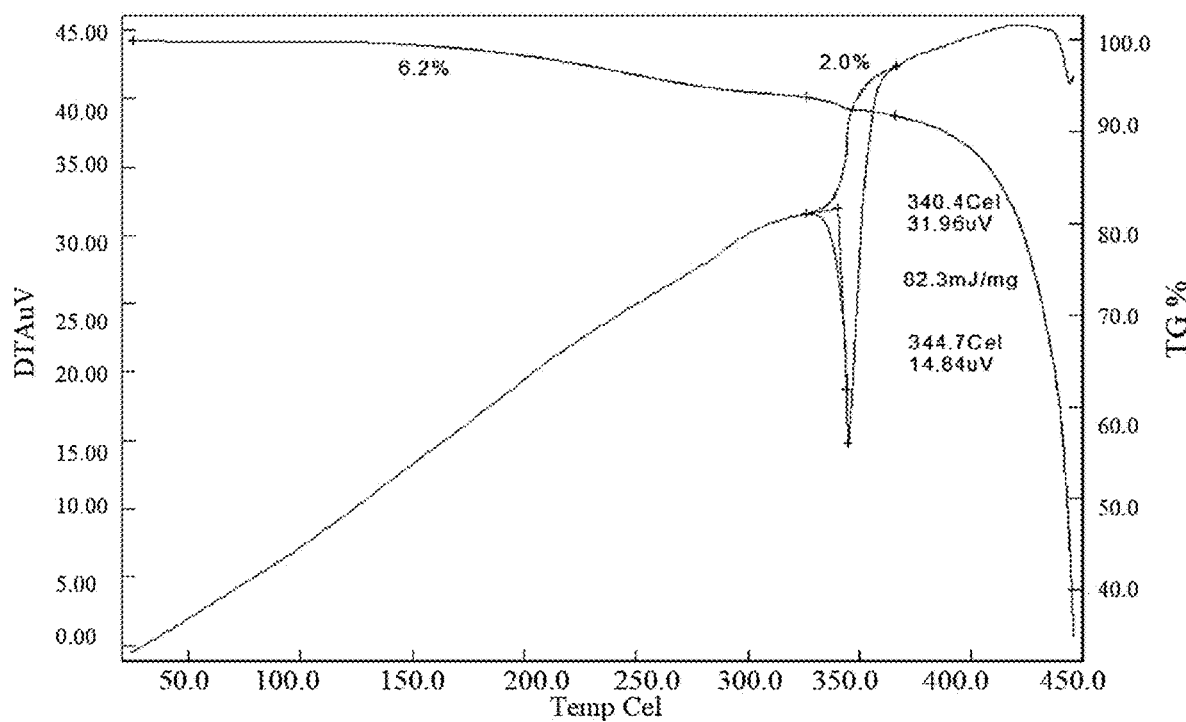

FIG. 63 is a TG/DTA thermogram of Pattern 7. The TG/DTA thermogram of Pattern 7 was obtained as described in Example 6. The thermogram shows a 6.2% weight loss between 150 and 340° C. and sample decomposition above 350° C. The thermogram also shows that the sample melted noted with onset at 340° C. and a peak at 345° C. The x-axis is Temp measured in degrees Celsius and the y-axis is intensity measured in DTAuV on the left and TG % on the right.

Figure 64:
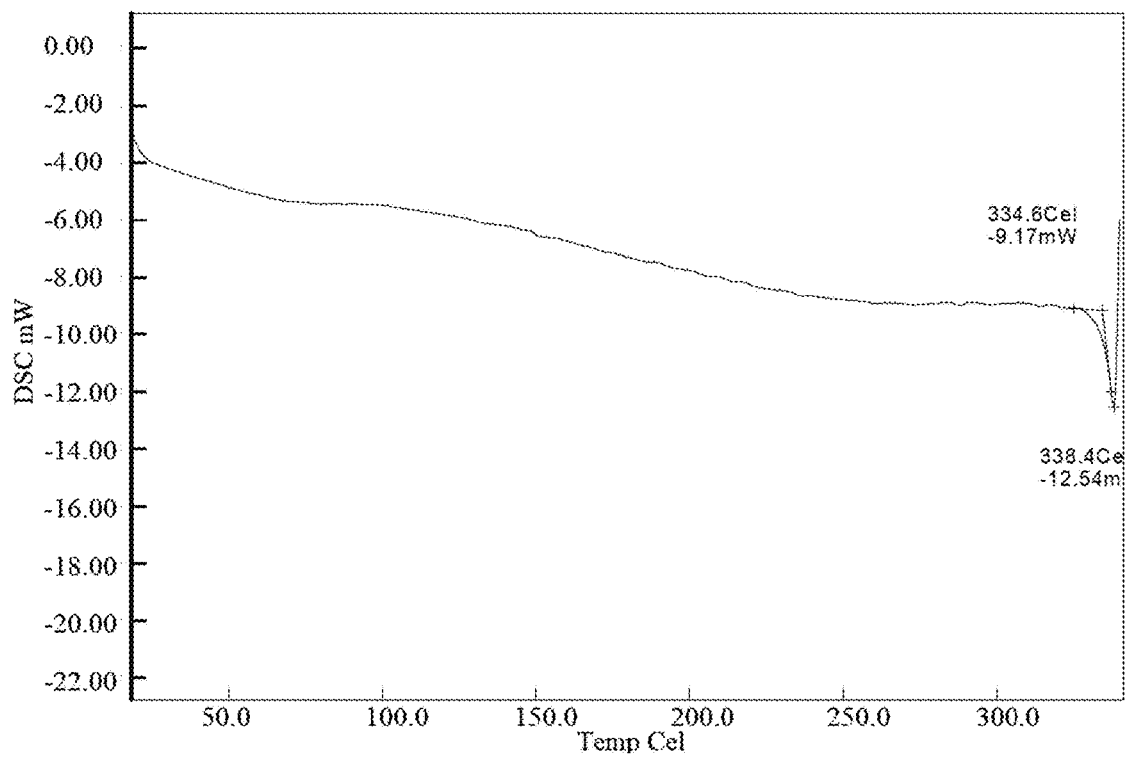

FIG. 64 is a DSC first heat thermogram of Pattern 7. The DSC thermogram of Pattern 7 was obtained as described in Example 7. The thermogram shows the sample melting event at 335° C. and a peak at 338° C. (consistent with TG/DTA data) during first heat. The x-axis is Temp measured in degrees Celsius and the y-axis is intensity measured in DSC mW.

Figure 65:
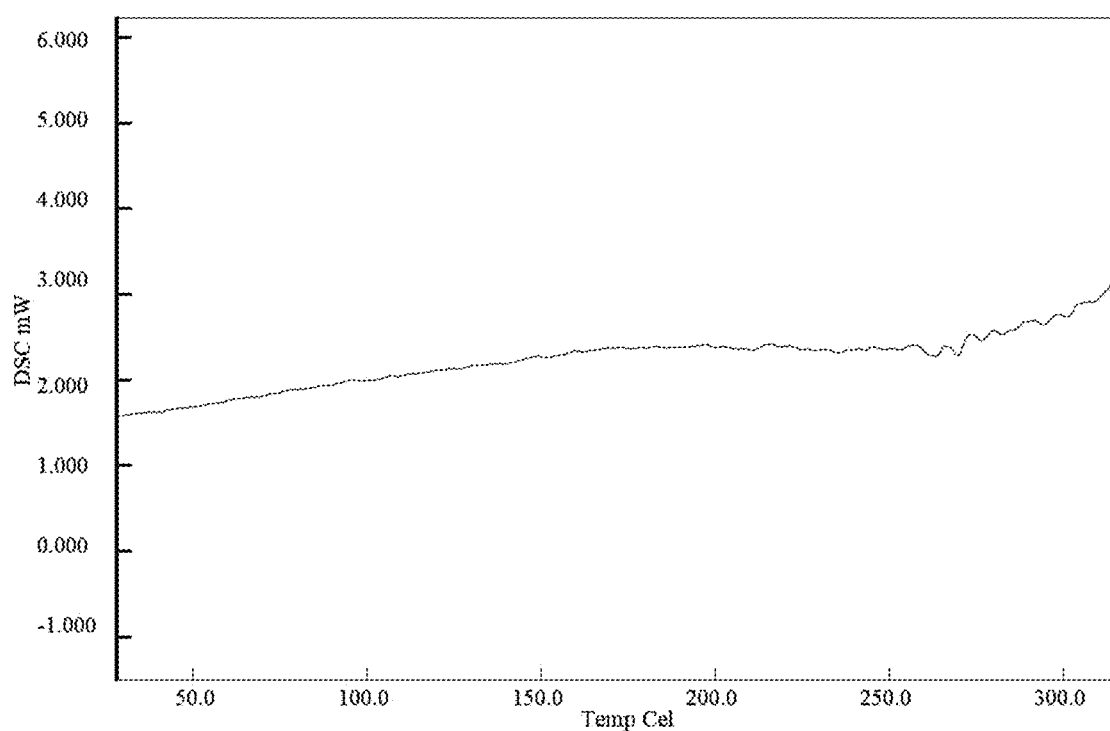

FIG. 65 is a DSC cool thermogram of Pattern 7. The DSC thermogram of Pattern 7 was obtained as described in Example 7. The thermogram shows no significant thermal events in the cool cycle. The x-axis is Temp measured in degrees Celsius and the y-axis is intensity measured in DSC mW.

Figure 66:
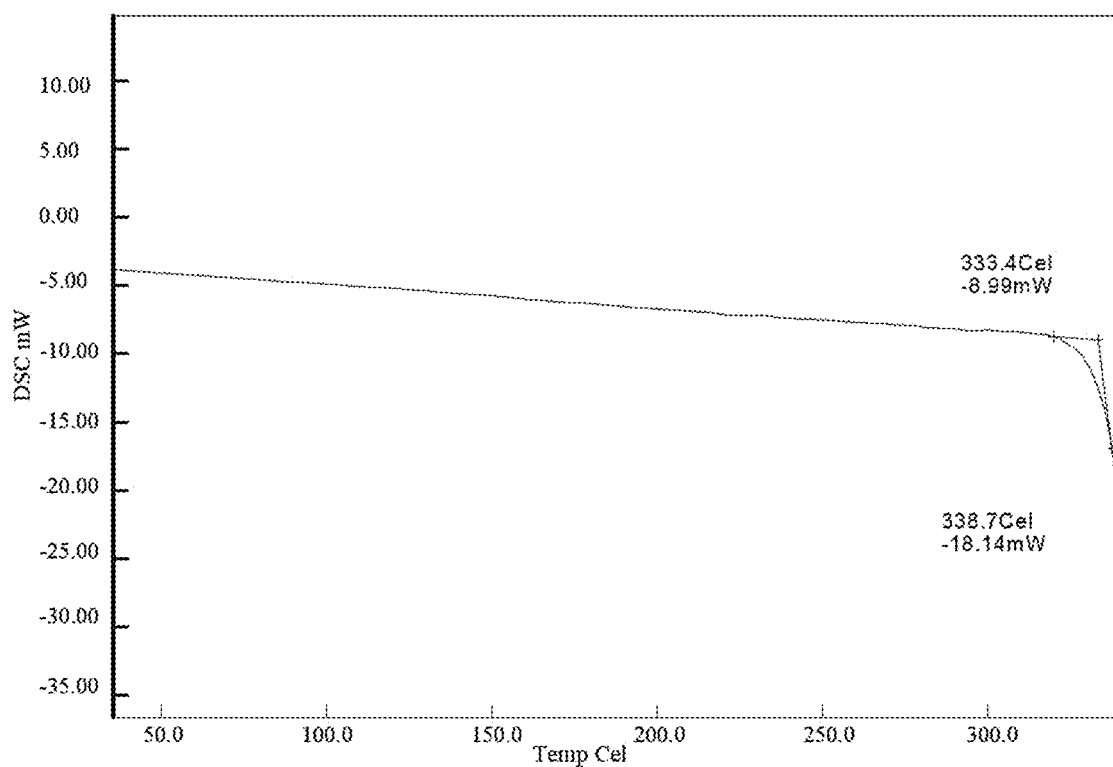

FIG. 66 is a DSC second heat thermogram of the crystalline Pattern 7. The DSC thermogram of Pattern 7 was obtained as described in Example 7. The second heat contained the melting event with onset 333° C. and a peak at 339° C. Possible incomplete melting during the initial heat cycle. The x-axis is Temp measured in degrees Celsius and the y-axis is intensity measured in DSC mW.

Figure 67:
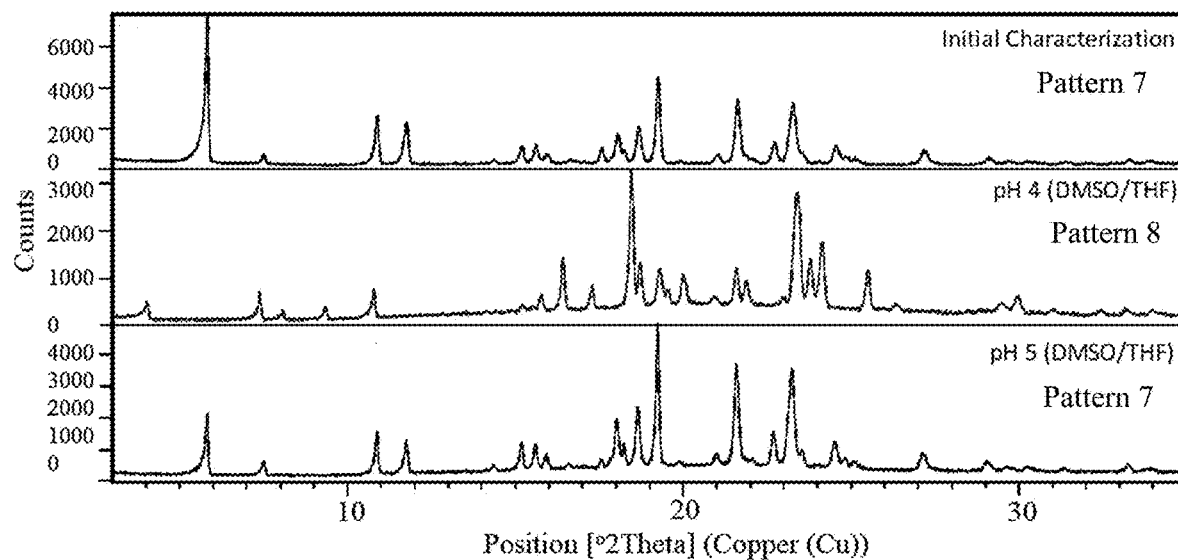

FIG. 67 is a comparison of XRPD diffractograms from pH solubility studies of Pattern 7 at various pHs. The material resulting from pH 4 was identified as Pattern 8. The diffractograms were obtained as described in Example 1 and the pH experiment was as described in Example 16. The x-axis is 2Theta measured in degrees and the y-axis is intensity measured in counts.

Figure 68:
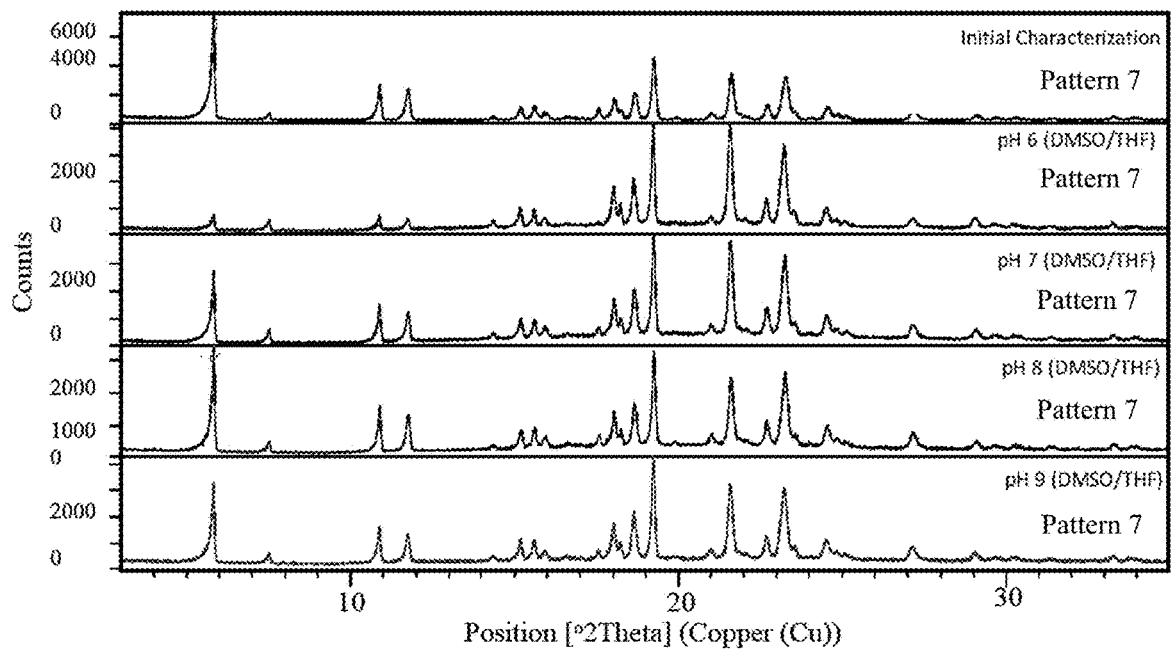

FIG. 68 is a comparison of XRPD diffractograms from pH solubility studies of Pattern 7 at various pHs. The diffractogram of Pattern 7 was obtained as described in Example 1 and Example 16. The x-axis is 2Theta measured in degrees and the y-axis is intensity measured in counts.

Figure 69:
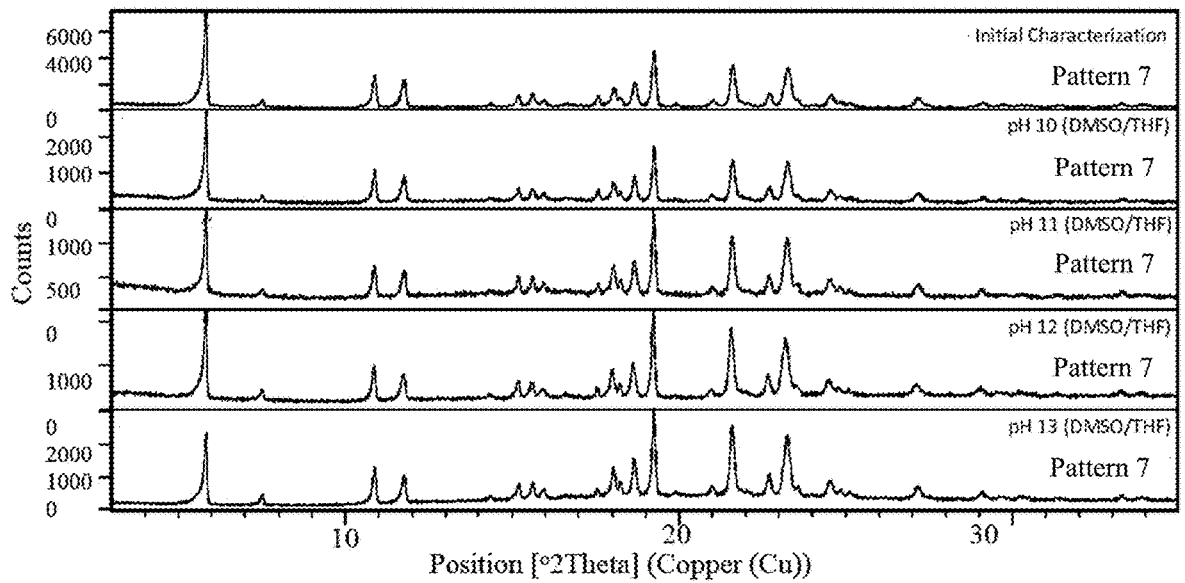

FIG. 69 is a comparison of XRPD diffractograms from pH solubility studies of Pattern 7 at various pH solvent systems. The diffractogram of Pattern 7 was obtained as described in Example 1 and Example 16. The x-axis is 2Theta measured in degrees and the y-axis is intensity measured in counts.

Figure 70:
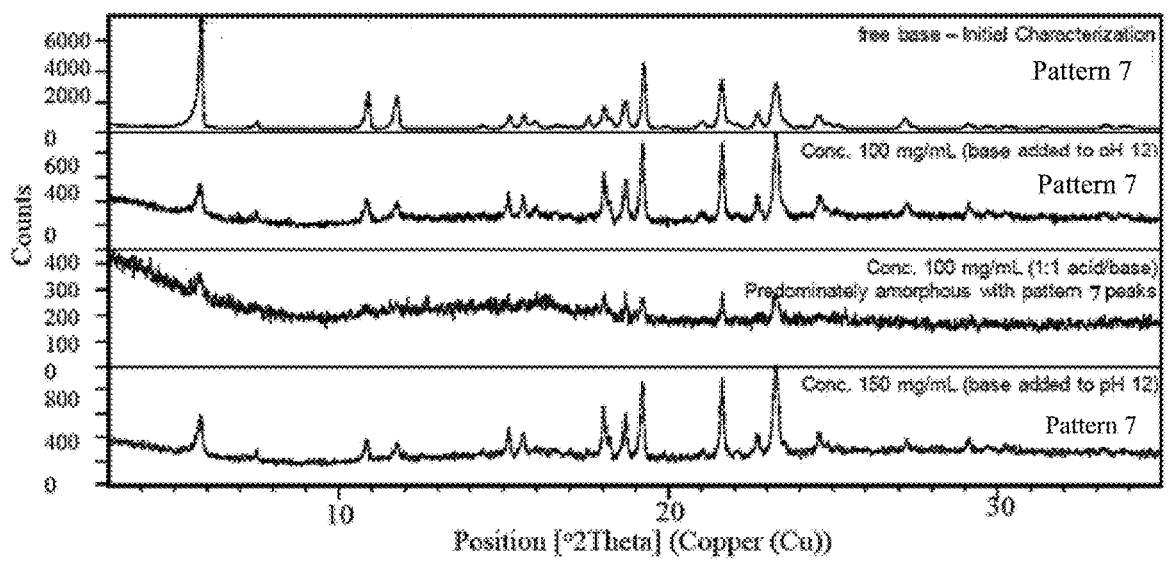

FIG. 70 is a comparison of XRPD diffractograms that resulted from crystallization set 1. The crystallizations were conducted as described in Example 17. The comparison shows the Pattern 7 and forms resulting from various concentrations in various pH solvent systems. The x-axis is 2Theta measured in degrees and the y-axis is intensity measured in counts.

Figure 71:
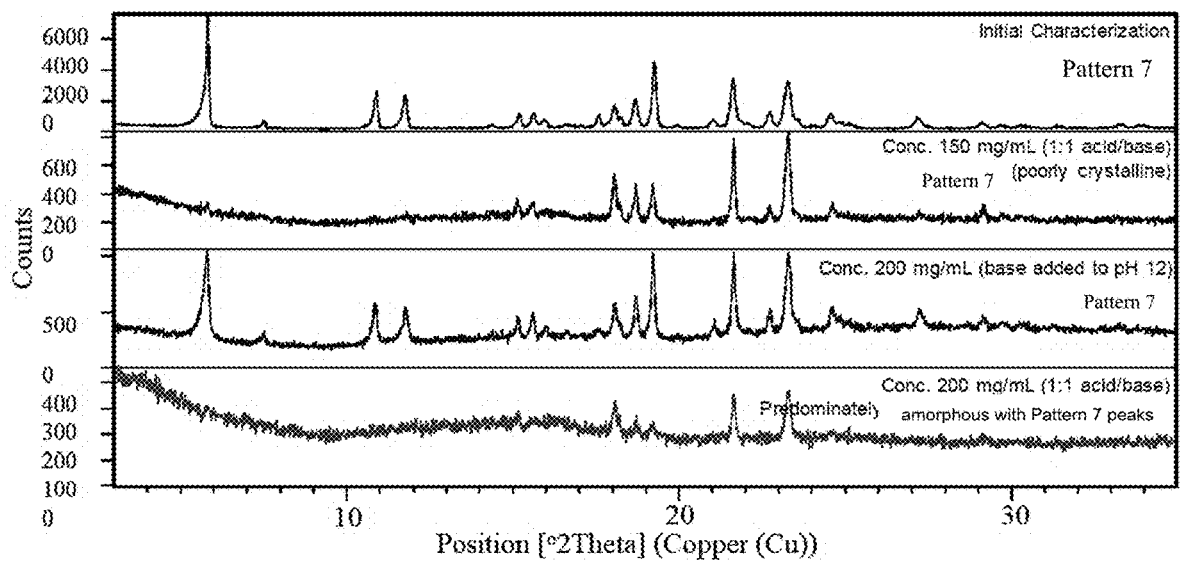

FIG. 71 is a comparison of XRPD diffractograms that resulted from crystallization sets 2 and 3. The crystallizations were conducted as described in Example 18 and Example 19. The comparison shows the Pattern 7 and forms resulting from various concentrations in various pH solvent systems. The x-axis is 2Theta measured in degrees and the y-axis is intensity measured in counts.

Figure 72:
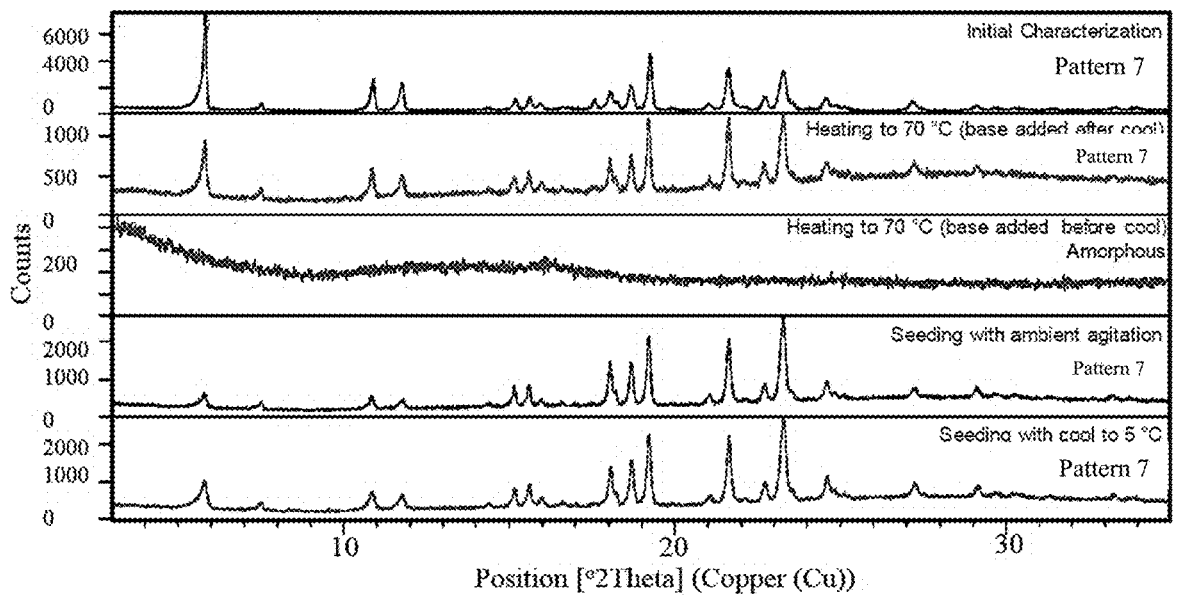

FIG. 72 is a comparison of XRPD diffractograms that resulted from crystallization sets 2 and 3. The crystallizations were conducted as described in Example 18 and Example 19. The comparison shows the Pattern 7 and forms resulting from various concentrations in various pH solvent systems. The x-axis is 2Theta measured in degrees and the y-axis is intensity measured in counts.

Figure 73:
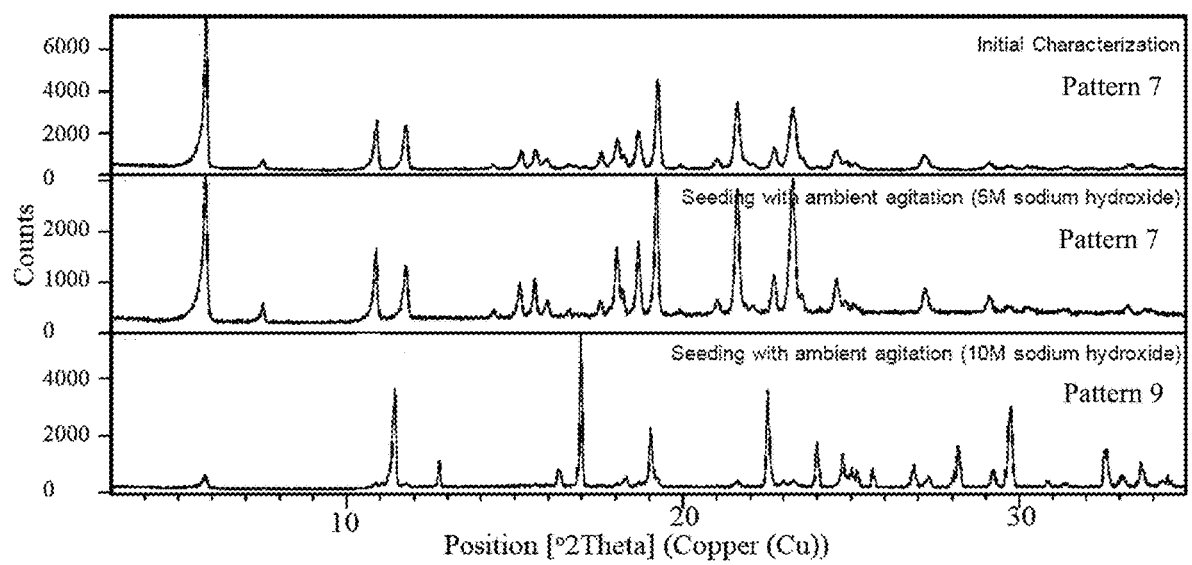

FIG. 73 is a comparison of XRPD diffractograms that resulted from crystallization set 4. The crystallizations were conducted as described in Example 20. The comparison shows the Pattern 7 and forms resulting from various concentrations in various pH solvent systems. The x-axis is 2Theta measured in degrees and the y-axis is intensity measured in counts.

Figure 74:
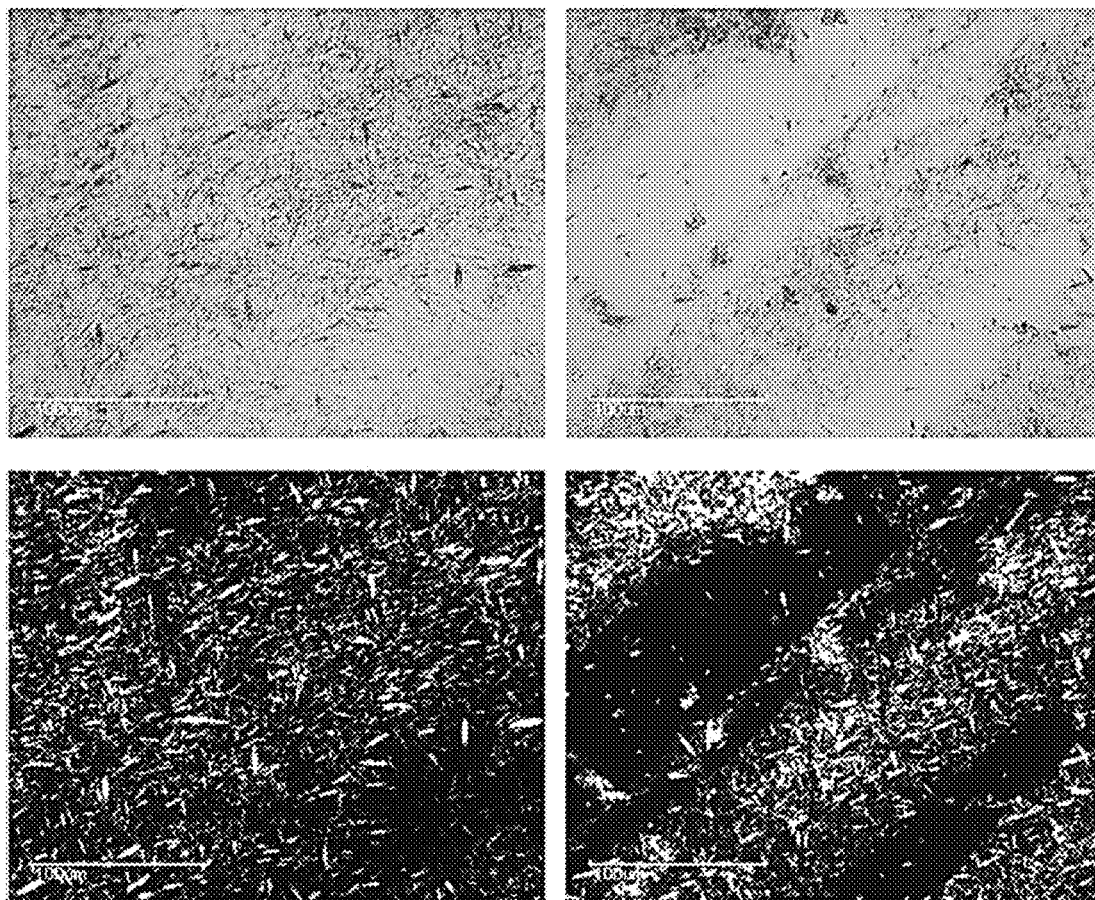

FIG. 74 is a PLM image corresponding to the material obtained from experiment 1 from Example 23. The polarized sample is shown in the bottom row and the non-polarized light sample is shown in the top row.

Figure 75:
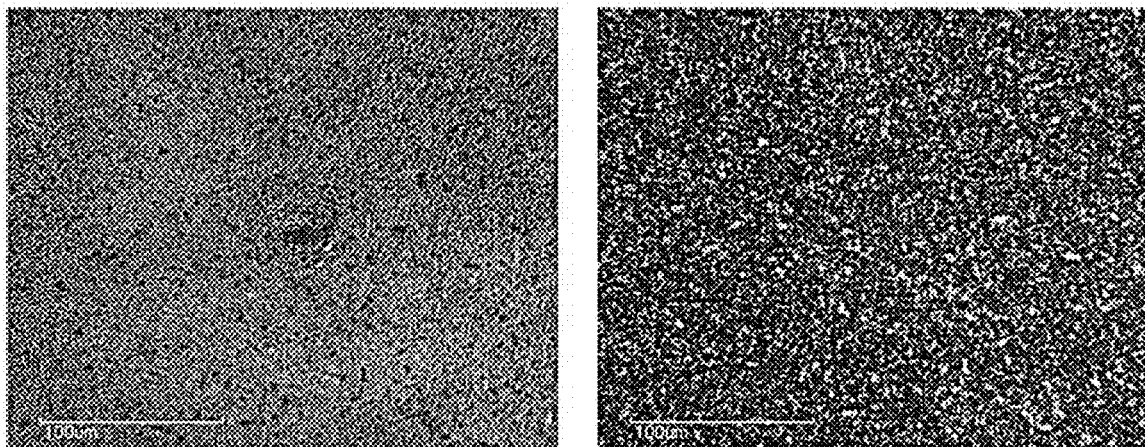

FIG. 75 is a PLM image corresponding to the material obtained from experiment 2 from Example 23. The PLM image was obtained as described in Example 5. The polarized sample is shown on the right and the non-polarized light sample is shown on the left.

Figure 76:
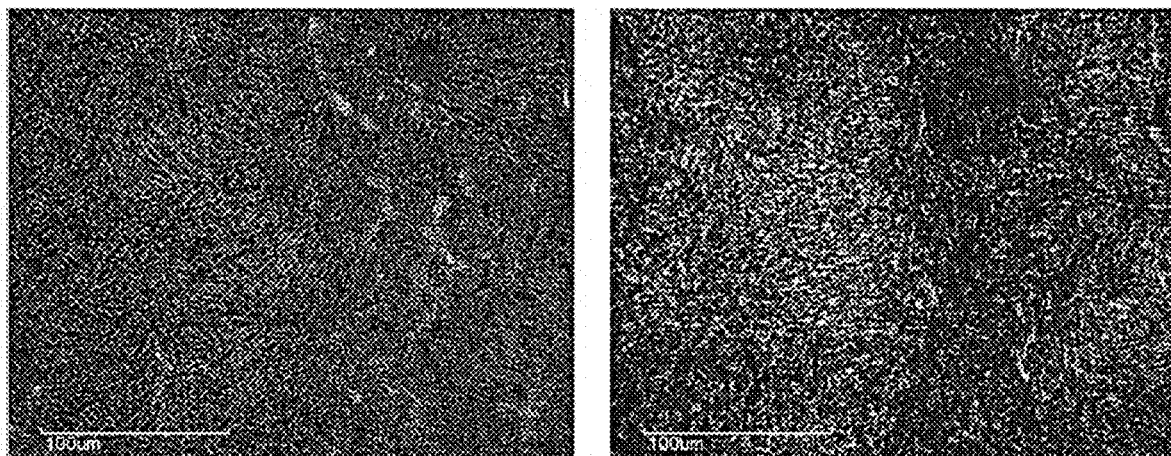

FIG. 76 is a PLM image corresponding to the material obtained from experiment 3 from Example 23. The PLM image was obtained as described in Example 5. The polarized sample is shown on the right and the non-polarized light sample is shown on the left.

Figure 77:
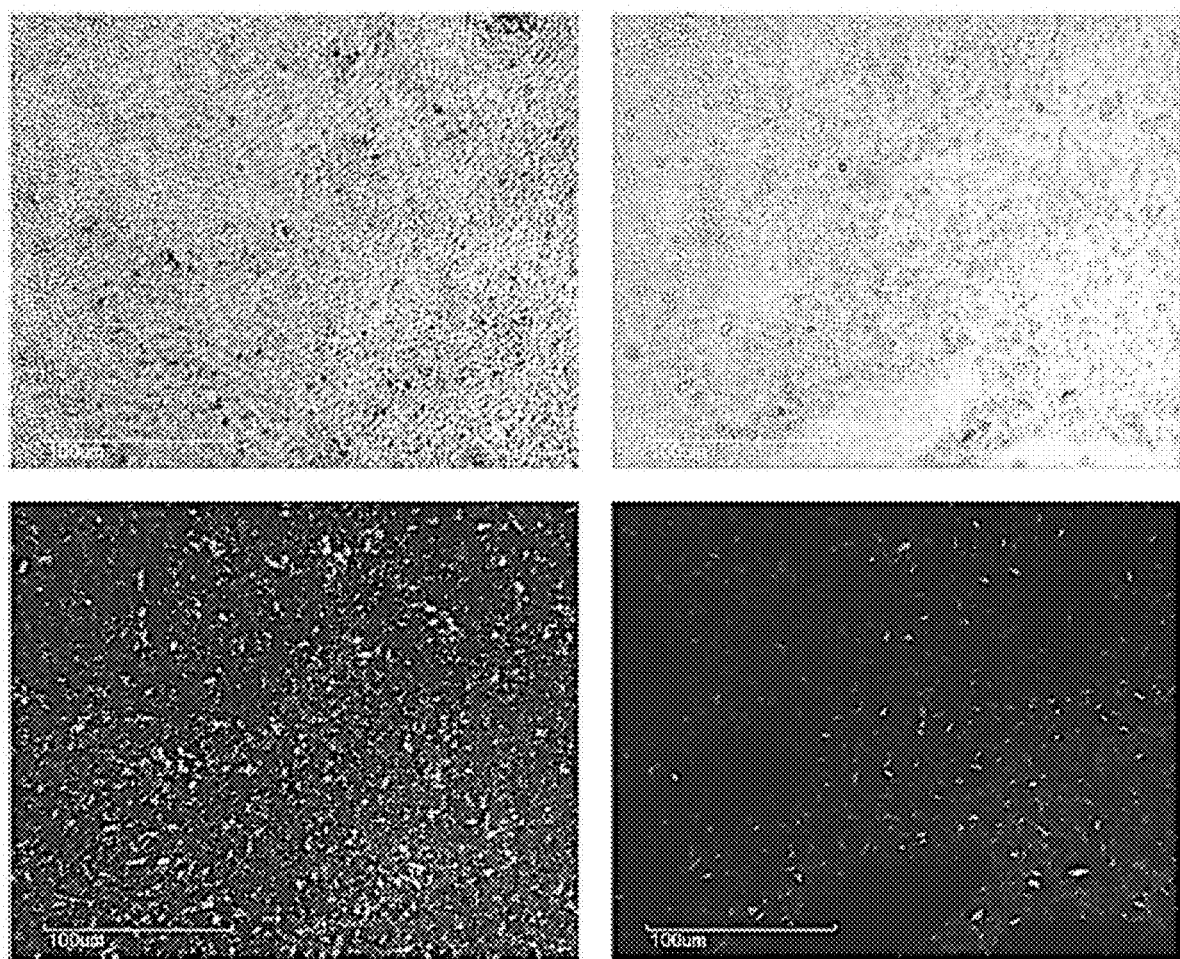

FIG. 77 is a PLM image corresponding to the material obtained from experiment 4 from Example 23. The PLM image was obtained as described in Example 5. The polarized sample is shown in the bottom row and the non-polarized light sample is shown in the top row.

Figure 78:
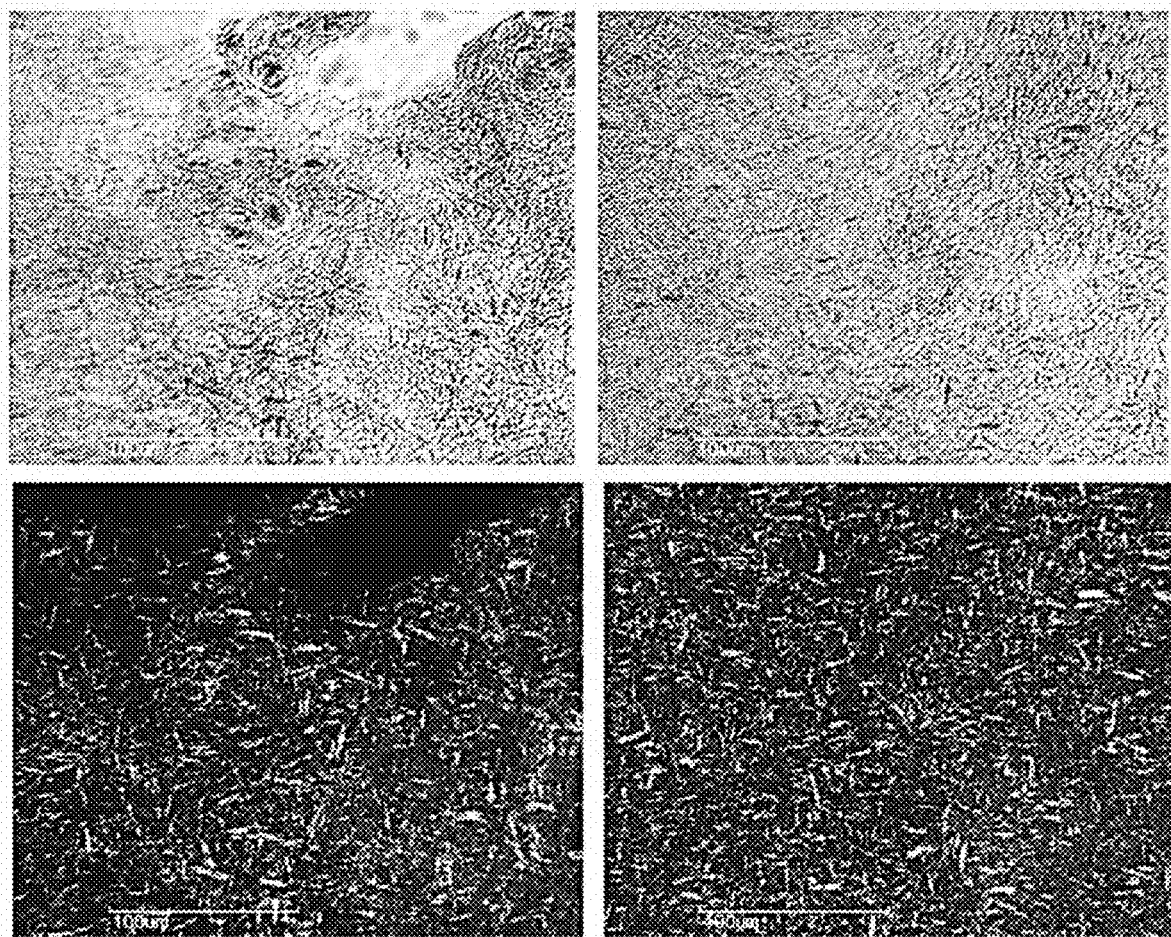

FIG. 78 is a PLM image corresponding to the material obtained from experiment 5 from Example 23. The PLM image was obtained as described in Example 5. The polarized sample is shown in the bottom row and the Non-Polarized Light sample is shown in the top row.

Figure 79:
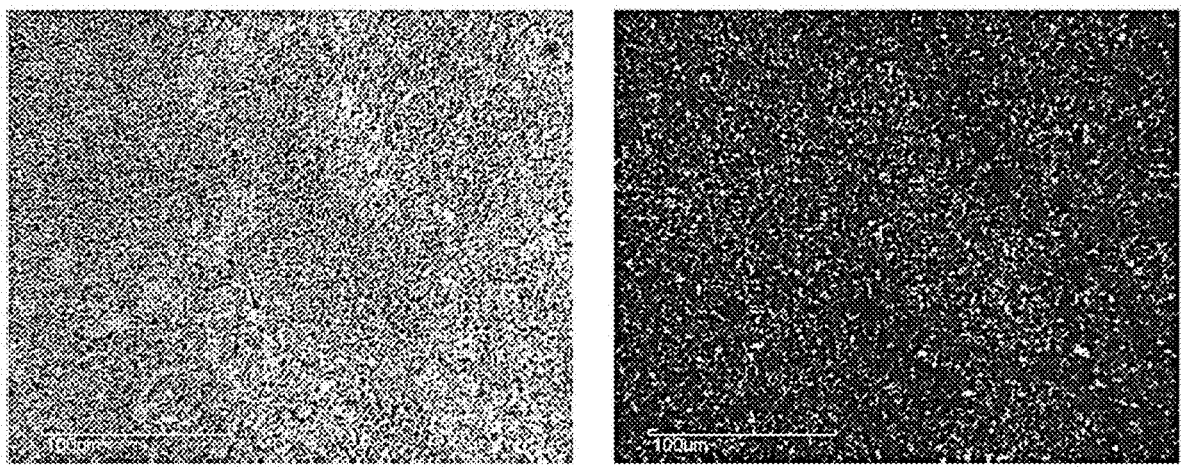

FIG. 79 is a PLM image corresponding to the material obtained from experiment 7 from Example 23. The PLM image was obtained as described in Example 5. The polarized sample is shown on the right and the non-polarized Light sample is shown on the left.

Figure 80:
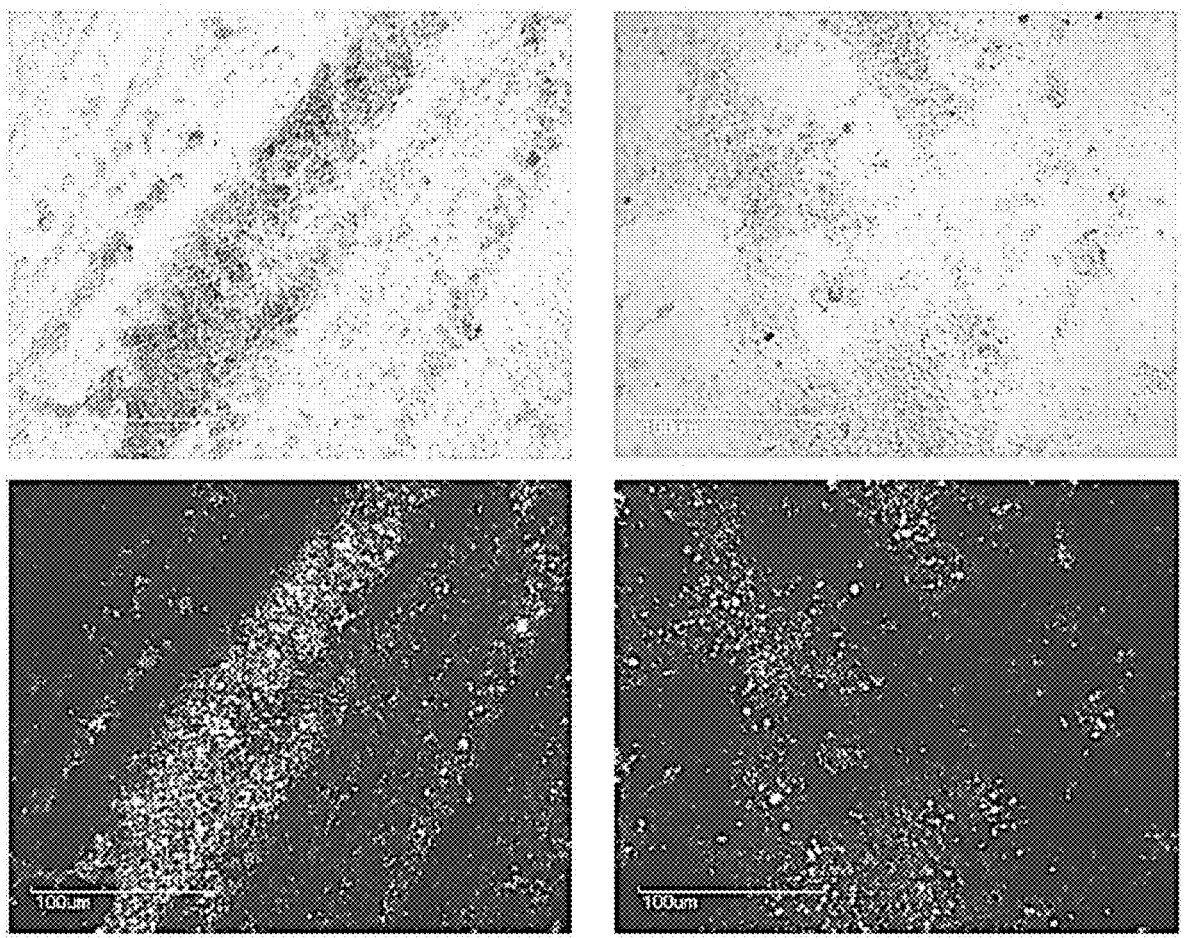

FIG. 80 is a PLM image corresponding to the material obtained from experiment 6 from Example 23. The PLM image was obtained as described in Example 5. The polarized sample is shown in the bottom row and the Non-Polarized Light sample is shown in the top row.

Figure 81:
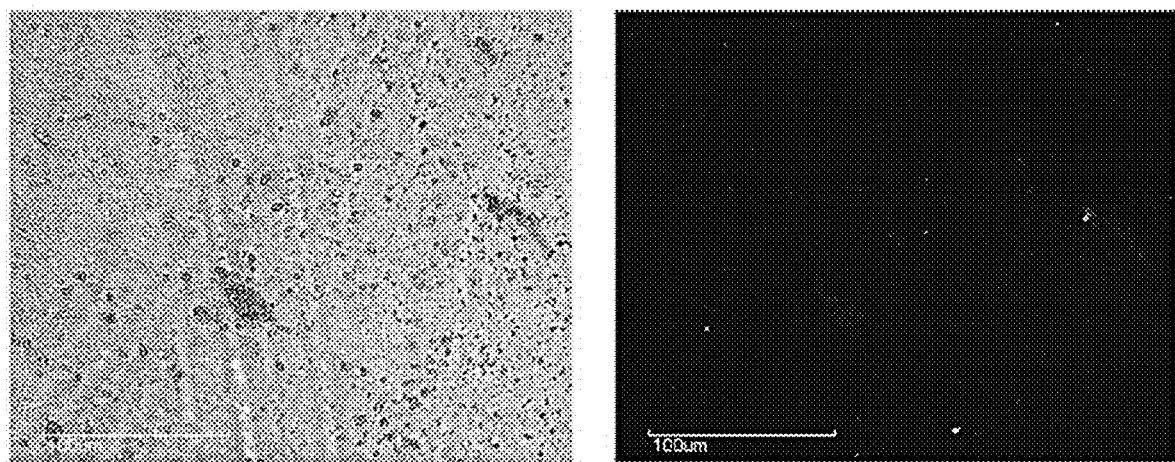

FIG. 81 is a PLM image corresponding to the material obtained from experiment 8 from Example 23. The polarized sample is shown on the right and the non-polarized Light sample is shown on the left.

Figure 82:
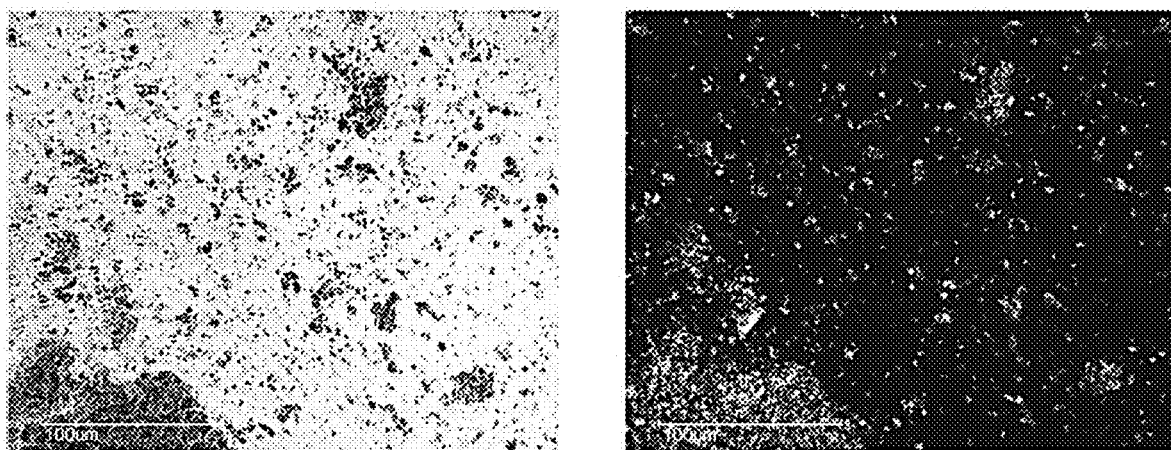

FIG. 82 is a PLM image corresponding to the material obtained from experiment 9 from Example 23. The PLM image was obtained as described in Example 5. The polarized sample is shown on the right and the non-polarized Light sample is shown on the left.

Figure 83:
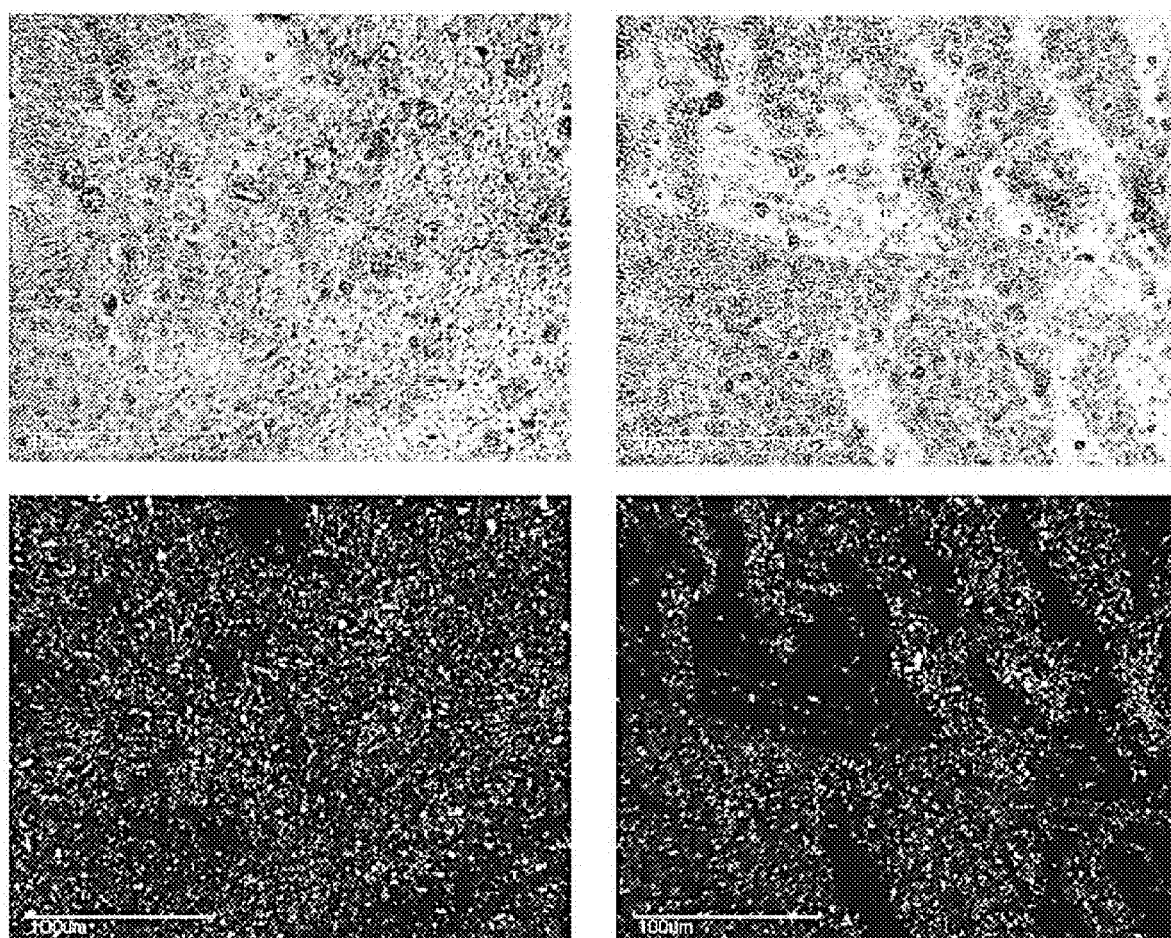

FIG. 83 is a PLM image corresponding to the material obtained from experiment 10 from Example 23. The polarized sample is shown in the bottom row and the Non-Polarized Light sample is shown in the top row.

Figure 84:
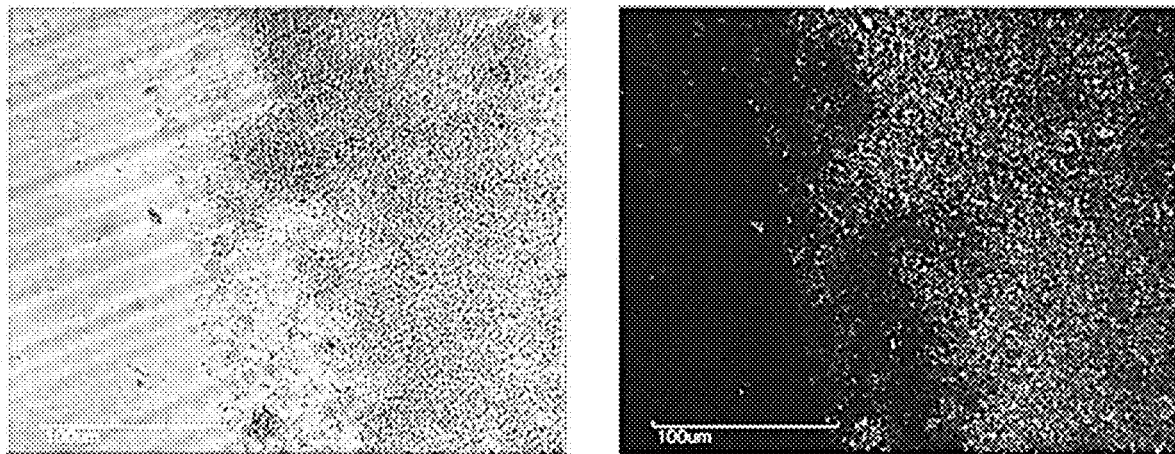

FIG. 84 is a PLM image corresponding to the material obtained from experiment 11 from Example 23. The polarized sample is shown on the right and the non-polarized Light sample is shown on the left.

Figure 85:
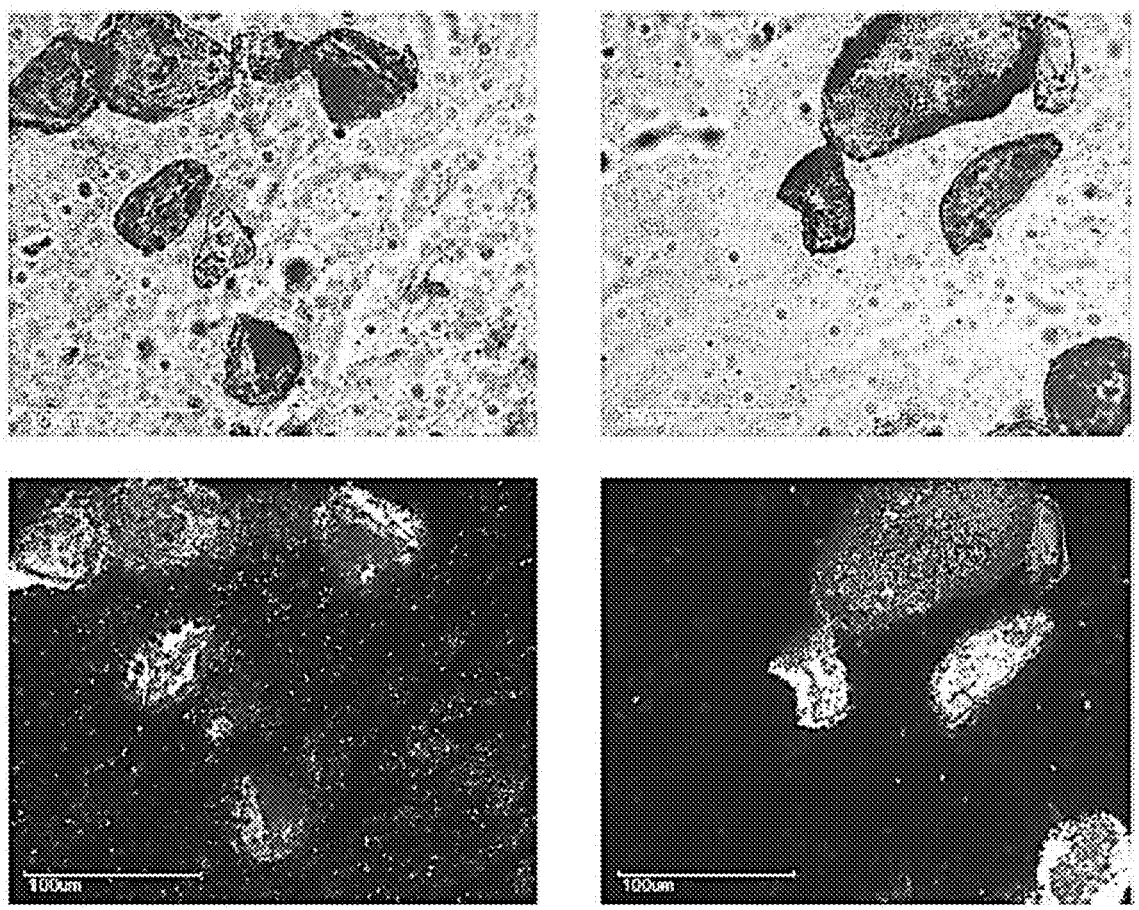

FIG. 85 is a PLM image corresponding to the material obtained from experiment 12 from Example 23. This material was identified as Pattern 9. The polarized sample is shown in the bottom row and the Non-Polarized Light sample is shown in the top row.

Figure 86:
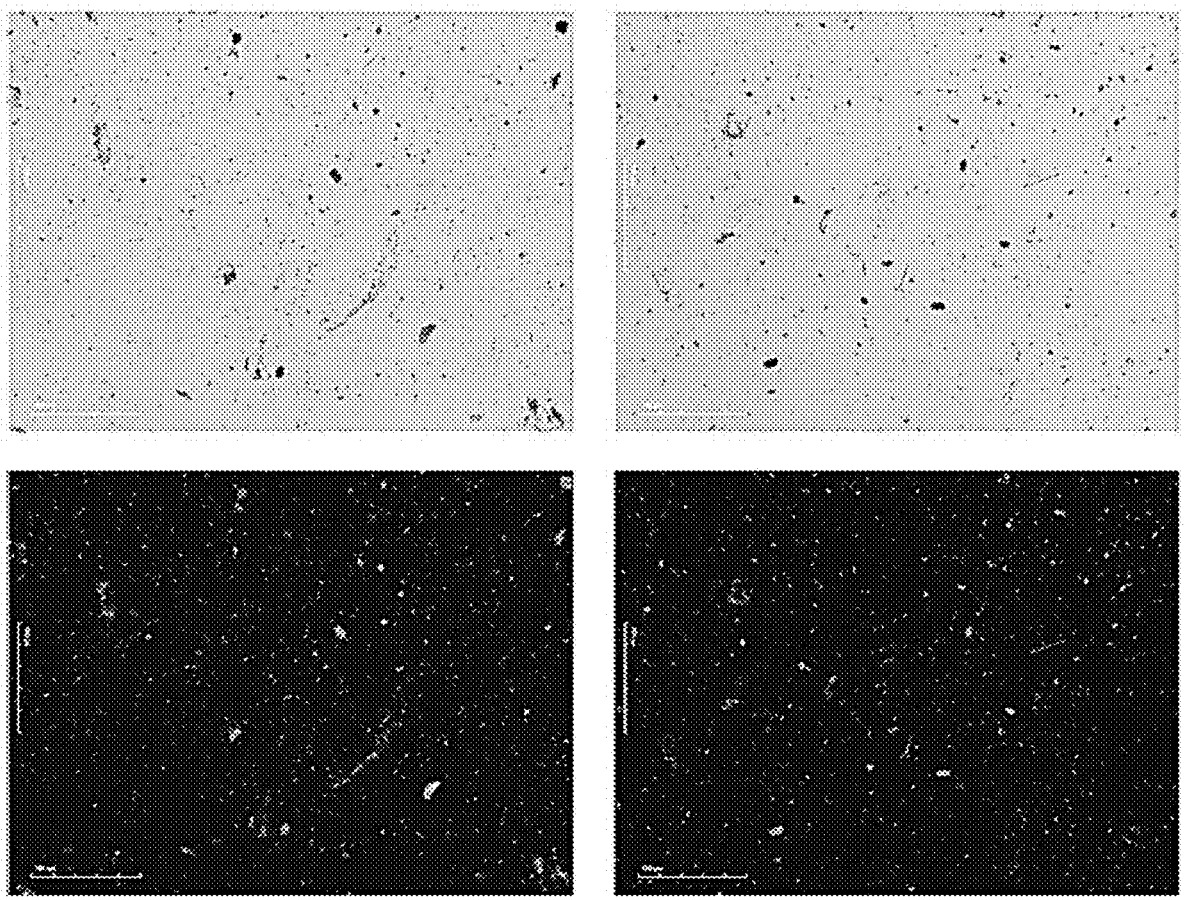

FIG. 86 is a PLM Images of the crystalline Pattern 10 at 200× Magnification. The PLM imaging of crystalline Pattern 7 was obtained as described in Example 5. The polarized sample is shown in the bottom row and the Non-Polarized Light sample is shown in the top row.

Figure 87:
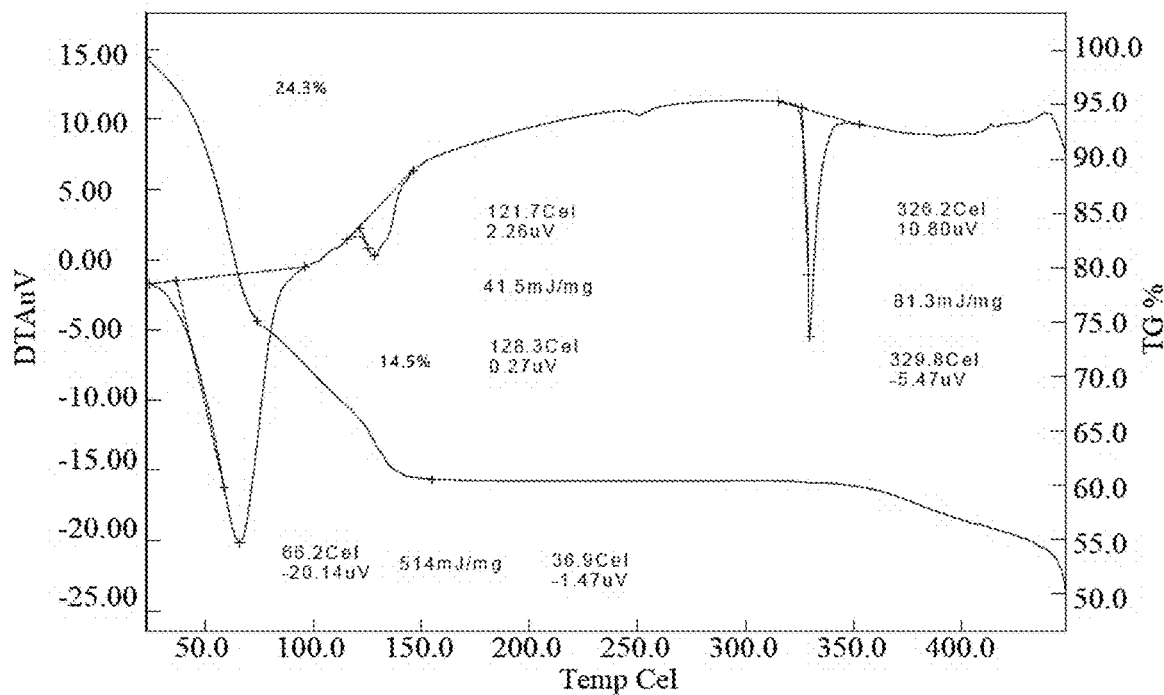

FIG. 87 is a TG/DTA thermogram of Pattern 9. The TG/DTA thermogram of Pattern 9 was obtained as described in Example 6. Pattern 9 exhibited a large weight loss of 24.3% from the onset of heating up to 150° C. Pattern 9 exhibited a second mass loss of 15 wt. % between 75° C. and 154° C. The DT trace identified two endothermic events associated with the mass losses at the first shown onset at 37° C. peaking at 66.2° C.; the second onset at 122° C. peaking at 128° C.; and the third and final endothermic event in the DT trace (sample melt) was observed with an onset of 326° C. and a peak at 330° C. The x-axis is Temp measured in degrees Celsius and the y-axis is intensity measured in DTAuV on the left and TG % on the right.

Figure 88:
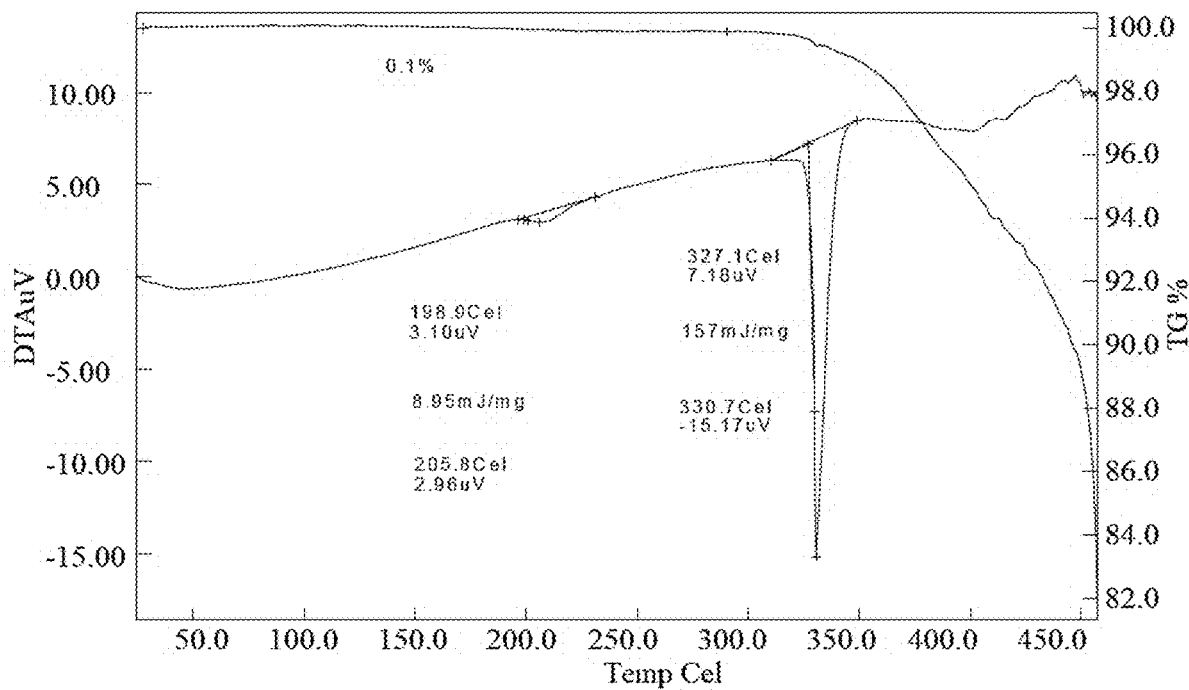

FIG. 88 is a TG/DTA thermogram of Pattern 10. The TG/DTA thermogram was obtained as described in Example 6. The thermogram shows showed minimal weight loss of 0.1% weight loss between 150 and 340° C. from onset of heating. The sample showed degradation above 320° C. The thermogram also shows two peaks, with the first onset at 199 and peaking at 206; and the second onset at 327° C. peaking at 331° C. The x-axis is Temp measured in degrees Celsius and the y-axis is intensity measured in DTAuV on the left and TG % on the right.

Figure 89:
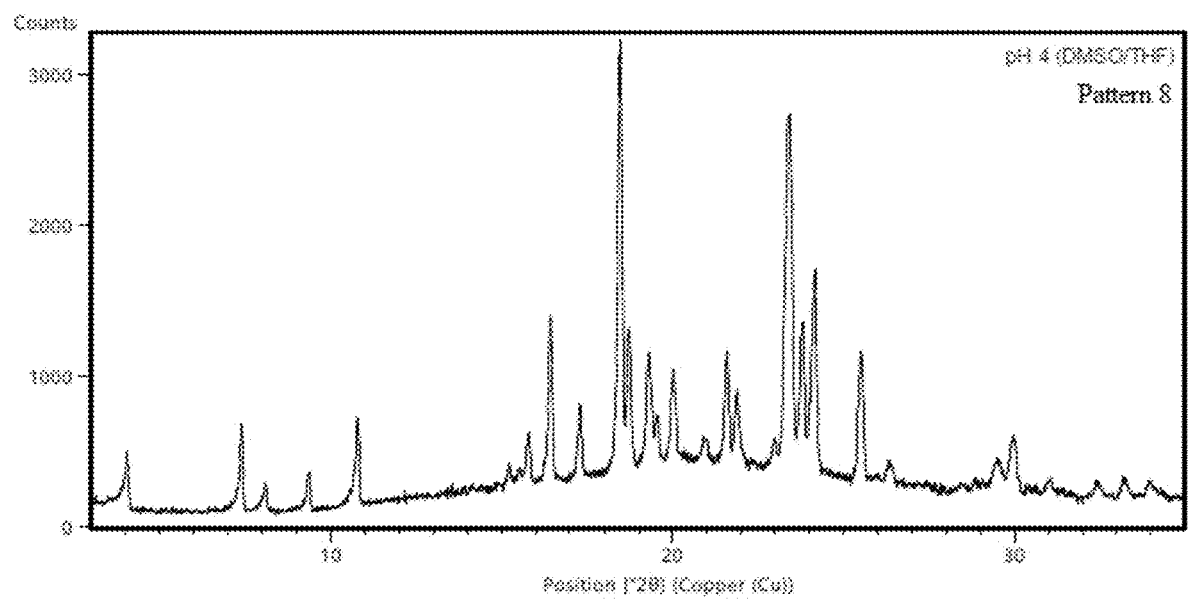

FIG. 89 is an XRPD Diffractogram of the crystalline Pattern 8. The crystal structure was obtained using the method described in Example 1 and the peaks are shown in Table 1. The x-axis is 2Theta measured in degrees and the y-axis is intensity measured in counts.

Figure 90:
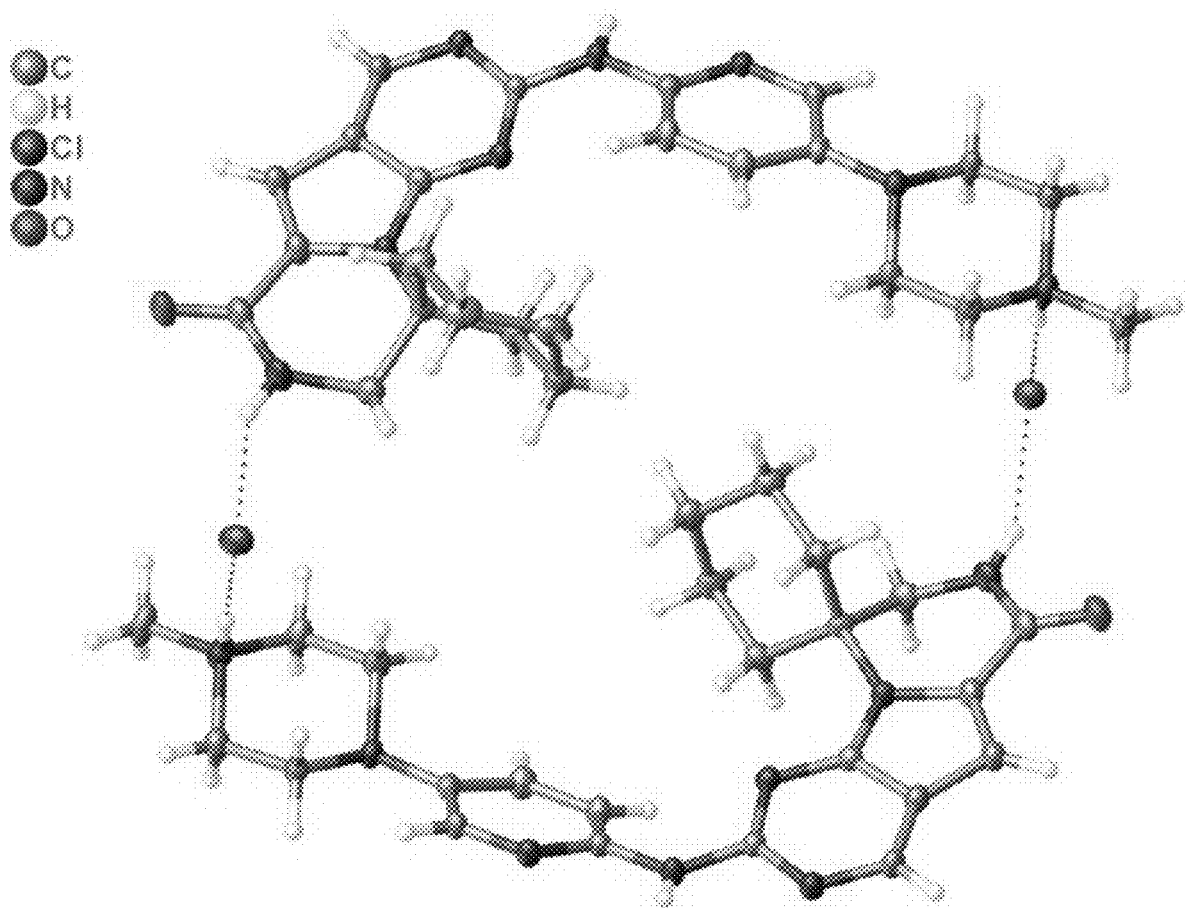

FIG. 90 is the crystal structure of Pattern 11. The crystal structure was solved as described in Example 25. Non-hydrogen atoms are shown with thermal ellipsoids set at 50% probability level.

Figure 91:
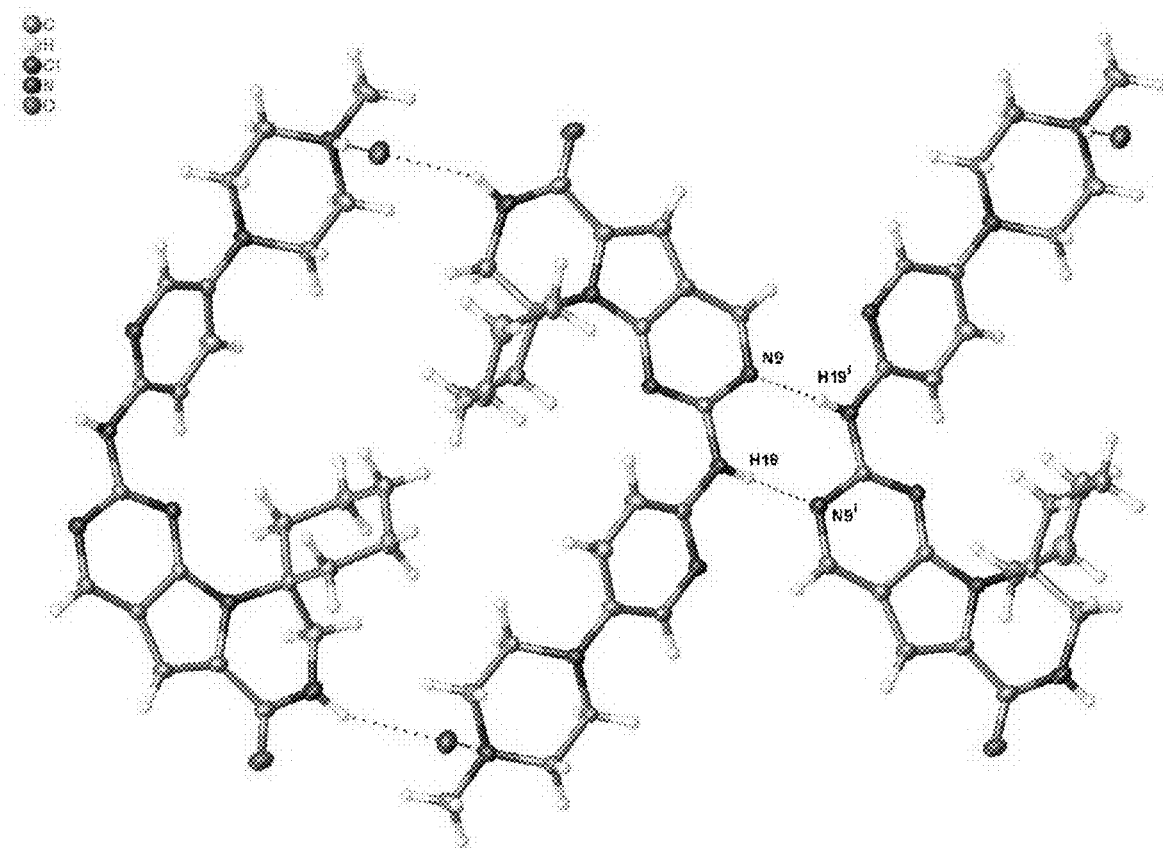

FIG. 91 is the crystal structure of Pattern 11 with hydrogen bonding depicted. The crystal structure was solved as described in Example 25. Non-hydrogen atoms are shown with thermal ellipsoids set at 50% probability level.

Figure 92:
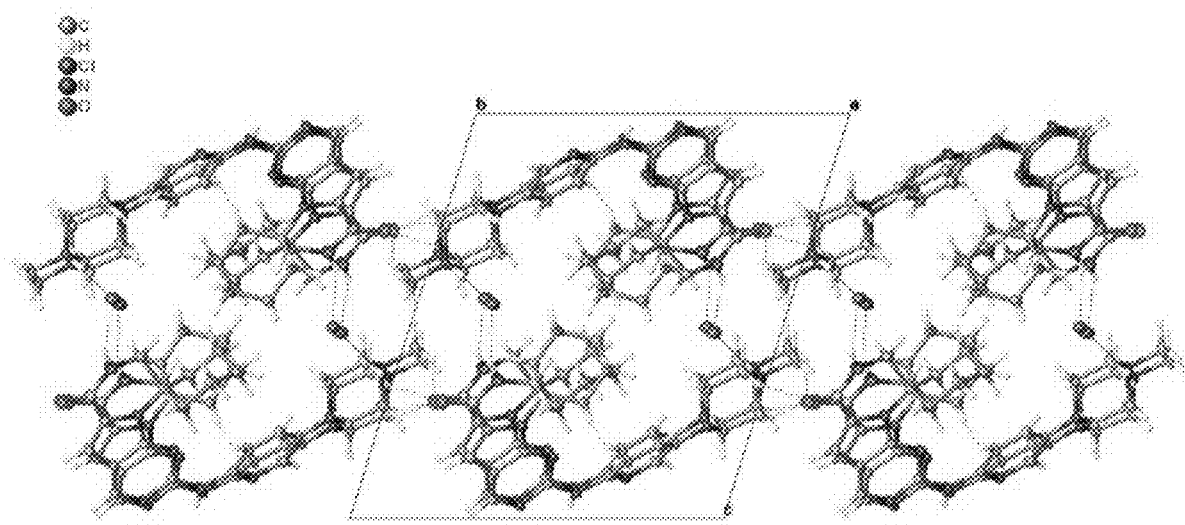

FIG. 92 is the crystal structure of Pattern 11 with the view set to the unit cell a axis. The crystal structure was solved as described in Example 25. Non-hydrogen atoms are shown with thermal ellipsoids set at 50% probability level.

Figure 93:
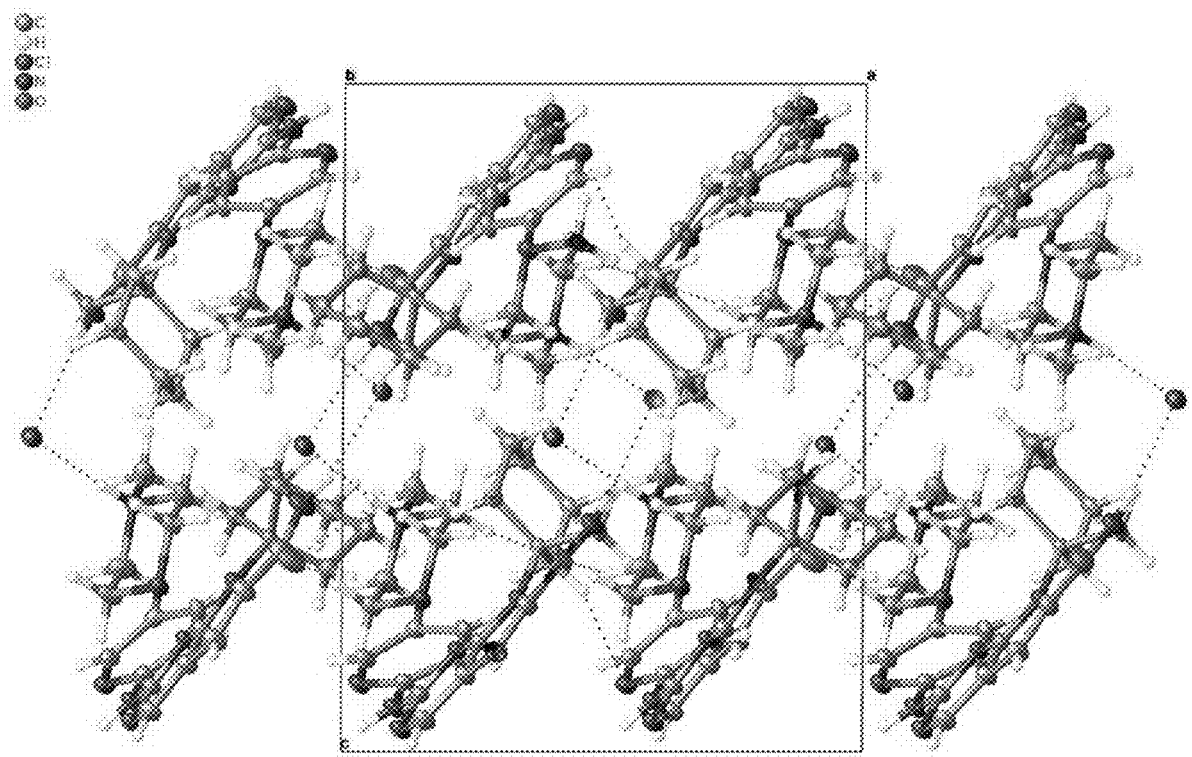

FIG. 93 is the crystal structure of Pattern 11 with the view set to the unit cell b axis. The crystal structure was solved as described in Example 25. Non-hydrogen atoms are shown with thermal ellipsoids set at 50% probability level.

Figure 94:
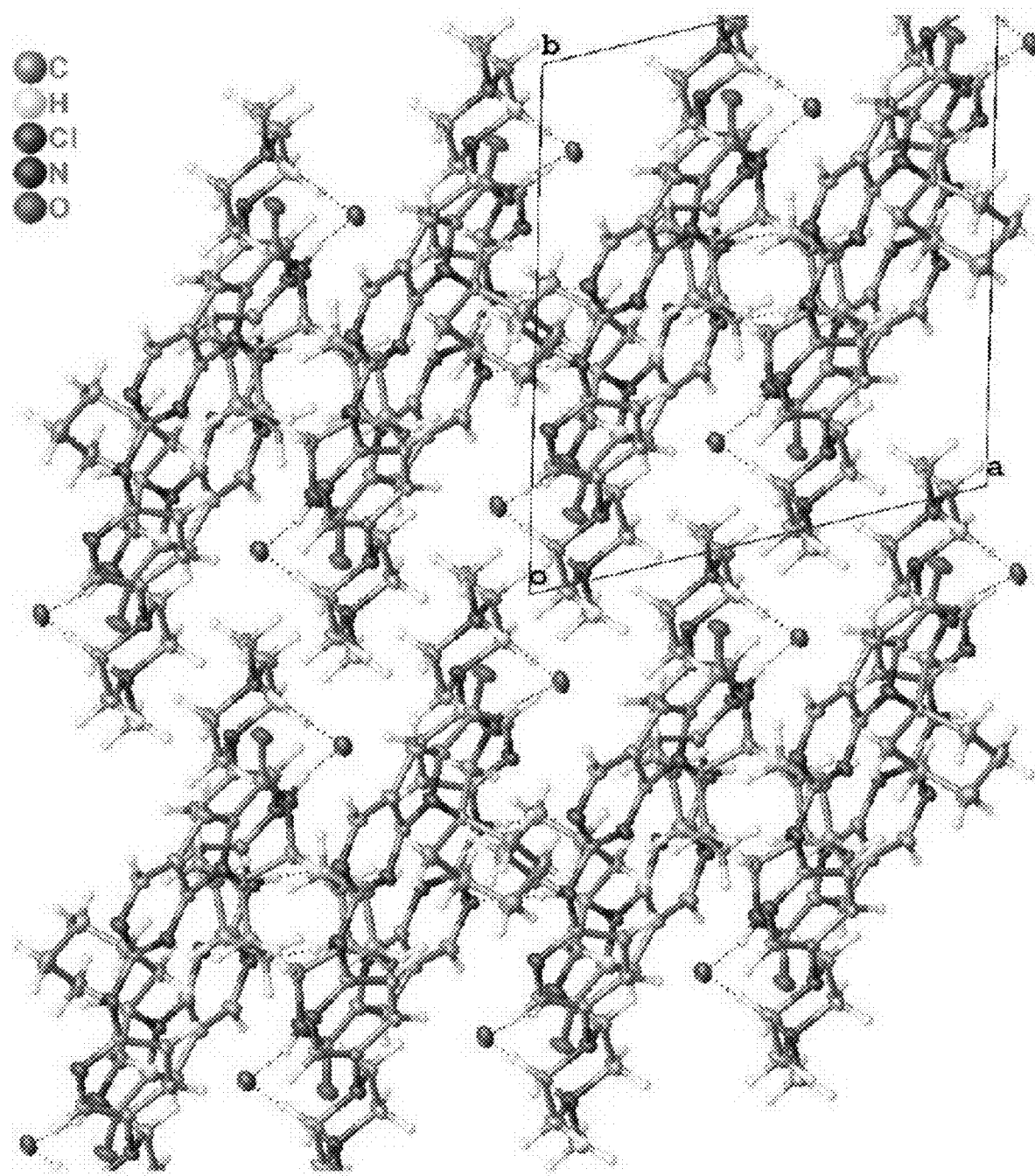

FIG. 94 is the crystal structure of Pattern 11 with the view set to the unit cell c axis. The crystal structure was solved as described in Example 25. Non-hydrogen atoms are shown with thermal ellipsoids set at 50% probability level.

Figure 95:
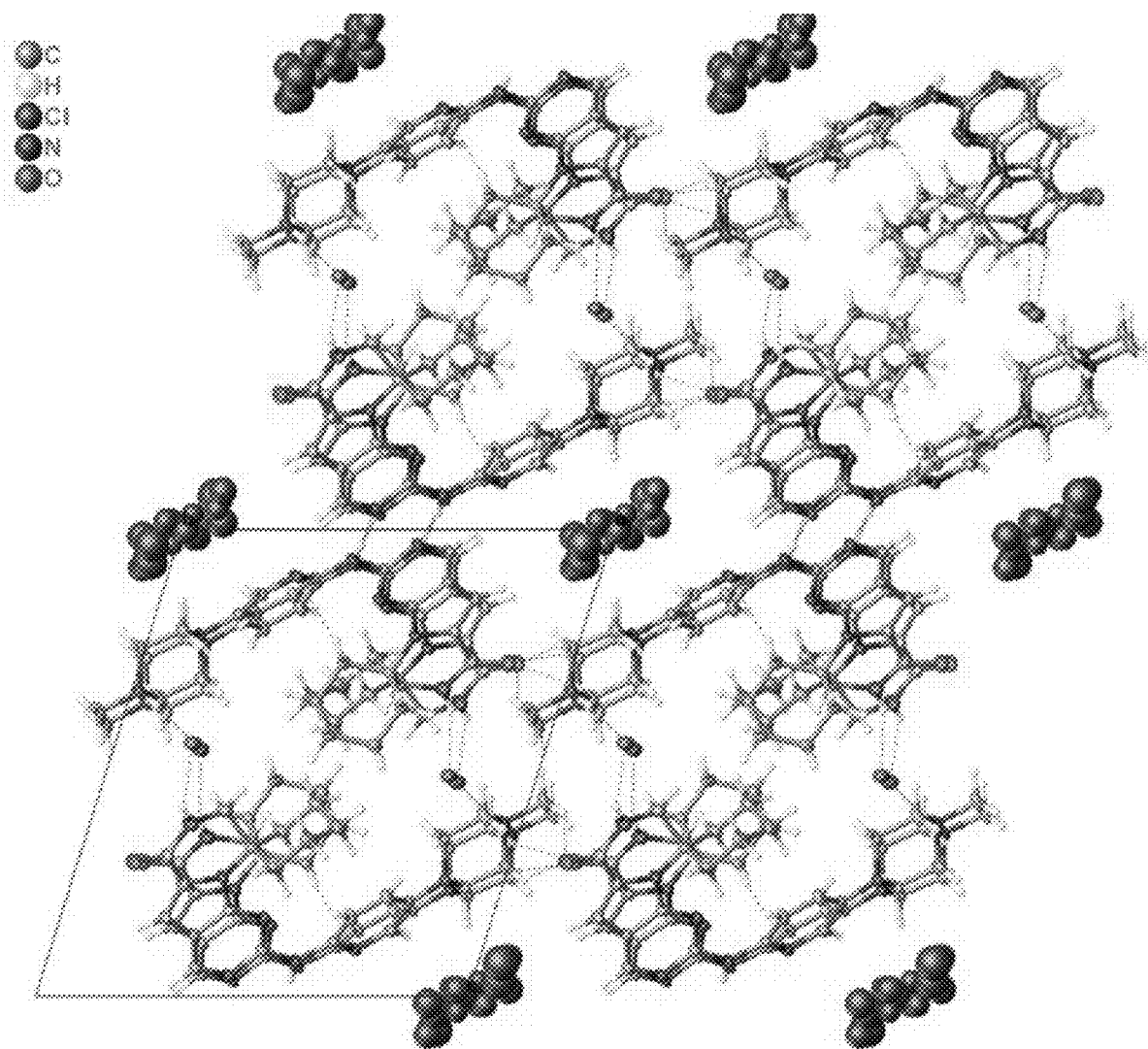

FIG. 95 is the crystal structure of Pattern 11 with the view set to the void view of the a axis. The crystal structure was solved as described in Example 25. Non-hydrogen atoms are shown with thermal ellipsoids set at 50% probability level.

Figure 96:
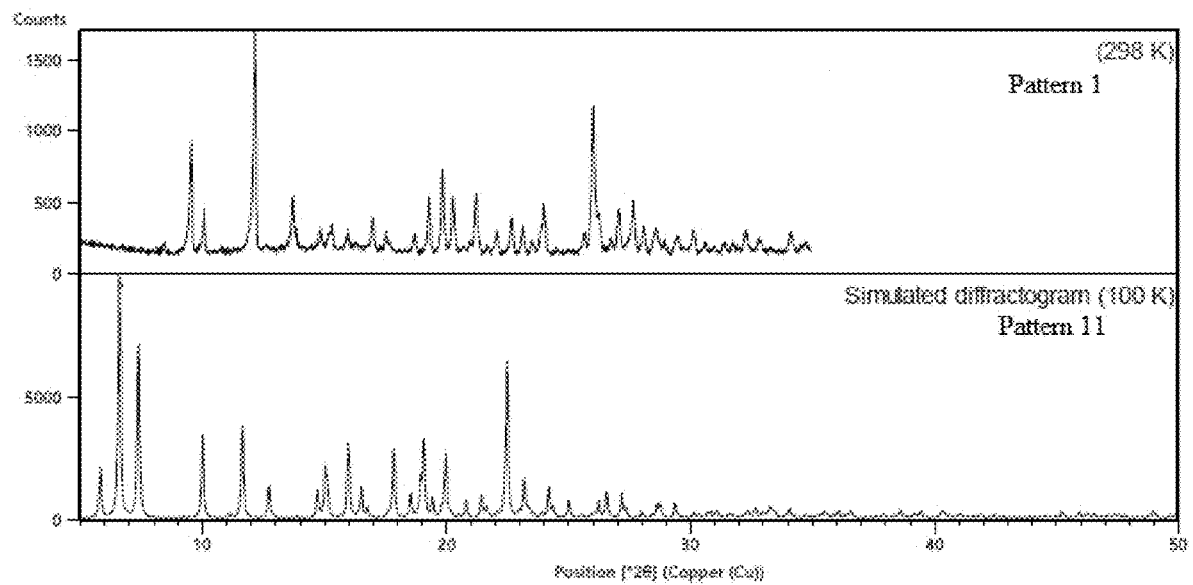

FIG. 96 is a comparison of the simulated XRPD pattern of Pattern 11 and the XRPD pattern of Pattern 1. The x-axis is 2Theta measured in degrees and the y-axis is intensity measured in counts.

Figure 97:
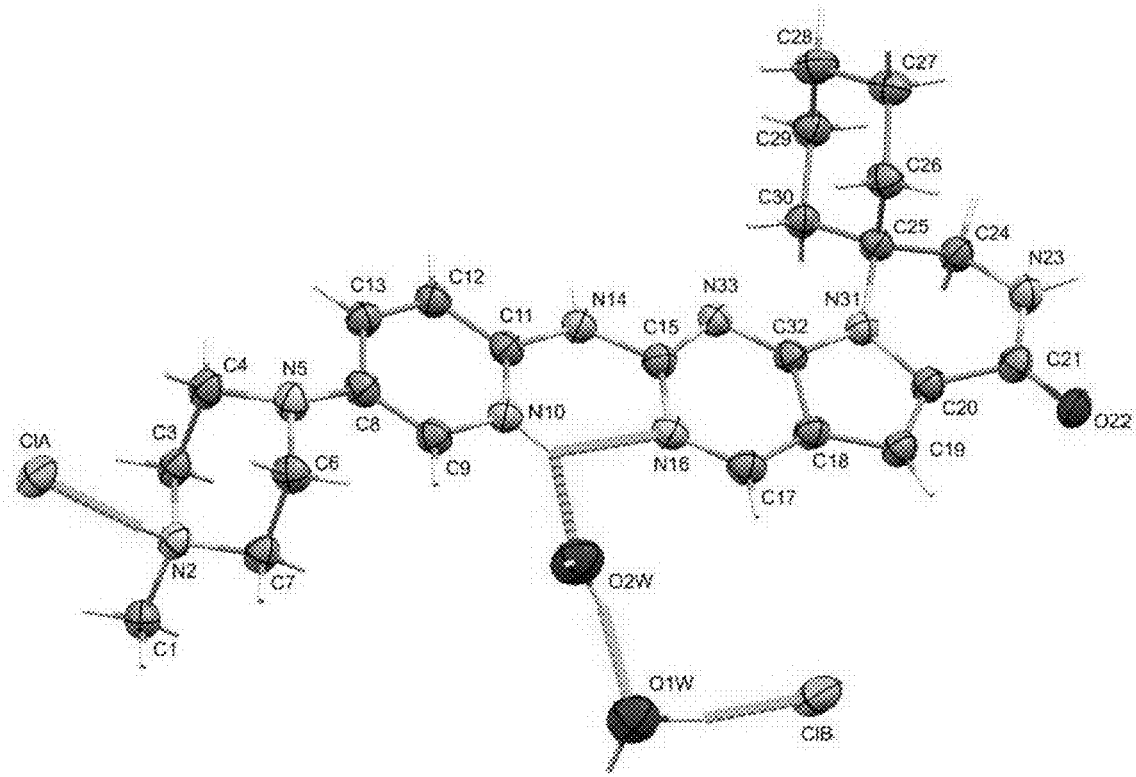

FIG. 97 is the crystal structure of Pattern 1 resulting from the x-ray crystallography discussed in Example 27.

Figure 98:
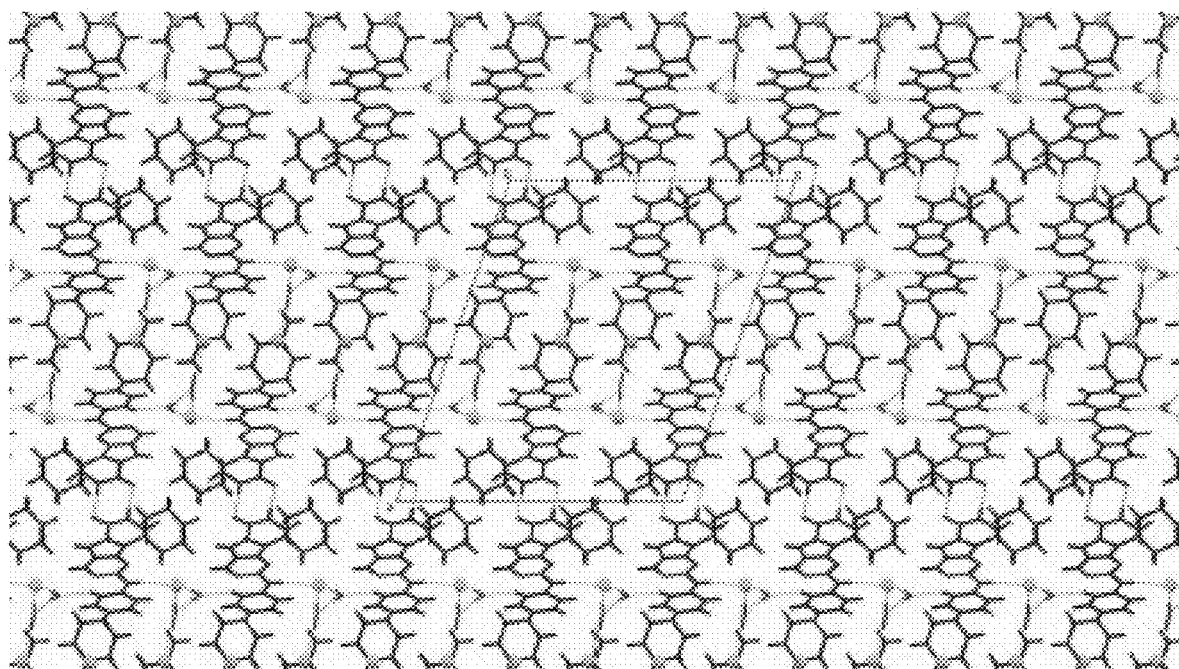

FIG. 98 is the crystal structure of Pattern 1 resulting from the x-ray crystallography discussed in Example 27 where the hydrogen bonds are shown explicitly.

Figure 99:
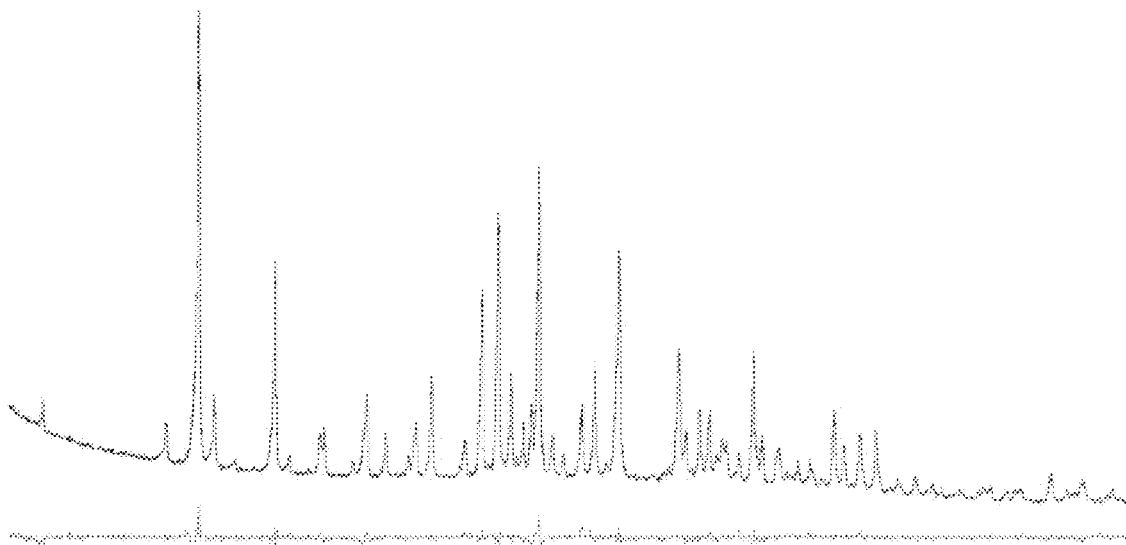

FIG. 99 is an overlay of the experimentally determined XRPD diffractogram of Pattern 1 with the simulated diffractogram that corresponds to the crystal structure shown in FIG. 97. The differences between these two lines is shown on the bottom line. As the bottom line is nearly flat the simulation strongly suggests that the crystal structure corresponds to the XRPD pattern.

DETAILED DESCRIPTION OF THE INVENTION

It cannot be predicted in advance whether a compound exists in more than one solid form or with which salt or solvate it exists or what the various properties of any solid form might be if one or more does exist, or whether the properties are advantageous for a therapeutic dosage form. As one example, the drug ritonavir is active in one morphic form and inactive in another form, and the inactive form is the more stable.

Trilaciclib is used in certain embodiments as a myelopreservation agent to protect healthy cells, notably hematopoietic cells, during chemotherapy. It is intended to be administered by intravenous injection for fast access to the blood stream just prior to administration of chemotherapy, typically also by IV injection. However, a problem is evident that trilaciclib is not very soluble in water, and also practically insoluble in DMSO. Further, it becomes less soluble as the pH increases. Blood typically has a pH of 7.35-7.45, which is mildly basic. Phosphate buffered saline typically has a pH of 7.2-7.4. Trilaciclib is not very soluble at this pH, and thus multiple problems can occur. Most importantly, a significant amount of trilaciclib is required to achieve a therapeutic effect. A typical dose is 240 mg/m$^2$ and can be estimated to be about a 300 mg dose for a normal adult. Because of the lack of solubility in water, it would take a dilute solution in a lot of fluid to provide this dosage of free base trilaciclib, which would have to be given over a long period of time, in contradiction to how it should be delivered. The trilaciclib IV is typically administered over about 30 minutes (20-60 minutes), which means that the drug has to be concentrated, not dilute, in the IV fluid. Also, when the free base trilaciclib is injected into blood, there is a real possibility of at least some of it falling out of solution because of the fact that blood is mildly basic. This can cause problems at the site of injection caused by drug deposition and a loss of activity.

It has been discovered that an IV solution of trilaciclib for injection to cancer patients to preserve healthy cells or for an antineoplastic treatment can be accomplished by administering it as a dihydrochloride or a dihydrochloride, dihydrate. This enables the intended therapeutic effect because it can be delivered quickly in a concentrated form directly to the blood stream. In a principal embodiment, the IV solution is prepared from a lyophilized powder of the dihydrochloride, dihydrate crystalline Pattern 1.

Pattern 1, Pattern 2, and Pattern 3 are highly crystalline forms of Compound 1 as a dihydrochloride. Pattern 1 is a useful dihydrochloride, dihydrate form of Compound 1. Pattern 4 is a crystalline solvate of Compound 1 as a dihydrochloride with acetonitrile. Pattern 5 is a crystalline form of Compound 1 as a dihydrochloride. Pattern 6 is a metastable form of Compound 1 as a dihydrochloride. Pattern 7 is a highly crystalline form of Compound 1 as a free base. Pattern 8 and Pattern 10 are crystalline forms of Compound 1 as a free base. Pattern 9 is a crystalline form of Compound 1 as a free base which may be either a solvate or hydrate. Pattern 11 is a crystalline form of Compound 1 as a dihydrochloride, hemi-hydrate.

In certain embodiments Pattern 1 dihydrochloride, dihydrate is the most stable morphic form of Compound 1 as a dihydrochloride and can be formed by competitive slurry experiments with either Pattern 2 or Pattern 3. In certain embodiments Pattern 1 regardless of its water content is the most stable morphic form of Compound 1 as a dihydrochloride and can be formed by competitive slurry experiments with either Pattern 2 or Pattern 3. In certain embodiments Pattern 7 is the most stable morphic form of Compound 1 as a free base.

Pattern 1 dihydrochloride, dihydrate has multiple therapeutic advantages over the other morphic forms of Compound 1. For example, Pattern 1 dihydrochloride, dihydrate is more easily used in an intravenous solution. Additionally, higher concentrations of Pattern 1 dihydrochloride, dihydrate can be achieved in water and/or DMSO.

Pattern 1 dihydrochloride, dihydrate has multiple manufacturing advantages over the other morphic forms of Compound 1. For example, Pattern 1 dihydrochloride, dihydrate typically has increased shelf stability, thermodynamic stability, and/or solubility in water than other morphic forms of Compound 1. In other embodiments the manufacture of Pattern 1 dihydrochloride, dihydrate is reproducibly more scalable than the manufacture of other morphic forms of Compound 1.

In one aspect of the present invention, isolated Pattern 1, optionally as a dihydrate, is used in the manufacture of a lyophilized form that is then formulated with a suitable solvent such as phosphate buffered saline for administration to a patient, for example, by intravenous delivery. In an alternative embodiment it can be formulated into a parenteral dosage form. This dosage form can be used, for example, in subcutaneous administration.

In one aspect of the present invention, isolated Pattern 2 is used in the manufacture of a lyophilized form that is then formulated with a suitable solvent such as phosphate buffered saline for administration to a patient, for example, by intravenous delivery. In an alternative embodiment it can be formulated into a parenteral dosage form. This dosage form can be used, for example, in subcutaneous administration.

In one aspect of the present invention, isolated Pattern 3 is used in the manufacture of a lyophilized form that is then formulated with a suitable solvent such as phosphate buffered saline for administration to a patient, for example, by intravenous delivery. In an alternative embodiment it can be formulated into a parenteral dosage form. This dosage form can be used, for example, in subcutaneous administration.

In one aspect of the present invention, isolated Pattern 7 is used in the manufacture of a lyophilized form that is then formulated with a suitable solvent such as phosphate buffered saline for administration to a patient, for example, by intravenous delivery. In an alternative embodiment it can be formulated into a parenteral dosage form. This dosage form can be used, for example, in subcutaneous administration.

Pattern 1

An isolated morphic form of Compound 1 as a dihydrochloride that has been designated Pattern 1 is provided in this invention.

Compound 1 Pattern 1 can be in the form of a dihydrochloride, dihydrate. Pattern 1 is typically, initially, in the form of a dihydrochloride, dihydrate after being formed and even after being dried will eventually revert to a dihydrochloride, dihydrate when exposed to air. Regardless of water content Pattern 1 can maintain its representative XRPD peaks as described in more detail below. For example, if the morphic form of Compound 1 is prepared as described herein to form Pattern 1 and then dried, the representative XRPD peaks will remain the same before and after drying.

In certain embodiments Compound 1 Pattern 1 is a dihydrochloride, dihydrate morphic form. In certain embodiments the invention provides the composition of Compound 1 as a dihydrochloride, dihydrate. In certain embodiments the invention provides the composition of Compound 1 Pattern 1 as a dihydrochloride salt dihydrate.

In certain embodiments Compound 1 Pattern 1 dihydrochloride, dihydrate is more stable than other hydrate forms of Compound 1. In another embodiment Compound 1 Pattern 1 dihydrochloride, dihydrate is more stable than non-hydrate forms of Compound 1. Compound 1 Pattern 1 as a dihydrochloride, dihydrate can be advantageous to the anhydrous, monohydrate, or even trihydrate versions of Compound 1 Pattern 1. For example, the dihydrate version of Compound 1 Pattern 1 dihydrochloride has increased shelf stability, thermodynamic stability, and/or solubility in water than the anhydrous, monohydrate, or even trihydrate versions of Compound 1 Pattern 1. In other embodiments the manufacture of Pattern 1 dihydrochloride, dihydrate is cheaper, faster, and/or more scalable than the manufacture of the anhydrous, monohydrate, or even trihydrate versions Compound 1 Pattern 1.

Figure 1:
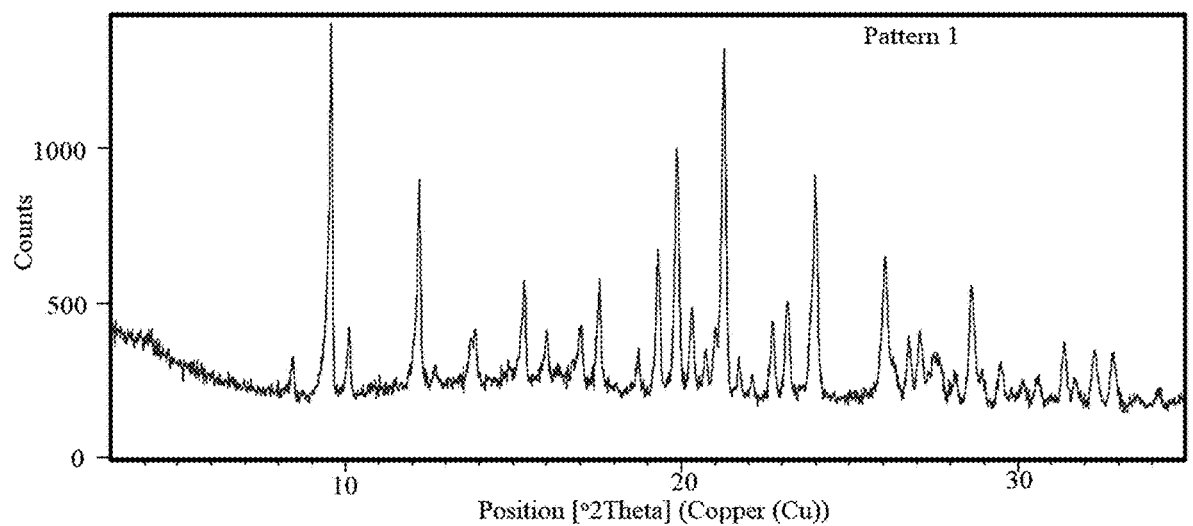
FIG. 1 is an XRPD Diffractogram of the crystalline Pattern 1. The crystal structure was obtained using the method described in Example 1 and the peaks are shown in Table 1. The x-axis is 2Theta measured in degrees and the y-axis is intensity measured in counts.
Figure 2:
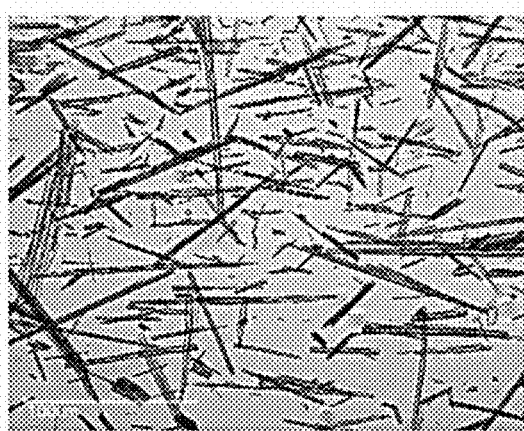
FIG. 2 is a PLM Imaging of the crystalline Pattern 1. The image was obtained using the method described in Example 5. Pattern 1 material appeared highly crystalline under PLM imaging with the non-polarized material shown on the left, and the polarized material shown on the right.
Figure 2:
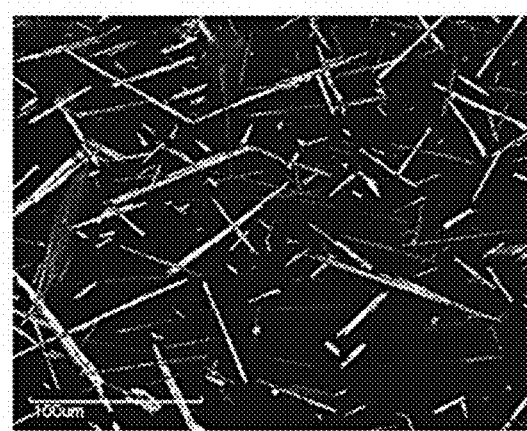
Figure 3:
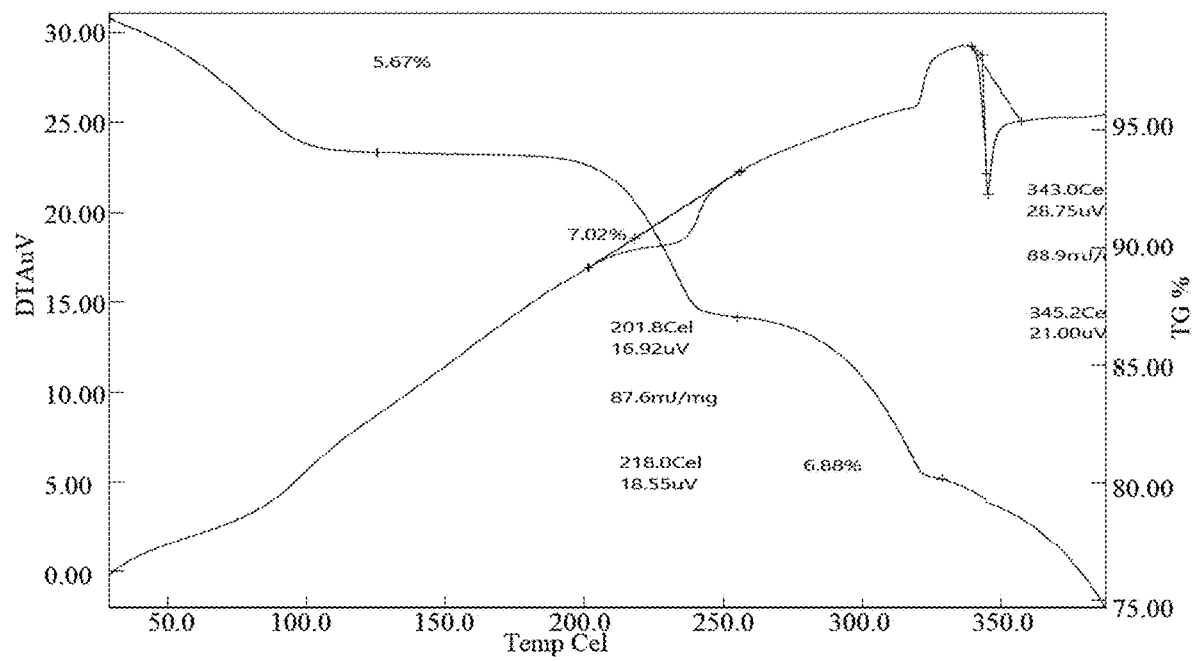
FIG. 3 is a thermogravimetric/differential thermal (TG/DTA) thermogram of crystalline Pattern 1. The TG/DTA thermogram of Pattern 1 was obtained as described in Example 6. The initial mass loss of ca. 6% from the onset of heating related to the loss of surface moisture. Two mass losses of ca. 7% were observed from ca. 200° C. peaking at 218° C. and 300° C. peaking at 343° C.
Figure 4:
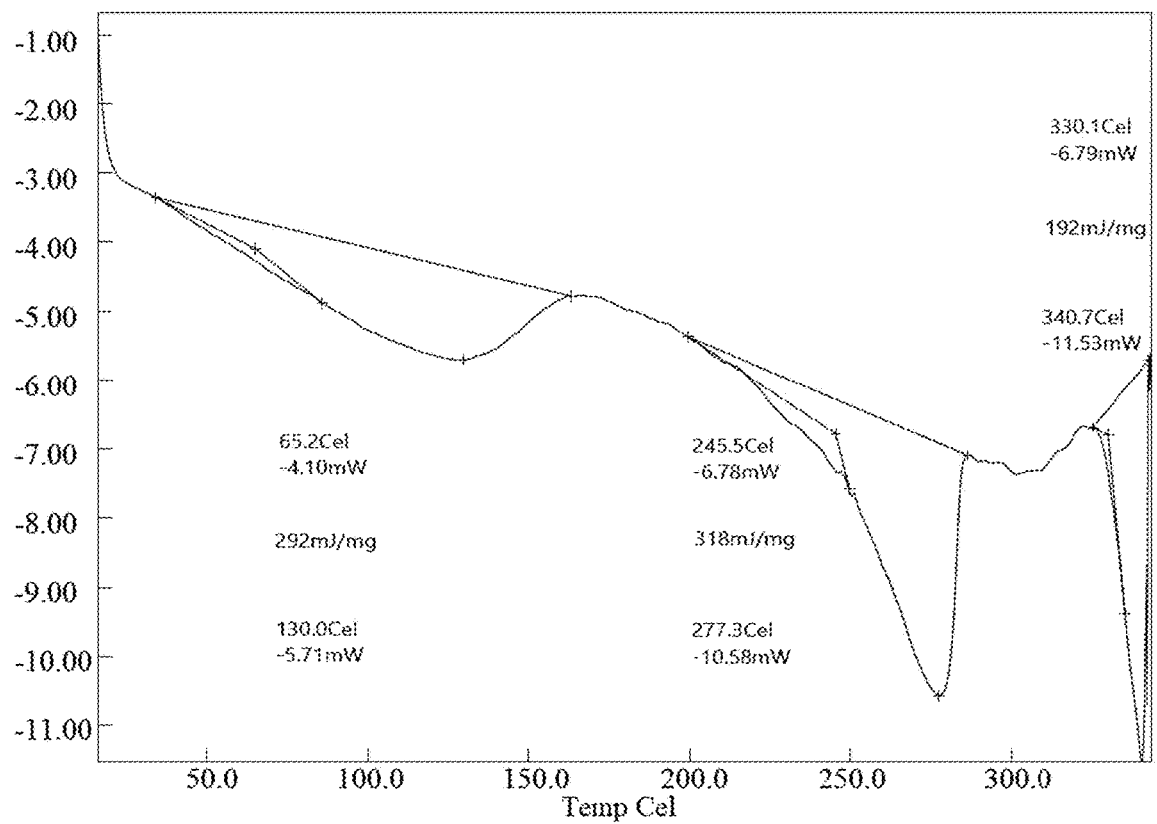
FIG. 4 is a Differential Scanning calorimetry (DSC) thermogram of the crystalline Pattern 1. The DSC thermogram of crystalline Pattern 1 was obtained as described in Example 7. DSC analysis showed 2 broad endotherms ca. 65° C. peaking at 130° C. and 245° C. peaking at 277° C. A sharp melting endotherm was observed from an onset of 330° C. peaking at 341° C.
Figure 5:
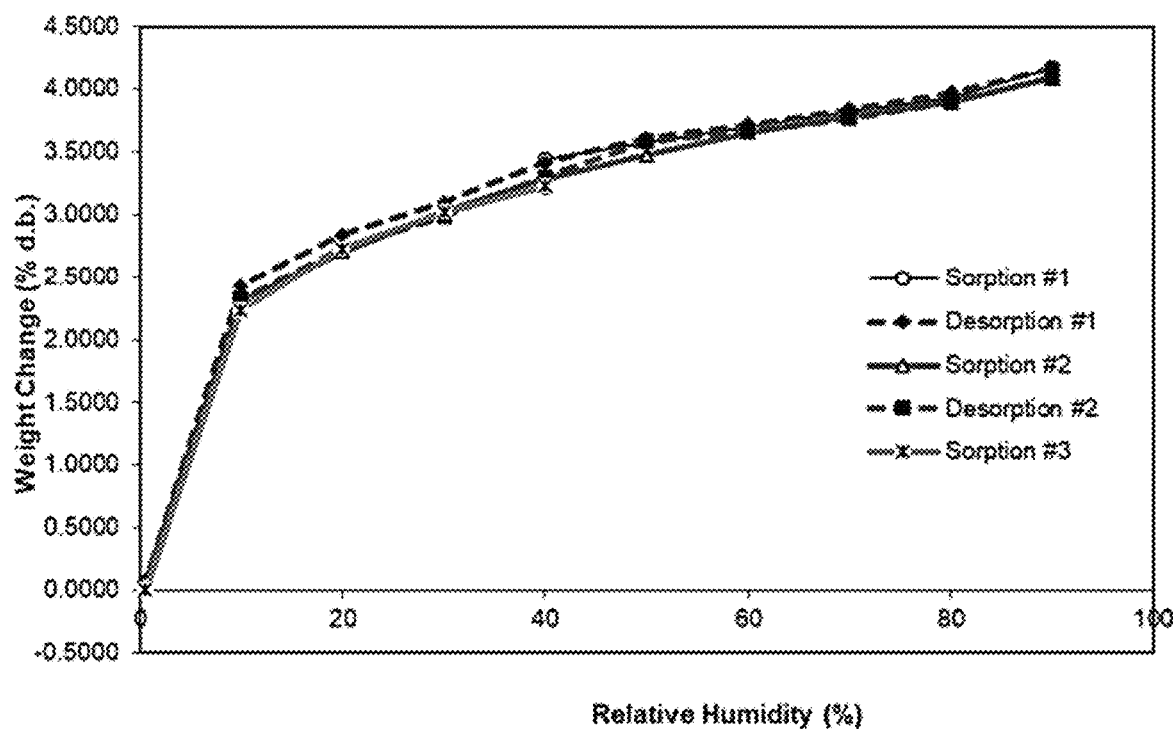
FIG. 5. is a Dynamic Vapor Sorption (DVS) analysis showing the results from a moisture sorption experiment of Pattern 1. DVS analysis of Pattern 1 was obtained as described in Example 3. The material was found to be stable and the XRPD analysis of a dried sample at the conclusion of the experiment confirmed Pattern 1. Pattern 1 adsorbed 3.00 wt % at 40% RH (relative humidity) and 4.00 wt % at 90% RH. The x-axis is relative humidity measured as a percent and the y-axis is weight of water of the material measured as a percent.
Figure 6:
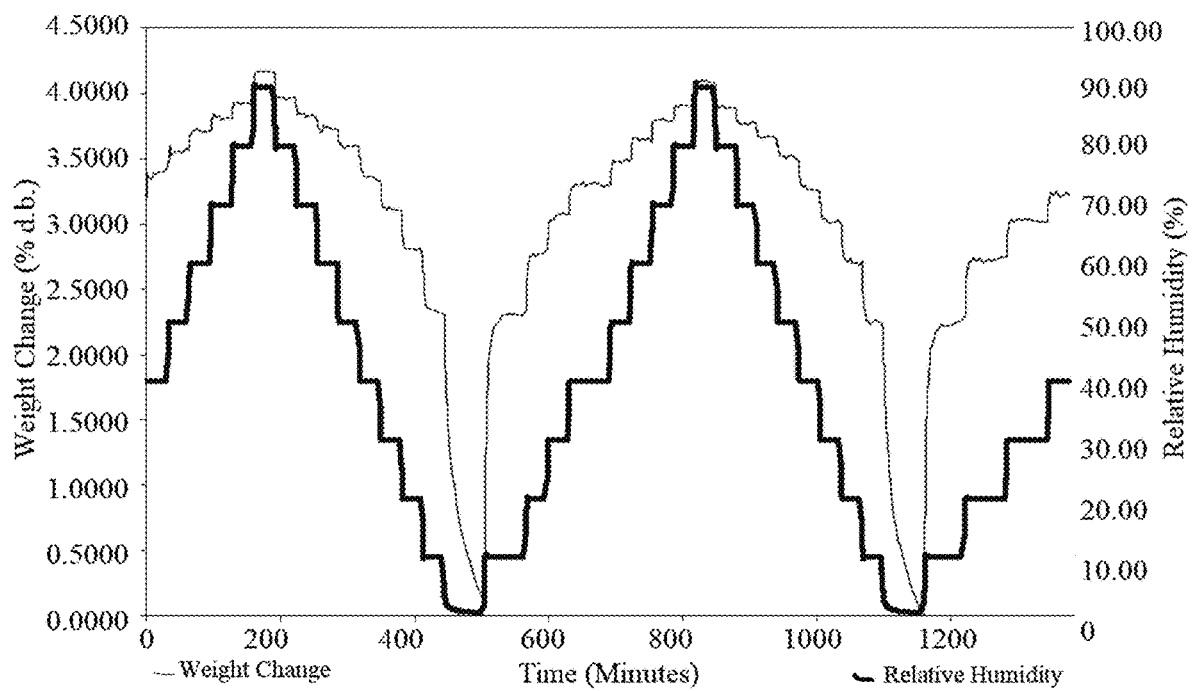
FIG. 6 is a Dynamic Vapor Sorption (DVS) Kinetic Plot of Pattern 1. DVS of Pattern 1 was obtained as described in Example 3. The sample was subjected to a ramping profile from 40-90% relative humidity (RH) at 10% increments, maintaining the sample at each step until a stable weight had been achieved (dm/dt 0.004%, minimum step length 30 minutes, maximum step length 500 minutes) at 25° C. After completion of the sorption cycle, the sample was dried using the same procedure to 0% RH and then a second sorption cycle back to 40% RH. Two cycles were performed. The material appeared hygroscopic by DVS with a mass increase of 4% between 0% and 90% RH. During the desorption cycles the material dehydrates.
Figure 7:
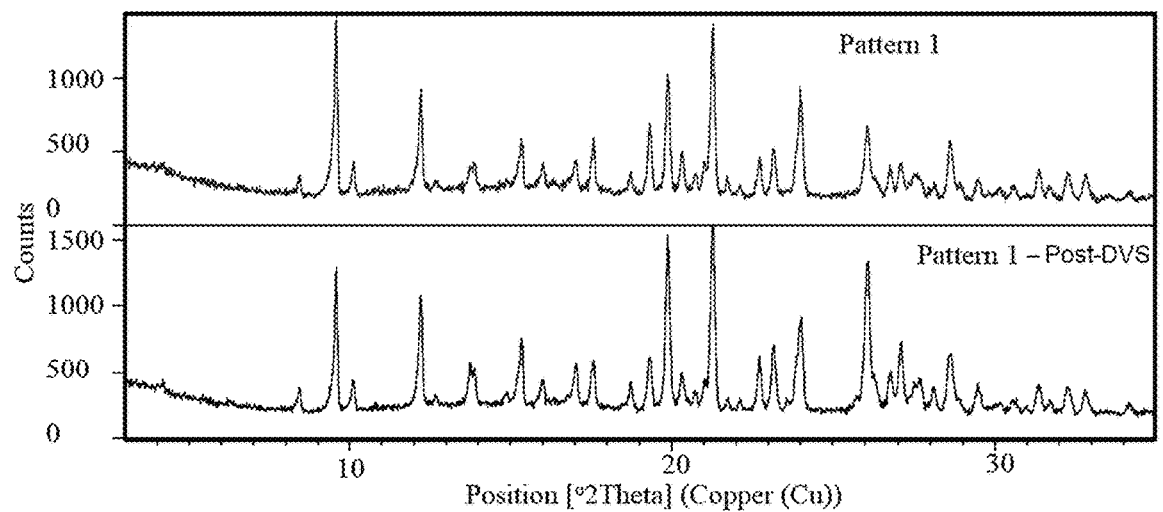
FIG. 7 is a comparison of XRPD diffractograms of Pattern 1 and Pattern 1 post-DVS. The diffractogram of Pattern 1 was obtained as described in Example 1; and post-DVS of Pattern 1 was obtained as described in Example 11. The material appeared hygroscopic by DVS with a mass increase of 4% between 0% and 90% RH. During the desorption cycles the material dehydrates. XRPD analysis post-DVS showed no change in Pattern 1. The x-axis is 2Theta measured in degrees and the y-axis is intensity measured in counts.

In certain embodiments, Compound 1 Pattern 1, optionally as a dihydrate, is characterized by an XRPD pattern that is substantially similar to that set forth in FIG. 1. In one embodiment, Compound 1 Pattern 1 optionally as a dihydrate, is characterized by an XRPD pattern comprising at least three 2theta values selected from about 9.6±0.2°, about 21.3±0.2°, about 19.8±0.2°, about 12.2±0.2°, about 24.0±0.2°, about 26.1±0.2°, about 19.3±0.2°, about 17.6±0.2°, and about 28.6±0.2°. In one embodiment, Compound 1 Pattern 1, optionally as a dihydrate, is characterized by an XRPD pattern comprising a peak with a 2theta value of about 9.6±0.2°.

In certain embodiments, Compound 1 Pattern 1, optionally as a dihydrate, is characterized as having a 6%±3% weight loss on the onset of heating the sample. In certain embodiments, Compound 1 Pattern 1, optionally as a dihydrate, is characterized as having a 7%±3% weight loss between about 200° C. and about 230° C. In certain embodiments, Compound 1 Pattern 1 is characterized as having a second 7%±3% weight loss between about 300° C. and about 380° C.

Compound 1 Pattern 1 can be prepared using selective crystallization. The method can be carried out by treating a solution comprising a suitable solvent(s) and Compound 1 as a dihydrochloride optionally in the presence of one or more seeds comprising Compound 1 Pattern 1 to conditions that provide for the crystallization of Compound 1 Pattern 1. If the solvent used is water or contains water then the resulting Compound 1 Pattern 1 is typically a dihydrochloride, dihydrate. The selective crystallization can be carried out in any suitable solvent. For example, it can be carried out in an aprotic solvent or a mixture thereof. Examples of aprotic solvents that can be used include tetrahydrofuran, dichloromethane, nitromethane, and dioxane. In another embodiment Compound 1 Pattern 1 is prepared from a protic solvent. Examples of protic solvents that can be used include water, methanol, and ethanol. In certain embodiments Compound 1 Pattern 1 is prepared from a mixture of an aprotic solvent and a protic solvent, such as for example a mixture of acetonitrile and water.

The selective crystallization can be carried out at, for example, a temperature in the range of about 20° C. to about 65° C. In another embodiment the selective crystallization can be carried out at, for example, a temperature in the range of about 35° C. to about 45° C. or at about 40° C.

In one embodiment, Compound 1 Pattern 1, optionally as a dihydrate, is produced by crystallization or recrystallization in an acidic solution. For example Compound 1 Pattern 1 can be produced in an aqueous hydrochloric acid solution.

In one embodiment Compound 1 Pattern 1 is produced by heating Compound 1 to about 80° C. and agitating for at least 30 minutes. The resulting solution is filtered into a reactor pre-heated to about 80° C., and the reaction mixture is cooled to about 70° C. Preheated (about 70° C.) purified water is added and the reaction mixture is cooled to below 20° C. with agitation. Compound 1 Pattern 1 can be isolated by filtration, washed with purified water and acetone, and dried under vacuum at an elevated temperature.

In certain embodiments Compound 1 Pattern 1, optionally as a dihydrate, is sieved using a mill. In certain embodiments the sieved Compound 1 Pattern 1 material is formulated for parenteral administration to a patient. In certain embodiments, Compound 1 Pattern 1, optionally as a dihydrate, is characterized by an XRPD pattern comprising at least 2 peaks selected from about 9.6±0.2°, about 12.2±0.2°, about 19.8±0.2°, about 21.2±0.2°, about 23.9±0.2° and about 26.1±0.2°.

In certain embodiments, Compound 1 Pattern 1, optionally as a dihydrate, is characterized by an XRPD pattern comprising at least 3 peaks selected from about 9.6±0.2°, about 12.2±0.2°, about 19.8±0.2°, about 21.2±0.2°, about 23.9±0.2° and about 26.1±0.2°.

In certain embodiments, Compound 1 Pattern 1, optionally as a dihydrate, is characterized by an XRPD pattern comprising at least 4 peaks selected from about 9.6±0.2°, about 12.2±0.2°, about 19.8±0.2°, about 21.2±0.2°, about 23.9±0.2° and about 26.1±0.2°.

In certain embodiments, Compound 1 Pattern 1, optionally as a dihydrate, is characterized by an XRPD pattern comprising at least 5 peaks selected from about 9.6±0.2°, about 12.2±0.2°, about 19.8±0.2°, about 21.2±0.2°, about 23.9±0.2° and about 26.1±0.2°.

In certain embodiments, Compound 1 Pattern 1, optionally as a dihydrate, is characterized by an XRPD pattern comprising the 2theta values selected from about 9.6±0.2°, about 12.2±0.2°, about 19.8±0.2°, about 21.2±0.2°, about 23.9±0.2° and about 26.1±0.2°.

In certain embodiments, Compound 1 Pattern 1, optionally as a dihydrate, is characterized by an XRPD pattern comprising all or at least 2, 3, 4, 5, 6, 7, 8, 9, 10, 11, 12, 13, 14, 15, 16, 17, 18, 19, or 20° 2theta values within ±0.4° 2theta of the peaks selected from:

a. 9.6, 21.3, 19.8, 12.2, 24.0, 26.1, 19.3, 17.6, 28.6, 15.3, 23.2, 20.3, 22.7, 27.1, 21.0, 17.0, 10.1, 16.0, 26.8, 31.4, 13.8, 32.3, 32.9, 20.7, 18.7, and 27.6 °2θ; or
b. 9.6, 21.3, 19.8, 12.2, 24.0, 26.1, 19.3, 17.6, 28.6, 15.3, 23.2, 20.3, 22.7, 27.1, 21.0, 17.0, 10.1, 16.0, 26.8, 31.4, 13.8, 32.3, 32.9, 20.7, and 18.7 °2θ; or
c. 9.6, 21.3, 19.8, 12.2, 24.0, 26.1, 19.3, 17.6, 28.6, 15.3, 23.2, 20.3, 22.7, 27.1, 21.0, 17.0, 10.1, 16.0, 26.8, 31.4, 13.8, 32.3, 32.9, and 20.7, °2θ; or
d. 9.6, 21.3, 19.8, 12.2, 24.0, 26.1, 19.3, 17.6, 28.6, 15.3, 23.2, 20.3, 22.7, 27.1, 21.0, 17.0, 10.1, 16.0, 26.8, 31.4, 13.8, 32.3, and 32.9, °2θ; or
e. 9.6, 21.3, 19.8, 12.2, 24.0, 26.1, 19.3, 17.6, 28.6, 15.3, 23.2, 20.3, 22.7, 27.1, 21.0, 17.0, 10.1, 16.0, 26.8, 31.4, 13.8, and 32.3, °2θ; or
f. 9.6, 21.3, 19.8, 12.2, 24.0, 26.1, 19.3, 17.6, 28.6, 15.3, 23.2, 20.3, 22.7, 27.1, 21.0, 17.0, 10.1, 16.0, 26.8, 31.4, and 13.8, °2θ; or
g. 9.6, 21.3, 19.8, 12.2, 24.0, 26.1, 19.3, 17.6, 28.6, 15.3, 23.2, 20.3, 22.7, 27.1, 21.0, 17.0, 10.1, 16.0, 26.8, and 31.4, °2θ; or
h. 9.6, 21.3, 19.8, 12.2, 24.0, 26.1, 19.3, 17.6, 28.6, 15.3, 23.2, 20.3, 22.7, 27.1, 21.0, 17.0, 10.1, 16.0, and 26.8, °2θ; or
i. 9.6, 21.3, 19.8, 12.2, 24.0, 26.1, 19.3, 17.6, 28.6, 15.3, 23.2, 20.3, 22.7, 27.1, 21.0, 17.0, 10.1, and 16.0, °2θ; or
j. 9.6, 21.3, 19.8, 12.2, 24.0, 26.1, 19.3, 17.6, 28.6, 15.3, 23.2, 20.3, 22.7, 27.1, 21.0, 17.0, and 10.1, °2θ; or
k. 9.6, 21.3, 19.8, 12.2, 24.0, 26.1, 19.3, 17.6, 28.6, 15.3, 23.2, 20.3, 22.7, 27.1, 21.0, and 17.0, °2θ; or
l. 9.6, 21.3, 19.8, 12.2, 24.0, 26.1, 19.3, 17.6, 28.6, 15.3, 23.2, 20.3, 22.7, 27.1, and 21.0, °2θ; or
m. 9.6, 21.3, 19.8, 12.2, 24.0, 26.1, 19.3, 17.6, 28.6, 15.3, 23.2, 20.3, 22.7, and 27.1, °2θ; or
n. 9.6, 21.3, 19.8, 12.2, 24.0, 26.1, 19.3, 17.6, 28.6, 15.3, 23.2, 20.3, and 22.7, °2θ; or
o. 9.6, 21.3, 19.8, 12.2, 24.0, 26.1, 19.3, 17.6, 28.6, 15.3, 23.2, and 20.3, °2θ; or
p. 9.6, 21.3, 19.8, 12.2, 24.0, 26.1, 19.3, 17.6, 28.6, 15.3, and 23.2, °2θ; or
q. 9.6, 21.3, 19.8, 12.2, 24.0, 26.1, 19.3, 17.6, 28.6, and 15.3, °2θ; or
r. 9.6, 21.3, 19.8, 12.2, 24.0, 26.1, 19.3, 17.6, and 28.6, °2θ; or
s. 9.6, 21.3, 19.8, 12.2, 24.0, 26.1, 19.3, and 17.6, °2θ; or
t. 9.6, 21.3, 19.8, 12.2, 24.0, 26.1, and 19.3, °2θ; or
u. 9.6, 21.3, 19.8, 12.2, 24.0, and 26.1, °2θ;
v. any of the above peak lists wherein the °2θ are ±0.1; or
w. any of the above peak lists wherein the °2θ are ±0.2; or
x. any of the above peak lists wherein the °2θ are ±0.3.

In one embodiment Compound 1 Pattern 1, optionally as a dihydrate, is characterized by an XRPD pattern described above and is further characterized by having no peaks greater than 15% relative intensity in between 4 and 9 °2θ. In one embodiment Compound 1 Pattern 1, optionally as a dihydrate, is characterized by an XRPD pattern described above and is further characterized by having no peaks greater than 10% relative intensity in between 4 and 9 °2θ. In one embodiment Compound 1 Pattern 1, optionally as a dihydrate, is characterized by an XRPD pattern described above and is further characterized by having no peaks greater than 5% relative intensity in between 4 and 9 °2θ. In one embodiment Compound 1 Pattern 1, optionally as a dihydrate, is characterized by an XRPD pattern described above and is further characterized by having no peaks greater than 3% relative intensity in between 4 and 9 °2θ.

In certain embodiments Compound 1 Pattern 1, optionally as a dihydrate, is used in the preparation of amorphous Compound 1 as a dihydrochloride. For example, the amorphous Compound 1 as a dihydrochloride can be formed by lyophilization or spray drying of Compound 1 Pattern 1, optionally as a dihydrate. This amorphous dihydrochloride may possess higher purity than if it were directly prepared by known synthetic methods. In addition, an advantage of first preparing Compound 1 Pattern 1, optionally as a dihydrate, and then converting it to an amorphic material may be that the total shelf life of the product is increased as a result.

In certain embodiments Compound 1 Pattern 1, optionally as a dihydrate, is used in the preparation of amorphous Compound 1 as a mono-HCl salt. For example, the amorphous Compound 1 as a mono-HCl salt can be formed by dissolving Compound 1 Pattern 1 and modifying the pH of the solution followed by removal of solvent. This amorphous mono-HCl salt may possess higher purity than if it was directly prepared by known synthetic methods. In addition, an advantage of first preparing Compound 1 Pattern 1, optionally as a dihydrate, and then converting it to an amorphic material may be that the total shelf life of the product is increased.

In certain embodiments Compound 1 Pattern 1, optionally as a dihydrate, is used in the preparation of amorphous Compound 1 as a free base. This amorphous free base may possess higher purity than if it was directly prepared by known synthetic methods. In addition, an advantage of first preparing Compound 1 Pattern 1, optionally as a dihydrate, and then converting it to an amorphic material may be that the total shelf life of the product is increased as a result.

In certain embodiments Compound 1 Pattern 1, optionally as a dihydrate, is used in the preparation of a liquid solution suitable for intravenous administration of Compound 1. This liquid solution of Compound 1 may possess higher purity than if it was directly prepared by known synthetic methods. In addition, an advantage of first preparing Compound 1

Pattern 1, optionally as a dihydrate, and then converting it to a liquid solution may be that the total shelf life of the product is increased as a result.

In certain embodiments Compound 1 Pattern 1, optionally as a dihydrate, is lyophilized. In these embodiments Compound 1 Pattern 1, optionally as a dihydrate, can optionally be mixed with one or more appropriate excipients before or after lyophilization. For example, in certain embodiments the invention provides a solid lyophilized composition comprising Compound 1 Pattern 1, optionally as a dihydrate. In certain embodiments the invention provides solid lyophilized composition comprising Compound 1 Pattern 1, optionally as a dihydrate, mannitol, and citric acid. In certain embodiments the invention provides solid lyophilized composition comprising Compound 1 Pattern 1 dihydrochloride, dihydrate, mannitol, and citric acid.

Non-Limiting Embodiments of the Present Invention
1. In certain embodiments a crystalline compound is provided of structure:

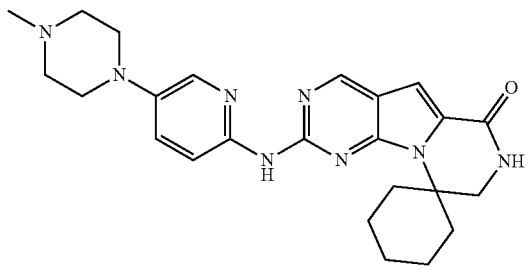 [SMILES: CN1CCN(c2ccc(Nc3ncc4cc5n(c4n3)C3(CCCCC3)CNC5=O)nc2)CC1]

which is a dihydrochloride, dihydrate.

Other non-limiting embodiments include:
2. The crystalline compound of embodiment 1 characterized by an X-ray powder diffraction (XRPD) pattern comprising at least three 2theta values selected from 9.6±0.2°, 21.3±0.2°, 19.8±0.2°, 12.2±0.2°, 24.0±0.2°, 26.1±0.2°, 19.3±0.2°, 17.6±0.2°, and 28.6±0.2°.
3. The crystalline compound of embodiment 2, wherein the XRPD pattern comprises at least four 2theta values selected from 9.6±0.2°, 21.3±0.2°, 19.8±0.2°, 12.2±0.2°, 24.0±0.2°, 26.1±0.2°, 19.3±0.2°, 17.6±0.2°, and 28.6±0.2°.
4. The crystalline compound of embodiment 2, wherein the XRPD pattern comprises at least five 2theta values selected from 9.6±0.2°, 21.3±0.2°, 19.8±0.2°, 12.2±0.2°, 24.0±0.2°, 26.1±0.2°, 19.3±0.2°, 17.6±0.2°, and 28.6±0.2°.
5. The crystalline compound of embodiment 2, wherein the XRPD pattern comprises at least six 2theta values selected from 9.6±0.2°, 21.3±0.2°, 19.8±0.2°, 12.2±0.2°, 24.0±0.2°, 26.1±0.2°, 19.3±0.2°, 17.6±0.2°, and 28.6±0.2°.
6. The crystalline compound of embodiment 2, wherein the XRPD pattern comprises at least the 2theta value of 9.6±0.2°.
7. The crystalline compound of embodiment 2, wherein the XRPD pattern comprises at least the 2theta values of 9.6±0.2°, 19.8±0.2°, and 21.3±0.2°.
8. In certain embodiments a lyophilized powder prepared from the crystalline compound of embodiment 1 is provided.
9. The lyophilized powder of embodiment 8, wherein the crystalline compound of embodiment 1 is characterized by an X-ray powder diffraction (XRPD) pattern comprising at least three 2theta values selected from 9.6±0.2°, 21.3±0.2°, 19.8±0.2°, 12.2±0.2°, 24.0±0.2°, 26.1±0.2°, 19.3±0.2°, 17.6±0.2°, and 28.6±0.2°.
10. The lyophilized powder of embodiment 9, wherein the crystalline compound of embodiment 1 is characterized by an XRPD pattern comprising at least four 2theta values selected from 9.6±0.2°, 21.3±0.2°, 19.8±0.2°, 12.2±0.2°, 24.0±0.2°, 26.1±0.2°, 19.3±0.2°, 17.6±0.2°, and 28.6±0.2°.
11. The lyophilized powder of embodiment 9, wherein the crystalline compound of embodiment 1 is characterized by an XRPD pattern comprising at least five 2theta values selected from 9.6±0.2°, 21.3±0.2°, 19.8±0.2°, 12.2±0.2°, 24.0±0.2°, 26.1±0.2°, 19.3±0.2°, 17.6±0.2°, and 28.6±0.2°.
12. The lyophilized powder of embodiment 9, wherein the crystalline compound of embodiment 1 is characterized by an XRPD pattern comprising at least six 2theta values selected from 9.6±0.2°, 21.3±0.2°, 19.8±0.2°, 12.2±0.2°, 24.0±0.2°, 26.1±0.2°, 19.3±0.2°, 17.6±0.2°, and 28.6±0.2°.
13. The lyophilized powder of embodiment 9 wherein the crystalline compound of embodiment 1 is characterized by an XRPD pattern comprising at least the 2theta value of 9.6±0.2°.
14. The lyophilized powder of embodiment 9, wherein the crystalline compound of embodiment 1 is characterized by an XRPD pattern comprising at least the 2theta values of 9.6±0.2°, 19.8±0.2°, and 21.3±0.2°.
15. In certain embodiments a pharmaceutical composition comprising the crystalline compound of embodiment 1 and a pharmaceutically acceptable excipient is provided.
16. The pharmaceutical composition of embodiment 15, wherein the pharmaceutical composition is suitable for intravenous delivery.
17. The pharmaceutical composition of embodiment 15 comprising about 200 milligrams to about 600 milligrams of the crystalline compound of embodiment 1.
18. The pharmaceutical composition of embodiment 15 comprising about 300 milligrams of the crystalline compound of embodiment 1.
19. The pharmaceutical composition of embodiment 15 comprising a dose of about 150 mg/m$^2$ to about 350 mg/m$^2$ of the crystalline compound of embodiment 1.
20. The pharmaceutical composition of embodiment 15 further comprising about 300 mg of mannitol and about 76 mg of citric acid.
21. The pharmaceutical composition of embodiment 15 comprising a dose of about 240 mg/m$^2$ of the crystalline compound of embodiment 1.
22. In certain embodiments a pharmaceutically acceptable reconstituted solution of the lyophilized powder of embodiment 8 is provided.
23. The pharmaceutical solution of embodiment 23, wherein the solution is aqueous.
24. The pharmaceutical solution of embodiment 23, wherein the pharmaceutical composition is suitable for intravenous delivery.
25. The pharmaceutical solution of embodiment 23 comprising about 200 milligrams to about 600 milligrams of the lyophilized powder of embodiment 8.
26. The pharmaceutical solution of embodiment 23 comprising about 300 milligrams of the lyophilized powder of embodiment 8.

27. The pharmaceutical solution of embodiment 23 comprising a dose of about 150 mg/m² to about 350 mg/m² of the lyophilized powder of embodiment 8.
28. The pharmaceutical solution of embodiment 23 further comprising about 300 mg of mannitol and about 76 mg of citric acid.
29. The pharmaceutical solution of embodiment 23 further comprising sodium hydroxide or hydrochloric acid.
30. The pharmaceutical solution of embodiment 23 comprising a dose of about 240 mg/m² of the lyophilized powder of embodiment 8.
31. A lyophilized powder comprising a compound of structure:

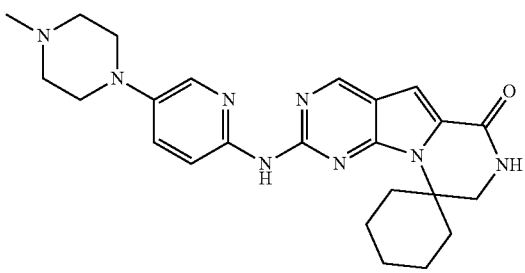 [SMILES: CN1CCN(c2ccc(Nc3ncc4cc5n(c4n3)C3(CCCCC3)CNC5=O)nc2)CC1]

which is a dihydrochloride, which optionally includes hydrate.
32. The lyophilized powder of embodiment 31, wherein the compound is characterized by an X-ray powder diffraction (XRPD) pattern comprising at least three 2theta values selected from 9.6±0.2°, 21.3±0.2°, 19.8±0.2°, 12.2±0.2°, 24.0±0.2°, 26.1±0.2°, 19.3±0.2°, 17.6±0.2°, and 28.6±0.2°.
33. The lyophilized powder of embodiment 31, wherein the compound is characterized by an XRPD pattern comprising at least four 2theta values selected from 9.6±0.2°, 21.3±0.2°, 19.8±0.2°, 12.2±0.2°, 24.0±0.2°, 26.1±0.2°, 19.3±0.2°, 17.6±0.2°, and 28.6±0.2°.
34. The lyophilized powder of embodiment 31, wherein the compound is characterized by an XRPD pattern comprising at least five 2theta values selected from 9.6±0.2°, 21.3±0.2°, 19.8±0.2°, 12.2±0.2°, 24.0±0.2°, 26.1±0.2°, 19.3±0.2°, 17.6±0.2°, and 28.6±0.2°.
35. The lyophilized powder of embodiment 31, wherein the compound is characterized by an XRPD pattern comprising at least six 2theta values selected from 9.6±0.2°, 21.3±0.2°, 19.8±0.2°, 12.2±0.2°, 24.0±0.2°, 26.1±0.2°, 19.3±0.2°, 17.6±0.2°, and 28.6±0.2°.
36. The lyophilized powder of embodiment 31, wherein the compound is characterized by an XRPD pattern comprising at least the 2theta value of 9.6±0.2°.
37. The lyophilized powder of embodiment 31, wherein the compound is characterized by an XRPD pattern comprising at least the 2theta values of 9.6±0.2°, 19.8±0.2°, and 21.3±0.2°.

Formulation of Compound 1 Pattern 1

In certain embodiments Compound 1 Pattern 1 in the form of a dihydrochloride, dihydrate in a formulation is provided. In certain embodiments the formulation comprises about 300-400 mg, about 350-400 mg, about 360-380 mg, or more particularly about 373 mg, of Compound 1 Pattern 1 dihydrochloride, dihydrate, about 50-100, about 60-80, or more particularly about 76 mg of citric acid monohydrate, and about 250-350 mg, about 280-320 mg, or more particularly about 300 mg of mannitol, and optionally sodium hydroxide and/or hydrochloric acid to adjust the pH as desired. In particular, 373 mg of the dihydrochloride, dihydrate will provide 300 mg of Trilaiclib free base.

In certain embodiments the formulation is lyophilized after Compound 1 Pattern 1 in the form of a dihydrochloride, dihydrate is mixed with citric acid and mannitol. In certain embodiments the formulation comprises lyophilized Compound 1 Pattern 1 in the form of a dihydrochloride, dihydrate mixed with citric acid and mannitol, wherein the citric acid and mannitol are added after Compound 1 Pattern 1 in the form of a dihydrochloride, dihydrate is lyophilized.

In certain embodiments Compound 1 Pattern 1 in the form of a dihydrochloride in a formulation is provided. In certain embodiments the formulation comprises about 300-400 mg, about 350-400 mg, or about 360-380 mg, or more particularly about 373 mg, of Compound 1 Pattern 1 dihydrochloride, dihydrate, about 50-100, about 60-80, or more particularly about 76 mg of citric acid monohydrate, and about 250-350 mg, about 280-320 mg or more particularly about 300 mg of mannitol, and optionally sodium hydroxide and/or hydrochloric acid to adjust the pH as desired for reconstitution.

In certain embodiments this formulation is sterile.

In certain embodiments the formulation is lyophilized after Compound 1 Pattern 1 in the form of a dihydrochloride, dihydrate is mixed with citric acid and mannitol. In certain embodiments the formulation comprises lyophilized Compound 1 Pattern 1 in the form of a dihydrochloride mixed with citric acid and mannitol, wherein the citric acid and mannitol are added after Compound 1 Pattern 1 in the form of a dihydrochloride, dihydrate is lyophilized.

In certain embodiments a formulation is provided wherein the formulation is prepared by lyophilizing about 300-400 mg, about 350-400 mg, or about 360-380 mg, or more particularly about 373 mg, of Compound 1 Pattern 1 dihydrochloride, dihydrate, about 50-100, about 60-80, or more particularly about 76 mg citric acid monohydrate, and about 250-350 mg, about 280-320 mg or more particularly about 300 mg of mannitol, and optionally sodium hydroxide and/or hydrochloric acid to adjust the pH as desired. In another embodiment the formulation results from lyophilizing Compound 1 Pattern 1 after it is mixed with about 50-100 mg, about 60-80 mg, or more particularly about 76 mg of citric acid monohydrate, and about 280-320 mg, or more particularly about 300 mg of mannitol.

Any of the formulations described above can be reconstituted with about 5-100, 5-50, 10-30, about 10-25, or more particularly about 19.5 mL of sterile water, phosphate buffered saline, dilute sugar, or another saline solution. In one non-limiting embodiment the reconstitution solution is a sterile sodium chloride solution, for example, comprising about 0.9% NaCl or a sterile sugar solution, for example, of about 5% dextrose solution. The resulting reconstituted solution will have any amount of trilaciclib needed for the intended purpose, such as for example, between about 5-50 mg/mL, about 10-25 mg/ml or even about 15 mg/mL of trilaciclib. In certain embodiments the resulting solution is then diluted prior to parenteral administration, such as intravenous delivery.

Non-limiting examples of typical quality standards and pharmaceutical function are provided in the table below.

| Components | Quantity (mg) per Vial[a] | Pharmaceutical Function | Quality Standards |
|---|---|---|---|
| trilaciclib[b] | 300 | Active | Internal |
| Mannitol | 300 | Bulking agent | USP/Ph. Eur. |
| Citric acid monohydrate | 75.6 | Buffer | USP/Ph. Eur. |
| Sodium hydroxide | q.s. | pH adjustment | NF/Ph. Eur. |
| Hydrochloric acid | q.s. | pH adjustment[c] | NF/Ph. Eur. |
| Water for Injection[d] | q.s. | Solvent | USP/Ph. Eur. |
| Nitrogen[e] | N/A | Process aide | NF |

NF = National Formulary;
USP = United States Pharmacopoeia;
Ph. Eur. = European Pharmacopoeia;
N/A = not applicable;
q.s. = quantity sufficient
[a]The target weight of solution filled into vials prior to lyophilization is 12.252 g (12 mL).
[b]Amount in terms of free base (equivalent to 373 mg of Compound 1 Pattern 1 dihydrochloride, dihydrate).
[c]May be used if necessary, to adjust the bulk solution pH.
[d]Essentially removed during lyophilization.
[e]Nitrogen is used as an inert gas at the end of the lyophilization process for vacuum adjustment.

The resulting formulation can be supplied in any appropriate container, for example in a 20 mL (Type 1) clear glass vial, sealed with a 20 mm gray chlorobutyl rubber stopper and secured with a 20 mm aluminum overseal with a plastic flip-off seal.

In certain embodiments the solid formulation is reconstituted with about 5-100, 5-50, 10-30, about 10-25, or more particularly about 19.5 mL of about 0.9% NaCl or a sterile sugar solution, for example, of about 5% dextrose solution, sodium hydroxide and/or hydrochloric acid is added to adjust pH, and then the reconstituted solution is diluted to the appropriate dose for administration to a human in need thereof, for example at a dosage of about 200-300 mg/m$^2$, for example 240 mg/m$^2$.

Chemical Description and Terminology

Compounds are described using standard nomenclature. Unless defined otherwise, all technical and scientific terms used herein have the same meaning as is commonly understood by one of skill in the art to which this invention belongs.

The terms "a" and "an" do not denote a limitation of quantity, but rather denote the presence of at least one of the referenced item. The term "or" means "and/or". Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable.

All methods described herein can be performed in any suitable order unless otherwise indicated herein or otherwise clearly contradicted by context. The use of any and all examples, or exemplary language (e.g., "such as"), is intended merely for illustration and does not pose a limitation on the scope of the invention unless otherwise claimed.

An "active agent" is a compound (including a compound disclosed herein), element, or mixture that when administered to a patient, alone or in combination with another compound, element, or mixture, confers, directly or indirectly, a physiological effect on the patient. The indirect physiological effect may occur via a metabolite or other indirect mechanism.

"Deuteration" and "deuterated" means that a hydrogen is replaced by a deuterium such that the deuterium exists over natural abundance and is thus "enriched". An enrichment of 50% means that rather than hydrogen at the specified position the deuterium content is 50%. For clarity, it is confirmed that the term "enriched" as used herein does not mean percentage enriched over natural abundance. In other embodiments, there will be at least 80%, at least 90%, or at least 95% deuterium enrichment at the specified deuterated position or positions. In other embodiments there will be at least 96%, at least 97%, at least 98%, or at least 99% deuterium enrichment at the specified deuterated position or positions indicated. In the absence of indication to the contrary, the enrichment of deuterium in the specified position of the compound described herein is at least 90%.

A "dosage form" means a unit of administration of an active agent. Non-limiting examples of dosage forms include tablets, capsules, injections, suspensions, liquids, intravenous fluids, emulsions, creams, ointments, suppositories, inhalable forms, transdermal forms, and the like.

"Pharmaceutical compositions" are compositions comprising at least one active agent, such as a compound or salt of one of the active compounds disclosed herein, and at least one other substance, such as a carrier. Pharmaceutical compositions optionally contain more than one active agent. "Pharmaceutical combinations" or "combination therapy" refers to the administration of at least two active agents, and in one embodiment, three or four or more active agents which may be combined in a single dosage form or provided together in separate dosage forms optionally with instructions that the active agents are to be used together to treat a disorder.

"Pharmaceutically acceptable salts" includes derivatives of the disclosed compounds in which the parent compound is modified by making inorganic and organic, suitably non-toxic, acid or base addition salts thereof. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. The pharmaceutically acceptable salt can be in the form of a pure crystal, or single morphic form, or can be used in non-crystalline or amorphic, glassy, or vitreous form, or a mixture thereof. In an alternative embodiment, the active compound can be provided in the form of a solvate.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—(CH$_2$)n-COOH where n is 0-4, and the like. Lists of additional suitable salts may be found, e.g., in Remington's Pharmaceutical Sciences, 17th ed., Mack Publishing Company, Easton, Pa., p. 1418 (1985).

The term "carrier" means a diluent, excipient, or vehicle with which an active compound is provided.

A "pharmaceutically acceptable excipient" means an excipient that is useful in preparing a pharmaceutical composition/combination that is generally safe, is sufficiently non-toxic, and neither biologically nor otherwise undesirable. A "pharmaceutically acceptable excipient" as used in the present application includes both one and more than one such excipient.

A "patient" or "host" is a human or non-human animal, including, but not limited to, simian, avian, feline, canine, bovine, equine or porcine in need of medical treatment. Medical treatment can include treatment of an existing condition, such as a disease or disorder, or a prophylactic or diagnostic treatment. In a particular embodiment, the patient or host is a human patient. The patient such as a host can be treated for any condition that is responsive to trilaciclib, including for myelopreservation or as an antineoplastic agent.

The term "isolated" as used herein refers to the material in substantially pure form. An isolated compound does not have another component that materially affects the properties of the compound. In particular embodiments, an isolated form is at least 50, 60, 70, 80, 90, 95, 98 or 99% pure.

Pharmaceutical Compositions and Dosage Forms

In one aspect of the invention a formulation is provided wherein the formulation is prepared by lyophilizing about 300 to 400 mg, about 350-400 mg or more particularly about 373 mg of Compound 1 Pattern 1 dihydrochloride, dihydrate (equivalent to about 300 mg of trilaciclib free base) and mixing it with about 50-100 mg, about 60-80 mg, or more particularly about 76 mg of citric acid monohydrate, and about 250-350 mg, about 280-320 mg or more particularly about 300 mg of mannitol, and optionally sodium hydroxide and/or hydrochloric acid to adjust the pH as desired. In another embodiment the formulation results from lyophilizing Compound 1 Pattern 1 after it is mixed with about 50-100 mg, about 60-80 mg, or more particularly about 76 mg of citric acid monohydrate, and about 250-350 mg, about 280-320 mg or more particularly about 300 mg of mannitol, and optionally sodium hydroxide and/or hydrochloric acid to adjust the pH as desired.

This formulation can be reconstituted with about 10-30, or more particularly about 5-100, 5-50, 10-30, about 10-25, or more particularly about 19.5 mL of sterile water, phosphate buffered saline, dilute sugar, or another saline solution. In one non-limiting embodiment the reconstitution solution is a sterile sodium chloride solution, for example, comprising about 0.9% NaCl or a sterile sugar solution, for example, of about 5% dextrose solution. The resulting reconstituted solution will have any amount of trilaciclib needed for the intended purpose, such as for example, between about 5-50 mg/mL, about 10-25 mg/ml or even about 15 mg/mL of trilaciclib. In certain embodiments the resulting solution is then diluted prior to parenteral administration, such as intravenous delivery.

The isolated Compound 1 Pattern 1 described herein, or an alternative salt, isotopic analog, or prodrug can be administered in an effective amount to a host to treat any of the disorders described herein using any suitable approach which achieves the desired therapeutic result. The amount and timing of the isolated Compound 1 Pattern 1 administered will, of course, be dependent on the host being treated, the instructions of the supervising medical specialist, on the time course of the exposure, on the manner of administration, on the pharmacokinetic properties of the particular active compound, and on the judgment of the prescribing physician. Thus, because of host to host variability, the dosages given below are a guideline and the physician can titrate doses of the compound to achieve the treatment that the physician considers appropriate for the host. In considering the degree of treatment desired, the physician can balance a variety of factors such as age and weight of the host, presence of preexisting disease, as well as presence of other diseases.

The pharmaceutical composition may be formulated as any pharmaceutically useful form, and typically a parenteral formulation, such as an intravenous, intramuscular, subcutaneous, or intradermal formulation. Other alternative formulations include oral, transdermal, or intranasal formulations. For example the pharmaceutical composition may be in the form of an I.V. bag a vial for injection, a pill, a capsule, a tablet, a transdermal patch, a subcutaneous patch, a dry powder, an inhalation formulation, in a medical device, suppository, buccal, or sublingual formulation. Some dosage forms, such as tablets and capsules, are subdivided into suitably sized unit doses containing appropriate quantities of the active components, e.g., an effective amount to achieve the desired purpose.

In certain embodiments the pharmaceutical composition is in a dosage form that contains from about 50 $mg/m^2$ to about 800 $mg/m^2$, from about 100 $mg/m^2$ to about 600 $mg/m^2$, from about 100 $mg/m^2$ to about 500 $mg/m^2$, from about 100 $mg/m^2$ to about 400 $mg/m^2$, from about 100 $mg/m^2$ to about 350 $mg/m^2$, from about 150 $mg/m^2$ to about 350 $mg/m^2$, from about 200 $mg/m^2$ to about 350 $mg/m^2$, or from about 200 $mg/m^2$ to about 300 $mg/m^2$. In one embodiment the pharmaceutical composition is in a dosage form that contains about 240 $mg/m^2$.

The therapeutically effective dosage of the isolated Compound 1 Pattern 1 described herein will be determined by the health care practitioner depending on the condition, size and age of the patient as well as the route of delivery. In one non-limited embodiment, a dosage from about 0.1 to about 200 mg/kg has therapeutic efficacy, with all weights being calculated based upon the weight of the active compound. In some embodiments, the dosage may be the amount of the isolated Compound 1 Pattern 1 needed to provide a serum concentration of the active compound of up to about 10 nM, 50 nM, 100 nM, 200 nM, 300 nM, 400 nM, 500 nM, 600 nM, 700 nM, 800 nM, 900 nM, 1 µM, 5 µM, 10 µM, 20 µM, 30 µM, or 40 µM.

In certain embodiments the pharmaceutical composition is in a dosage form that contains from about 0.1 mg to about 2000 mg, from about 10 mg to about 1000 mg, from about 100 mg to about 800 mg, or from about 200 mg to about 600 mg of the active compound and optionally from about 0.1 mg to about 2000 mg, from about 10 mg to about 1000 mg, from about 100 mg to about 800 mg, or from about 200 mg to about 600 mg, for example from about 300 mg to about 400 mg of the isolated Compound 1 Pattern 1, measured alternatively either as the free base or its salt, in a unit dosage form, for example for parenteral deliver such as an I.V. bag. Examples are dosage forms with at least 5, 10, 15, 20, 25, 50, 100, 200, 250, 300, 400, 500, 600, 700, or 750 mg of active compound, or its salt. The pharmaceutical composition may also include a molar ratio of the isolated Compound 1 Pattern 1 and an additional active agent, in a ratio that achieves the desired results.

The isolated Compound 1 Pattern 1 disclosed herein or used as described herein may be administered parenterally, intravaneously, orally, topically, by inhalation or spray, sublingually, via implant, including ocular implant, transdermally, via buccal administration, rectally, intramuscular, inhalation, intra-aortal, intracranial, subdermal, intraperitioneal, subcutaneous, transnasal, sublingual, or rectal or by other means, in dosage unit formulations containing conventional pharmaceutically acceptable carriers.

In accordance with the presently disclosed methods, a parenteral dosage form can be made from Compound 1 Pattern 1, for example Compound 1 Pattern 1 dihydrochloride, dihydrate. This dosage form can include any pharmaceutically acceptable excipient, for example a liquid excipient. Non-limiting examples of liquid excipients include phosphate buffered saline, unbuffered or buffered saline (e.g. NaCl solution without buffering agents), a sugar solution (e.g. a solution of dextrose, or a combination thereof as desired. When being prepared for parenteral dosing Compound 1 Pattern 1, for example Compound 1 Pattern 1 dihydrochloride, dihydrate, may be dissolved in a concentrated solution of an appropriate liquid excipient. This concentrated solution of Compound 1 may then be diluted with the same or different liquid excipient to the appropriate dose for treating a human in need thereof. In certain embodiments the pH of the solution (either before or after dilution) is adjusted with a pH adjusting reagent (for example HCl or NaOH). In certain embodiments an additional therapeutic or non-therapeutic agent is added to the solution before administration or to improve shelf life.

In accordance with the presently disclosed methods, an oral administration can be in any desired form in which the isolated Compound 1 Pattern 1 is stable as a solid. In certain embodiments, the isolated Compound 1 Pattern 1 is delivered in a solid microparticle or nanoparticle. When administered through inhalation the isolated Compound 1 Pattern 1 may be in the form of a plurality of solid particles or droplets having any desired particle size, and for example, from about 0.01, 0.1 or 0.5 to about 5, 10, 20 or more microns, and optionally from about 1 to about 2 microns. The isolated Compound 1 Pattern 1 as disclosed in the present invention has good pharmacokinetic and pharmacodynamics properties, for instance when administered by the oral or intravenous routes.

The pharmaceutical formulations can comprise the isolated Compound 1 Pattern 1 described herein or an alternative pharmaceutically acceptable salt thereof, in any pharmaceutically acceptable carrier.

Carriers include excipients and diluents and must be of sufficiently high purity and sufficiently low toxicity to render them suitable for administration to the patient being treated. The carrier can be inert or it can possess pharmaceutical benefits of its own. The amount of carrier employed in conjunction with the compound is sufficient to provide a practical quantity of material for administration per unit dose of the compound.

Classes of carriers include, but are not limited to binders, buffering agents, coloring agents, diluents, di sintegrants, emulsifiers, flavorants, glidents, lubricants, preservatives, stabilizers, surfactants, tableting agents, and wetting agents. Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin; talc, and vegetable oils. Optional active agents may be included in a pharmaceutical composition, which do not substantially interfere with the activity of the compound of the present invention.

Depending on the intended mode of administration, the pharmaceutical compositions can be in the form of solid form or a semi-solid dosage form that the isolated Compound 1 Pattern 1 is stable in, such as, for example, tablets, suppositories, pills, capsules, powders, or the like, preferably in unit dosage form suitable for single administration of a precise dosage. The compositions will include an effective amount of the selected drug in combination with a pharmaceutically acceptable carrier and, in addition, can include other pharmaceutical agents, adjuvants, diluents, buffers, and the like.

Thus, the compositions of the disclosure can be administered as pharmaceutical formulations including those suitable for oral (including buccal and sub-lingual), rectal, nasal, topical, pulmonary, vaginal administration or in a form suitable for administration by inhalation or insufflation. The preferred manner of administration is oral using a convenient daily dosage regimen which can be adjusted according to the degree of affliction. For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like.

In yet another embodiment is the use of permeation enhancer excipients including polymers such as: polycations (chitosan and its quaternary ammonium derivatives, poly-L-arginine, aminated gelatin); polyanions (N-carboxymethyl chitosan, poly-acrylic acid); and, thiolated polymers (carboxymethyl cellulose-cysteine, polycarbophil-cysteine, chitosan-thiobutylamidine, chitosan-thioglycolic acid, chitosan-glutathione conjugates).

For oral administration, the composition will generally take the form of a tablet or capsule. Tablets and capsules are preferred oral administration forms. Tablets and capsules for oral use can include one or more commonly used carriers such as lactose and corn starch. Lubricating agents, such as magnesium stearate, are also typically added. Typically, the compositions of the disclosure can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

In addition to the active compounds or their salts, the pharmaceutical formulations can contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the formulations can contain antimicrobial preservatives. Useful antimicrobial preservatives include methylparaben, propylparaben, and benzyl alcohol. An antimicrobial preservative is typically employed when the formulations is placed in a vial designed for multi-dose use. The pharmaceutical formulations described herein can be lyophilized using techniques well known in the art.

For oral administration a pharmaceutical composition can take the form of a tablet, pill, capsule, powder, and the like. Tablets containing various excipients such as sodium citrate, calcium carbonate and calcium phosphate may be employed along with various disintegrants such as starch (e.g., potato or tapioca starch) and certain complex silicates, together with binding agents such as polyvinylpyrrolidone, sucrose, gelatin and acacia. Additionally, lubricating agents such as magnesium stearate, sodium lauryl sulfate, and talc are often very useful for tableting purposes. Solid compositions of a similar type may be employed as fillers in soft and hard-filled gelatin capsules.

Pharmaceutical formulations also are provided which provide a controlled release of a compound described herein, including through the use of a degradable polymer, as known in the art.

The term "pharmaceutically acceptable salts" as used herein refers to those salts which are, within the scope of sound medical judgment, suitable for use in contact with hosts (e.g., human hosts) without undue toxicity, irritation, allergic response, and the like, commensurate with a reasonable benefit/risk ratio, and effective for their intended use, as well as the zwitterionic forms, where possible, of the compounds of the presently disclosed host matter.

In an alternative embodiment Compound 1 Pattern 1 is not a HCl salt, but is instead a salt described below.

In one embodiment the additional therapeutic agent described in the Combination Section below is administered as a pharmaceutically acceptable salt, for example, a salt described below.

Thus, the term "salts" refers to the relatively non-toxic, inorganic and organic acid addition salts of the presently disclosed compounds. These salts can be prepared during the final isolation and purification of the compounds or by separately reacting the purified compound in its free base form with a suitable organic or inorganic acid and isolating the salt thus formed. Basic compounds are capable of forming a wide variety of different salts with various inorganic and organic acids. Acid addition salts of the basic compounds are prepared by contacting the free base form with a sufficient amount of the desired acid to produce the salt in the conventional manner. The free base form can be regenerated by contacting the salt form with a base and isolating the free base in the conventional manner. The free base forms may differ from their respective salt forms in certain physical properties such as solubility in polar solvents. Pharmaceutically acceptable base addition salts may be formed with metals or amines, such as alkali and alkaline earth metal hydroxides, or of organic amines. Examples of metals used as cations, include, but are not limited to, sodium, potassium, magnesium, calcium, and the like. Examples of suitable amines include, but are not limited to, N,N'-dibenzylethylenediamine, chloroprocaine, choline, diethanolamine, ethylenediamine, N-methylglucamine, and procaine. The base addition salts of acidic compounds are prepared by contacting the free acid form with a sufficient amount of the desired base to produce the salt in the conventional manner. The free acid form can be regenerated by contacting the salt form with an acid and isolating the free acid in a conventional manner. The free acid forms may differ from their respective salt forms somewhat in certain physical properties such as solubility in polar solvents.

Salts can be prepared from inorganic acids sulfate, pyrosulfate, bisulfate, sulfite, bisulfite, nitrate, phosphate, monohydrogenphosphate, dihydrogenphosphate, metaphosphate, pyrophosphate, chloride, bromide, iodide such as hydrochloric, nitric, phosphoric, sulfuric, hydrobromic, hydriodic, phosphorus, and the like. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, laurylsulphonate and isethionate salts, and the like. Salts can also be prepared from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. and the like. Representative salts include acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like.

Pharmaceutically acceptable salts can include cations based on the alkali and alkaline earth metals, such as sodium, lithium, potassium, calcium, magnesium and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. Also contemplated are the salts of amino acids such as arginate, gluconate, galacturonate, and the like. See, for example, Berge et al., J. Pharm. Sci., 1977, 66, 1-19, which is incorporated herein by reference.

Formulations suitable for rectal administration are typically presented as unit dose suppositories. These may be prepared by admixing the active disclosed compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil, which maintain the stability of the isolated Compound 1 Pattern 1. Carriers which may be used include petroleum jelly, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3 (6):318 (1986)) and typically take the form of an optionally buffered aqueous solution of the active compound. In one embodiment, microneedle patches or devices are provided for delivery of drugs across or into biological tissue, particularly the skin. The microneedle patches or devices permit drug delivery at clinically relevant rates across or into skin or other tissue barriers, with minimal or no damage, pain, or irritation to the tissue.

Formulations suitable for administration to the lungs can be delivered by a wide range of passive breath driven and active power driven single/-multiple dose dry powder inhalers (DPI). The devices most commonly used for respiratory delivery include nebulizers, metered-dose inhalers, and dry powder inhalers. Several types of nebulizers are available, including jet nebulizers, ultrasonic nebulizers, and vibrating mesh nebulizers. Selection of a suitable lung delivery device depends on parameters, such as nature of the drug and its formulation, the site of action, and pathophysiology of the lung.

Advantageous Pharmaceutical Form of Trilaciclib for Effective Therapy

In certain embodiments the morphic form of Compound 1, for example Compound 1 dihydrochloride, dihydrate, is used to produce an intravenous formulation as a myelopreservation agent or alternatively when given along with chemotherapy to treat cancer optionally along with the standard of care for the cancer being treated. The standard of care for treating a particular cancer includes the use of therapies that are approved by a regulatory agency, for example the U.S. Food and Drug Administration (FDA), European Medicines Agency (EMA), or the Chinese National Medical Products Administration (NMPA) for the cancer being treated. In other embodiments a pharmaceutical formulation as described herein is selected and managed by the patient's healthcare practitioner.

(i) Myelopreseryation

When used as a myelopreservation agent, it can be administered, for example as taught in WO 2014/144326, WO 2016/040848, WO 2018/106729, or PCT/US20/38557. For example, in certain embodiments Compound 1 Pattern 1 dihydrochloride, dihydrate or an intravenous solution prepared from it is administered on each day of a treatment cycle on which chemotherapy is administered. For example, if the chemotherapy is given on day 1, day 2, and/or day 3 of a treatment cycle then the intravenous solution is also administered on day 1, day 2, and/or day 3 of the treatment cycle (for example on day 1 or day 1 and day 2 of the treatment cycle). In another embodiment the intravenous solution is administered on day 1 and day 8 of a 21 day treatment cycle, and as non-limiting examples, in combination with gemcitabine, carboplatin, or topotecan.

In certain embodiments, the isolated Compound 1 Pattern 1 of the present invention decreases the effect of chemotherapeutic agent toxicity on CDK4/6 replication dependent healthy cells, such as hematopoietic stem cells and hematopoietic progenitor cells (together referred to as HSPCs), and/or renal epithelial cells, in subjects, typically humans, that will be, are being, or have been exposed to the chemotherapeutic agent (typically a DNA-damaging agent).

In one embodiment, the subject has been exposed to a chemotherapeutic agent, and, using the intravenous solution described herein, the subject's CDK4/6-replication dependent healthy cells are placed in G1 arrest following exposure in order to mitigate, for example, DNA damage. In one embodiment, the compound is administered at least ½ hour, at least 1 hour, at least 2 hours, at least 3 hours, at least 4 hours, at least 5 hours, at least 6 hours, at least 7 hours, at least 8 hours, at least 10 hours, at least 12 hours, at least 14 hours, at least 16 hours, at least 18 hours, at least 20 hours or more post chemotherapeutic agent exposure. In an alternative embodiment, Compound 1 Pattern 1 dihydrochloride, dihydrate or an intravenous solution prepared from it is administered at least ½ hour, at least 1 hour, at least 2 hours, at least 3 hours, at least 4 hours, at least 5 hours, at least 6 hours, at least 7 hours, at least 8 hours, at least 10 hours, at least 12 hours, at least 14 hours, at least 16 hours, at least 18 hours, at least 20 hours or more prior to chemotherapeutic agent exposure. In certain embodiments Compound 1 Pattern 1 dihydrochloride, dihydrate or an intravenous solution prepared from it is administered about 4 hours before chemotherapy.

In one embodiment, an intravenous solution prepared from Compound 1 Pattern 1 dihydrochloride, dihydrate is administered in combination with a chemotherapeutic agent including but not limited to a treatment regimen wherein the chemotherapeutic agent is administered: on day 1-3 every 21 days; on days 1-3 every 28 days; on day 1 every 3 weeks; on day 1, day 8, and day 15 every 28 days, on day 1 and day 8 every 28 days; on days 1 and 8 every 21 days; on days 1-5 every 21 days; 1 day a week for 6-8 weeks; on days 1, 22, and 43; days 1 and 2 weekly; days 1-4 and 22-25; days 1-4, 22-25, and 43-46; and similar type-regimens, wherein the CDK4/6-replication dependent cells are arrested at the G1 phase during chemotherapeutic agent exposure.

In one embodiment, the isolated Compound 1 Pattern 1 can allow for dose intensification (e.g., more therapy can be given in a fixed period of time) in medically related chemotherapies, which will translate to better efficacy. Therefore, the presently disclosed methods can result in chemotherapy regimens that are less toxic and more effective.

In some embodiments, the use of the isolated Compound 1 Pattern 1 described herein may result in reduced or substantially limited off-target effects, for example, related to inhibition of kinases other than CDK4 and/or CDK6 such as CDK2. Furthermore, in certain embodiments, the use of the isolated Compound 1 Pattern 1 described herein should not induce cell cycle arrest in CDK4/6 replication independent cells.

In some embodiments, the use of the isolated Compound 1 Pattern 1 described herein reduces the risk of undesirable off-target effects including, but not limited to, long term toxicity, anti-oxidant effects, and estrogenic effects. Anti-oxidant effects can be determined by standard assays known in the art. For example, a compound with no significant anti-oxidant effects is a compound that does not significantly scavenge free-radicals, such as oxygen radicals. The anti-oxidant effects of a compound can be compared to a compound with known anti-oxidant activity, such as genistein. Thus, a compound with no significant anti-oxidant activity can be one that has less than about 2, 3, 5, 10, 30, or 100 fold anti-oxidant activity relative to genistein. Estrogenic activities can also be determined via known assays. For instance, a non-estrogenic compound is one that does not significantly bind and activate the estrogen receptor. A compound that is substantially limited estrogenic effects can be one that has less than about 2, 3, 5, 10, 20, or 100-fold estrogenic activity relative to a compound with estrogenic activity, e.g., genistein.

Compound 1 Pattern 1, for example Compound 1 Pattern 1 dihydrochloride, dihydrate, or a formulation produced from it may be administered parenterally, for example, intravenously, to a patient prior to administration of an immune-response inducing chemotherapy such as an ICD-inducing chemotherapy. In some embodiments, Compound 1 is administered up to about 24 hours or less, or up to about 20, 15, 10, 5, or 4 hours or less for example about 30-60 minutes or less, prior to administration of the chemotherapy. In some embodiments, Compound 1 is administered approximately about 22 to 26 hours before administration of the chemotherapy, and again about 4 hours or less, for example about 30-60 minutes or less, prior to administration of the chemotherapy. In some embodiments, the dose of Compound 1 administered is between about 180 and about 280 mg/m$^2$. For example, the dose is up to about 100, 125, 150, 180, 185, 190, 195, 200, 205, 210, 215, 220, 225, 230, 235, 240, 245, 250, 255, 260, 265, 270, 275, or 280 mg/m$^2$ or any dose in between these numbers as determined desirable by the healthcare practitioner. In a particular embodiment, the dose is about 240 mg/m$^2$.

Typically, Compound 1 Pattern 1, for example Compound 1 Pattern 1 dihydrochloride, dihydrate, or a formulation produced from it is administered to the subject prior to treatment with the chemotherapeutic agent such that its concentration reaches peak serum levels before or during treatment with the chemotherapeutic agent, allowing for the inhibition of proliferation of immune effector cells, thus protecting them from the harmful effects of chemotherapy. In some embodiments, Compound 1 Pattern 1, for example Compound 1 Pattern 1 dihydrochloride, dihydrate, or a formulation produced from it is administered concomitantly, or closely thereto, with the chemotherapeutic agent exposure. Alternatively, the CDK4/6 inhibitor described herein can be administered following exposure to the chemotherapeutic agent if desired to mitigate immune effector cell damage associated with chemotherapeutic agent exposure. In one embodiment, an aqueous solution produced form Compound 1 Pattern 1 is administered to a patient in need thereof.

In some embodiments, Compound 1 Pattern 1, for example Compound 1 Pattern 1 dihydrochloride, dihydrate, or a formulation produced from it is administered to the subject less than about 24 hours, about 20 hours, about 16 hours, about 12 hours, about 8 hours, about 4 hours, about 2.5 hours, about 2 hours, about 1 hour, about ½ hour or less prior to treatment with the chemotherapeutic agent. In a particular embodiment, Compound 1 Pattern 1, for example Compound 1 Pattern 1 dihydrochloride, dihydrate, or a formulation produced from it is administered about ½ hour prior to administration of the chemotherapeutic agent.

In some embodiments, Compound 1 Pattern 1, for example Compound 1 Pattern 1 dihydrochloride, dihydrate, or a formulation produced from it is administered to the subject twice before administration of the chemotherapy. For example, in some embodiments, Compound 1 Pattern 1, for example Compound 1 Pattern 1 dihydrochloride, dihydrate, or a formulation produced from it is administered between about 18 and 28 hours before the administration of the chemotherapy, and then once again at less than about 4 hours, about 2.5 hours, about 2 hours, about 1 hour, about ½ hour or less prior to treatment with the chemotherapeutic agent. In a particular embodiment, Compound 1 Pattern 1, for example Compound 1 Pattern 1 dihydrochloride, dihydrate, or a formulation produced from it is administered between about 22 and 26 hours prior to administration of the chemotherapeutic agent and again about ½ hour or less prior to administration of the chemotherapeutic agent.

In certain embodiments, Compound 1 Pattern 1, for example Compound 1 Pattern 1 dihydrochloride, dihydrate, or a formulation produced from it is administered prior to or concomitantly with the administration of a chemotherapeutic agent, wherein the chemotherapeutic agent is administered: for example, on day 1-3 every 21 days; on days 1-3 every 28 days; on day 1 every 3 weeks; on day 1, day 8, and day 15 every 28 days, on day 1 and day 8 every 28 days; on days 1 and day 8 every 21 days; on days 1-5 every 21 days; 1 day a week for 6-8 weeks; on days 1, 22, and 43; days 1 and 2 weekly; days 1-4 and 22-25; days 1-4; days 22-25, and days 43-46; and similar type chemotherapeutic regimens. In some embodiments, Compound 1 Pattern 1, for example Compound 1 Pattern 1 dihydrochloride, dihydrate, or a formulation produced from it is administered prior to or concomitantly with at least one administration of the chemotherapeutic agent during a chemotherapeutic treatment regimen. In some embodiments, Compound 1 Pattern 1, for example Compound 1 Pattern 1 dihydrochloride, dihydrate, or a formulation produced from it is administered prior to or concomitantly with one or more administrations of the chemotherapeutic agent during a chemotherapeutic treatment regimen. In one embodiment, Compound 1 Pattern 1, for example Compound 1 Pattern 1 dihydrochloride, dihydrate, or a formulation produced from it is administered prior to or concomitantly with each administration of the chemotherapeutic agent during a chemotherapeutic treatment regimen.

In some embodiments, Compound 1 Pattern 1, for example Compound 1 Pattern 1 dihydrochloride, dihydrate, or a formulation produced from it is administered prior to or concomitantly with each administration of a chemotherapeutic agent for example during a standard chemotherapeutic protocol such as, for example, a 21-day cycle. Following cessation of the standard chemotherapeutic protocol, Compound 1 Pattern 1, for example Compound 1 Pattern 1 dihydrochloride, dihydrate, or a formulation produced from it can be further administered alone in a maintenance dose. In some embodiments, Compound 1 Pattern 1, for example Compound 1 Pattern 1 dihydrochloride, dihydrate, or a formulation produced from it is further administered once a week for at least 3, 4, 5, 6, 7, 8, 9, 10, 11, 12, 13, 14, 15, 16, 26, 52, 104 weeks, or longer. In some embodiments, Compound 1 Pattern 1, for example Compound 1 Pattern 1 dihydrochloride, dihydrate, or a formulation produced from it is administered once every 21 days following the cessation of the chemotherapeutic protocol. In one embodiment, Compound 1 Pattern 1, for example Compound 1 Pattern 1 dihydrochloride, dihydrate, or a formulation produced from it is a fast-acting, short half-life CDK4/6 inhibitor.

In some embodiments, Compound 1 Pattern 1, for example Compound 1 Pattern 1 dihydrochloride, dihydrate, or a formulation produced from it is administered with a chemotherapy agent in a maintenance therapy treatment regimen following cessation of the standard chemotherapeutic protocol. Maintenance therapy can comprise either continuation of an agent given as part of the first-line or previous regimen (continuation maintenance) or treatment with a new agent (switch maintenance).

In some embodiments, Compound 1 Pattern 1, for example Compound 1 Pattern 1 dihydrochloride, dihydrate, or a formulation produced from it is further administered in a maintenance-type therapeutic regimen, wherein Compound 1 Pattern 1, for example Compound 1 Pattern 1 dihydrochloride, dihydrate, or a formulation produced from it is administered in combination with a reduced maintenance dose of chemotherapy at a regular dosing interval for example but not limited to, once a week, once every two weeks, once every three weeks, once a month, once every six weeks, once every two months, once every three months, or once every six months following the completion of the initial chemotherapy treatment. In some embodiments, Compound 1 Pattern 1, for example Compound 1 Pattern 1 dihydrochloride, dihydrate, or a formulation produced from it is administered with the same agent used in the previous phase of chemotherapy treatment. In some embodiments, Compound 1 Pattern 1, for example Compound 1 Pattern 1 dihydrochloride, dihydrate, or a formulation produced from it is administered with a different chemotherapy agent than was used in the previous phase of chemotherapy treatment.

Standard cancer chemotherapy can promote tumor immunity in two major ways: (i) inducing immunogenic cell death as part of its intended therapeutic effect; and (ii) disrupting strategies that tumors use to evade the immune response. A large body of data demonstrates that some chemotherapy drugs at their standard dose and schedule mediate their antitumor effect, at least in part, by inducing immunogenic cell death (see, e.g., Emens et al., *Chemotherapy: friend of foe to cancer vaccines*? Curr Opin Mol Ther 2001; 3:77-84; Vanmeerbeek et al., *Trial Watch: Chemotherapy-Induced Immunogenic Cell Death in Immuni-Oncology*. Oncoimmunology Vol. 9, No. 1 2020: e1703449, both incorporated by reference herein).

Immunogenic cell death (ICD) is a type of cell death characterized by, for example, cell surface translocation of calreticulin (CRT), extracellular release of ATP and high mobility group box 1 (HMBG1), and stimulation of type I interferon (IFN) responses. ICD in cancer cells may prime an anticancer immune response. A variety of chemotherapeutic agents can induce ICD, as indicated by the alterations in tumor-infiltrating lymphocytes (TIL) abundance and composition.

In response to ICD-inducing chemotherapeutics, tumor cells expose CRT on cell surface prior to death, and release damage-associated molecular pattern (DAMP) molecules such as ATP during apoptosis or HMGB1 upon secondary necrosis. These DAMPs stimulate the recruitment of dendritic cells (DCs) into the tumor bed, the uptake and processing of tumor antigens, and the optimal antigen presentation to T cells. Cross-priming of CD8+ T-cells is triggered by mature DCs and γδ T-cells in an IL-1β and IL-17 dependent manner. Primed CTLs then elicit a direct cytotoxic response to kill remaining tumor cells through the generation of IFN-γ, perforin-1 and granzyme B. In certain embodiments Compound 1 Pattern 1, for example Compound 1 Pattern 1 dihydrochloride, dihydrate, or a formulation produced from it is used for myelopreservation in combination with ICD-inducing chemotherapy.

ICD-inducing chemotherapies for use in the present invention include alkylating agents such as cyclophosphamide, trabectedin, temozolomide, melphalan, dacarbazine, and oxaliplatin; antimetabolites such as methotrexate, mitroxantrone, gemcitabine, and 5-fluorouracil (5-FU); cytotoxic antibiotics such as bleomycin and anthracyclines, including doxorubicin, daunorubicin, epirubicin, idarubicin, and valrubicin; taxanes, such as paclitaxel, cabazitaxel, and docetaxel; topoisomerase inhibitors such as topotecan, irinotecan, and etoposide; platinum compounds such as carboplatin and cisplatin; anti-microtubule vinca alkaloid agents such as vinblastine, vincristine, vinorelbine, and vindesine. Other ICD-inducing chemotherapies include bortezomib, an inhibitor of the 26S proteasome subunit, mechlorethamine, diaziquone, mitomycin C, fludarabine and cytosine arabinoside. In some embodiments, the ICD-inducing chemotherapy is selected from idarubicin, epirubicin, doxorubicin, mitoxantrone, oxaliplatin, bortezomib, gemcitabine, and cyclophosphamide, and combinations thereof. In an alternative embodiment, the chemotherapeutic administered is capable of inducing an immune-response may modulate tumor immunity by mechanisms distinct from immunogenic cell death. Various chemotherapy drugs can modulate the activity of distinct immune cell subsets or the immune phenotype of tumor cells through enhancing antigen presentation, enhancing expression of costimulatory molecules including B7.1 (CD80) and B7.2 (CD86), down-regulating checkpoint molecules such as programmed death-ligand 1 (PD-L1), or promoting tumor cell death through the fas, perforin, or Granzyme B pathways. Chemotherapies that modulate tumor immunity may do so by: abrogating myeloid-derived suppressor cell (MDSC) activity, for example gemcitabine, 5-fluoruracil, cisplatin, and doxorubicin; abrogating Treg activity, for example cyclophosphamide, 5-fluorouracil; paclitaxel, cisplatin, and fludarabine; enhancement of T-cell cross priming, for example gemcitabine and anthracyclines such as doxorubicin, daunorubicin, epirubicin, valrubicin and idarubicin.; augmenting dendritic cell activation, for example anthracyclines, taxanes, cyclo-phosphamide, vinca alkaloids, methotrexate, and mitomycin C; promoting anti-tumor CD4+ T-cell phenotype, for example cyclophosphamide and paclitaxel; and promoting tumor cell recognition and lysis, for example cyclophosphamide, 5-fluorouracil, paclitaxel, doxorubicin, cisplatin, and cytosine arabinoside.

In some embodiments, a method for selecting a patient or patient population for cancer therapy that includes the administration of Compound 1 Pattern 1, for example Compound 1 Pattern 1 dihydrochloride, dihydrate, or a formulation produced from it with chemotherapy in a manner that increases the progression free survival or overall survival of the patient or patient population is provided comprising, determining if the cancer has a surrounding microenvironment that is favorable to immune modulation, is immunogenically susceptible to CDK4/6 inhibitor treatment, or is immunogenic, and if so, administering to the patient an effective amount of Compound 1 Pattern 1, for example Compound 1 Pattern 1 dihydrochloride, dihydrate, or a formulation produced from it in combination with an effective amount of an alkylating agent such as cyclophosphamide, trabectedin, temozolomide, melphalan, dacarbazine, or oxaliplatin; an antimetabolite such as methotrexate, mitroxantrone, gemcitabine, or 5-fluorouracil (5-FU); a cytotoxic antibiotic such as bleomycin or an anthracycline such as doxorubicin, daunorubicin, epirubicin, idarubicin, or valrubicin; a taxane, such as paclitaxel, cabazitaxel, and docetaxel; topoisomerase inhibitors such as topotecan, irinotecan, and etoposide; platinum compounds such as carboplatin and cisplatin; anti-microtubule vinca alkaloid agents such as vinblastine, vincristine, vinorelbine and vindesine; bortezomib; mechlorethamine; diaziquone; fludarabine; mitomycin C; and cytosine arabinoside. In some embodiments, the administration of Compound 1 Pattern 1, for example Compound 1 Pattern 1 dihydrochloride, dihydrate, or a formulation produced from it in combination with the chemotherapy does not include administering an immune checkpoint inhibitor. In some embodiments, the patient has a tumor classified as immunogenic. In some embodiments, the patient has a hot immune tumor. In some embodiments, the patient has an altered-immunosuppressed immune tumor. In some embodiments, the patient has an altered-excluded immune tumor. In some embodiments, the patient has a cold tumor. In some embodiments, the patient has a tumor that is classified as a C2 "IFN-γ Dominant" class cancer. In some embodiments, the patient has a tumor that is classified as a high "IFN-γ Signature" or a high "Expanded Immune Signature." In some embodiments, the patient has a tumor that is PD-L1 positive.

In some embodiments, a method for selecting a patient or patient population for cancer therapy that includes the administration of Compound 1 Pattern 1, for example Compound 1 Pattern 1 dihydrochloride, dihydrate, or a formulation produced from it with chemotherapy in a manner that increases the progression free survival or overall survival of the patient or patient population is provided comprising, determining if the cancer has a surrounding microenvironment that is favorable to immune modulation, is immunogenically susceptible to CDK4/6 inhibitor treatment, or is immunogenic, and if so, administering to the patient an effective amount of Compound 1 Pattern 1, for example Compound 1 Pattern 1 dihydrochloride, dihydrate, or a formulation produced from it in combination with an effective amount of cyclophosphamide. In some embodiments, the administration of Compound 1 Pattern 1, for example Compound 1 Pattern 1 dihydrochloride, dihydrate, or a formulation produced from it in combination with cyclophosphamide does not include administering an immune checkpoint inhibitor. In some embodiments, the patient has a tumor classified as immunogenic. In some embodiments, the patient has a hot immune tumor. In some embodiments, the patient has an altered-immunosuppressed immune tumor. In some embodiments, the patient has an altered-excluded immune tumor. In some embodiments, the patient has a cold tumor. In some embodiments, the patient has a tumor that is classified as a C2 "IFN-γ Dominant" class cancer. In some embodiments, the patient has a tumor that is classified as a high "IFN-γ Signature" or a high "Expanded Immune Signature." In some embodiments, the patient has a tumor that is PD-L1 positive.

In some embodiments, a method for selecting a patient or patient population for cancer therapy that includes the administration of a CDK 4/6 inhibitor with chemotherapy in a manner that increases the progression free survival or overall survival of the patient or patient population is provided comprising, determining if the cancer has a surrounding microenvironment that is favorable to immune modulation, is immunogenically susceptible to CDK4/6 inhibitor treatment, or is immunogenic, and if so, administering to the patient an effective amount of Compound 1 Pattern 1, for example Compound 1 Pattern 1 dihydrochloride, dihydrate, or a formulation produced from it in combination with an effective amount of trabectedin. In some embodiments, the administration of Compound 1 Pattern 1, for example Compound 1 Pattern 1 dihydrochloride, dihydrate, or a formulation produced from it in combination with trabectedin does not include administering an immune checkpoint inhibitor. In some embodiments, the patient has a tumor classified as immunogenic. In some embodiments, the patient has a hot immune tumor. In some embodiments, the patient has an altered-immunosuppressed immune tumor. In some embodiments, the patient has an altered-excluded immune tumor. In some embodiments, the patient has a cold tumor. In some embodiments, the patient has a tumor that is classified as a C2 "IFN-γ Dominant" class cancer. In some embodiments, the patient has a tumor that is classified as a high "IFN-γ Signature" or a high "Expanded Immune Signature." In some embodiments, the patient has a tumor that is PD-L1 positive.

In some embodiments, a method for selecting a patient or patient population for cancer therapy that includes the administration of Compound 1 Pattern 1, for example Compound 1 Pattern 1 dihydrochloride, dihydrate, or a formulation produced from it with chemotherapy in a manner that increases the progression free survival or overall survival of the patient or patient population is provided comprising, determining if the cancer has a surrounding microenvironment that is favorable to immune modulation, is immunogenically susceptible to CDK4/6 inhibitor treatment, or is immunogenic, and if so, administering to the patient an effective amount of Compound 1 Pattern 1, for example Compound 1 Pattern 1 dihydrochloride, dihydrate, or a formulation produced from it in combination with an effective amount of temozolomide. In some embodiments, the administration of Compound 1 Pattern 1, for example Compound 1 Pattern 1 dihydrochloride, dihydrate, or a formulation produced from it inhibitor in combination with temozolomide does not include administering an immune checkpoint inhibitor. In some embodiments, the patient has a tumor classified as immunogenic. In some embodiments, the patient has a hot immune tumor. In some embodiments, the patient has an altered-immunosuppressed immune tumor. In some embodiments, the patient has an altered-excluded immune tumor. In some embodiments, the patient has a cold tumor. In some embodiments, the patient has a tumor that is classified as a C2 "IFN-γ Dominant" class cancer. In some embodiments, the patient has a tumor that is classified as a high "IFN-γ Signature" or a high "Expanded Immune Signature." In some embodiments, the patient has a tumor that is PD-L1 positive.

In some embodiments, a method for selecting a patient or patient population for cancer therapy that includes the administration of Compound 1 Pattern 1, for example Compound 1 Pattern 1 dihydrochloride, dihydrate, or a formulation produced from it r with chemotherapy in a manner that increases the progression free survival or overall survival of the patient or patient population is provided comprising, determining if the cancer has a surrounding microenvironment that is favorable to immune modulation, is immunogenically susceptible to CDK4/6 inhibitor treatment, or is immunogenic, and if so, administering to the patient an effective amount of Compound 1 Pattern 1, for example Compound 1 Pattern 1 dihydrochloride, dihydrate, or a formulation produced from it in combination with an effective amount of melphalan. In some embodiments, the patient has a tumor classified as immunogenic. In some embodiments, the patient has a hot immune tumor. In some embodiments, the patient has an altered-immunosuppressed immune tumor. In some embodiments, the patient has an altered-excluded immune tumor. In some embodiments, the patient has a cold tumor. In some embodiments, the patient has a tumor that is classified as a C2 "IFN-γ Dominant" class cancer. In some embodiments, the patient has a tumor that is classified as a high "IFN-γ Signature" or a high "Expanded Immune Signature." In some embodiments, the patient has a tumor that is PD-L1 positive.

In some embodiments, a method for selecting a patient or patient population for cancer therapy that includes the administration of a CDK 4/6 inhibitor with chemotherapy in a manner that increases the progression free survival or overall survival of the patient or patient population is provided comprising, determining if the cancer has a surrounding microenvironment that is favorable to immune modulation, is immunogenically susceptible to CDK4/6 inhibitor treatment, or is immunogenic, and if so, administering to the patient an effective amount of Compound 1 Pattern 1, for example Compound 1 Pattern 1 dihydrochloride, dihydrate, or a formulation produced from it in combination with an effective amount of dacarbazine. In some embodiments, the patient has a tumor classified as immunogenic. In some embodiments, the patient has a hot immune tumor. In some embodiments, the patient has an altered-immunosuppressed immune tumor. In some embodiments, the patient has an altered-excluded immune tumor. In some embodiments, the patient has a cold tumor. In some embodiments, the patient has a tumor that is classified as a C2 "IFN-γ Dominant" class cancer. In some embodiments, the patient has a tumor that is classified as a high "IFN-γ Signature" or a high "Expanded Immune Signature." In some embodiments, the patient has a tumor that is PD-L1 positive.

In some embodiments, a method for selecting a patient or patient population for cancer therapy that includes the administration of Compound 1 Pattern 1, for example Compound 1 Pattern 1 dihydrochloride, dihydrate, or a formulation produced from it with chemotherapy in a manner that increases the progression free survival or overall survival of the patient or patient population is provided comprising, determining if the cancer has a surrounding microenvironment that is favorable to immune modulation, is immunogenically susceptible to CDK4/6 inhibitor treatment, or is immunogenic, and if so, administering to the patient an effective amount of Compound 1 Pattern 1, for example Compound 1 Pattern 1 dihydrochloride, dihydrate, or a formulation produced from it in combination with an effective amount of oxaliplatin. In some embodiments, the patient has a tumor classified as immunogenic. In some embodiments, the patient has a hot immune tumor. In some embodiments, the patient has an altered-immunosuppressed immune tumor. In some embodiments, the patient has an altered-excluded immune tumor. In some embodiments, the patient has a cold tumor. In some embodiments, the patient has a tumor that is classified as a C2 "IFN-γ Dominant" class cancer. In some embodiments, the patient has a tumor that is classified as a high "IFN-γ Signature" or a high "Expanded Immune Signature." In some embodiments, the patient has a tumor that is PD-L1 positive.

In some embodiments, a method for selecting a patient or patient population for cancer therapy that includes the administration of Compound 1 Pattern 1, for example Compound 1 Pattern 1 dihydrochloride, dihydrate, or a formulation produced from it with chemotherapy in a manner that increases the progression free survival or overall survival of the patient or patient population is provided comprising, determining if the cancer has a surrounding microenvironment that is favorable to immune modulation, is immunogenically susceptible to CDK4/6 inhibitor treatment, or is immunogenic, and if so, administering to the patient an effective amount of Compound 1 Pattern 1, for example Compound 1 Pattern 1 dihydrochloride, dihydrate, or a formulation produced from it in combination with an effective amount of methotrexate. In some embodiments, the patient has a tumor classified as immunogenic. In some embodiments, the patient has a hot immune tumor. In some embodiments, the patient has an altered-immunosuppressed immune tumor. In some embodiments, the patient has an altered-excluded immune tumor. In some embodiments, the patient has a cold tumor. In some embodiments, the patient has a tumor that is classified as a C2 "IFN-γ Dominant" class cancer. In some embodiments, the patient has a tumor that is classified as a high "IFN-γ Signature" or a high "Expanded Immune Signature." In some embodiments, the patient has a tumor that is PD-L1 positive.

In some embodiments, a method for selecting a patient or patient population for cancer therapy that includes the administration of a CDK 4/6 inhibitor with chemotherapy in a manner that increases the progression free survival or overall survival of the patient or patient population is provided comprising, determining if the cancer has a surrounding microenvironment that is favorable to immune modulation, is immunogenically susceptible to CDK4/6 inhibitor treatment, or is immunogenic, and if so, administering to the patient an effective amount of Compound 1 Pattern 1, for example Compound 1 Pattern 1 dihydrochloride, dihydrate, or a formulation produced from it in combination with an effective amount of 5-fluorouracil (5-FU). In some embodiments, the patient has a tumor classified as immunogenic. In some embodiments, the patient has a hot immune tumor. In some embodiments, the patient has an altered-immunosuppressed immune tumor. In some embodiments, the patient has an altered-excluded immune tumor. In some embodiments, the patient has a cold tumor. In some embodiments, the patient has a tumor that is classified as a C2 "IFN-γ Dominant" class cancer. In some embodiments, the patient has a tumor that is classified as a high "IFN-γ Signature" or a high "Expanded Immune Signature." In some embodiments, the patient has a tumor that is PD-L1 positive.

In some embodiments, a method for selecting a patient or patient population for cancer therapy that includes the administration of Compound 1 Pattern 1, for example Compound 1 Pattern 1 dihydrochloride, dihydrate, or a formulation produced from it with chemotherapy in a manner that increases the progression free survival or overall survival of the patient or patient population is provided comprising, determining if the cancer has a surrounding microenvironment that is favorable to immune modulation, is immunogenically susceptible to CDK4/6 inhibitor treatment, or is immunogenic, and if so, administering to the patient an effective amount of Compound 1 Pattern 1, for example Compound 1 Pattern 1 dihydrochloride, dihydrate, or a formulation produced from it in combination with an effective amount of gemcitabine. In some embodiments, the patient has a tumor classified as immunogenic. In some embodiments, the patient has a hot immune tumor. In some embodiments, the patient has an altered-immunosuppressed immune tumor. In some embodiments, the patient has an altered-excluded immune tumor. In some embodiments, the patient has a cold tumor. In some embodiments, the patient has a tumor that is classified as a C2 "IFN-γ Dominant" class cancer. In some embodiments, the patient has a tumor that is classified as a high "IFN-γ Signature" or a high "Expanded Immune Signature."

In some embodiments, a method for selecting a patient or patient population for cancer therapy that includes the administration of Compound 1 Pattern 1, for example Compound 1 Pattern 1 dihydrochloride, dihydrate, or a formulation produced from it with chemotherapy in a manner that increases the progression free survival or overall survival of the patient or patient population is provided comprising, determining if the cancer has a surrounding microenvironment that is favorable to immune modulation, is immunogenically susceptible to CDK4/6 inhibitor treatment, or is immunogenic, and if so, administering to the patient an effective amount of Compound 1 Pattern 1, for example Compound 1 Pattern 1 dihydrochloride, dihydrate, or a formulation produced from it in combination with an effective amount of mitoxantrone. In some embodiments, the patient has a tumor classified as immunogenic. In some embodiments, the patient has a hot immune tumor. In some embodiments, the patient has an altered-immunosuppressed immune tumor. In some embodiments, the patient has an altered-excluded immune tumor. In some embodiments, the patient has a cold tumor. In some embodiments, the patient has a tumor that is classified as a C2 "IFN-γ Dominant" class cancer. In some embodiments, the patient has a tumor that is classified as a high "IFN-γ Signature" or a high "Expanded Immune Signature." In some embodiments, the patient has a tumor that is PD-L1 positive.

In some embodiments, a method for selecting a patient or patient population for cancer therapy that includes the administration of a CDK 4/6 inhibitor with chemotherapy in a manner that increases the progression free survival or overall survival of the patient or patient population is provided comprising, determining if the cancer has a surrounding microenvironment that is favorable to immune modulation, is immunogenically susceptible to CDK4/6 inhibitor treatment, or is immunogenic, and if so, administering to the patient an effective amount of Compound 1 Pattern 1, for example Compound 1 Pattern 1 dihydrochloride, dihydrate, or a formulation produced from it in combination with an effective amount of doxorubicin. In some embodiments, the administration of Compound 1 Pattern 1, for example Compound 1 Pattern 1 dihydrochloride, dihydrate, or a formulation produced from it in combination with doxorubicin does not include administering an immune checkpoint inhibitor. In some embodiments, the patient has a tumor classified as immunogenic. In some embodiments, the patient has a hot immune tumor. In some embodiments, the patient has an altered-immunosuppressed immune tumor. In some embodiments, the patient has an altered-excluded immune tumor. In some embodiments, the patient has a cold tumor. In some embodiments, the patient has a tumor that is classified as a C2 "IFN-γ Dominant" class cancer. In some embodiments, the patient has a tumor that is classified as a high "IFN-γ Signature" or a high "Expanded Immune Signature." In some embodiments, the patient has a tumor that is PD-L1 positive.

In some embodiments, a method for selecting a patient or patient population for cancer therapy that includes the administration of Compound 1 Pattern 1, for example Compound 1 Pattern 1 dihydrochloride, dihydrate, or a formulation produced from it with chemotherapy in a manner that increases the progression free survival or overall survival of the patient or patient population is provided comprising, determining if the cancer has a surrounding microenvironment that is favorable to immune modulation, is immunogenically susceptible to CDK4/6 inhibitor treatment, or is immunogenic, and if so, administering to the patient an effective amount of Compound 1 Pattern 1, for example Compound 1 Pattern 1 dihydrochloride, dihydrate, or a formulation produced from it in combination with an effective amount of daunorubicin. In some embodiments, the patient has a tumor classified as immunogenic. In some embodiments, the patient has a hot immune tumor. In some embodiments, the patient has an altered-immunosuppressed immune tumor. In some embodiments, the patient has an altered-excluded immune tumor. In some embodiments, the patient has a cold tumor. In some embodiments, the patient has a tumor that is classified as a C2 "IFN-γ Dominant" class cancer. In some embodiments, the patient has a tumor that is classified as a high "IFN-γ Signature" or a high "Expanded Immune Signature." In some embodiments, the patient has a tumor that is PD-L1 positive.

In some embodiments, a method for selecting a patient or patient population for cancer therapy that includes the administration of Compound 1 Pattern 1, for example Compound 1 Pattern 1 dihydrochloride, dihydrate, or a formulation produced from it with chemotherapy in a manner that increases the progression free survival or overall survival of the patient or patient population is provided comprising, determining if the cancer has a surrounding microenvironment that is favorable to immune modulation, is immunogenically susceptible to CDK4/6 inhibitor treatment, or is immunogenic, and if so, administering to the patient an effective amount of Compound 1 Pattern 1, for example Compound 1 Pattern 1 dihydrochloride, dihydrate, or a formulation produced from it in combination with an effective amount of idarubicin In some embodiments, the patient has a tumor classified as immunogenic. In some embodiments, the patient has a hot immune tumor. In some embodiments, the patient has an altered-immunosuppressed immune tumor. In some embodiments, the patient has an altered-excluded immune tumor. In some embodiments, the patient has a cold tumor. In some embodiments, the patient has a tumor that is classified as a C2 "IFN-γ Dominant" class cancer. In some embodiments, the patient has a tumor that is classified as a high "IFN-γ Signature" or a high "Expanded Immune Signature." In some embodiments, the patient has a tumor that is PD-L1 positive.

In some embodiments, a method for selecting a patient or patient population for cancer therapy that includes the administration of Compound 1 Pattern 1, for example Compound 1 Pattern 1 dihydrochloride, dihydrate, or a formulation produced from it with chemotherapy in a manner that increases the progression free survival or overall survival of the patient or patient population is provided comprising, determining if the cancer has a surrounding microenvironment that is favorable to immune modulation, is immunogenically susceptible to CDK4/6 inhibitor treatment, or is immunogenic, and if so, administering to the patient an effective amount of Compound 1 Pattern 1, for example Compound 1 Pattern 1 dihydrochloride, dihydrate, or a formulation produced from it in combination with an effective amount of valrubicin. In some embodiments, the patient has a tumor classified as immunogenic. In some embodiments, the patient has a hot immune tumor. In some embodiments, the patient has an altered-immunosuppressed immune tumor. In some embodiments, the patient has an altered-excluded immune tumor. In some embodiments, the patient has a cold tumor. In some embodiments, the patient has a tumor that is classified as a C2 "IFN-γ Dominant" class cancer. In some embodiments, the patient has a tumor that is classified as a high "IFN-γ Signature" or a high "Expanded Immune Signature." In some embodiments, the patient has a tumor that is PD-L1 positive.

In some embodiments, a method for selecting a patient or patient population for cancer therapy that includes the administration of a CDK 4/6 inhibitor with chemotherapy in a manner that increases the progression free survival or overall survival of the patient or patient population is provided comprising, determining if the cancer has a surrounding microenvironment that is favorable to immune modulation, is immunogenically susceptible to CDK4/6 inhibitor treatment, or is immunogenic, and if so, administering to the patient an effective amount of Compound 1 Pattern 1, for example Compound 1 Pattern 1 dihydrochloride, dihydrate, or a formulation produced from it in combination with an effective amount of epirubicin. In some embodiments, the patient has a tumor classified as immunogenic. In some embodiments, the patient has a hot immune tumor. In some embodiments, the patient has an altered-immunosuppressed immune tumor. In some embodiments, the patient has an altered-excluded immune tumor. In some embodiments, the patient has a cold tumor. In some embodiments, the patient has a tumor that is classified as a C2 "IFN-γ Dominant" class cancer. In some embodiments, the patient has a tumor that is classified as a high "IFN-γ Signature" or a high "Expanded Immune Signature." In some embodiments, the patient has a tumor that is PD-L1 positive.

In some embodiments, a method for selecting a patient or patient population for cancer therapy that includes the administration of Compound 1 Pattern 1, for example Compound 1 Pattern 1 dihydrochloride, dihydrate, or a formulation produced from it with chemotherapy in a manner that increases the progression free survival or overall survival of the patient or patient population is provided comprising, determining if the cancer has a surrounding microenvironment that is favorable to immune modulation, is immunogenically susceptible to CDK4/6 inhibitor treatment, or is immunogenic, and if so, administering to the patient an effective amount of Compound 1 Pattern 1, for example Compound 1 Pattern 1 dihydrochloride, dihydrate, or a formulation produced from it combination with an effective amount of bleomycin. In some embodiments, the administration of Compound 1 Pattern 1, for example Compound 1 Pattern 1 dihydrochloride, dihydrate, or a formulation produced from it in combination with bleomycin does not include administering an immune checkpoint inhibitor. In some embodiments, the patient has a hot immune tumor. In some embodiments, the patient has a tumor classified as immunogenic. In some embodiments, the patient has a hot immune tumor. In some embodiments, the patient has an altered-immunosuppressed immune tumor. In some embodiments, the patient has an altered-excluded immune tumor. In some embodiments, the patient has a cold tumor. In some embodiments, the patient has a tumor that is classified as a C2 "IFN-γ Dominant" class cancer. In some embodiments, the patient has a tumor that is classified as a high "IFN-γ Signature" or a high "Expanded Immune Signature."

In some embodiments, a method for selecting a patient or patient population for cancer therapy that includes the administration of Compound 1 Pattern 1, for example Compound 1 Pattern 1 dihydrochloride, dihydrate, or a formulation produced from it with chemotherapy in a manner that increases the progression free survival or overall survival of the patient or patient population is provided comprising, determining if the cancer has a surrounding microenvironment that is favorable to immune modulation, is immunogenically susceptible to CDK4/6 inhibitor treatment, or is immunogenic, and if so, administering to the patient an effective amount of Compound 1 Pattern 1, for example Compound 1 Pattern 1 dihydrochloride, dihydrate, or a formulation produced from it in combination with an effective amount of bortezomib. In some embodiments, the administration of Compound 1 Pattern 1, for example Compound 1 Pattern 1 dihydrochloride, dihydrate, or a formulation produced from it in combination with bortezomib does not include administering an immune checkpoint inhibitor. In some embodiments, the patient has a tumor classified as immunogenic. In some embodiments, the patient has a hot immune tumor. In some embodiments, the patient has an altered-immunosuppressed immune tumor. In some embodiments, the patient has an altered-excluded immune tumor. In some embodiments, the patient has a cold tumor. In some embodiments, the patient has a tumor that is classified as a C2 "IFN-γ Dominant" class cancer. In some embodiments, the patient has a tumor that is classified as a high "IFN-γ Signature" or a high "Expanded Immune Signature." In some embodiments, the patient has a tumor that is PD-L1 positive.

In some embodiments, a method for selecting a patient or patient population for cancer therapy that includes the administration of Compound 1 Pattern 1, for example Compound 1 Pattern 1 dihydrochloride, dihydrate, or a formulation produced from it with chemotherapy in a manner that increases the progression free survival or overall survival of the patient or patient population is provided comprising, determining if the cancer has a surrounding microenvironment that is favorable to immune modulation, is immunogenically susceptible to CDK4/6 inhibitor treatment, or is immunogenic, and if so, administering to the patient an effective amount of Compound 1 Pattern 1, for example Compound 1 Pattern 1 dihydrochloride, dihydrate, or a formulation produced from it in combination with an effective amount of paclitaxel. In some embodiments, the administration of Compound 1 Pattern 1, for example Compound 1 Pattern 1 dihydrochloride, dihydrate, or a formulation produced from it in combination with paclitaxel does not include administering an immune checkpoint inhibitor. In some embodiments, the patient has a tumor classified as immunogenic. In some embodiments, the patient has a hot immune tumor. In some embodiments, the patient has an altered-immunosuppressed immune tumor. In some embodiments, the patient has an altered-excluded immune tumor. In some embodiments, the patient has a cold tumor. In some embodiments, the patient has a tumor that is classified as a C2 "IFN-γ Dominant" class cancer. In some embodiments, the patient has a tumor that is classified as a high "IFN-γ Signature" or a high "Expanded Immune Signature." In some embodiments, the patient has a tumor that is PD-L1 positive.

In some embodiments, a method for selecting a patient or patient population for cancer therapy that includes the administration of Compound 1 Pattern 1, for example Compound 1 Pattern 1 dihydrochloride, dihydrate, or a formulation produced from it with chemotherapy in a manner that increases the progression free survival or overall survival of the patient or patient population is provided comprising, determining if the cancer has a surrounding microenvironment that is favorable to immune modulation, is immunogenically susceptible to CDK4/6 inhibitor treatment, or is immunogenic, and if so, administering to the patient an effective amount of Compound 1 Pattern 1, for example Compound 1 Pattern 1 dihydrochloride, dihydrate, or a formulation produced from it Compound 1 Pattern 1, for example Compound 1 Pattern 1 dihydrochloride, dihydrate, or a formulation produced from it in combination with an effective amount of docetaxel. In some embodiments, the administration of Compound 1 Pattern 1, for example Compound 1 Pattern 1 dihydrochloride, dihydrate, or a formulation produced from it in combination with docetaxel does not include administering an immune checkpoint inhibitor. In some embodiments, the patient has a tumor classified as immunogenic. In some embodiments, the patient has a hot immune tumor. In some embodiments, the patient has an altered-immunosuppressed immune tumor. In some embodiments, the patient has an altered-excluded immune tumor. In some embodiments, the patient has a cold tumor. In some embodiments, the patient has a tumor that is classified as a C2 "IFN-γ Dominant" class cancer. In some embodiments, the patient has a tumor that is classified as a high "IFN-γ Signature" or a high "Expanded Immune Signature." In some embodiments, the patient has a tumor that is PD-L1 positive.

In some embodiments, a method for selecting a patient or patient population for cancer therapy that includes the administration of Compound 1 Pattern 1, for example Compound 1 Pattern 1 dihydrochloride, dihydrate, or a formulation produced from it with chemotherapy in a manner that increases the progression free survival or overall survival of the patient or patient population is provided comprising, determining if the cancer has a surrounding microenvironment that is favorable to immune modulation, is immunogenically susceptible to CDK4/6 inhibitor treatment, or is immunogenic, and if so, administering to the patient an effective amount of Compound 1 Pattern 1, for example Compound 1 Pattern 1 dihydrochloride, dihydrate, or a formulation produced from it in combination with an effective amount of cabazitaxel. In some embodiments, the administration of Compound 1 Pattern 1, for example Compound 1 Pattern 1 dihydrochloride, dihydrate, or a formulation produced from it in combination with cabazitaxel does not include administering an immune checkpoint inhibitor. In some embodiments, the patient has a tumor classified as immunogenic. In some embodiments, the patient has a hot immune tumor. In some embodiments, the patient has an altered-immunosuppressed immune tumor. In some embodiments, the patient has an altered-excluded immune tumor. In some embodiments, the patient has a cold tumor. In some embodiments, the patient has a tumor that is classified as a C2 "IFN-γ Dominant" class cancer. In some embodiments, the patient has a tumor that is classified as a high "IFN-γ

Signature" or a high "Expanded Immune Signature." In some embodiments, the patient has a tumor that is PD-L1 positive.

In some embodiments, a method for selecting a patient or patient population for cancer therapy that includes the administration of a CDK 4/6 inhibitor with chemotherapy in a manner that increases the progression free survival or overall survival of the patient or patient population is provided comprising, determining if the cancer has a surrounding microenvironment that is favorable to immune modulation, is immunogenically susceptible to CDK4/6 inhibitor treatment, or is immunogenic, and if so, administering to the patient an effective amount of Compound 1 Pattern 1, for example Compound 1 Pattern 1 dihydrochloride, dihydrate, or a formulation produced from it in combination with an effective amount of topotecan. In some embodiments, the administration of Compound 1 Pattern 1, for example Compound 1 Pattern 1 dihydrochloride, dihydrate, or a formulation produced from it in combination with topotecan does not include administering an immune checkpoint inhibitor. In some embodiments, the patient has a tumor classified as immunogenic. In some embodiments, the patient has a hot immune tumor. In some embodiments, the patient has an altered-immunosuppressed immune tumor. In some embodiments, the patient has an altered-excluded immune tumor. In some embodiments, the patient has a cold tumor. In some embodiments, the patient has a tumor that is classified as a C2 "IFN-γ Dominant" class cancer. In some embodiments, the patient has a tumor that is classified as a high "IFN-γ Signature" or a high "Expanded Immune Signature." In some embodiments, the patient has a tumor that is PD-L1 positive.

In some embodiments, a method for selecting a patient or patient population for cancer therapy that includes the administration of Compound 1 Pattern 1, for example Compound 1 Pattern 1 dihydrochloride, dihydrate, or a formulation produced from it with chemotherapy in a manner that increases the progression free survival or overall survival of the patient or patient population is provided comprising, determining if the cancer has a surrounding microenvironment that is favorable to immune modulation, is immunogenically susceptible to CDK4/6 inhibitor treatment, or is immunogenic, and if so, administering to the patient an effective amount of Compound 1 Pattern 1, for example Compound 1 Pattern 1 dihydrochloride, dihydrate, or a formulation produced from it in combination with an effective amount of etoposide. In some embodiments, the administration of Compound 1 Pattern 1, for example Compound 1 Pattern 1 dihydrochloride, dihydrate, or a formulation produced from it in combination with etoposide does not include administering an immune checkpoint inhibitor. In some embodiments, the patient has a tumor classified as immunogenic. In some embodiments, the patient has a hot immune tumor. In some embodiments, the patient has an altered-immunosuppressed immune tumor. In some embodiments, the patient has an altered-excluded immune tumor. In some embodiments, the patient has a cold tumor. In some embodiments, the patient has a tumor that is classified as a C2 "IFN-γ Dominant" class cancer. In some embodiments, the patient has a tumor that is classified as a high "IFN-γ Signature" or a high "Expanded Immune Signature." In some embodiments, the patient has a tumor that is PD-L1 positive.

In some embodiments, a method for selecting a patient or patient population for cancer therapy that includes the administration of Compound 1 Pattern 1, for example Compound 1 Pattern 1 dihydrochloride, dihydrate, or a formulation produced from it with chemotherapy in a manner that increases the progression free survival or overall survival of the patient or patient population is provided comprising, determining if the cancer has a surrounding microenvironment that is favorable to immune modulation, is immunogenically susceptible to CDK4/6 inhibitor treatment, or is immunogenic, and if so, administering to the patient an effective amount of Compound 1 Pattern 1, for example Compound 1 Pattern 1 dihydrochloride, dihydrate, or a formulation produced from it in combination with an effective amount of irinotecan. In some embodiments, the administration of Compound 1 Pattern 1, for example Compound 1 Pattern 1 dihydrochloride, dihydrate, or a formulation produced from it in combination with irinotecan does not include administering an immune checkpoint inhibitor. In some embodiments, the patient has a tumor classified as immunogenic. In some embodiments, the patient has a hot immune tumor. In some embodiments, the patient has an altered-immunosuppressed immune tumor. In some embodiments, the patient has an altered-excluded immune tumor. In some embodiments, the patient has a cold tumor. In some embodiments, the patient has a tumor that is classified as a C2 "IFN-γ Dominant" class cancer. In some embodiments, the patient has a tumor that is classified as a high "IFN-γ Signature" or a high "Expanded Immune Signature." In some embodiments, the patient has a tumor that is PD-L1 positive.

In some embodiments, a method for selecting a patient or patient population for cancer therapy that includes the administration of Compound 1 Pattern 1, for example Compound 1 Pattern 1 dihydrochloride, dihydrate, or a formulation produced from it with chemotherapy in a manner that increases the progression free survival or overall survival of the patient or patient population is provided comprising, determining if the cancer has a surrounding microenvironment that is favorable to immune modulation, is immunogenically susceptible to CDK4/6 inhibitor treatment, or is immunogenic, and if so, administering to the patient an effective amount of Compound 1 Pattern 1, for example Compound 1 Pattern 1 dihydrochloride, dihydrate, or a formulation produced from it in combination with an effective amount of cisplatin. In some embodiments, the administration of Compound 1 Pattern 1, for example Compound 1 Pattern 1 dihydrochloride, dihydrate, or a formulation produced from it in combination with cisplatin does not include administering an immune checkpoint inhibitor. In some embodiments, the patient has a tumor classified as immunogenic. In some embodiments, the patient has a hot immune tumor. In some embodiments, the patient has an altered-immunosuppressed immune tumor. In some embodiments, the patient has an altered-excluded immune tumor. In some embodiments, the patient has a cold tumor. In some embodiments, the patient has a tumor that is classified as a C2 "IFN-γ Dominant" class cancer. In some embodiments, the patient has a tumor that is classified as a high "IFN-γ Signature" or a high "Expanded Immune Signature." In some embodiments, the patient has a tumor that is PD-L1 positive.

In some embodiments, a method for selecting a patient or patient population for cancer therapy that includes the administration of Compound 1 Pattern 1, for example Compound 1 Pattern 1 dihydrochloride, dihydrate, or a formulation produced from it with chemotherapy in a manner that increases the progression free survival or overall survival of the patient or patient population is provided comprising, determining if the cancer has a surrounding microenvironment that is favorable to immune modulation, is immunogenically susceptible to CDK4/6 inhibitor treatment, or is immunogenic, and if so, administering to the patient an effective amount of Compound 1 Pattern 1, for example Compound 1 Pattern 1 dihydrochloride, dihydrate, or a formulation produced from it in combination with an effective amount of carboplatin. In some embodiments, the administration of Compound 1 Pattern 1, for example Compound 1 Pattern 1 dihydrochloride, dihydrate, or a formulation produced from it in combination with carboplatin does not include administering an immune checkpoint inhibitor. In some embodiments, the patient has a tumor classified as immunogenic. In some embodiments, the patient has a hot immune tumor. In some embodiments, the patient has an altered-immunosuppressed immune tumor. In some embodiments, the patient has an altered-excluded immune tumor. In some embodiments, the patient has a cold tumor. In some embodiments, the patient has a tumor that is classified as a C2 "IFN-γ Dominant" class cancer. In some embodiments, the patient has a tumor that is classified as a high "IFN-γ Signature" or a high "Expanded Immune Signature." In some embodiments, the patient has a tumor that is PD-L1 positive.

In some embodiments, a method for selecting a patient or patient population for cancer therapy that includes the administration of Compound 1 Pattern 1, for example Compound 1 Pattern 1 dihydrochloride, dihydrate, or a formulation produced from it with chemotherapy in a manner that increases the progression free survival or overall survival of the patient or patient population is provided comprising, determining if the cancer has a surrounding microenvironment that is favorable to immune modulation, is immunogenically susceptible to CDK4/6 inhibitor treatment, or is immunogenic, and if so, administering to the patient an effective amount of Compound 1 Pattern 1, for example Compound 1 Pattern 1 dihydrochloride, dihydrate, or a formulation produced from it in combination with an effective amount of vinblastine. In some embodiments, the administration of Compound 1 Pattern 1, for example Compound 1 Pattern 1 dihydrochloride, dihydrate, or a formulation produced from it in combination with vinblastine does not include administering an immune checkpoint inhibitor. In some embodiments, the patient has a tumor classified as immunogenic. In some embodiments, the patient has a hot immune tumor. In some embodiments, the patient has an altered-immunosuppressed immune tumor. In some embodiments, the patient has an altered-excluded immune tumor. In some embodiments, the patient has a cold tumor. In some embodiments, the patient has a tumor that is classified as a C2 "IFN-γ Dominant" class cancer. In some embodiments, the patient has a tumor that is classified as a high "IFN-γ Signature" or a high "Expanded Immune Signature." In some embodiments, the patient has a tumor that is PD-L1 positive.

In some embodiments, a method for selecting a patient or patient population for cancer therapy that includes the administration of Compound 1 Pattern 1, for example Compound 1 Pattern 1 dihydrochloride, dihydrate, or a formulation produced from it with chemotherapy in a manner that increases the progression free survival or overall survival of the patient or patient population is provided comprising, determining if the cancer has a surrounding microenvironment that is favorable to immune modulation, is immunogenically susceptible to CDK4/6 inhibitor treatment, or is immunogenic, and if so, administering to the patient an effective amount of Compound 1 Pattern 1, for example Compound 1 Pattern 1 dihydrochloride, dihydrate, or a formulation produced from it in combination with an effective amount of vincristine. In some embodiments, the administration of Compound 1 Pattern 1, for example Compound 1 Pattern 1 dihydrochloride, dihydrate, or a formulation produced from it in combination with vincristine does not include administering an immune checkpoint inhibitor. In some embodiments, the patient has a tumor classified as immunogenic. In some embodiments, the patient has a hot immune tumor. In some embodiments, the patient has an altered-immunosuppressed immune tumor. In some embodiments, the patient has an altered-excluded immune tumor. In some embodiments, the patient has a cold tumor. In some embodiments, the patient has a tumor that is classified as a C2 "IFN-γ Dominant" class cancer. In some embodiments, the patient has a tumor that is classified as a high "IFN-γ Signature" or a high "Expanded Immune Signature." In some embodiments, the patient has a tumor that is PD-L1 positive.

In some embodiments, a method for selecting a patient or patient population for cancer therapy that includes the administration of Compound 1 Pattern 1, for example Compound 1 Pattern 1 dihydrochloride, dihydrate, or a formulation produced from it with chemotherapy in a manner that increases the progression free survival or overall survival of the patient or patient population is provided comprising, determining if the cancer has a surrounding microenvironment that is favorable to immune modulation, is immunogenically susceptible to CDK4/6 inhibitor treatment, or is immunogenic, and if so, administering to the patient an effective amount of Compound 1 Pattern 1, for example Compound 1 Pattern 1 dihydrochloride, dihydrate, or a formulation produced from it in combination with an effective amount of vinorelbine. In some embodiments, the administration of Compound 1 Pattern 1, for example Compound 1 Pattern 1 dihydrochloride, dihydrate, or a formulation produced from it in combination with vinorelbine does not include administering an immune checkpoint inhibitor. In some embodiments, the patient has a tumor classified as immunogenic. In some embodiments, the patient has a hot immune tumor. In some embodiments, the patient has an altered-immunosuppressed immune tumor. In some embodiments, the patient has an altered-excluded immune tumor. In some embodiments, the patient has a cold tumor. In some embodiments, the patient has a tumor that is classified as a C2 "IFN-γ Dominant" class cancer. In some embodiments, the patient has a tumor that is classified as a high "IFN-γ Signature" or a high "Expanded Immune Signature." In some embodiments, the patient has a tumor that is PD-L1 positive.

In some embodiments, a method for selecting a patient or patient population for cancer therapy that includes the administration of Compound 1 Pattern 1, for example Compound 1 Pattern 1 dihydrochloride, dihydrate, or a formulation produced from it with chemotherapy in a manner that increases the progression free survival or overall survival of the patient or patient population is provided comprising, determining if the cancer has a surrounding microenvironment that is favorable to immune modulation, is immunogenically susceptible to CDK4/6 inhibitor treatment, or is immunogenic, and if so, administering to the patient an effective amount of Compound 1 Pattern 1, for example Compound 1 Pattern 1 dihydrochloride, dihydrate, or a formulation produced from it in combination with an effective amount of vindesine. In some embodiments, the administration of Compound 1 Pattern 1, for example Compound 1 Pattern 1 dihydrochloride, dihydrate, or a formulation produced from it in combination with vindesine does not include administering an immune checkpoint inhibitor. In some embodiments, the patient has a tumor classified as immunogenic. In some embodiments, the patient has a hot immune tumor. In some embodiments, the patient has an altered-immunosuppressed immune tumor. In some embodiments, the patient has an altered-excluded immune tumor. In some embodiments, the patient has a cold tumor. In some embodiments, the patient has a tumor that is classified as a C2 "IFN-γ Dominant" class cancer. In some embodiments, the patient has a tumor that is classified as a high "IFN-γ Signature" or a high "Expanded Immune Signature." In some embodiments, the patient has a tumor that is PD-L1 positive.

In some embodiments, a method for selecting a patient or patient population for cancer therapy that includes the administration of Compound 1 Pattern 1, for example Compound 1 Pattern 1 dihydrochloride, dihydrate, or a formulation produced from it with chemotherapy in a manner that increases the progression free survival or overall survival of the patient or patient population is provided comprising, determining if the cancer has a surrounding microenvironment that is favorable to immune modulation, is immunogenically susceptible to CDK4/6 inhibitor treatment, or is immunogenic, and if so, administering to the patient an effective amount of Compound 1 Pattern 1, for example Compound 1 Pattern 1 dihydrochloride, dihydrate, or a formulation produced from it in combination with an effective amount of diaziquone. In some embodiments, the administration of Compound 1 Pattern 1, for example Compound 1 Pattern 1 dihydrochloride, dihydrate, or a formulation produced from it in combination with diaziquone does not include administering an immune checkpoint inhibitor. In some embodiments, the patient has a tumor classified as immunogenic. In some embodiments, the patient has a hot immune tumor. In some embodiments, the patient has an altered-immunosuppressed immune tumor. In some embodiments, the patient has an altered-excluded immune tumor. In some embodiments, the patient has a cold tumor. In some embodiments, the patient has a tumor that is classified as a C2 "IFN-γ Dominant" class cancer. In some embodiments, the patient has a tumor that is classified as a high "IFN-γ Signature" or a high "Expanded Immune Signature." In some embodiments, the patient has a tumor that is PD-L1 positive.

In some embodiments, a method for selecting a patient or patient population for cancer therapy that includes the administration of Compound 1 Pattern 1, for example Compound 1 Pattern 1 dihydrochloride, dihydrate, or a formulation produced from it with chemotherapy in a manner that increases the progression free survival or overall survival of the patient or patient population is provided comprising, determining if the cancer has a surrounding microenvironment that is favorable to immune modulation, is immunogenically susceptible to CDK4/6 inhibitor treatment, or is immunogenic, and if so, administering to the patient an effective amount of Compound 1 Pattern 1, for example Compound 1 Pattern 1 dihydrochloride, dihydrate, or a formulation produced from it in combination with an effective amount of mechlorethamine. In some embodiments, the administration of Compound 1 Pattern 1, for example Compound 1 Pattern 1 dihydrochloride, dihydrate, or a formulation produced from it in combination with mechlorethamine does not include administering an immune checkpoint inhibitor. In some embodiments, the patient has a tumor classified as immunogenic. In some embodiments, the patient has a hot immune tumor. In some embodiments, the patient has an altered-immunosuppressed immune tumor. In some embodiments, the patient has an altered-excluded immune tumor. In some embodiments, the patient has a cold tumor. In some embodiments, the patient has a tumor that is classified as a C2 "IFN-γ Dominant" class cancer. In some embodiments, the patient has a tumor that is classified as a high "IFN-γ Signature" or a high "Expanded Immune Signature." In some embodiments, the patient has a tumor that is PD-L1 positive.

In some embodiments, a method for selecting a patient or patient population for cancer therapy that includes the administration of Compound 1 Pattern 1, for example Compound 1 Pattern 1 dihydrochloride, dihydrate, or a formulation produced from it with chemotherapy in a manner that increases the progression free survival or overall survival of the patient or patient population is provided comprising, determining if the cancer has a surrounding microenvironment that is favorable to immune modulation, is immunogenically susceptible to CDK4/6 inhibitor treatment, or is immunogenic, and if so, administering to the patient an effective amount of Compound 1 Pattern 1, for example Compound 1 Pattern 1 dihydrochloride, dihydrate, or a formulation produced from it in combination with an effective amount of mitomycin C. In some embodiments, the administration of Compound 1 Pattern 1, for example Compound 1 Pattern 1 dihydrochloride, dihydrate, or a formulation produced from it in combination with mitomycin C does not include administering an immune checkpoint inhibitor. In some embodiments, the patient has a tumor classified as immunogenic. In some embodiments, the patient has a hot immune tumor. In some embodiments, the patient has an altered-immunosuppressed immune tumor. In some embodiments, the patient has an altered-excluded immune tumor. In some embodiments, the patient has a cold tumor. In some embodiments, the patient has a tumor that is classified as a C2 "IFN-γ Dominant" class cancer. In some embodiments, the patient has a tumor that is classified as a high "IFN-γ Signature" or a high "Expanded Immune Signature." In some embodiments, the patient has a tumor that is PD-L1 positive.

In some embodiments, a method for selecting a patient or patient population for cancer therapy that includes the administration of Compound 1 Pattern 1, for example Compound 1 Pattern 1 dihydrochloride, dihydrate, or a formulation produced from it with chemotherapy in a manner that increases the progression free survival or overall survival of the patient or patient population is provided comprising, determining if the cancer has a surrounding microenvironment that is favorable to immune modulation, is immunogenically susceptible to CDK4/6 inhibitor treatment, or is immunogenic, and if so, administering to the patient an effective amount of Compound 1 Pattern 1, for example Compound 1 Pattern 1 dihydrochloride, dihydrate, or a formulation produced from it in combination with an effective amount of fludarabine. In some embodiments, the administration of Compound 1 Pattern 1, for example Compound 1 Pattern 1 dihydrochloride, dihydrate, or a formulation produced from it in combination with fludarabine does not include administering an immune checkpoint inhibitor. In some embodiments, the patient has a tumor classified as immunogenic. In some embodiments, the patient has a hot immune tumor. In some embodiments, the patient has an altered-immunosuppressed immune tumor. In some embodiments, the patient has an altered-excluded immune tumor. In some embodiments, the patient has a cold tumor. In some embodiments, the patient has a tumor that is classified as a C2 "IFN-γ Dominant" class cancer. In some embodiments, the patient has a tumor that is classified as a high "IFN-γ

Signature" or a high "Expanded Immune Signature." In some embodiments, the patient has a tumor that is PD-L1 positive.

In some embodiments, a method for selecting a patient or patient population for cancer therapy that includes the administration of Compound 1 Pattern 1, for example Compound 1 Pattern 1 dihydrochloride, dihydrate, or a formulation produced from it with chemotherapy in a manner that increases the progression free survival or overall survival of the patient or patient population is provided comprising, determining if the cancer has a surrounding microenvironment that is favorable to immune modulation, is immunogenically susceptible to CDK4/6 inhibitor treatment, or is immunogenic, and if so, administering to the patient an effective amount of Compound 1 Pattern 1, for example Compound 1 Pattern 1 dihydrochloride, dihydrate, or a formulation produced from it in combination with an effective amount of cytosine arabinoside. In some embodiments, the administration of Compound 1 Pattern 1, for example Compound 1 Pattern 1 dihydrochloride, dihydrate, or a formulation produced from it in combination with cytosine arobinoside does not include administering an immune checkpoint inhibitor. In some embodiments, the patient has a tumor classified as immunogenic. In some embodiments, the patient has a hot immune tumor. In some embodiments, the patient has an altered-immunosuppressed immune tumor. In some embodiments, the patient has an altered-excluded immune tumor. In some embodiments, the patient has a cold tumor. In some embodiments, the patient has a tumor that is classified as a C2 "IFN-γ Dominant" class cancer. In some embodiments, the patient has a tumor that is classified as a high "IFN-γ Signature" or a high "Expanded Immune Signature." In some embodiments, the patient has a tumor that is PD-L1 positive.

In any of the above embodiments, the patient to be treated has been determined to have a cancer having a surrounding microenvironment that is favorable to immune modulation, is immunogenic, or is immunogenically susceptible to CDK4/6 inhibitor treatment. Accordingly, provided the cancer fits into the category as described herein, the patient may be suitable for the described treatments. In some embodiments, the cancer to be treated is selected from the group consisting of breast cancer, including but not limited to estrogen receptor (ER)-positive breast cancer and triple negative breast cancer, non-small cell lung carcinoma, head and neck squamous cell cancer, classical Hodgkin lymphoma (cHL), diffuse large B-cell lymphoma, bladder cancer, primary mediastinal B-cell lymphoma (PBMCL), urothelial carcinoma, microsatellite instability-high (MSI-H) solid tumors, mismatch repair deficient (dMMR) solid tumor, gastric or gastroesophageal junction (GEJ) adenocarcinoma, squamous cell carcinoma of the esophagus, cervical cancer, endometrial cancer, cholangiocarcinoma, hepatocellular carcinoma, Merkel cell carcinoma, renal cell carcinoma, ovarian cancer, anal canal cancer, colorectal cancer, skin cutaneous melanoma and melanoma.

In some embodiments, the patient is not administered a check point inhibitor.

In some embodiments, the patient is administered a check point inhibitor.

(ii) Anti-Neoplastic Therapy

In addition to being used in the production of advantageous intravenous solutions for myelopreservation, Compound 1 Pattern 1 dihydrochloride, dihydrate can be used to treat an abnormal cellular proliferation disorder, inflammatory disorder, immune disorder, or autoimmune disorder.

In one aspect, a method of treating a proliferative disorder in a host, including a human, is provided comprising administering isolated Compound 1 Pattern 1, for example as a dihydrochloride, dihydrate, optionally in a pharmaceutically acceptable carrier. Non-limiting examples of disorders include tumors, cancers, disorders related to abnormal cellular proliferation, inflammatory disorders, immune disorders, and autoimmune disorders.

In one embodiment Compound 1 Pattern 1 is administered parentally. This administration can be daily or with treatment holidays for myelopreservation.

Compound 1 Pattern 1 is useful as a therapeutic agent in a dosage form when administered in an effective amount to a host, including a human, to treat a tumor, cancer (solid, non-solid, diffuse, hematological, etc.), abnormal cellular proliferation, immune disorder, inflammatory disorder, blood disorder, a myelo- or lymphoproliferative disorder such as B- or T-cell lymphomas, multiple myeloma, breast cancer, prostate cancer, AML, ALL, ACL, lung cancer, pancreatic cancer, colon cancer, skin cancer, melanoma, Waldenstrom's macroglobulinemia, Wiskott-Aldrich syndrome, or a post-transplant lymphoproliferative disorder; an autoimmune disorder, for example, Lupus, Crohn' s Disease, Addison disease, Celiac disease, dermatomyositis, Graves disease, thyroiditis, multiple sclerosis, pernicious anemia, reactive arthritis, or type I diabetes; a disease of cardiologic malfunction, including hypercholesterolemia; an infectious disease, including a viral and/or bacterial infection; an inflammatory condition, including asthma, chronic peptic ulcers, tuberculosis, rheumatoid arthritis, periodontitis, ulcerative colitis, or hepatitis.

Exemplary proliferative disorders include, but are not limited to, benign growths, neoplasms, tumors, cancer (Rb positive or Rb negative), autoimmune disorders, inflammatory disorders graft-versus-host rejection, and fibrotic disorders.

Non-limiting examples of cancers that can be treated according to the present invention include, but are not limited to, acoustic neuroma, adenocarcinoma, adrenal gland cancer, anal cancer, angiosarcoma (e.g., lymphangiosarcoma, lymphangioendotheliosarcoma, hemangiosarcoma), appendix cancer, benign monoclonal gammopathy, biliary cancer (e.g., cholangiocarcinoma), bladder cancer, breast cancer (e.g., adenocarcinoma of the breast, papillary carcinoma of the breast, mammary cancer, medullary carcinoma of the breast), brain cancer (e.g., meningioma; glioma, e.g., astrocytoma, oligodendroglioma; medulloblastoma), bronchus cancer, carcinoid tumor, cervical cancer (e.g., cervical adenocarcinoma), choriocarcinoma, chordoma, craniopharyngioma, colorectal cancer (e.g., colon cancer, rectal cancer, colorectal adenocarcinoma), epithelial carcinoma, ependymoma, endotheliosarcoma (e.g., Kaposi's sarcoma, multiple idiopathic hemorrhagic sarcoma), endometrial cancer (e.g., uterine cancer, uterine sarcoma), esophageal cancer (e.g., adenocarcinoma of the esophagus, Barrett's adenocarinoma), Ewing's sarcoma, eye cancer (e.g., intraocular melanoma, retinoblastoma), familiar hypereosinophilia, gall bladder cancer, gastric cancer (e.g., stomach adenocarcinoma), gastrointestinal stromal tumor (GIST), head and neck cancer (e.g., head and neck squamous cell carcinoma, oral cancer (e.g., oral squamous cell carcinoma (OSCC), throat cancer (e.g., laryngeal cancer, pharyngeal cancer, nasopharyngeal cancer, oropharyngeal cancer)), hematopoietic cancers (e.g., leukemia such as acute lymphocytic leukemia (ALL)—also known as acute lymphoblastic leukemia or acute lymphoid leukemia (e.g., B-cell ALL, T-cell ALL), acute myelocytic leukemia (AML)

(e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma (DLBCL)), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., "Waldenstrom's macroglobulinemia"), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, anaplastic large cell lymphoma); a mixture of one or more leukemia/lymphoma as described above; and multiple myeloma (MM)), heavy chain disease (e.g., alpha chain disease, gamma chain disease, mu chain disease), hemangioblastoma, inflammatory myofibroblastic tumors, immunocytic amyloidosis, kidney cancer (e.g., nephroblastoma a.k.a. Wilms' tumor, renal cell carcinoma), liver cancer (e.g., hepatocellular cancer (HCC), malignant hepatoma), lung cancer (e.g., bronchogenic carcinoma, small cell lung cancer (SCLC), non-small cell lung cancer (NSCLC), adenocarcinoma of the lung), leiomyosarcoma (LMS), mastocytosis (e.g., systemic mastocytosis), myelodysplastic syndrome (MDS), mesothelioma, myeloproliferative disorder (MPD) (e.g., polycythemia Vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)), neuroblastoma, neurofibroma (e.g., neurofibromatosis (NF) type 1 or type 2, schwannomatosis), neuroendocrine cancer (e.g., gastroenteropancreatic neuroendoctrine tumor (GEP-NET), carcinoid tumor), osteosarcoma, ovarian cancer (e.g., cystadenocarcinoma, ovarian embryonal carcinoma, ovarian adenocarcinoma), papillary adenocarcinoma, pancreatic cancer (e.g., pancreatic andenocarcinoma, intraductal papillary mucinous neoplasm (IPMN), Islet cell tumors), penile cancer (e.g., Paget's disease of the penis and scrotum), pinealoma, primitive neuroectodermal tumor (PNT), prostate cancer (e.g., prostate adenocarcinoma), rectal cancer, rhabdomyosarcoma, salivary gland cancer, skin cancer (e.g., squamous cell carcinoma (SCC), keratoacanthoma (KA), melanoma, basal cell carcinoma (BCC)), small bowel cancer (e.g., appendix cancer), soft tissue sarcoma (e.g., malignant fibrous histiocytoma (MFH), liposarcoma, malignant peripheral nerve sheath tumor (MPNST), chondrosarcoma, fibrosarcoma, myxosarcoma), sebaceous gland carcinoma, sweat gland carcinoma, synovioma, testicular cancer (e.g., seminoma, testicular embryonal carcinoma), thyroid cancer (e.g., papillary carcinoma of the thyroid, papillary thyroid carcinoma (PTC), medullary thyroid cancer), urethral cancer, vaginal cancer and vulvar cancer (e.g., Paget's disease of the vulva).

In certain aspects, the invention includes the use of an effective amount of the isolated Compound 1 Pattern 1, or its pharmaceutically acceptable salt, prodrug or isotopic variant optionally in a pharmaceutical composition, to treat a host, typically a human, with a selected cancer, tumor, hyperproliferative condition or an inflammatory or immune disorder. Compound 1 Pattern 1 is also active against T-cell proliferation. Given the paucity of drugs for T-cell cancers and abnormal proliferation, the identification of such uses represents a substantial improvement in the medical therapy for these diseases.

In another embodiment, the disorder is myelodysplastic syndrome (MDS).

In certain embodiments, the cancer is a hematopoietic cancer. In certain embodiments, the hematopoietic cancer is a lymphoma. In certain embodiments, the hematopoietic cancer is a leukemia. In certain embodiments, the leukemia is acute myelocytic leukemia (AML).

In certain embodiments, the proliferative disorder is a myeloproliferative neoplasm. In certain embodiments, the myeloproliferative neoplasm (MPN) is primary myelofibrosis (PMF).

In certain embodiments, the cancer is a solid tumor. A solid tumor, as used herein, refers to an abnormal mass of tissue that usually does not contain cysts or liquid areas. Different types of solid tumors are named for the type of cells that form them. Examples of classes of solid tumors include, but are not limited to, sarcomas, carcinomas, and lymphomas, as described above herein. Additional examples of solid tumors include, but are not limited to, squamous cell carcinoma, colon cancer, breast cancer, prostate cancer, lung cancer, liver cancer, pancreatic cancer, and melanoma.

In certain embodiments, the condition treated with Compound 1 Pattern 1 is a disorder related to abnormal cellular proliferation.

Abnormal cellular proliferation, notably hyperproliferation, can occur as a result of a wide variety of factors, including genetic mutation, infection, exposure to toxins, autoimmune disorders, and benign or malignant tumor induction.

There are a number of skin disorders associated with cellular hyperproliferation. Psoriasis, for example, is a benign disease of human skin generally characterized by plaques covered by thickened scales. The disease is caused by increased proliferation of epidermal cells of unknown cause. Chronic eczema is also associated with significant hyperproliferation of the epidermis. Other diseases caused by hyperproliferation of skin cells include atopic dermatitis, lichen planus, warts, pemphigus vulgaris, actinic keratosis, basal cell carcinoma and squamous cell carcinoma.

Other hyperproliferative cell disorders include blood vessel proliferation disorders, fibrotic disorders, autoimmune disorders, graft-versus-host rejection, tumors and cancers.

Blood vessel proliferative disorders include angiogenic and vasculogenic disorders. Proliferation of smooth muscle cells in the course of development of plaques in vascular tissue cause, for example, restenosis, retinopathies and atherosclerosis. Both cell migration and cell proliferation play a role in the formation of atherosclerotic lesions.

Fibrotic disorders are often due to the abnormal formation of an extracellular matrix. Examples of fibrotic disorders include hepatic cirrhosis and mesangial proliferative cell disorders. Hepatic cirrhosis is characterized by the increase in extracellular matrix constituents resulting in the formation of a hepatic scar. Hepatic cirrhosis can cause diseases such as cirrhosis of the liver. An increased extracellular matrix resulting in a hepatic scar can also be caused by viral infection such as hepatitis. Lipocytes appear to play a major role in hepatic cirrhosis.

Mesangial disorders are brought about by abnormal proliferation of mesangial cells. Mesangial hyperproliferative cell disorders include various human renal diseases, such as glomerulonephritis, diabetic nephropathy, malignant nephrosclerosis, thrombotic micro-angiopathy syndromes, transplant rejection, and glomerulopathies.

Another disease with a proliferative component is rheumatoid arthritis. Rheumatoid arthritis is generally considered an autoimmune disease that is thought to be associated with activity of autoreactive T cells, and to be caused by autoantibodies produced against collagen and IgE.

Other disorders that can include an abnormal cellular proliferative component include Bechet's syndrome, acute respiratory distress syndrome (ARDS), ischemic heart disease, post-dialysis syndrome, leukemia, acquired immune deficiency syndrome, vasculitis, lipid histiocytosis, septic shock and inflammation in general.

In certain embodiments a compound of the present invention and its pharmaceutically acceptable derivatives or pharmaceutically acceptable formulations containing these compounds are also useful in the prevention and treatment of HBV infections and other related conditions such as anti-HBV antibody positive and HBV-positive conditions, chronic liver inflammation caused by HBV, cirrhosis, acute hepatitis, fulminant hepatitis, chronic persistent hepatitis, and fatigue. These compounds or formulations can also be used prophylactically to prevent or retard the progression of clinical illness in individuals who are anti-HBV antibody or HBV-antigen positive or who have been exposed to HBV.

In certain embodiments, the condition is associated with an immune response.

Cutaneous contact hypersensitivity and asthma are just two examples of immune responses that can be associated with significant morbidity. Others include atopic dermatitis, eczema, Sjogren's Syndrome, including keratoconjunctivitis sicca secondary to Sjogren's Syndrome, alopecia areata, allergic responses due to arthropod bite reactions, Crohn's disease, aphthous ulcer, iritis, conjunctivitis, keratoconjunctivitis, ulcerative colitis, cutaneous lupus erythematosus, scleroderma, vaginitis, proctitis, and drug eruptions. These conditions may result in any one or more of the following symptoms or signs: itching, swelling, redness, blisters, crusting, ulceration, pain, scaling, cracking, hair loss, scarring, or oozing of fluid involving the skin, eye, or mucosal membranes.

In atopic dermatitis, and eczema in general, immunologically mediated leukocyte infiltration (particularly infiltration of mononuclear cells, lymphocytes, neutrophils, and eosinophils) into the skin importantly contributes to the pathogenesis of these diseases. Chronic eczema also is associated with significant hyperproliferation of the epidermis. Immunologically mediated leukocyte infiltration also occurs at sites other than the skin, such as in the airways in asthma and in the tear producing gland of the eye in keratoconjunctivitis sicca.

In one non-limiting embodiment compounds of the present invention are used as topical agents in treating contact dermatitis, atopic dermatitis, eczematous dermatitis, psoriasis, Sjogren's Syndrome, including keratoconjunctivitis sicca secondary to Sjogren's Syndrome, alopecia areata, allergic responses due to arthropod bite reactions, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, and drug eruptions. The novel method may also be useful in reducing the infiltration of skin by malignant leukocytes in diseases such as mycosis fungoides. These compounds can also be used to treat an aqueous-deficient dry eye state (such as immune mediated keratoconjunctivitis) in a patient suffering therefrom, by administering the compound topically to the eye.

The term "neoplasia" or "cancer" is used throughout the specification to refer to the pathological process that results in the formation and growth of a cancerous or malignant neoplasm, i.e., abnormal tissue (solid) or cells (non-solid) that grow by cellular proliferation, often more rapidly than normal and continues to grow after the stimuli that initiated the new growth cease. Malignant neoplasms show partial or complete lack of structural organization and functional coordination with the normal tissue and most invade surrounding tissues, can metastasize to several sites, are likely to recur after attempted removal and may cause the death of the patient unless adequately treated. As used herein, the term neoplasia is used to describe all cancerous disease states and embraces or encompasses the pathological process associated with malignant hematogenous, ascitic and solid tumors. Exemplary cancers which may be treated by the present disclosed compounds either alone or in combination with at least one additional anti-cancer agent include squamous-cell carcinoma, basal cell carcinoma, adenocarcinoma, hepatocellular carcinomas, and renal cell carcinomas, cancer of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas; bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor and teratocarcinomas. Additional cancers which may be treated using the disclosed compounds according to the present invention include, for example, acute granulocytic leukemia, acute lymphocytic leukemia (ALL), acute myelogenous leukemia (AML), adenocarcinoma, adenosarcoma, adrenal cancer, adrenocortical carcinoma, anal cancer, anaplastic astrocytoma, angiosarcoma, appendix cancer, astrocytoma, Basal cell carcinoma, B-Cell lymphoma, bile duct cancer, bladder cancer, bone cancer, bone marrow cancer, bowel cancer, brain cancer, brain stem glioma, breast cancer, triple (estrogen, progesterone and HER-2) negative breast cancer, double negative breast cancer (two of estrogen, progesterone and HER-2 are negative), single negative (one of estrogen, progesterone and HER-2 is negative), estrogen-receptor positive, HER2-negative breast cancer, estrogen receptor-negative breast cancer, estrogen receptor positive breast cancer, metastatic breast cancer, luminal A breast cancer, luminal B breast cancer, Her2-negative breast cancer, HER2-positive or negative breast cancer, progesterone receptor-negative breast cancer, progesterone receptor-positive breast cancer, recurrent breast cancer, carcinoid tumors, cervical cancer, cholangiocarcinoma, chondrosarcoma, chronic lymphocytic leukemia (CLL), chronic myelogenous leukemia (CML), colon cancer, colorectal cancer, craniopharyngioma, cutaneous lymphoma, cutaneous melanoma, diffuse astrocytoma, ductal carcinoma in situ (DCIS), endometrial cancer, ependymoma, epithelioid sarcoma, esophageal cancer, ewing sarcoma, extrahepatic bile duct cancer, eye cancer, fallopian tube cancer, fibrosarcoma, gallbladder cancer, gastric cancer, gastrointestinal cancer, gastrointestinal carcinoid cancer, gastrointestinal stromal tumors (GIST), germ cell tumor glioblastoma multiforme (GBM), glioma, hairy cell leukemia, head and neck cancer, hemangioendothelioma, Hodgkin lymphoma, hypopharyngeal cancer, infiltrating ductal carcinoma (IDC), infiltrating lobular carcinoma (ILC), inflammatory breast cancer (IBC), intestinal Cancer, intrahepatic bile duct cancer, invasive/infiltrating breast cancer, Islet cell cancer, jaw cancer, Kaposi sarcoma, kidney cancer, laryngeal cancer, leiomyosarcoma, leptomeningeal metastases, leukemia, lip cancer, liposarcoma, liver cancer, lobular carcinoma in situ, low-grade astrocytoma, lung cancer, lymph node cancer, lymphoma, male breast cancer, medullary carcinoma, medulloblastoma, melanoma, meningioma, Merkel cell carcinoma, mesenchymal chondrosarcoma, mesenchymous, mesothelioma metastatic breast cancer, metastatic melanoma metastatic squamous neck cancer, mixed gliomas, monodermal teratoma, mouth cancer mucinous carcinoma, mucosal melanoma, multiple myeloma, Mycosis Fungoides, myelodysplastic syndrome, nasal cavity cancer, nasopharyngeal cancer, neck cancer, neuroblastoma, neuroendocrine tumors (NETs), non-Hodgkin's lymphoma, non-small cell lung cancer (NSCLC), oat cell cancer, ocular cancer, ocular melanoma, oligodendroglioma, oral cancer, oral cavity cancer, oropharyngeal cancer, osteogenic sarcoma, osteosarcoma, ovarian cancer, ovarian epithelial cancer ovarian germ cell tumor, ovarian primary peritoneal carcinoma, ovarian sex cord stromal tumor, Paget's disease, pancreatic cancer, papillary carcinoma, paranasal sinus cancer, parathyroid cancer, pelvic cancer, penile cancer, peripheral nerve cancer, peritoneal cancer, pharyngeal cancer, pheochromocytoma, pilocytic astrocytoma, pineal region tumor, pineoblastoma, pituitary gland cancer, primary central nervous system (CNS) lymphoma, prostate cancer, rectal cancer, renal cell carcinoma, renal pelvis cancer, rhabdomyosarcoma, salivary gland cancer, soft tissue sarcoma, bone sarcoma, sarcoma, sinus cancer, skin cancer, small cell lung cancer (SCLC), small intestine cancer, spinal cancer, spinal column cancer, spinal cord cancer, squamous cell carcinoma, stomach cancer, synovial sarcoma, T-cell lymphoma, testicular cancer, throat cancer, thymoma/thymic carcinoma, thyroid cancer, tongue cancer, tonsil cancer, transitional cell cancer, tubal cancer, tubular carcinoma, undiagnosed cancer, ureteral cancer, urethral cancer, uterine adenocarcinoma, uterine cancer, uterine sarcoma, vaginal cancer, vulvar cancer, T-cell lineage acute lymphoblastic leukemia (T-ALL), T-cell lineage lymphoblastic lymphoma (T-LL), peripheral T-cell lymphoma, Adult T-cell leukemia, Pre-B ALL, Pre-B lymphomas, large B-cell lymphoma, Burkitts lymphoma, B-cell ALL, Philadelphia chromosome positive ALL, Philadelphia chromosome positive CML, juvenile myelomonocytic leukemia (JMML), acute promyelocytic leukemia (a subtype of AML), large granular lymphocytic leukemia, Adult T-cell chronic leukemia, diffuse large B cell lymphoma, follicular lymphoma; Mucosa-Associated Lymphatic Tissue lymphoma (MALT), small cell lymphocytic lymphoma, mediastinal large B cell lymphoma, nodal marginal zone B cell lymphoma (NMZL); splenic marginal zone lymphoma (SMZL); intravascular large B-cell lymphoma; primary effusion lymphoma; or lymphomatoid granulomatosis; B-cell prolymphocytic leukemia; splenic lymphoma/leukemia, unclassifiable, splenic diffuse red pulp small B-cell lymphoma; lymphoplasmacytic lymphoma; heavy chain diseases, for example, Alpha heavy chain disease, Gamma heavy chain disease, Mu heavy chain disease, plasma cell myeloma, solitary plasmacytoma of bone; extraosseous plasmacytoma; primary cutaneous follicle center lymphoma, T cell/histocyte rich large B-cell lymphoma, DLBCL associated with chronic inflammation; Epstein-Barr virus (EBV)+ DLBCL of the elderly; primary mediastinal (thymic) large B-cell lymphoma, primary cutaneous DLBCL, leg type, ALK+ large B-cell lymphoma, plasmablastic lymphoma; large B-cell lymphoma arising in HHV8-associated multicentric, Castleman disease; B-cell lymphoma, unclassifiable, with features intermediate between diffuse large B-cell lymphoma, or B-cell lymphoma, unclassifiable, with features intermediate between diffuse large B-cell lymphoma and classical Hodgkin lymphoma.

In another aspect, a method of increasing BIM expression (e.g., BCLC2L11 expression) is provided to induce apoptosis in a cell comprising contacting a compound of the present invention or a pharmaceutically acceptable composition, salt, isotopic analog, or prodrug thereof with the cell. In certain embodiments, the method is an in vitro method. In certain embodiments, the method is an in vivo method. BCL2L11 expression is tightly regulated in a cell. BCL2L11 encodes for BIM, a proapoptotic protein. BCL2L11 is downregulated in many cancers and BIM is inhibited in many cancers, including chronic myelocytic leukemia (CML) and non-small cell lung cancer (NSCLC) and that suppression of BCL2L11 expression can confer resistance to tyrosine kinase inhibitors. See, e.g., Ng et al., Nat. Med. (2012) 18:521-528.

In yet another aspect, a method of treating a condition associated with angiogenesis is provided, such as, for example, a diabetic condition (e.g., diabetic retinopathy), an inflammatory condition (e.g., rheumatoid arthritis), macular degeneration, obesity, atherosclerosis, or a proliferative disorder, comprising administering to a subject in need thereof a compound of the present invention or a pharmaceutically acceptable composition, salt, isotopic analog, or prodrug thereof.

In certain embodiments, the condition associated with angiogenesis is macular degeneration. In certain embodiments, provided is a method of treating macular degeneration comprising administering to a subject in need thereof a compound of the present invention or a pharmaceutically acceptable composition, salt, isotopic analog, or prodrug thereof.

In certain embodiments, the condition associated with angiogenesis is obesity. As used herein, "obesity" and "obese" as used herein, refers to class I obesity, class II obesity, class III obesity and pre-obesity (e.g., being "overweight") as defined by the World Health Organization. In certain embodiments, a method of treating obesity is provided comprising administering to a subject in need thereof a compound of the present invention or a pharmaceutically acceptable composition, salt, isotopic analog, or prodrug thereof.

In certain embodiments, the condition associated with angiogenesis is atherosclerosis. In certain embodiments, provided is a method of treating atherosclerosis comprising administering to a subject in need thereof a compound of the present invention or a pharmaceutically acceptable composition, salt, isotopic analog, or prodrug thereof.

In certain embodiments, the condition associated with angiogenesis is a proliferative disorder. In certain embodiments, provided is a method of treating a proliferative disorder comprising administering to a subject in need thereof a compound of the present invention or a pharmaceutically acceptable composition, salt, isotopic analog, or prodrug thereof.

In an alternative embodiment the compound is administered at a dose of about 50 mg/m$^2$ to about 800 mg/m$^2$, from about 100 mg/m$^2$ to about 600 mg/m$^2$, from about 100 mg/m$^2$ to about 500 mg/m$^2$, from about 100 mg/m$^2$ to about 400 mg/m$^2$, from about 100 mg/m$^2$ to about 350 mg/m$^2$, from about 150 mg/m$^2$ to about 350 mg/m$^2$, from about 200 mg/m$^2$ to about 350 mg/m$^2$, or from about 200 mg/m$^2$ to about 300 mg/m$^2$.

Isolated Compound 1 Pattern 1 can be used in an effective amount alone or in combination with another compound of the present invention or another bioactive agent to treat a host such as a human with a disorder as described herein.

The isolated Compound 1 Pattern 1 described herein can be used in an effective amount alone or in combination with another compound of the present invention or another bioactive agent to treat a host such as a human with a disorder as described herein.

The term "bioactive agent" is used to describe an agent, other than the selected compound according to the present invention, which can be used in combination or alternation with a compound of the present invention to achieve a desired result of therapy. In one embodiment, the compound of the present invention and the bioactive agent are administered in a manner that they are active in vivo during overlapping time periods, for example, have time-period overlapping Cmax, Tmax, AUC or other pharmacokinetic parameter. In another embodiment, isolated Compound 1 Pattern 1 and the bioactive agent are administered to a host in need thereof that do not have overlapping pharmacokinetic parameter, however, one has a therapeutic impact on the therapeutic efficacy of the other.

In one aspect of this embodiment, the bioactive agent is an immune modulator, including but not limited to a checkpoint inhibitor, including as non-limiting examples, a PD-1 inhibitor, PD-L1 inhibitor, PD-L2 inhibitor, CTLA-4 inhibitor, LAG-3 inhibitor, TIM-3 inhibitor, V-domain Ig suppressor of T-cell activation (VISTA) inhibitors, small molecule, peptide, nucleotide, or other inhibitor. In certain aspects, the immune modulator is an antibody, such as a monoclonal antibody.

PD-1 inhibitors that blocks the interaction of PD-1 and PD-L1 by binding to the PD-1 receptor, and in turn inhibit immune suppression include, for example, nivolumab (Opdivo), pembrolizumab (Keytruda), pidilizumab, AMP-224 (AstraZeneca and MedImmune), PF-06801591 (Pfizer), MEDI0680 (AstraZeneca), PDR001 (Novartis), REGN2810 (Regeneron), SHR-12-1 (Jiangsu Hengrui Medicine Company and Incyte Corporation), TSR-042 (Tesaro), and the PD-L1/VISTA inhibitor CA-170 (Curis Inc.). PD-L1 inhibitors that block the interaction of PD-1 and PD-L1 by binding to the PD-L1 receptor, and in turn inhibits immune suppression, include for example, atezolizumab (Tecentriq), durvalumab (AstraZeneca and MedImmune), KN035 (Alphamab), and BMS-936559 (Bristol-Myers Squibb). CTLA-4 checkpoint inhibitors that bind to CTLA-4 and inhibits immune suppression include, but are not limited to, ipilimumab, tremelimumab (AstraZeneca and MedImmune), AGEN1884 and AGEN2041 (Agenus). LAG-3 checkpoint inhibitors, include, but are not limited to, BMS-986016 (Bristol-Myers Squibb), GSK2831781 (GlaxoSmithKline), IMP321 (Prima BioMed), LAG525 (Novartis), and the dual PD-1 and LAG-3 inhibitor MGD013 (MacroGenics). An example of a TIM-3 inhibitor is TSR-022 (Tesaro).

In yet another embodiment, isolated Compound 1 Pattern 1 as described herein can be administered in an effective amount for the treatment of abnormal tissue of the female reproductive system such as breast, ovarian, endometrial, or uterine cancer, in combination or alternation with an effective amount of an estrogen inhibitor including but not limited to a SERM (selective estrogen receptor modulator), a SERD (selective estrogen receptor degrader), a complete estrogen receptor degrader, or another form of partial or complete estrogen antagonist or agonist. Partial anti-estrogens like raloxifene and tamoxifen retain some estrogen-like effects, including an estrogen-like stimulation of uterine growth, and also, in some cases, an estrogen-like action during breast cancer progression which actually stimulates tumor growth. In contrast, fulvestrant, a complete anti-estrogen, is limited estrogen-like action on the uterus and is effective in tamoxifen-resistant tumors. Non-limiting examples of anti-estrogen compounds are provided in WO 2014/19176 assigned to Astra Zeneca, WO2013/090921, WO 2014/203129, WO 2014/203132, and US2013/0178445 assigned to Olema Pharmaceuticals, and U.S. Pat. Nos. 9,078,871, 8,853,423, and 8,703, 810, as well as US 2015/0005286, WO 2014/205136, and WO 2014/205138.

Additional non-limiting examples of anti-estrogen compounds include: SERMS such as anordrin, bazedoxifene, broparestriol, chlorotrianisene, clomiphene citrate, cyclofenil, lasofoxifene, ormeloxifene, raloxifene, tamoxifen, toremifene, and fulvestrant; aromatase inhibitors such as aminoglutethimide, testolactone, anastrozole, exemestane, fadrozole, formestane, and letrozole; and antigonadotropins such as leuprorelin, cetrorelix, allylestrenol, chloromadinone acetate, cyproterone acetate, delmadinone acetate, dydrogesterone, medroxyprogesterone acetate, megestrol acetate, nomegestrol acetate, norethisterone acetate, progesterone, and spironolactone. Other estrogenic ligands that can be used according to the present invention are described in U.S. Pat. Nos. 4,418,068; 5,478,847; 5,393,763; and 5,457,117, WO2011/156518, U.S. Pat. Nos. 8,455,534 and 8,299,112, 9,078,871; 8,853,423; 8,703,810; US 2015/0005286; and WO 2014/205138, US2016/0175289, US2015/0258080, WO 2014/191726, WO 2012/084711; WO 2002/013802; WO 2002/004418; WO 2002/003992; WO 2002/003991; WO 2002/003990; WO 2002/003989; WO 2002/003988; WO 2002/003986; WO 2002/003977; WO 2002/003976; WO 2002/003975; WO 2006/078834; U.S. Pat. No. 6,821,989; US 2002/0128276; U.S. Pat. No. 6,777,424; US 2002/0016340; U.S. Pat. Nos. 6,326,392; 6,756,401; US 2002/0013327; U.S. Pat. Nos. 6,512,002; 6,632,834; US 2001/0056099; U.S. Pat. Nos. 6,583,170; 6,479,535; WO 1999/024027; U.S. Pat. No. 6,005,102; EP 0802184; U.S. Pat. Nos. 5,998,402; 5,780,497, 5,880,137, WO 2012/048058 and WO 2007/087684.

In another embodiment, the isolated Compound 1 Pattern 1 described herein can be administered in an effective amount for the treatment of abnormal tissue of the male reproductive system such as prostate or testicular cancer, in combination or alternation with an effective amount of an androgen (such as testosterone) inhibitor including but not limited to a selective androgen receptor modulator, a selective androgen receptor degrader, a complete androgen receptor degrader, or another form of partial or complete androgen antagonist. In one embodiment, the prostate or testicular cancer is androgen-resistant. Non-limiting examples of anti-androgen compounds are provided in WO 2011/156518 and U.S. Pat. Nos. 8,455,534 and 8,299,112. Additional non-limiting examples of anti-androgen compounds include: enzalutamide, apalutamide, cyproterone acetate, chlormadinone acetate, spironolactone, canrenone, drospirenone, ketoconazole, topilutamide, abiraterone acetate, and cimetidine.

In one embodiment, an effective amount of Compound 1 Pattern 1 is administered in combination with an effective amount of abiraterone acetate (Zytiga) for the treatment of abnormal tissue of the male reproductive system.

In one embodiment, an effective amount of Compound 1 Pattern 1 is administered in combination with an effective amount of abiraterone acetate (Zytiga) for the treatment of prostate cancer.

In one embodiment, an effective amount of Compound 1 Pattern 1 is administered in combination with an effective amount of enzalutamide for the treatment of prostate cancer.

In one embodiment, the bioactive agent is an ALK inhibitor. Examples of ALK inhibitors include but are not limited to Crizotinib, Alectinib, ceritinib, TAE684 (NVP-TAE684), GSK1838705A, AZD3463, ASP3026, PF-06463922, entrectinib (RXDX-101), and AP26113. In one embodiment, the bioactive agent is an EGFR inhibitor. Examples of EGFR inhibitors include erlotinib (Tarceva), gefitinib (Iressa), afatinib (Gilotrif), rociletinib (CO-1686), osimertinib (Tagrisso), olmutinib (Olita), naquotinib (ASP8273), nazartinib (EGF816), PF-06747775 (Pfizer), icotinib (BPI-2009), neratinib (HKI-272; PB272); avitinib (AC0010), EAI045, tarloxotinib (TH-4000; PR-610), PF-06459988 (Pfizer), tesevatinib (XL647; EXEL-7647; KD-019), transtinib, WZ-3146, WZ8040, CNX-2006, dacomitinib (PF-00299804; Pfizer), brigatinib (Alunbrig), lorlatinib, and PF-06747775 (PF7775).

In one embodiment, an effective amount of Compound 1 Pattern 1 is administered in combination with an effective amount of afatinib dimaleate (Gilotrif) for the treatment of non-small cell lung cancer.

In one embodiment, an effective amount of Compound 1 Pattern 1 is administered in combination with an effective amount of alectinib (Alecensa) for the treatment of non-small cell lung cancer.

In one embodiment, an effective amount of Compound 1 Pattern 1 is administered in combination with an effective amount of ceritinib (Zykadia) for the treatment of non-small cell lung cancer.

In one embodiment, an effective amount of Compound 1 Pattern 1 is administered in combination with an effective amount of crizotinib (Xalkori) for the treatment of non-small cell lung cancer.

In one embodiment, an effective amount of Compound 1 Pattern 1 is administered in combination with an effective amount of osimertinib (Tagrisso) for the treatment of non-small cell lung cancer.

In one embodiment, an effective amount of Compound 1 Pattern 1 is administered in combination with an effective amount of brigatinib (Alunbrig) for the treatment of non-small cell lung cancer.

In one embodiment, an effective amount of Compound 1 Pattern 1 is administered in combination with an effective amount of lorlatinib for the treatment of non-small cell lung cancer.

In one embodiment, the bioactive agent is an HER-2 inhibitor. Examples of HER-2 inhibitors include trastuzumab, lapatinib, ado-trastuzumab emtansine, and pertuzumab.

In one embodiment, an effective amount of Compound 1 Pattern 1 is administered in combination with an effective amount of lapatinib ditosylate for the treatment of breast cancer.

In one embodiment, an effective amount of Compound 1 Pattern 1 is administered in combination with an effective amount of lapatinib ditosylate for the treatment of HER2+ breast cancer.

In one embodiment, an effective amount of Compound 1 Pattern 1 is administered in combination with an effective amount of PF7775 for the treatment of non-small cell lung cancer.

In one embodiment, the bioactive agent is a CD20 inhibitor. Examples of CD20 inhibitors include obinutuzumab, rituximab, fatumumab, ibritumomab, tositumomab, and ocrelizumab.

In one embodiment, the bioactive agent is a JAK3 inhibitor. Examples of JAK3 inhibitors include tasocitinib.

In one embodiment, the bioactive agent is a BCL-2 inhibitor. Examples of BCL-2 inhibitors include venetoclax, ABT-199 (4-[4-[[2-(4-Chlorophenyl)-4,4-dimethylcyclohex-1-en-1-yl]methyl]piperazin-1-yl]-N-[[3-nitro-4-[[(tetrahydro-2H-pyran-4-yl)methyl]amino]phenyl]sulfonyl]-2-[(1H-pyrrolo[2,3-b]pyridin-5-yl)oxy]benzamide), ABT-737 (4-[4-[[2-(4-chlorophenyl)phenyl]methyl]piperazin-1-yl]-N-[4-[[(2R)-4-(dimethylamino)-1-phenylsulfanylbutan-2-yl]amino]-3-nitrophenyl]sulfonylbenzamide) (navitoclax), ABT-263 ((R)-4-(4-((4'-chloro-4,4-dimethyl-3,4,5,6-tetrahydro-[1,1'-biphenyl]-2-yl)methyl)piperazin-1-yl)-N-((4-((4-morpholino-1-(phenylthio)butan-2-yl)amino)-3((trifluoromethyl)sulfonyl)phenyl)sulfonyl)benzamide), GX15-070 (obatoclax mesylate, (2Z)-2-[(5Z)-5-[(3,5-dimethyl-1H-pyrrol-2-yl)methylidene]-4-methoxypyrrol-2-ylidene]indole; methanesulfonic acid))), 2-methoxy-antimycin A3, YC137 (4-(4,9-dioxo-4,9-dihydronaphtho[2,3-d]thiazol-2-ylamino)-phenyl ester), pogosin, ethyl 2-amino-6-bromo-4-(1-cyano-2-ethoxy-2-oxoethyl)-4H-chromene-3-carboxylate, Nilotinib-d3, TW-37 (N-[4-[[2-(1,1-Dimethylethyl)phenyl]sulfonyl]phenyl]-2,3,4-trihydroxy-5-[[2-(1-methylethyl)phenyl]methyl]benzamide), Apogossypolone (ApoG2), HA14-1, AT101, sabutoclax, gambogic acid, or G3139 (Oblimersen).

In one aspect, a treatment regimen is provided comprising the administration of Compound 1 Pattern 1 in combination with at least one additional chemotherapeutic agent. The combinations disclosed herein can be administered for beneficial, additive, or synergistic effect in the treatment of abnormal cellular proliferative disorders.

In specific embodiments, the treatment regimen includes the administration of isolated Compound 1 Pattern 1 in combination with at least one kinase inhibitor. In one embodiment, the at least one kinase inhibitor is selected from a phosphoinositide 3-kinase (PI3K) inhibitor, a Bruton's tyrosine kinase (BTK) inhibitor, or a spleen tyrosine kinase (Syk) inhibitor, or a combination thereof.

PI3k inhibitors that may be used in the present invention are well known. Examples of PI3 kinase inhibitors include but are not limited to Wortmannin, demethoxyviridin, perifosine, idelalisib, Pictilisib, Palomid 529, ZSTK474, PWT33597, CUDC-907, and AEZS-136, duvelisib, GS-9820, BKM120, GDC-0032 (Taselisib), (2-[4-[2-(2-Isopropyl-5-methyl-1,2,4-triazol-3-yl)-5,6-dihydroimidazo[1,2-d][1,4]benzoxazepin-9-yl]pyrazol-1-yl]-2-methylpropanamide), MLN-1117 ((2R)-1-Phenoxy-2-butanyl hydrogen (S)-methylphosphonate; or Methyl(oxo) {[(2R)-1-phenoxy-2-butanyl]oxy}phosphonium)), BYL-719 ((2S)—N1-[4-Methyl-5-[2-(2,2,2-trifluoro-1,1-dimethylethyl)-4-pyridinyl]-2-thiazolyl]-1,2-pyrrolidinedicarboxamide), GSK2126458 (2,4-Difluoro-N-{2-(methyl oxy)-5-[4-(4-pyridazinyl)-6-quinolinyl]-3-pyridinyl}benzenesulfonamide) (omipalisib), TGX-221 ((±)-7-Methyl-2-(morpholin-4-yl)-9-(1-phenylaminoethyl)-pyrido[1,2-a]-pyrimidin-4-one), GSK2636771 (2-Methyl-1-(2-methyl-3-(trifluoromethyl)benzyl)-6-morpholino-1H-benzo[d]imidazole-4-carboxylic acid dihydrochloride), KIN-193 ((R)-2-((1-(7-methyl-2-morpholino-4-oxo-4H-pyrido[1,2-a]pyrimidin-9-yl)ethyl)amino)benzoic acid), TGR-1202/RP5264, GS-9820 ((S)-1-(4-((2-(2-aminopyrimidin-5-yl)-7-methyl-4-mohydroxypropan-1-one), GS-1101 (5-fluoro-3-phenyl-2-([S)]-1-[9H-purin-6-ylamino]-propyl)-3H-quinazolin-4-one), AMG-319, GSK-2269557, SAR245409 (N-(4-(N-(3-((3,5-dimethoxyphenyl)amino)quinoxalin-2-yl)sulfamoyl)phenyl)-3-methoxy-4 methylbenzamide), BAY80-6946 (2-amino-N-(7-methoxy-8-(3-morpholinopropoxy)-2,3-dihydroimidazo[1,2-c]quinaz), AS 252424 (5-[1-[5-(4-Fluoro-2-hydroxy-phenyl)-furan-2-yl]-meth-(Z)-ylidene]-thiazolidine-2,4-dione), CZ 24832 (5-(2-amino-8-fluoro-[1,2,4]triazolo[1,5-a]pyridin-6-yl)-N-tert-butylpyridine-3-sulfonamide), Buparlisib (5-[2,6-Di(4-morpholinyl)-4-pyrimidinyl]-4-(trifluoromethyl)-2-pyridinamine), GDC-0941 (2-(1H-Indazol-4-yl)-6-[[4-(methylsulfonyl)-1-piperazinyl]methyl]-4-(4-morpholinyl)thieno[3,2-d]pyrimidine), GDC-0980 ((S)-1-(4-((2-(2-aminopyrimidin-5-yl)-7-methyl-4-morpholinothieno[3,2-d]pyrimidin-6 yl)methyl)piperazin-1-yl)-2-hydroxypropan-1-one (also known as RG7422)), SF1126 ((8S,14S,17S)-14-(carboxymethyl)-8-(3-guanidinopropyl)-17-(hydroxymethyl)-3,6,9,12,15-pentaoxo-1-(4-(4-oxo-8-phenyl-4H-chromen-2-yl)morpholino-4-ium)-2-oxa-7,10, 13,16-tetraazaoctadecan-18-oate), PF-05212384 (N-[4-[[4-(Dimethylamino)-1-piperidinyl]carbonyl]phenyl]-N'-[4-(4, 6-di-4-morpholinyl-1,3,5-triazin-2-yl)phenyl]urea) (gedatolisib), LY3023414, BEZ235 (2-Methyl-2-{4-[3 methyl-2-oxo-8-(quinolin-3-yl)-2,3-dihydro-1H-imidazo[4, 5-c]quinolin-1-yl]phenyl}propanenitrile) (dactolisib), XL-765 (N-(3-(N-(3-(3,5-dimethoxyphenylamino)quinoxalin-2-yl)sulfamoyl)phenyl)-3-methoxy-4-methylbenzamide), and GSK1059615 (5-[[4-(4-Pyridinyl)-6-quinolinyl]methylene]-2,4-thiazolidenedione), PX886 ([(3aR,6E, 9S,9aR,10R,11aS)-6-[[bis(prop-2-enyl)amino] methylidene]-5-hydroxy-9-(methoxymethyl)-9a,11a-dimethyl-1,4,7-trioxo-2,3,3a,9,10,11-hexahydroindeno[4, 5h]isochromen-10-yl]acetate (also known as sonolisib)) LY294002, AZD8186, PF-4989216, pilaralisib, GNE-317, PI-3065, PI-103, NU7441 (KU-57788), HS 173, VS-5584 (SB2343), CZC24832, TG100-115, A66, YM201636, CAY10505, PIK-75, PIK-93, AS-605240, BGT226 (NVP-BGT226), AZD6482, voxtalisib, alpelisib, IC-87114, TGI100713, CH5132799, PKI-402, copanlisib (BAY 80-6946), XL 147, PIK-90, PIK-293, PIK-294, 3-MA (3-methyladenine), AS-252424, AS-604850, apitolisib (GDC-0980; RG7422), and the structures described in WO2014/071109. In one embodiment, isolated Compound 1 Pattern 1 is combined in a single dosage form with the PIk3 inhibitor.

In one embodiment, an effective amount of Compound 1 Pattern 1 is administered in combination with an effective amount of alpelisib for the treatment of solid tumors.

In one embodiment, an effective amount of Compound 1 Pattern 1 is administered in combination with an effective amount of alpelisib for the treatment of abnormal tissue of the female reproductive system.

In one embodiment, an effective amount of Compound 1 Pattern 1 is administered in combination with an effective amount of alpelisib for the treatment of breast cancer.

In one embodiment, an effective amount of Compound 1 Pattern 1 is administered in combination with an effective amount of copanlisib hydrochloride (Aliqopa) for the treatment of lymphoma.

In one embodiment, an effective amount of Compound 1 Pattern 1 is administered in combination with an effective amount of copanlisib hydrochloride (Aliqopa) for the treatment of follicular lymphoma.

In one embodiment, an effective amount of Compound 1 Pattern 1 is administered in combination with an effective amount of idelalisib (Zydelig) for the treatment of chronic lymphocytic leukemia.

In one embodiment, an effective amount of Compound 1 Pattern 1 is administered in combination with an effective amount of idelalisib (Zydelig) for the treatment of Non-Hodgkin lymphoma, including follicular B-cell non-Hodgkin lymphoma or small lymphocytic lymphoma.

BTK inhibitors for use in the present invention are well known. Examples of BTK inhibitors include ibrutinib (also known as PCI-32765)(Imbruvica™)(1-[(3R)-3-[4-amino-3-(4-phenoxy-phenyl)pyrazolo[3,4-d]pyrimidin-1-yl]piperidin-1-yl]prop-2-en-1-one), dianilinopyrimidine-based inhibitors such as AVL-101 and AVL-291/292 (N-(3-((5-fluoro-2-((4-(2-methoxyethoxy)phenyl)amino)pyrimidin-4-yl)amino)phenyl)acryl amide) (Avila Therapeutics) (see US Patent Publication No 2011/0117073, incorporated herein in its entirety), Dasatinib ([N-(2-chloro-6-methylphenyl)-2-(6-(4-(2-hydroxyethyl)piperazin-1-yl)-2-methylpyrimidin-4-ylamino)thiazole-5-carboxamide], LFM-A13 (alpha-cyano-beta-hydroxy-beta-methyl-N-(2,5-ibromophenyl) propenamide), GDC-0834 ([R—N-(3-(6-(4-(1,4-dimethyl-3-oxopiperazin-2-yl)phenylamino)-4-methyl-5-oxo-4, 5-dihydropyrazin-2-yl)-2-methylphenyl)-4,5,6,7-tetrahydrobenzo[b]thiophene-2-carboxamide], CGI-560 4-(tert-butyl)-N-(3-(8-(phenylamino)imidazo[1,2-a]pyrazin-6-yl) phenyl)benzamide, CGI-1746 (4-(tert-butyl)-N-(2-methyl-3-(4-methyl-6-((4-(morpholine-4-carbonyl)phenyl)amino)-5-oxo-4,5-dihydropyrazin-2-yl)phenyl)benzamide), CNX-774 (4-(4-(4-((3-acrylamidophenyl)amino)-5-fluoropyrimidin-2-yl)amino)phenoxy)-N-methylpicolinamide), CTA056 (7-benzyl-1-(3-(piperidin-1-yl)propyl)-2-(4-(pyridin-4-yl)phenyl)-1H-imidazo[4,5-g] quinoxalin-6(5H)-one), GDC-0834 ((R)—N-(3-(6-((4-(1,4-dimethyl-3-oxopiperazin-2-yl)phenyl)amino)-4-methyl-5-oxo-4,5-dihydropyrazin-2-yl)-2-methylphenyl)-4,5,6,7-tetrahydrobenzo[b]thiophene-2-carboxamide), GDC-0837 ((R)—N-(3-(6-((4-(1,4-dimethyl-3-oxopiperazin-2-yl)phenyl)amino)-4-methyl-5-oxo-4,5-dihydropyrazin-2-yl)-2-methylphenyl)-4,5,6,7-tetrahydrobenzo[b]thiophene-2-carboxamide), HM-71224, ACP-196, ONO-4059 (Ono Pharmaceuticals), PRT062607 (4-((3-(2H-1,2,3-triazol-2-yl)phenyl)amino)-2-(((1R,2S)-2-aminocyclohexyl)amino) pyrimidine-5-carboxamide hydrochloride), QL-47 (1-(1-acryloylindolin-6-yl)-9-(1-methyl-1H-pyrazol-4-yl)benzo [h][1,6]naphthyridin-2(1H)-one), and RN486 (6-cyclopropyl-8-fluoro-2-(2-hydroxymethyl-3-{1-methyl-5-[5-(4-methyl-piperazin-1-yl)-pyridin-2-ylamino]-6-oxo-1,6-dihydro-pyridin-3-yl}-phenyl)-2H-isoquinolin-1-one), and other molecules capable of inhibiting BTK activity, for example those BTK inhibitors disclosed in Akinleye et ah, Journal of Hematology & Oncology, 2013, 6:59, the entirety of which is incorporated herein by reference. In one embodiment, an effective amount of the isolated Compound 1 Pattern 1 is combined in a single dosage form with the BTK inhibitor.

In one embodiment, an effective amount of Compound 1 Pattern 1 is administered in combination with an effective amount of ibrutinib (Imbruvica) for the treatment of chronic lymphocytic leukemia.

In one embodiment, an effective amount of Compound 1 Pattern 1 is administered in combination with an effective amount of ibrutinib (Imbruvica) for the treatment of lymphoma, including small lymphocytic lymphoma, mantle cell lymphoma, marginal zone lymphoma, or Waldenström macroglobulinemia.

Syk inhibitors for use in the present invention are well known, and include, for example, Cerdulatinib (4-(cyclopropylamino)-2-((4-(4-(ethylsulfonyl)piperazin-1-yl)phenyl)amino)pyrimidine-5-carboxamide), entospletinib (6-(1H-indazol-6-yl)-N-(4-morpholinophenyl)imidazo[1,2-a]pyrazin-8-amine), fostamatinib ([6-({5-Fluoro-2-[(3,4,5-trimethoxyphenyl)amino]-4-pyrimidinyl}amino)-2,2-dimethyl-3-oxo-2,3-dihydro-4H-pyrido[3,2-b][1,4]oxazin-4-yl]methyl dihydrogen phosphate), fostamatinib disodium salt (sodium (6-((5-fluoro-2-((3,4,5-trimethoxyphenyl)amino)pyrimidin-4-yl)amino)-2,2-dimethyl-3-oxo-2H-pyrido[3,2-b][1,4]oxazin-4(3H)-yl)methyl phosphate), BAY 61-3606 (2-(7-(3,4-Dimethoxyphenyl)-imidazo[1,2-c]pyrimidin-5-ylamino)-nicotinamide HCl), RO9021 (6-[(1R,2S)-2-Amino-cyclohexylamino]-4-(5,6-dimethyl-pyridin-2-ylamino)-pyridazine-3-carboxylic acid amide), imatinib (Gleevac; 4-[(4-methylpiperazin-1-yl)methyl]-N-(4-methyl-3-{[4-(pyridin-3-yl)pyrimidin-2-yl]amino}phenyl)benzamide), staurosporine, GSK143 (2-(((3R,4R)-3-aminotetrahydro-2H-pyran-4-yl)amino)-4-(p-tolylamino)pyrimidine-5-carboxamide), PP2 (1-(tert-butyl)-3-(4-chlorophenyl)-1H-pyrazolo[3,4-d]pyrimidin-4-amine), PRT-060318 (2-(((1R,2S)-2-aminocyclohexyl)amino)-4-(m-tolylamino)pyrimidine-5-carboxamide), PRT-062607 (4-((3-(2H-1,2,3-triazol-2-yl)phenyl)amino)-2-(((1R,2S)-2-aminocyclohexyl)amino)pyrimidine-5-carboxamide hydrochloride), R112 (3,3'-((5-fluoropyrimidine-2,4-diyl)bis(azanediyl))diphenol), R348 (3-Ethyl-4-methylpyridine), R406 (6-((5-fluoro-2-((3,4,5-trimethoxyphenyl)amino)pyrimidin-4-yl)amino)-2,2-dimethyl-2H-pyrido[3,2-b][1,4]oxazin-3 (4H)-one), piceatannol (3-Hydroxyresveratol), YM193306(see Singh et al. Discovery and Development of Spleen Tyrosine Kinase (SYK) Inhibitors, J. Med. Chem. 2012, 55, 3614-3643), 7-azaindole, piceatannol, ER-27319 (see Singh et al. Discovery and Development of Spleen Tyrosine Kinase (SYK) Inhibitors, J. Med. Chem. 2012, 55, 3614-3643 incorporated in its entirety herein), Compound D (see Singh et al. Discovery and Development of Spleen Tyrosine Kinase (SYK) Inhibitors, J. Med. Chem. 2012, 55, 3614-3643 incorporated in its entirety herein), PRT060318 (see Singh et al. Discovery and Development of Spleen Tyrosine Kinase (SYK) Inhibitors, J. Med. Chem. 2012, 55, 3614-3643 incorporated in its entirety herein), luteolin (see Singh et al. Discovery and Development of Spleen Tyrosine Kinase (SYK) Inhibitors, J. Med. Chem. 2012, 55, 3614-3643 incorporated in its entirety herein), apigenin (see Singh et al. Discovery and Development of Spleen Tyrosine Kinase (SYK) Inhibitors, J. Med. Chem. 2012, 55, 3614-3643 incorporated in its entirety herein), quercetin (see Singh et al. Discovery and Development of Spleen Tyrosine Kinase (SYK) Inhibitors, J. Med. Chem. 2012, 55, 3614-3643 incorporated in its entirety herein), fisetin (see Singh et al. Discovery and Development of Spleen Tyrosine Kinase (SYK) Inhibitors, J. Med. Chem. 2012, 55, 3614-3643 incorporated in its entirety herein), myricetin (see Singh et al. Discovery and Development of Spleen Tyrosine Kinase (SYK) Inhibitors, J. Med. Chem. 2012, 55, 3614-3643 incorporated in its entirety herein), morin (see Singh et al. Discovery and Development of Spleen Tyrosine Kinase (SYK) Inhibitors, J. Med. Chem. 2012, 55, 3614-3643 incorporated in its entirety herein). In one embodiment an effective amount of the isolated Compound 1 Pattern 1 is combined in a single dosage form with the Syk inhibitor.

In one embodiment, the at least one additional chemotherapeutic agent is a protein cell death-1 (PD-1) inhibitor. PD-1 inhibitors are known in the art, and include, for example, nivolumab (BMS), pembrolizumab (Merck), pidilizumab (CureTech/Teva), AMP-244 (Amplimmune/GSK), BMS-936559 (BMS), and MEDI4736 (Roche/Genentech). In one embodiment, an effective amount of the isolated Compound 1 Pattern 1 is combined in a single dosage form with the PD-1 inhibitor.

In one embodiment, the at least one additional chemotherapeutic agent is a B-cell lymphoma 2 (Bcl-2) protein inhibitor. BCL-2 inhibitors are known in the art, and include, for example, ABT-199 (4-[4-[[2-(4-Chlorophenyl)-4,4-dimethylcyclohex-1-en-1-yl]methyl]piperazin-1-yl]-N-[[3-nitro-4-[[(tetrahydro-2H-pyran-4-yl)methyl]amino]phenyl]sulfonyl]-2-[(1H-pyrrolo[2,3-b]pyridin-5-yl)oxy]benzamide), ABT-737 (4-[4-[[2-(4-chlorophenyl)phenyl]methyl]piperazin-1-yl]-N-[4-[[[(2R)-4-(dimethylamino)-1-phenylsulfanylbutan-2-yl]amino]-3-nitrophenyl]sulfonylbenzamide), ABT-263 ((R)-4-(4-((4'-chloro-4,4-dimethyl-3,4,5,6-tetrahydro-[1,1'-biphenyl]-2-yl)methyl)piperazin-1-yl)-N-((4-((4-morpholino-1-(phenylthio)butan-2-yl)amino)-3((trifluoromethyl)sulfonyl)phenyl)sulfonyl)benzamide), GX15-070 (obatoclax mesylate, (2Z)-2-[(5Z)-5-[(3,5-dimethyl-1H-pyrrol-2-yl)methylidene]-4-methoxypyrrol-2-ylidene]indole; methanesulfonic acid))), 2-methoxy-antimycin A3, YC137 (4-(4,9-dioxo-4,9-dihydronaphtho[2,3-d]thiazol-2-ylamino)-phenyl ester), pogosin, ethyl 2-amino-6-bromo-4-(1-cyano-2-ethoxy-2-oxoethyl)-4H-chromene-3-carboxylate, Nilotinib-d3, TW-37 (N-[4-[[2-(1,1-Dimethylethyl)phenyl]sulfonyl]phenyl]-2,3,4-trihydroxy-5-[[2-(1-methylethyl)phenyl]methyl]benzamide), Apogossypolone (ApoG2), or G3139 (Oblimersen). In one embodiment, an effective amount of the isolated Compound 1 Pattern 1 is combined in a single dosage form with the at least one BCL-2 inhibitor.

In one embodiment, a combination described herein can be further combined with an additional therapeutic to treat the cancer. The second therapy can be an immunotherapy. As discussed in more detail below, an effective amount of the isolated Compound 1 Pattern 1 can be conjugated to an antibody, radioactive agent, or other targeting agent that directs the compound to the diseased or abnormally proliferating cell. In another embodiment, the combination is used in combination with another pharmaceutical or a biologic agent (for example an antibody) to increase the efficacy of treatment with a combined or a synergistic approach. In an embodiment, combination can be used with T-cell vaccination, which typically involves immunization with inactivated autoreactive T cells to eliminate a cancer cell population as described herein. In another embodiment, the combination is used in combination with a bispecific T-cell Engager (BiTE), which is an antibody designed to simultaneously bind to specific antigens on endogenous T cells and cancer cells as described herein, linking the two types of cells.

In one embodiment, the bioactive agent is a MEK inhibitor. MEK inhibitors are well known, and include, for example, trametinib/GSK1120212 (N-(3-{3-Cyclopropyl-5-[(2-fluoro-4-iodophenyl)amino]-6,8-dimethyl-2,4,7-trioxo-3,4,6,7-tetrahydropyrido[4,3-d]pyrimidin-1(2H-yl}phenyl) acetamide), selumetinib (6-(4-bromo-2-chloroanilino)-7-fluoro-N-(2-hydroxyethoxy)-3-methylbenzimidazole-5-carboxamide), pimasertib/AS703026/MSC 1935369 ((S)—N-(2,3-dihydroxypropyl)-3-((2-fluoro-4-iodophenyl)amino) isonicotinamide), XL-518/GDC-0973 (1-({3,4-difluoro-2-[(2-fluoro-4-iodophenyl)amino]phenyl}carbonyl)-3-[(2S)-piperidin-2-yl]azetidin-3-ol), refametinib/BAY869766/RDEA1 19 (N-(3,4-difluoro-2-(2-fluoro-4-iodophenylamino)-6-methoxyphenyl)-1-(2,3-dihydroxypropyl)cyclopropane-1-sulfonamide), PD-0325901 (N-[(2R)-2,3-Dihydroxypropoxy]-3,4-difluoro-2-[(2-fluoro-4-iodophenyl)amino]-benzamide), TAK733 ((R)-3-(2,3-Dihydroxypropyl)-6-fluoro-5-(2-fluoro-4-iodophenylamino)-8-methylpyrido[2,3-d]pyrimidine-4,7(3H,8H)-dione), MEK162/ARRY438162 (5-[(4-Bromo-2-fluorophenyl)amino]-4-fluoro-N-(2-hydroxyethoxy)-1-methyl-1H-benzimidazole-6-carboxamide), RO5126766 (3-[[3-Fluoro-2-(methylsulfamoylamino)-4-pyridyl]methyl]-4-methyl-7-pyrimidin-2-yloxychromen-2-one), WX-554, RO4987655/CH4987655 (3,4-difluoro-2-((2-fluoro-4-iodophenyl) amino)-N-(2-hydroxyethoxy)-5-((3-oxo-1,2-oxazinan-2yl) methyl)benzamide), or AZD8330 (2-((2-fluoro-4-iodophenyl)amino)-N-(2 hydroxyethoxy)-1,5-dimethyl-6-oxo-1,6-dihydropyridine-3-carboxamide), U0126-EtOH, PD184352 (CI-1040), GDC-0623, BI-847325, cobimetinib, PD98059, BIX 02189, BIX 02188, binimetinib, SL-327, TAK-733, PD318088.

In one embodiment, an effective amount of Compound 1 Pattern 1 is administered in combination with an effective amount of binimetinib for the treatment of melanoma, including BRAF-mutant melanoma and NRAS-mutant melanoma.

In one embodiment, an effective amount of Compound 1 Pattern 1 is administered in combination with an effective amount of cobimetinib (Cotellic) for the treatment of melanoma, including BRAF-mutant melanoma and NRAS-mutant melanoma.

In one embodiment, an effective amount of Compound 1 Pattern 1 is administered in combination with an effective amount of binimetinib for the treatment of ovarian cancer.

In one embodiment, an effective amount of Compound 1 Pattern 1 is administered in combination with an effective amount of selumetinib for the treatment of non-small cell lung cancer.

In one embodiment, an effective amount of Compound 1 Pattern 1 is administered in combination with an effective amount of selumetinib for the treatment of thyroid cancer.

In one embodiment, an effective amount of Compound 1 Pattern 1 is administered in combination with an effective amount of trametinib (Mekinist) for the treatment of thyroid cancer.

In one embodiment, an effective amount of Compound 1 Pattern 1 is administered in combination with an effective amount of trametinib (Mekinist) for the treatment of melanoma.

In one embodiment, an effective amount of Compound 1 Pattern 1 is administered in combination with an effective amount of trametinib (Mekinist) for the treatment of non-small cell lung cancer.

In one embodiment, the bioactive agent is a Raf inhibitor. Raf inhibitors are known and include, for example, Vemurafinib (N-[3-[[5-(4-Chlorophenyl)-1H-pyrrolo[2,3-b]pyridin-3-yl]carbonyl]-2,4-difluorophenyl]-1-propanesulfonamide), sorafenib tosylate (4-[4-[[4-chloro-3-(trifluoromethyl)phenyl]carbamoylamino]phenoxy]-N-methylpyridine-2-carboxamide;4-methylbenzenesulfonate), AZ628 (3-(2-cyanopropan-2-yl)-N-(4-methyl-3-(3-methyl-4-oxo-3,4-dihydroquinazolin-6-ylamino)phenyl)benzamide), NVP-BHG712 (4-methyl-3-(1-methyl-6-(pyridin-3-yl)-1H-pyrazolo[3,4-d]pyrimidin-4-ylamino)-N-(3-(trifluoromethyl)phenyl)benzamide), RAF-265 (1-methyl-5-[2-[5-(trifluoromethyl)-1H-imidazol-2-yl]pyridin-4-yl]oxy-N-[4-(trifluoromethyl)phenyl]benzimidazol-2-amine), 2-Bromoaldisine (2-Bromo-6,7-dihydro-1H,5H-pyrrolo[2,3-c]azepine-4,8-dione), Raf Kinase Inhibitor IV (2-chloro-5-(2-phenyl-5-(pyridin-4-yl)-1H-imidazol-4-yl)phenol), Sorafenib N-Oxide (4-[4-[[[[4-Chloro-3(trifluoroMethyl) phenyl]aMino]carbonyl]aMino]phenoxy]-N-Methyl-2pyridinecarboxaMide 1-Oxide), PLX-4720, dabrafenib (GSK2118436), GDC-0879, RAF265, AZ 628, SB590885, ZM336372, GW5074, TAK-632, CEP-32496, LY3009120, and GX818 (Encorafenib).

In one embodiment, an effective amount of Compound 1 Pattern 1 is administered in combination with an effective amount of dabrafenib (Tafinlar) for the treatment of thyroid cancer.

In one embodiment, an effective amount of Compound 1 Pattern 1 is administered in combination with an effective amount of dabrafenib (Tafinlar) for the treatment of melanoma.

In one embodiment, an effective amount of Compound 1 Pattern 1 is administered in combination with an effective amount of dabrafenib (Tafinlar) for the treatment of non-small cell lung cancer.

In one embodiment, an effective amount of Compound 1 Pattern 1 is administered in combination with an effective amount of encorafenib for the treatment of melanoma, including BRAF-mutant melanoma.

In one embodiment, the additional therapy is a monoclonal antibody (MAb). Some MAbs stimulate an immune response that destroys cancer cells. Similar to the antibodies produced naturally by B cells, these MAbs "coat" the cancer cell surface, triggering its destruction by the immune system. For example, bevacizumab targets vascular endothelial growth factor(VEGF), a protein secreted by tumor cells and other cells in the tumor's microenvironment that promotes the development of tumor blood vessels. When bound to bevacizumab, VEGF cannot interact with its cellular receptor, preventing the signaling that leads to the growth of new blood vessels. Similarly, cetuximab and panitumumab target the epidermal growth factor receptor (EGFR), and trastuzumab targets the human epidermal growth factor receptor 2 (HER-2). MAbs that bind to cell surface growth factor receptors prevent the targeted receptors from sending their normal growth-promoting signals. They may also trigger apoptosis and activate the immune system to destroy tumor cells.

Another group of cancer therapeutic MAbs are the immunoconjugates. These MAbs, which are sometimes called immunotoxins or antibody-drug conjugates, consist of an antibody attached to a cell-killing substance, such as a plant or bacterial toxin, a chemotherapy drug, or a radioactive molecule. The antibody latches onto its specific antigen on the surface of a cancer cell, and the cell-killing substance is taken up by the cell. FDA-approved conjugated MAbs that work this way include ado-trastuzumab emtansine, which targets the HER-2 molecule to deliver the drug DM1, which inhibits cell proliferation, to HER-2 expressing metastatic breast cancer cells.

Immunotherapies with T cells engineered to recognize cancer cells via bispecific antibodies (bsAbs) or chimeric antigen receptors (CARs) are approaches with potential to ablate both dividing and non/slow-dividing subpopulations of cancer cells.

Bispecific antibodies, by simultaneously recognizing target antigen and an activating receptor on the surface of an immune effector cell, offer an opportunity to redirect immune effector cells to kill cancer cells. The other approach is the generation of chimeric antigen receptors by fusing extracellular antibodies to intracellular signaling domains. Chimeric antigen receptor-engineered T cells are able to specifically kill tumor cells in a MHC-independent way.

In some embodiments, the combination can be administered to the subject in further combination with other chemotherapeutic agents. If convenient, the combination described herein can be administered at the same time as another chemotherapeutic agent, in order to simplify the treatment regimen. In some embodiments, the combination and the other chemotherapeutic can be provided in a single formulation. In one embodiment, the use of the compounds described herein is combined in a therapeutic regime with other agents. Such agents may include, but are not limited to, tamoxifen, midazolam, letrozole, bortezomib, anastrozole, goserelin, an mTOR inhibitor, a PI3 kinase inhibitors, dual mTOR-PI3K inhibitors, MEK inhibitors, RAS inhibitors, ALK inhibitors, HSP inhibitors (for example, HSP70 and HSP 90 inhibitors, or a combination thereof), BCL-2 inhibitors, apopotoic inducing compounds, AKT inhibitors, including but not limited to, MK-2206, GSK690693, Perifosine, (KRX-0401), GDC-0068, Triciribine, AZD5363, Honokiol, PF-04691502, and ipatasertib, Miltefosine; PD-1 inhibitors including but not limited to, Nivolumab, CT-011, MK-3475, BMS936558, and AMP-514 or FLT-3 inhibitors, including but not limited to, P406, Dovitinib, Quizartinib (AC220), Amuvatinib (MP-470), Tandutinib (MLN518), ENMD-2076, and KW-2449, or combinations thereof.

In one embodiment, an effective amount of Compound 1 Pattern 1 is administered in combination with an effective amount of ipatasertib for the treatment of breast cancer, including triple negative breast cancer.

In one embodiment, the bioactive agent is an mTOR inhibitor. Examples of mTOR inhibitors include but are not limited to vistusertib and rapamycin and its analogs, everolimus (Afinitor), temsirolimus, ridaforolimus, sirolimus, and deforolimus. Examples of MEK inhibitors include but are not limited to tametinib/GSK1120212 (N-(3-{3-Cyclopropyl-5-[(2-fluoro-4-iodophenyl)amino]-6,8-dimethyl-2,4,7-trioxo-3,4,6,7-tetrahydropyrido[4,3-d]pyrimidin-1(2H-yl}phenyl)acetamide), selumetinob (6-(4-bromo-2-chloroanilino)-7-fluoro-N-(2-hydroxyethoxy)-3-methylbenzimidazole-5-carboxamide), pimasertib/AS703026/MSC1935369 ((S)—N-(2,3-dihydroxypropyl)-3-((2-fluoro-4-iodophenyl)amino)isonicotinamide), XL-518/GDC-0973 (1-({3,4-difluoro-2-[(2-fluoro-4-iodophenyl)amino]phenyl}carbonyl)-3-[(2S)-piperidin-2-yl] azetidin-3-ol), refametinib/BAY869766/RDEA119 (N-(3,4-difluoro-2-(2-fluoro-4-iodophenylamino)-6-methoxyphenyl)-1-(2,3-dihydroxypropyl)cyclopropane-1-sulfonamide), PD-0325901 (N-[(2R)-2,3-Dihydroxypropoxy]-3,4-difluoro-2-[(2-fluoro-4-iodophenyl)amino]-benzamide), TAK733 ((R)-3-(2,3-Dihydroxypropyl)-6-fluoro-5-(2-fluoro-4-iodophenylamino)-8-methylpyrido[2,3d]pyrimidine-4,7 (3H,8H)-dione), MEK162/ARRY438162 (5-[(4-Bromo-2-fluorophenyl)amino]-4-fluoro-N-(2-hydroxyethoxy)-1-methyl-1H-benzimidazole-6 carboxami de), R05126766 (3-[[3-Fluoro-2-(methylsulfamoylamino)-4-pyridyl]methyl]-4-methyl-7-pyrimidin-2-yloxychromen-2-one), WX-554, R04987655/CH4987655 (3,4-difluoro-2-((2-fluoro-4-iodophenyl)amino)-N-(2-hydroxyethoxy)-5-((3-oxo-1,2-oxazinan-2 yl)methyl)benzamide), or AZD8330 (2-((2-fluoro-4-iodophenyl)amino)-N-(2-hydroxyethoxy)-1,5-dimethyl-6-oxo-1,6-dihydropyridine-3-carboxamide).

In one embodiment, the bioactive agent is a RAS inhibitor. Examples of RAS inhibitors include but are not limited to Reolysin and siG12D LODER.

In one embodiment, the bioactive agent is an ALK inhibitor. Examples of ALK inhibitors include but are not limited to Crizotinib, AP26113, and LDK378.

In one embodiment, the bioactive agent is a HSP inhibitor. HSP inhibitors include but are not limited to Geldanamycin or 17-N-Allylamino-17-demethoxygeldanamycin (17AAG), and Radicicol. In a particular embodiment, a compound described herein is administered in combination with letrozole and/or tamoxifen. Other chemotherapeutic agents that can be used in combination with the compounds described herein include, but are not limited to, chemotherapeutic agents that do not require cell cycle activity for their anti-neoplastic effect.

Additional bioactive compounds include, for example, everolimus, trabectedin, abraxane, TLK 286, AV-299, DN-101, pazopanib, GSK690693, RTA 744, ON 0910. Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an aurora kinase inhibitor, a PIK-1 modulator, an HDAC inhibitor, a c-MET inhibitor, a PARP inhibitor, a Cdk inhibitor, an IGFR-TK inhibitor, an anti-HGF antibody, a focal adhesion kinase inhibitor, a Map kinase (mek) inhibitor, a VEGF trap antibody, pemetrexed, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdR₁ KRX-0402, lucanthone, LY317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo [2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES (diethylstilbestrol), estradiol, estrogen, conjugated estrogen, bevacizumab, IMC-1C11, CHIR-258); 3-[5-(methyl sulfonylpiperadinemethyl)-indolyl-quinolone, vatalanib, AG-013736, AVE-0005, goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, Ionafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, amsacrine, anagrelide, L-asparaginase, Bacillus Calmette-Guerin (BCG) vaccine, adriamycin, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gleevec, gemcitabine, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonist, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, a platelet-derived growth factor receptor alpha (PDGFR-α) antibody, epoetin alfa, darbepoetin alfa and mixtures thereof.

In one embodiment, an effective amount of the isolated Compound 1 Pattern 1 described herein can be combined with a PARP inhibitor selected from niraparib tosylate monohydrate (Zejula), olaparib (Lynparza), rucaparib camsylate (Rubraca), and talazoparib.

In one embodiment, an effective amount of Compound 1 Pattern 1 is administered in combination with an effective amount of niraparib tosylate monohydrate (Zejula) for the treatment of abnormal tissue of the female reproductive system, including ovarian epithelial cancer or fallopian tube cancer.

In one embodiment, an effective amount of Compound 1 Pattern 1 is administered in combination with an effective amount of niraparib tosylate monohydrate (Zejula) for the treatment of peritoneal cancer.

In one embodiment, an effective amount of Compound 1 Pattern 1 is administered in combination with an effective amount of olaparib (Lynparza) for the treatment of abnormal tissue of the female reproductive system, including breast cancer, ovarian cancer, ovarian epithelial cancer or fallopian tube cancer.

In one embodiment, an effective amount of Compound 1 Pattern 1 is administered in combination with an effective amount of olaparib (Lynparza) for the treatment of BRAC1 or BRAC2-mutated breast cancer.

In one embodiment, an effective amount of Compound 1 Pattern 1 is administered in combination with an effective amount of olaparib (Lynparza) for the treatment of HER2-breast cancer.

In one embodiment, an effective amount of Compound 1 Pattern 1 is administered in combination with an effective amount of olaparib (Lynparza) for the treatment of peritoneal cancer.

In one embodiment, an effective amount of Compound 1 Pattern 1 is administered in combination with an effective amount of rucaparib camsylate (Rubraca) for the treatment of abnormal tissue of the female reproductive system, including breast cancer, ovarian cancer, ovarian epithelial cancer or fallopian tube cancer.

In one embodiment, an effective amount of Compound 1 Pattern 1 is administered in combination with an effective amount of rucaparib camsylate (Rubraca) for the treatment of peritoneal cancer.

In one embodiment, an effective amount of Compound 1 Pattern 1 is administered in combination with an effective amount of talazoparib for the treatment of abnormal tissue of the female reproductive system, including breast cancer, ovarian cancer, ovarian epithelial cancer or fallopian tube cancer.

In one embodiment, an effective amount of Compound 1 Pattern 1 is administered in combination with an effective amount of talazoparib for the treatment of BRAC1 or BRAC2-mutated breast cancer.

In one embodiment, an effective amount of Compound 1 Pattern 1 is administered in combination with an effective amount of olaratumab for the treatment of soft tissue sarcoma.

In one embodiment, an effective amount of Compound 1 Pattern 1 is administered in combination with an effective amount of savolitinib for the treatment of adenocarcinoma.

In one embodiment, an effective amount of Compound 1 Pattern 1 is administered in combination with an effective amount of savolitinib for the treatment of non-small cell lung cancer.

In one embodiment, an effective amount of Compound 1 Pattern 1 is administered in combination with an effective amount of savolitinib for the treatment of renal cell carcinoma.

In one embodiment, an effective amount of Compound 1 Pattern 1 is administered in combination with an effective amount of vistusertib for the treatment of advanced breast cancer.

In one embodiment, an effective amount of Compound 1 Pattern 1 is administered in combination with an effective amount of vistusertib for the treatment of advanced breast cancer.

In one embodiment, an effective amount of the isolated Compound 1 Pattern 1 described herein can be combined with a chemotherapeutic selected from, but are not limited to, Imatinib mesylate (Gleevac®), Dasatinib (Sprycel®), Nilotinib (Tasigna®), Bosutinib (Bosulif®), Trastuzumab (Herceptin®), Pertuzumab (Perjeta™), Lapatinib (Tykerb®), Gefitinib (Iressa®), Erlotinib (Tarceva®), Cetuximab (Erbitux®), Panitumumab (Vectibix®), Vandetanib (Caprelsa®), Vemurafenib (Zelboraf®), Vorinostat (Zolinza®), Romidepsin (Istodax®), Bexarotene (Tagretin®), Alitretinoin (Panretin®), Tretinoin (Vesanoid®), Carfilizomib (Kyprolis™), Pralatrexate (Folotyn®), Bevacizumab (Avastin®), Ziv-aflibercept (Zaltrap®), Sorafenib (Nexavar®), Sunitinib (Sutent®), Pazopanib (Votrient®), Regorafenib (Stivarga®), and Cabozantinib (Cometriq™).

In one embodiment, an effective amount of the isolated Compound 1 Pattern 1 described herein can be combined with a CD4/6 inhibitor including abemaciclib (Versenio), palbociclib (Ibrance), or trilaciclib.

In one embodiment, an effective amount of Compound 1 Pattern 1 is administered in combination with an effective amount of abemaciclib (Versenio) for the treatment of breast cancer.

In one embodiment, an effective amount of Compound 1 Pattern 1 is administered in combination with an effective amount of abemaciclib (Versenio) for the treatment of HR+HER2-breast cancer.

In one embodiment, an effective amount of Compound 1 Pattern 1 is administered in combination with an effective amount of palbociclib (Ibrance) for the treatment of breast cancer.

In one embodiment, an effective amount of Compound 1 Pattern 1 is administered in combination with an effective amount of palbociclib (Ibrance) for the treatment of HR+HER2-breast cancer.

In one embodiment, an effective amount of Compound 1 Pattern 1 is administered in combination with an effective amount of palbociclib (Ibrance) for the treatment of breast cancer.

In one embodiment, an effective amount of Compound 1 Pattern 1 is administered in combination with an effective amount of palbociclib (Ibrance) for the treatment of metastatic triple negative breast cancer.

In one embodiment, an effective amount of Compound 1 Pattern 1 is administered in combination with an effective amount of palbociclib (Ibrance) for the treatment of small cell lung cancer.

In one embodiment, an effective amount of Compound 1 Pattern 1 is administered in combination with an effective amount of cabozantinib S-malate (Cometrig™) for the treatment of thyroid cancer.

In one embodiment, an effective amount of Compound 1 Pattern 1 is administered in combination with an effective amount of cabozantinib S-maleate (Cometrig™) for the treatment of renal cell carcinoma.

In one embodiment, an effective amount of Compound 1 Pattern 1 is administered in combination with an effective amount of dasatinib (Sprycel) for the treatment of leukemia, including acute lymphoblastic leukemia or chronic myelogenous leukemia.

In one embodiment, an effective amount of Compound 1 Pattern 1 is administered in combination with an effective amount of dasatinib (Sprycel) for the treatment of prostate cancer.

In one embodiment, an effective amount of Compound 1 Pattern 1 is administered in combination with an effective amount of Erlotinib (Tarceva®) for the treatment of prostate cancer.

In one embodiment, an effective amount of Compound 1 Pattern 1 is administered in combination with an effective amount of Gefitinib (Iressa®) for the treatment of prostate cancer.

In one embodiment, an effective amount of Compound 1 Pattern 1 is administered in combination with an effective amount of imatinib mesylate (Gleevec) for the treatment of leukemia, including acute lymphoblastic leukemia, chronic eosinophilic leukemia, hypereosinophilic syndrome, or chronic myelogenous leukemia.

In one embodiment, an effective amount of Compound 1 Pattern 1 is administered in combination with an effective amount of trastuzumab (Herceptin) for the treatment of adenocarcinoma.

In one embodiment, an effective amount of Compound 1 Pattern 1 is administered in combination with an effective amount of trastuzumab (Herceptin) for the treatment of breast cancer, including HER2+ breast cancer.

In one embodiment, an effective amount of Compound 1 Pattern 1 is administered in combination with an effective amount of imatinib mesylate (Gleevec) for the treatment of tumors, including but not limited to dermatofibrosarcoma protuberans and gastrointestinal stromal tumors.

In one embodiment, an effective amount of Compound 1 Pattern 1 is administered in combination with an effective amount of imatinib mesylate (Gleevec) for the treatment of myelodysplastic/myeloproliferative neoplasms.

In one embodiment, an effective amount of Compound 1 Pattern 1 is administered in combination with an effective amount of imatinib mesylate (Gleevec) for the treatment of systemic mastocytosis.

In one embodiment, an effective amount of Compound 1 Pattern 1 is administered in combination with an effective amount of nilotinib (Tasigna) for the treatment of chronic myelogenous leukemia, including Philadelphia chromosome positive chronic myeloid leukemia (Ph+CML).

In one embodiment, an effective amount of Compound 1 Pattern 1 is administered in combination with an effective amount of pazopanib hydrochloride (Votrient) for the treatment of renal cell carcinoma.

In one embodiment, an effective amount of Compound 1 Pattern 1 is administered in combination with an effective amount of pazopanib hydrochloride (Votrient) for the treatment of soft tissue sarcoma.

In one embodiment, an effective amount of Compound 1 Pattern 1 is administered in combination with an effective amount of regorafenib (Stivarga) for the treatment of colorectal cancer.

In one embodiment, an effective amount of Compound 1 Pattern 1 is administered in combination with an effective amount of regorafenib (Stivarga) for the treatment of gastrointestinal stromal tumor.

In one embodiment, an effective amount of Compound 1 Pattern 1 is administered in combination with an effective amount of regorafenib (Stivarga) for the treatment of hepatocellular carcinoma.

In one embodiment, an effective amount of Compound 1 Pattern 1 is administered in combination with an effective amount of sorafenib Tosylate (Nexavar) for the treatment of carcinoma, including hepatocellular carcinoma or renal cell carcinoma.

In one embodiment, an effective amount of Compound 1 Pattern 1 is administered in combination with an effective amount of sunitinib malate (Sutent) for the treatment of gastrointestinal stromal tumor.

In one embodiment, an effective amount of Compound 1 Pattern 1 is administered in combination with an effective amount of sunitinib malate (Sutent) for the treatment of pancreatic cancer.

In one embodiment, an effective amount of Compound 1 Pattern 1 is administered in combination with an effective amount of sunitinib malate (Sutent) for the treatment of renal cell carcinoma.

In one embodiment, an effective amount of Compound 1 Pattern 1 is administered in combination with an effective amount of vemurafenib (Zelboraf) for the treatment of Erdheim-Chester disease.

In one embodiment, an effective amount of Compound 1 Pattern 1 is administered in combination with an effective amount of vemurafenib (Zelboraf) for the treatment of melanoma.

In certain aspects, the additional therapeutic agent is an anti-inflammatory agent, a chemotherapeutic agent, a radio-therapeutic, additional therapeutic agents, or immunosuppressive agents.

Suitable chemotherapeutic agents include, but are not limited to, radioactive molecules, toxins, also referred to as cytotoxins or cytotoxic agents, which includes any agent that is detrimental to the viability of cells, agents, and liposomes or other vesicles containing chemotherapeutic compounds. General anticancer pharmaceutical agents include: Vincristine (Oncovin®) or liposomal vincristine (Marqibo®), Daunorubicin (daunomycin or Cerubidine®) or doxorubicin (Adriamycin®), Cytarabine (cytosine arabinoside, ara-C, or Cytosar®), L-asparaginase (Elspar®) or PEG-L-asparaginase (pegaspargase or Oncaspar®), Etoposide (VP-16), Teniposide (Vumon®), 6-mercaptopurine (6-MP or Purinethol®), Methotrexate, Cyclophosphamide (Cytoxan®), Prednisone, Dexamethasone (Decadron), imatinib (Gleevec®), dasatinib (Sprycel®), nilotinib (Tasigna®), bosutinib (Bosulif®), and ponatinib (Iclusig™) Examples of additional suitable chemotherapeutic agents include but are not limited to 1-dehydrotestosterone, 5-fluorouracil decarbazine, 6-mercaptopurine, 6-thioguanine, actinomycin D, adriamycin, aldesleukin, alkylating agents, allopurinol sodium, altretamine, amifostine, anastrozole, anthramycin (AMC)), anti-mitotic agents, cis-dichlorodiamine platinum (II) (DDP) cisplatin, diamino dichloro platinum, anthracycline, an antibiotic, an antimetabolite, asparaginase, BCG live (intravesical), betamethasone sodium phosphate and betamethasone acetate, bicalutamide, bleomycin sulfate, busulfan, calcium leucouorin, calicheamicin, capecitabine, carboplatin, lomustine (CCNU), carmustine (BSNU), Chlorambucil, Cisplatin, Cladribine, Colchicin, conjugated estrogens, Cyclophosphamide, Cyclothosphamide, Cytarabine, Cytarabine, cytochalasin B, Cytoxan, Dacarbazine, Dactinomycin, dactinomycin (formerly actinomycin), daunirubicin HCl, daunorucbicin citrate, denileukin diftitox, Dexrazoxane, Dibromomannitol, dihydroxy anthracin dione, Docetaxel, dolasetron mesylate, doxorubicin HCl, dronabinol, E. coli L-asparaginase, emetine, epoetin-α, Erwinia L-asparaginase, esterified estrogens, estradiol, estramustine phosphate sodium, ethidium bromide, ethinyl estradiol, etidronate, etoposide citrororum factor, etoposide phosphate, filgrastim, floxuridine, fluconazole, fludarabine phosphate, fluorouracil, flutamide, folinic acid, gemcitabine HCl, glucocorticoids, goserelin acetate, gramicidin D, granisetron HCl, hydroxyurea, idarubicin HCl, ifosfamide, interferon α-2b, irinotecan HCl, letrozole, leucovorin calcium, leuprolide acetate, levamisole HCl, lidocaine, lomustine, maytansinoid, mechlorethamine HCl, medroxyprogesterone acetate, megestrol acetate, melphalan HCl, mercaptipurine, mesna, methotrexate, methyltestosterone, mithramycin, mitomycin C, mitotane, mitoxantrone, nilutamide, octreotide acetate, ondansetron HCL, paclitaxel, pamidronate disodium, pentostatin, pilocarpine HCl, plimycin, polifeprosan 20 with carmustine implant, porfimer sodium, procaine, procarbazine HCl, propranolol, rituximab, sargmostim, streptozotocin, tamoxifen, taxol, teniposide, tenoposide, testolactone, tetracaine, thioepa chlorambucil, thioguanine, thiotepa, topotecan HCl, toremifene citrate, trastuzumab, tretinoin, valrubicin, vinblastine sulfate, vincristine sulfate, and vinorelbine tartrate.

In one embodiment, an effective amount of Compound 1 Pattern 1 is administered in combination with an effective amount of bosutinib (Bosulif®) for the treatment of chronic myelogenous leukemia (CML).

In one embodiment, an effective amount of Compound 1 Pattern 1 is administered in combination with an effective amount of ponatinib hydrochloride (Iclusig) for the treatment of leukemia, including acute lymphoblastic leukemia and chronic myelogenous leukemia.

Additional therapeutic agents that can be administered in combination with a compound disclosed herein can include bevacizumab, sutinib, sorafenib, 2-methoxyestradiol or 2ME2, finasunate, vatalanib, vandetanib, aflibercept, volociximab, etaracizumab (MEDI-522), cilengitide, erlotinib, cetuximab, panitumumab, gefitinib, trastuzumab, dovitinib, figitumumab, atacicept, rituximab, alemtuzumab, aldesleukine, atlizumab, tocilizumab, temsirolimus, everolimus, lucatumumab, dacetuzumab, HLL1, huN901-DM1, atiprimod, natalizumab, bortezomib, carfilzomib, marizomib, tanespimycin, saquinavir mesylate, ritonavir, nelfinavir mesylate, indinavir sulfate, belinostat, panobinostat, mapatumumab, lexatumumab, dulanermin, ABT-737, oblimersen, plitidepsin, talmapimod, P276-00, enzastaurin, tipifarnib, perifosine, imatinib, dasatinib, lenalidomide, thalidomide, simvastatin, celecoxib, bazedoxifene, AZD4547, rilotumumab, oxaliplatin (Eloxatin), PD0332991, ribociclib (LEE011), amebaciclib (LY2835219), HDM201, fulvestrant (Faslodex), exemestane (Aromasin), PIM447, ruxolitinib (INC424), BGJ398, necitumumab, pemetrexed (Alimta), and ramucirumab (IMC-1121B).

In one embodiment, an effective amount of Compound 1 Pattern 1 is administered in combination with an effective amount of everolimus (Afinitor) for the treatment of breast cancer.

In one embodiment, an effective amount of Compound 1 Pattern 1 is administered in combination with an effective amount of everolimus (Afinitor) for the treatment of HR+, HER2-breast cancer.

In one embodiment, an effective amount of Compound 1 Pattern 1 is administered in combination with an effective amount of everolimus (Afinitor) for the treatment of pancreatic cancer.

In one embodiment, an effective amount of Compound 1 Pattern 1 is administered in combination with an effective amount of everolimus (Afinitor) for the treatment of gastrointestinal cancer.

In one embodiment, an effective amount of Compound 1 Pattern 1 is administered in combination with an effective amount of everolimus (Afinitor) for the treatment of lung cancer.

In one embodiment, an effective amount of Compound 1 Pattern 1 is administered in combination with an effective amount of everolimus (Afinitor) for the treatment of renal cell carcinoma.

In one embodiment, an effective amount of Compound 1 Pattern 1 is administered in combination with an effective amount of everolimus (Afinitor) for the treatment of astrocytoma, including subependymal giant cell astrocytoma.

In one embodiment, an effective amount of Compound 1 Pattern 1 is administered in combination with an effective amount of fulvestrant (Faslodex) for the treatment of breast cancer.

In one embodiment, an effective amount of Compound 1 Pattern 1 is administered in combination with an effective amount of fulvestrant (Faslodex) for the treatment of HR+, HER2-breast cancer.

In one embodiment, an effective amount of Compound 1 Pattern 1 is administered in combination with an effective amount of ramucirumab for the treatment of adenocarcinoma.

In one embodiment, an effective amount of Compound 1 Pattern 1 is administered in combination with an effective amount of ramucirumab for the treatment of non-small cell lung cancer.

In one embodiment, an effective amount of Compound 1 Pattern 1 is administered in combination with an effective amount of ramucirumab for the treatment of colorectal cancer.

In one embodiment, an effective amount of Compound 1 Pattern 1 is administered in combination with an effective amount of ribociclib (Kisqali) for the treatment of breast cancer.

In one embodiment, an effective amount of Compound 1 Pattern 1 is administered in combination with an effective amount of ribociclib (Kisqali) for the treatment of HR+ and HER2-breast cancer.

In one aspect of the present invention, a compound described herein can be combined with at least one IDH1 or IDH2 inhibitor. In one embodiment, an effective amount of Compound 1 Pattern 1 is administered in combination with an effective amount of enasidenib mesylate (Idhifa) for the treatment of acute myeloid leukemia.

In one aspect of the present invention, a compound described herein can be combined with at least one fibroblast growth factor receptor (FGFR) tyrosine kinase inhibitor. In one embodiment, an effective amount of Compound 1 Pattern 1 is administered in combination with an effective amount of erdafitinib for the treatment of urothelial cancer, including metastatic urothelial cancer.

In one aspect of the present invention, a compound described herein can be combined with at least one ERK inhibitor.

In one embodiment, an effective amount of Compound 1 Pattern 1 is administered in combination with an effective amount of SCH772984 for the treatment of melanoma, including BRAF-mutant melanoma or NRAS-mutant melanoma.

In one embodiment, an effective amount of Compound 1 Pattern 1 is administered in combination with an effective amount of ulixertinib for the treatment of melanoma, including uveal melanoma.

In one embodiment, an effective amount of Compound 1 Pattern 1 is administered in combination with an effective amount of ulixertinib for the treatment of pancreatic cancer.

In one aspect of the present invention, a compound described herein can be combined with at least one immunosuppressive agent. The immunosuppressive agent is preferably selected from the group consisting of a calcineurin inhibitor, e.g. a cyclosporin or an ascomycin, e.g. Cyclosporin A (NEORAL®), FK506 (tacrolimus), pimecrolimus, a mTOR inhibitor, e.g. rapamycin or a derivative thereof, e.g. Sirolimus (RAPAMUNE®), Everolimus (Certican®), temsirolimus, zotarolimus, biolimus-7, biolimus-9, a rapalog, e.g., ridaforolimus, azathioprine, campath 1H, a SIP receptor modulator, e.g. fingolimod or an analogue thereof, an anti IL-8 antibody, mycophenolic acid or a salt thereof, e.g. sodium salt, or a prodrug thereof, e.g. Mycophenolate Mofetil (CELLCEPT®), OKT3 (ORTHOCLONE OKT3®), Prednisone, ATGAM®, THYMOGLOBULIN®, Brequinar Sodium, OKT4, T10B9. A-3A, 33B3.1, 15-deoxyspergualin, tresperimus, Leflunomide ARAVA®, CTLAI-Ig, anti-CD25, anti-IL2R, Basiliximab (SIMULECT®), Daclizumab (ZENAPAX®), mizorbine, methotrexate, dexamethasone, ISAtx-247, SDZ ASM 981 (pimecrolimus, Elidel®), CTLA41g (Abatacept), belatacept, LFA31g, etanercept (sold as Enbrel® by Immunex), adalimumab (Humira®), infliximab (Remicade®), an anti-LFA-1 antibody, natalizumab (Antegren®), Enlimomab, gavilimomab, anti-thymocyte immunoglobulin, siplizumab, Alefacept efalizumab, pentasa, mesalazine, asacol, codeine phosphate, benorylate, fenbufen, naprosyn, diclofenac, etodolac and indomethacin, aspirin and ibuprofen.

In certain embodiments, a compound described herein is administered to the subject prior to treatment with another chemotherapeutic agent, during treatment with another chemotherapeutic agent, after administration of another chemotherapeutic agent, or a combination thereof.

In some embodiments, an effective amount of the isolated Compound 1 Pattern 1 can be administered to the subject such that the other chemotherapeutic agent can be administered either at higher doses (increased chemotherapeutic dose intensity) or more frequently (increased chemotherapeutic dose density). Dose-dense chemotherapy is a chemotherapy treatment plan in which drugs are given with less time between treatments than in a standard chemotherapy treatment plan. Chemotherapy dose intensity represents unit dose of chemotherapy administered per unit time. Dose intensity can be increased or decreased through altering dose administered, time interval of administration, or both.

In one embodiment of the invention, the compounds described herein can be administered in a concerted regimen with another agent such as a non-DNA-damaging, targeted anti-neoplastic agent or a hematopoietic growth factor agent. It has been recently been reported that the untimely administration of hematopoietic growth factors can have serious side effects. For example, the use of the EPO family of growth factors has been associated with arterial hypertension, cerebral convulsions, hypertensive encephalopathy, thromboembolism, iron deficiency, influenza like syndromes and venous thrombosis. The G-CSF family of growth factors has been associated with spleen enlargement and rupture, respiratory distress syndrome, allergic reactions and sickle cell complications. As such, in one embodiment, the use of the compounds or methods described herein is combined with the use of hematopoietic growth factors including, but not limited to, granulocyte colony stimulating factor (G-CSF, for example, sold as Neupogen (filgrastin), Neulasta (peg-filgrastin), or lenograstin), granulocyte-macrophage colony stimulating factor (GM-CSF, for example sold as molgramostim and sargramostim (Leukine)), M-CSF (macrophage colony stimulating factor), thrombopoietin (megakaryocyte growth development factor (MGDF), for example sold as Romiplostim and Eltrombopag) interleukin (IL)-12, interleukin-3, interleukin-11 (adipogenesis inhibiting factor or oprelvekin), SCF (stem cell factor, steel factor, kit-ligand, or KL) and erythropoietin (EPO), and their derivatives (sold as for example epoetin-α as Darbopoetin, Epocept, Nanokine, Epofit, Epogin, Eprex and Procrit; epoetin-β sold as for example NeoRecormon, Recormon and Micera), epoetin-delta (sold as for example Dynepo), epoetin-omega (sold as for example Epomax), epoetin zeta (sold as for example Silapo and Reacrit) as well as for example Epocept, EPOTrust, Erypro Safe, Repoeitin, Vintor, Epofit, Erykine, Wepox, Espogen, Relipoeitin, Shanpoietin, Zyrop and EPIAO). In one embodiment, an effective amount of the isolated Compound 1 Pattern 1 is administered prior to administration of the hematopoietic growth factor. In one embodiment, the hematopoietic growth factor administration is timed so that the compound's effect on HSPCs has dissipated. In one embodiment, the growth factor is administered at least 20 hours after the administration of a compound described herein.

If desired, multiple doses of a compound described herein can be administered to the subject. Alternatively, the subject can be given a single dose of a compound described herein.

In one aspect of the invention, a compound disclosed herein can be beneficially administered in combination with any therapeutic regimen entailing radiotherapy, chemotherapy, or other therapeutic agents. In additional embodiments the compounds disclosed herein can be beneficially administered in combination with therapeutic agents targeting auto-immune disorders.

EXAMPLES

Example 1. X-Ray Powder Diffraction (XRPD)

XRPD analysis was carried out on a PANalytical X'pert pro, scanning the samples between 3 and 35° 2θ. The material was gently grounded to release any agglomerates and loaded onto a multi-well plate with Kapton or Mylar polymer film to support the sample. The multi-well plate was then placed into the diffractometer and analyzed using Cu K radiation (α1 λ, =1.54060 Å; α2=1.54443 Å; β=1.39225 Å; α1: α2 ratio=0.5) running in transmission mode (step size 0.0130° 2θ) using 40 kV/40 mA generator settings. The above technique was used to generate the images in FIG. 1, FIG. 7, FIG. 8 through FIG. 19, FIG. 21 through FIG. 32, FIG. 36, FIG. 38, FIG. 42, FIG. 43, FIG. 49 through FIG. 59, FIG. 61, FIG. 67 through FIG. 69, and FIG. 89.

Table 1 below provides the XRPD Peak List for Pattern 1 with >10% relative intensity peaks. The XRPD performed on Pattern 1 exhibited sharp peaks, indicating the sample was composed of crystalline material. Significant peaks were observed in the XRPD on Pattern 1 at about 9.6±0.2°, about 12.2±0.2°, about 15.3±0.2°, about 17.6±0.2°, about 19.3±0.2°, about 19.8±0.2°, about 21.3±0.2°, about 22.7±0.2°, about 24.0±0.2°, about 26.1±0.2°, and about 28.6±0.2°.

TABLE 1

| XRPD Peak List for Pattern 1 | | |
|---|---|---|
| Pos. [°2θ] | d-spacing [Å] | Rel. Int. [%] |
| 9.57 | 9.24 | 100.0 |
| 10.12 | 8.74 | 16.80 |
| 12.20 | 7.26 | 57.10 |
| 13.82 | 6.41 | 14.30 |
| 15.33 | 5.78 | 27.70 |
| 15.99 | 5.54 | 16.60 |
| 17.00 | 5.22 | 17.80 |
| 17.56 | 5.05 | 31.70 |
| 18.71 | 4.74 | 11.50 |
| 19.28 | 4.60 | 35.70 |
| 19.84 | 4.47 | 65.40 |
| 20.30 | 4.37 | 23.30 |
| 20.71 | 4.29 | 11.80 |
| 20.98 | 4.23 | 17.90 |
| 21.27 | 4.18 | 89.10 |
| 22.71 | 3.91 | 20.90 |
| 23.19 | 3.84 | 24.70 |
| 23.97 | 3.71 | 53.30 |
| 26.06 | 3.42 | 37.00 |
| 26.76 | 3.33 | 16.40 |

TABLE 1-continued

| XRPD Peak List for Pattern 1 | | |
|---|---|---|
| Pos. [°2θ] | d-spacing [Å] | Rel. Int. [%] |
| 27.09 | 3.29 | 18.20 |
| 27.56 | 3.24 | 11.30 |
| 28.61 | 3.12 | 30.20 |
| 31.38 | 2.85 | 14.90 |
| 32.30 | 2.77 | 13.60 |
| 32.87 | 2.72 | 13.00 |

In certain embodiments, the morphic form is Pattern 1 and is characterized by an XRPD pattern comprising at least 2 peaks selected from about 9.6±0.2°, about 12.2±0.2°, about 15.3±0.2°, about 17.6±0.2°, about 19.3±0.2°, about 19.8±0.2°, about 21.2±0.2°, about 22.7±0.2°, about 23.9±0.2°, about 26.1±0.2°, and about 28.6±0.2°.

In certain embodiments, the morphic form is Pattern 1 and is characterized by an XRPD pattern comprising at least 3 peaks selected from about 9.6±0.2°, about 12.2±0.2°, about 15.3±0.2°, about 17.6±0.2°, about 19.3±0.2°, about 19.8±0.2°, about 21.2±0.2°, about 22.7±0.2°, about 23.9±0.2°, about 26.1±0.2°, and about 28.6±0.2°.

In certain embodiments, the morphic form is Pattern 1 and is characterized by an XRPD pattern comprising at least 4 peaks selected from about 9.6±0.2°, about 12.2±0.2°, about 15.3±0.2°, about 17.6±0.2°, about 19.3±0.2°, about 19.8±0.2°, about 21.2±0.2°, about 22.7±0.2°, about 23.9±0.2°, about 26.1±0.2°, and about 28.6±0.2°.

In certain embodiments, the morphic form is Pattern 1 and is characterized by an XRPD pattern comprising at least 5 peaks selected from about 9.6±0.2°, about 12.2±0.2°, about 15.3±0.2°, about 17.6±0.2°, about 19.3±0.2°, about 19.8±0.2°, about 21.2±0.2°, about 22.7±0.2°, about 23.9±0.2°, about 26.1±0.2°, and about 28.6±0.2°.

In certain embodiments, the morphic form is Pattern 1 and is characterized by an XRPD pattern comprising at least 6 peaks selected from about 9.6±0.2°, about 12.2±0.2°, about 15.3±0.2°, about 17.6±0.2°, about 19.3±0.2°, about 19.8±0.2°, about 21.2±0.2°, about 22.7±0.2°, about 23.9±0.2°, about 26.1±0.2°, and about 28.6±0.2°.

In certain embodiments, the morphic form is Pattern 1 and is characterized by an XRPD pattern comprising at least 7 peaks selected from about 9.6±0.2°, about 12.2±0.2°, about 15.3±0.2°, about 17.6±0.2°, about 19.3±0.2°, about 19.8±0.2°, about 21.2±0.2°, about 22.7±0.2°, about 23.9±0.2°, about 26.1±0.2°, and about 28.6±0.2°.

In certain embodiments, the morphic form is Pattern 1 and is characterized by an XRPD pattern comprising at least 8 peaks selected from about 9.6±0.2°, about 12.2±0.2°, about 15.3±0.2°, about 17.6±0.2°, about 19.3±0.2°, about 19.8±0.2°, about 21.2±0.2°, about 22.7±0.2°, about 23.9±0.2°, about 26.1±0.2°, and about 28.6±0.2°.

In certain embodiments, the morphic form is Pattern 1 and is characterized by an XRPD pattern comprising at least 9 peaks selected from about 9.6±0.2°, about 12.2±0.2°, about 15.3±0.2°, about 17.6±0.2°, about 19.3±0.2°, about 19.8±0.2°, about 21.2±0.2°, about 22.7±0.2°, about 23.9±0.2°, about 26.1±0.2°, and about 28.6±0.2°.

In certain embodiments, the morphic form is Pattern 1 and is characterized by an XRPD pattern comprising at least 10 peaks selected from about 9.6±0.2°, about 12.2±0.2°, about 15.3±0.2°, about 17.6±0.2°, about 19.3±0.2°, about 19.8±0.2°, about 21.2±0.2°, about 22.7±0.2°, about 23.9±0.2°, about 26.1±0.2°, and about 28.6±0.2°.

In certain embodiments, the morphic form is Pattern 1 and is characterized by an XRPD pattern comprising the 2theta values selected from about 9.6±0.2°, about 12.2±0.2°, about 15.3±0.2°, about 17.6±0.2°, about 19.3±0.2°, about 19.8±0.2°, about 21.2±0.2°, about 22.7±0.2°, about 23.9±0.2°, about 26.1±0.2°, and about 28.6±0.2°.

Table 2 below provides the results of the XRPD performed on Pattern 2. The XRPD exhibited sharp peaks, indicating the sample was composed of crystalline material. Significant peaks were observed in the XRPD on Pattern 2 at 6.7±0.2°, 11.1±0.2°, 16.3±0.2°, 17.2±0.2°, 18.2±0.2°, 19.8±0.2°, 20.4±0.2°, 20.6±0.2°, 26.4±0.2°, and 27.3±0.2°.

TABLE 2

XRPD peaks of Pattern 2.

| Pos. [°2θ] | d-spacing [Å] | Rel. Int. [%] |
|---|---|---|
| 6.77 | 13.050 | 100 |
| 11.15 | 7.933 | 58.67 |
| 14.06 | 6.300 | 14.44 |
| 14.77 | 5.996 | 24.21 |
| 15.08 | 5.875 | 19.26 |
| 16.29 | 5.442 | 63.87 |
| 16.96 | 5.227 | 26.73 |
| 17.24 | 5.144 | 36.62 |
| 18.19 | 4.878 | 39.51 |
| 19.81 | 4.482 | 36.17 |
| 20.42 | 4.350 | 33.11 |
| 20.64 | 4.303 | 31.36 |
| 21.55 | 4.125 | 23.41 |
| 22.72 | 3.914 | 22.54 |
| 23.11 | 3.849 | 28.74 |
| 24.90 | 3.576 | 16.55 |
| 25.55 | 3.486 | 14.30 |
| 26.41 | 3.375 | 99.54 |
| 27.28 | 3.269 | 49.45 |
| 28.46 | 3.137 | 27.85 |
| 30.35 | 2.945 | 10.69 |

In certain embodiments, the morphic form is Pattern 2 and is characterized by an XRPD pattern comprising at least 2 peaks selected from 6.7±0.2°, 11.1±0.2°, 16.3±0.2°, 17.2±0.2°, 18.2±0.2°, 19.8±0.2°, 20.4±0.2°, 20.6±0.2°, 26.4±0.2°, and 27.3±0.2°.

In certain embodiments, the morphic form is Pattern 2 and is characterized by an XRPD pattern comprising at least 3 peaks selected from 6.7±0.2°, 11.1±0.2°, 16.3±0.2°, 17.2±0.2°, 18.2±0.2°, 19.8±0.2°, 20.4±0.2°, 20.6±0.2°, 26.4±0.2°, and 27.3±0.2°.

In certain embodiments, the morphic form is Pattern 2 and is characterized by an XRPD pattern comprising at least 4 peaks selected from 6.7±0.2°, 11.1±0.2°, 16.3±0.2°, 17.2±0.2°, 18.2±0.2°, 19.8±0.2°, 20.4±0.2°, 20.6±0.2°, 26.4±0.2°, and 27.3±0.2°.

In certain embodiments, the morphic form is Pattern 2 and is characterized by an XRPD pattern comprising at least 5 peaks selected from 6.7±0.2°, 11.1±0.2°, 16.3±0.2°, 17.2±0.2°, 18.2±0.2°, 19.8±0.2°, 20.4±0.2°, 20.6±0.2°, 26.4±0.2°, and 27.3±0.2°.

In certain embodiments, the morphic form is Pattern 2 and is characterized by an XRPD pattern comprising at least 6 peaks selected from 6.7±0.2°, 11.1±0.2°, 16.3±0.2°, 17.2±0.2°, 18.2±0.2°, 19.8±0.2°, 20.4±0.2°, 20.6±0.2°, 26.4±0.2°, and 27.3±0.2°.

In certain embodiments, the morphic form is Pattern 2 and is characterized by an XRPD pattern comprising at least 7 peaks selected from 6.7±0.2°, 11.1±0.2°, 16.3±0.2°, 17.2±0.2°, 18.2±0.2°, 19.8±0.2°, 20.4±0.2°, 20.6±0.2°, 26.4±0.2°, and 27.3±0.2°.

In certain embodiments, the morphic form is Pattern 2 and is characterized by an XRPD pattern comprising at least 8 peaks selected from 6.7±0.2°, 11.1±0.2°, 16.3±0.2°, 17.2±0.2°, 18.2±0.2°, 19.8±0.2°, 20.4±0.2°, 20.6±0.2°, 26.4±0.2°, and 27.3±0.2°.

In certain embodiments, the morphic form is Pattern 2 and is characterized by an XRPD pattern comprising at least 9 peaks selected from 6.7±0.2°, 11.1±0.2°, 16.3±0.2°, 17.2±0.2°, 18.2±0.2°, 19.8±0.2°, 20.4±0.2°, 20.6±0.2°, 26.4±0.2°, and 27.3±0.2°.

In certain embodiments, the morphic form is Pattern 2 and is characterized by an XRPD pattern comprising the 2theta values selected from 6.7±0.2°, 11.1±0.2°, 16.3±0.2°, 17.2±0.2°, 18.2±0.2°, 19.8±0.2°, 20.4±0.2°, 20.6±0.2°, 26.4±0.2°, and 27.3±0.2°.

Table 4 below provides the results of the XRPD performed on Pattern 5. Significant peaks were observed in the XRPD on Pattern 5 at 6.3±0.2°, 6.8±0.2°, 8.1±0.2°, 11.2±0.2°, 16.2±0.2°, 26.5±0.2°, 27.4±0.2°, 27.8±0.2°, and 28.6±0.2°.

Table 2 below provides the results of the XRPD performed on Pattern 3 scale-up. The XRPD exhibited sharp peaks, indicating the sample was composed of crystalline material. Significant peaks were observed in the XRPD on Pattern 3 scale-up at about 8.1±0.2°, about 14.8±0.2°, about 16.5±0.2°, about 18.2±0.2°, about 19.7±0.2°, about 24.8±0.2°, about 25.6±0.2° and about 27.7±0.2°.

TABLE 3

XRPD peaks for Pattern 3.

| Pos. [°2θ] | d-spacing [Å] | Rel. Int. [%] |
|---|---|---|
| 8.12 | 10.885 | 100 |
| 16.50 | 5.371 | 59.88 |
| 24.84 | 3.584 | 40.08 |
| 14.80 | 5.986 | 37.36 |
| 18.16 | 4.884 | 33.40 |
| 27.72 | 3.218 | 31.65 |
| 25.56 | 3.485 | 28.53 |
| 19.74 | 4.497 | 27.61 |
| 17.13 | 5.177 | 27.38 |
| 12.99 | 6.817 | 26.27 |
| 15.98 | 5.548 | 25.23 |
| 22.20 | 4.005 | 21.04 |
| 26.76 | 3.331 | 19.56 |
| 24.30 | 3.662 | 19.00 |
| 31.30 | 2.858 | 18.31 |
| 5.13 | 17.212 | 17.64 |
| 29.87 | 2.992 | 13.67 |
| 33.15 | 2.703 | 11.17 |
| 29.06 | 3.073 | 10.28 |

In certain embodiments, the morphic form is Pattern 3 is characterized by an XRPD pattern comprising at least 2 peaks selected from 8.1±0.2°, 14.8±0.2°, 16.5±0.2°, 18.1±0.2°, 19.7±0.2°, 24.84±0.2°, and 27.7±0.2°.

In certain embodiments, the morphic form is Pattern 3 is characterized by an XRPD pattern comprising at least 3 peaks selected from 8.1±0.2°, 14.8±0.2°, 16.5±0.2°, 18.1±0.2°, 19.7±0.2°, 24.84±0.2°, and 27.7±0.2°.

In certain embodiments, the morphic form is Pattern 3 is characterized by an XRPD pattern comprising at least 4 peaks selected from 8.1±0.2°, 14.8±0.2°, 16.5±0.2°, 18.1±0.2°, 19.7±0.2°, 24.84±0.2°, and 27.7±0.2°.

In certain embodiments, the morphic form is Pattern 3 is characterized by an XRPD pattern comprising at least 5 peaks selected from 8.1±0.2°, 14.8±0.2°, 16.5±0.2°, 18.1±0.2°, 19.7±0.2°, 24.84±0.2°, and 27.7±0.2°.

In certain embodiments, the morphic form is Pattern 3 is characterized by an XRPD pattern comprising at least 6 peaks selected from 8.1±0.2°, 14.8±0.2°, 16.5±0.2°, 18.1±0.2°, 19.7±0.2°, 24.84±0.2°, and 27.7±0.2°.

In certain embodiments, the morphic form is Pattern 3 is characterized by an XRPD pattern comprising the 2theta values selected from 8.1±0.2°, 14.8±0.2°, 16.5±0.2°, 18.1±0.2°, 19.7±0.2°, 24.84±0.2°, and 27.7±0.2°.

TABLE 4

XRPD peaks of Pattern 4.

| Pos. [°2θ] | d-spacing [Å] | Rel. Int. [%] |
|---|---|---|
| 6.36 | 13.896 | 35.99 |
| 6.79 | 13.009 | 95.80 |
| 8.11 | 10.903 | 41.76 |
| 11.21 | 7.892 | 49.51 |
| 13.59 | 6.518 | 13.93 |
| 14.12 | 6.274 | 16.30 |
| 14.87 | 5.960 | 23.31 |
| 15.16 | 5.843 | 23.61 |
| 16.24 | 5.457 | 70.61 |
| 17.30 | 5.125 | 31.55 |
| 18.27 | 4.855 | 36.30 |
| 18.98 | 4.677 | 17.47 |
| 19.89 | 4.464 | 28.00 |
| 20.49 | 4.334 | 26.21 |
| 20.72 | 4.288 | 27.97 |
| 21.65 | 4.105 | 17.94 |
| 22.82 | 3.897 | 17.26 |
| 23.21 | 3.833 | 24.78 |
| 24.76 | 3.595 | 19.75 |
| 25.63 | 3.476 | 17.12 |
| 26.53 | 3.360 | 100 |
| 27.41 | 3.254 | 56.04 |
| 27.85 | 3.203 | 37.88 |
| 28.61 | 3.120 | 41.94 |
| 29.39 | 3.039 | 12.96 |
| 30.02 | 2.977 | 13.48 |
| 30.42 | 2.939 | 16.39 |
| 31.42 | 2.847 | 10.75 |
| 32.50 | 2.755 | 13.49 |
| 33.07 | 2.709 | 12.96 |

In certain embodiments, the morphic form is Pattern 5 and is characterized by an XRPD pattern comprising at least 2 peaks selected from 6.3±0.2°, 6.8±0.2°, 8.1±0.2°, 11.2±0.2°, 16.2±0.2°, 26.5±0.2°, 27.4±0.2°, 27.8±0.2°, and 28.6±0.2°.

In certain embodiments, the morphic form is Pattern 5 and is characterized by an XRPD pattern comprising at least 3 peaks selected from 6.3±0.2°, 6.8±0.2°, 8.1±0.2°, 11.2±0.2°, 16.2±0.2°, 26.5±0.2°, 27.4±0.2°, 27.8±0.2°, and 28.6±0.2°.

In certain embodiments, the morphic form is Pattern 5 and is characterized by an XRPD pattern comprising at least 4 peaks selected from 6.3±0.2°, 6.8±0.2°, 8.1±0.2°, 11.2±0.2°, 16.2±0.2°, 26.5±0.2°, 27.4±0.2°, 27.8±0.2°, and 28.6±0.2°.

In certain embodiments, the morphic form is Pattern 5 and is characterized by an XRPD pattern comprising at least 5 peaks selected from 6.3±0.2°, 6.8±0.2°, 8.1±0.2°, 11.2±0.2°, 16.2±0.2°, 26.5±0.2°, 27.4±0.2°, 27.8±0.2°, and 28.6±0.2°.

In certain embodiments, the morphic form is Pattern 5 and is characterized by an XRPD pattern comprising at least 6 peaks selected from 6.3±0.2°, 6.8±0.2°, 8.1±0.2°, 11.2±0.2°, 16.2±0.2°, 26.5±0.2°, 27.4±0.2°, 27.8±0.2°, and 28.6±0.2°.

In certain embodiments, the morphic form is Pattern 5 and is characterized by an XRPD pattern comprising at least 7 peaks selected from 6.3±0.2°, 6.8±0.2°, 8.1±0.2°, 11.2±0.2°, 16.2±0.2°, 26.5±0.2°, 27.4±0.2°, 27.8±0.2°, and 28.6±0.2°.

In certain embodiments, the morphic form is Pattern 5 and is characterized by an XRPD pattern comprising at least 8 peaks selected from 6.3±0.2°, 6.8±0.2°, 8.1±0.2°, 11.2±0.2°, 16.2±0.2°, 26.5±0.2°, 27.4±0.2°, 27.8±0.2°, and 28.6±0.2°.

In certain embodiments, the morphic form is Pattern 5 and is characterized by an XRPD pattern comprising the 2theta values selected from 6.3±0.2°, 6.8±0.2°, 8.1±0.2°, 11.2±0.2°, 16.2±0.2°, 26.5±0.2°, 27.4±0.2°, 27.8±0.2°, and 28.6±0.2°.

\ Table 5 below provides the results of the XRPD performed on Pattern 6 exhibited sharp peaks, indicating the sample was composed of crystalline material. Tabulated peak picks for Pattern 6>10% relative intensity. Significant peaks were observed in the XRPD on Pattern 6 at 6.7±0.2°, 11.1±0.2°, 16.26±0.2°, 26.3±0.2°, and 27.2±0.2°.

TABLE 5

XRPD peaks for Pattern 6 scale-up.

| Pos. [°2θ] | d-spacing [Å] | Rel. Int. [%] |
|---|---|---|
| 6.77 | 13.051 | 100 |
| 9.54 | 9.273 | 15.73 |
| 11.15 | 7.938 | 55.43 |
| 14.74 | 6.012 | 12.56 |
| 16.26 | 5.452 | 55.44 |
| 16.94 | 5.234 | 21.60 |
| 17.23 | 5.146 | 32.11 |
| 18.16 | 4.885 | 33.45 |
| 19.78 | 4.490 | 33.56 |
| 20.39 | 4.355 | 24.11 |
| 20.62 | 4.308 | 23.52 |
| 21.20 | 4.192 | 18.54 |
| 21.51 | 4.131 | 14.66 |
| 22.68 | 3.920 | 14.28 |
| 23.08 | 3.853 | 27.52 |
| 23.91 | 3.721 | 12.10 |
| 24.85 | 3.582 | 11.69 |
| 26.02 | 3.424 | 20.04 |
| 26.36 | 3.381 | 83.70 |
| 27.26 | 3.271 | 42.92 |
| 28.43 | 3.140 | 27.55 |

In certain embodiments, the morphic form is Pattern 6 and is characterized by an XRPD pattern comprising at least 2 peaks selected from 6.7±0.2°, 11.1±0.2°, 16.26±0.2°, 26.3±0.2°, and 27.2±0.2°.

In certain embodiments, the morphic form is Pattern 6 and is characterized by an XRPD pattern comprising at least 3 peaks selected from 6.7±0.2°, 11.1±0.2°, 16.26±0.2°, 26.3±0.2°, and 27.2±0.2°.

In certain embodiments, the morphic form is Pattern 6 and is characterized by an XRPD pattern comprising at least 4 peaks selected from 6.7±0.2°, 11.1±0.2°, 16.26±0.2°, 26.3±0.2°, and 27.2±0.2°.

In certain embodiments, the morphic form is Pattern 6 and is characterized by an XRPD pattern comprising the 2theta values selected from 6.7±0.2°, 11.1±0.2°, 16.26±0.2°, 26.3±0.2°, and 27.2±0.2°.

Example 2. General Technique for Using Gravimetric Vapor Sorption (GVS)

Approximately 10-20 mg of sample was placed into a mesh vapor sorption balance pan and loaded into an IGAS-orp Moisture Sorption Analyzer balance by Hiden Analytical. The sample was subjected to a ramping profile from 40-90% relative humidity (RH) at 10% increments, maintaining the sample at each step until a stable weight had been achieved (98% step completion, minimum step length 30 minutes, maximum step length 60 minutes) at 25° C. After completion of the sorption cycle, the sample was dried using the same procedure to 0% RH, and finally taken back to the starting point of 40% RH. Three cycles were performed. The weight change during the sorption/desorption cycles were plotted, allowing for the hygroscopic nature of the sample to be determined. The above technique was used to generate the images in FIG. 40 and FIG. 41.

Table 6 below provides tabulated GVS data for Pattern 1 showing the difference in water vapor uptake between the sorption and desorption isotherms. The weight change during the sorption/desorption cycles were plotted, allowing for the hygroscopic nature of the sample to be determined.

TABLE 6

Tabulated GVS data for Pattern 1

| | Target | Change in Mass (%) - ref | |
| --- | --- | --- | --- |
| | (RH (%)) | Sorption | Desorption |
| Cycle 1 | 0 | | 0.180 |
| | 10 | | 2.320 |
| | 20 | | 2.820 |
| | 30 | | 3.110 |
| | 40 | 3.420 | 3.340 |
| | 50 | 3.560 | 3.580 |
| | 60 | 3.720 | 3.730 |
| | 70 | 3.800 | 3.820 |
| | 80 | 3.920 | 3.970 |
| | 90 | 4.160 | 4.160 |
| Cycle 2 | 0 | 0.180 | 0.000 |
| | 10 | 2.300 | 2.240 |
| | 20 | 2.770 | 2.680 |
| | 30 | 3.030 | 3.020 |
| | 40 | 3.290 | 3.260 |
| | 50 | 3.470 | 3.500 |
| | 60 | 3.660 | 3.670 |
| | 70 | 3.780 | 3.780 |
| | 80 | 3.900 | 3.890 |
| | 90 | 4.080 | 4.080 |
| Cycle 3 | 0.000 | 0.000 | |
| | 10.000 | 2.250 | |
| | 20.000 | 2.740 | |
| | 30.000 | 3.020 | |
| | 40.000 | 3.220 | |

In certain embodiments, the sample was subjected to a ramping profile from 40-90% relative humidity (RH) at 10% increments.

In certain embodiments, at least two sorption cycles are performed.

In certain embodiments, three sorption cycles are performed.

Table 7 below provides the results of the GVS data for the mixture of Pattern 2 and pattern 6, showing the difference in water vapor uptake between the sorption and desorption isotherms. The weight change during the sorption/desorption cycles were plotted, allowing for the hygroscopic nature of the sample to be determined.

TABLE 7

GVS data of Pattern 2 and Pattern 6 mixture

| | Target | Change in Mass (%) - ref | |
| --- | --- | --- | --- |
| | (RH (%)) | Sorption | Desorption |
| Cycle 1 | 0 | | 0.000 |
| | 10 | | 3.118 |
| | 20 | | 3.734 |
| | 30 | | 4.148 |
| | 40 | 4.737 | 4.497 |
| | 50 | 5.420 | 4.806 |

TABLE 7-continued

GVS data of Pattern 2 and Pattern 6 mixture

| | Target | Change in Mass (%) - ref | |
| --- | --- | --- | --- |
| | (RH (%)) | Sorption | Desorption |
| | 60 | 7.044 | 5.181 |
| | 70 | 6.346 | 5.653 |
| | 80 | 6.770 | 6.343 |
| | 90 | 7.898 | 7.898 |
| Cycle 2 | 0 | 0.000 | 0.059 |
| | 10 | 2.731 | 3.200 |
| | 20 | 3.470 | 3.820 |
| | 30 | 3.969 | 4.205 |
| | 40 | 4.353 | 4.512 |
| | 50 | 4.661 | 4.848 |
| | 60 | 4.999 | 5.157 |
| | 70 | 5.436 | 5.572 |
| | 80 | 5.976 | 6.181 |
| | 90 | 7.039 | 7.039 |
| Cycle 3 | 0 | 0.059 | |
| | 10 | 2.708 | |
| | 20 | 3.502 | |
| | 30 | 4.027 | |
| | 40 | 4.335 | |

In certain embodiments, the sample was subjected to a ramping profile from 40-90% relative humidity (RH) at 10% increments.

In certain embodiments, at least two sorption cycles are performed.

In certain embodiments, three sorption cycles are performed.

Example 3. Dynamic Vapor Sorption (DVS)

Approximately, 10-20 mg of sample was placed into a mesh vapor sorption balance pan and loaded into a DVS Intrinsic dynamic vapor sorption balance by Surface Measurement Systems. The sample was subjected to a ramping profile from 40-90% relative humidity (RH) at 10% increments, maintaining the sample at each step until a stable weight had been achieved (dm/dt 0.004%, minimum step length 30 minutes, maximum step length 500 minutes) at 25° C. After completion of the sorption cycle, the sample was dried using the same procedure to 0% RH and then a second sorption cycle back to 40% RH. Two cycles were performed. The weight change during the sorption/desorption cycles were plotted, allowing for the hygroscopic nature of the sample to be determined. XRPD analysis was then carried out on any solid retained. The above technique was used to generate the images in FIG. 5, FIG. 6, FIG. 47 and FIG. 48.

TABLE 8 provides results for the tabulated DVS data of Pattern 3 scale-up.

| | Target | Change in Mass (%) - ref | | |
| --- | --- | --- | --- | --- |
| | (RH (%)) | Sorption | Desorption | Hysteresis |
| Cycle 1 | 0 | | 0.000 | |
| | 10 | | 0.863 | |
| | 20 | | 1.274 | |
| | 30 | | 1.818 | |
| | 40 | 2.516 | 2.223 | −0.292 |
| | 50 | 2.780 | 2.491 | −0.289 |
| | 60 | 2.970 | 2.727 | −0.242 |
| | 70 | 3.115 | 2.940 | −0.175 |
| | 80 | 3.288 | 3.171 | −0.117 |
| | 90 | 3.555 | 3.555 | |

TABLE 8-continued provides results for the tabulated DVS data of Pattern 3 scale-up.

| | Target | Change in Mass (%) - ref | | |
|---|---|---|---|---|
| | (RH (%)) | Sorption | Desorption | Hysteresis |
| Cycle 2 | 0 | 0.000 | 0.075 | |
| | 10 | 0.831 | 0.885 | 0.054 |
| | 20 | 1.198 | 1.290 | 0.091 |
| | 30 | 1.468 | 1.711 | 0.243 |
| | 40 | 1.853 | 1.977 | 0.124 |
| | 50 | 2.092 | 2.171 | 0.080 |
| | 60 | 2.271 | 2.337 | 0.066 |
| | 70 | 2.461 | 2.510 | 0.050 |
| | 80 | 2.700 | 2.717 | 0.018 |
| | 90 | 3.093 | 3.093 | |
| Cycle 3 | 0 | 0.075 | | |
| | 10 | 0.861 | | |
| | 20 | 1.198 | | |
| | 30 | 1.443 | | |
| | 40 | 1.757 | | |

The material appeared hygroscopic by DVS with a mass increase of ca. 4% at 90% RH. During the desorption cycles the material loses mass, likely due to the loss of surface water present in the sample and the crystallization of amorphous content present in the sample. The material adsorbed 2.5 wt % moisture at 40% RH, 3.1 wt % moisture at 60% and 3.5 wt % at 90% RH.

In certain embodiments, at least two sorption cycles are performed. In certain embodiments, three sorption cycles are performed.

Example 4. Tabulated Peak Picks of Pattern 4>5% Relative Intensity

XRPD analysis was carried out on a PANalytical X'pert pro, scanning the samples between 3 and 35° 2θ. The material was gently ground to release any agglomerates and loaded onto a multi-well plate with Kapton or Mylar polymer film to support the sample. The multi-well plate was then placed into the diffractometer and analyzed using Cu K radiation (α1 λ, =1.54060 Å; α2=1.54443 Å; β=1.39225 Å; α1:α2 ratio=0.5) running in transmission mode (step size 0.0130° 2θ) using 40 kV/40 mA generator settings. The above technique was used to generate the images in FIG. 13, FIG. 20 and FIG. 27.

Table 9 below provides the results of the XRPD performed on Pattern 4 exhibited sharp peaks, indicating the sample was composed of crystalline material. Significant peaks were observed in the XRPD on Pattern 4 at 6.1±0.2°, 15.0±0.2°, 27.5±0.2°, and 28.1±0.2°.

TABLE 9

XRPD peaks for Pattern 4

| Pos. [°2θ] | d-spacing [Å] | Rel. Int. [%] |
|---|---|---|
| 6.13 | 14.416 | 100 |
| 9.55 | 9.265 | 20.37 |
| 14.64 | 6.049 | 14.50 |
| 15.03 | 5.896 | 21.29 |
| 17.84 | 4.971 | 12.89 |
| 18.44 | 4.811 | 12.04 |
| 20.24 | 4.387 | 6.94 |
| 21.25 | 4.181 | 10.22 |
| 21.97 | 4.046 | 5.55 |
| 25.73 | 3.462 | 6.79 |
| 26.42 | 3.374 | 6.40 |
| 27.55 | 3.238 | 29.60 |

TABLE 9-continued

XRPD peaks for Pattern 4

| Pos. [°2θ] | d-spacing [Å] | Rel. Int. [%] |
|---|---|---|
| 28.15 | 3.170 | 29.11 |
| 29.61 | 3.017 | 6.00 |

In certain embodiments, the morphic form is Pattern 4 and is characterized by an XRPD pattern comprising at least 2 peaks selected from 6.1±0.2°, 15.0±0.2°, 27.5±0.2°, and 28.1±0.2 °.

In certain embodiments, the morphic form is Pattern 4 and is characterized by an XRPD pattern comprising at least 3 peaks selected from 6.1±0.2°, 15.0±0.2°, 27.5±0.2°, and 28.1±0.2°.

In certain embodiments, the morphic form is Pattern 4 and is characterized by an XRPD pattern comprising the 2theta values selected from 6.1±0.2°, 15.0±0.2°, 27.5±0.2°, and 28.1±0.2°.

Example 5. PLM Imaging

PLM imaging was carried out in the presence of crystallinity (birefringence). PLM imaging was determined using an Olympus BX50 polarizing microscope, equipped with a Motic camera and image capture software (Motic Images Plus 2.0). All images were recorded using the 20× objective, unless otherwise stated. The above technique was used to generate the images in FIG. 2, FIG. 37, FIG. 44, FIG. 62, and FIG. 74 through FIG. 86.

Example 6. Thermogravimetric Analysis (TGA)

Approximately 5 mg of material was weighed into an open aluminum pan and loaded into a simultaneous thermogravimetric/differential thermal analyzer (TG/DTA) and held at room temperature. The sample was then heated at a rate of 10° C./min from 20° C. to 300° C. during which time the change in sample weight was recorded along with any differential thermal events (DTA). Nitrogen was used as the purge gas, at a flow rate of 300 cm³/min. The above technique was used to generate the images in FIG. 3, FIG. 33, FIG. 34, FIG. 35, FIG. 38, FIG. 45, FIG. 63, FIG. 87 and FIG. 88.

Example 7. Differential Scanning Calorimetry (DSC)

Approximately, 5 mg of material was weighed into an aluminum DSC pan and sealed non-hermetically with a pierced aluminum lid. The sample pan was then loaded into a Seiko DSC6200 (equipped with a cooler) cooled and held at 20° C. Once a stable heat-flow response was obtained, the sample and reference were heated to 360° C. at a scan rate of 10° C./min and the resulting heat flow response monitored. Nitrogen was used as the purge gas, at a flow rate of 50 cm³/min. The above technique was used to generate the images in FIG. 4, FIG. 39, FIG. 46, FIG. 64, FIG. 65 and FIG. 66.

Example 8. Crystallization and Competitive Slurry Experiments

Competitive slurry experiments were carried out using ca. 10 mg of Pattern 1, Pattern 2/6 mixture and Pattern 3 were weighed out and added to a 1.5 mL glass vial. Samples were prepared using 100 μL aliquots of solvent until a mobile slurry was formed. Samples were stirred at ambient temperature for 48 hours. A second set of samples were stirred at 60° C. for 48 hours. All samples were collected, and the solids were isolated and analyzed by XRPD. The above technique was used to generate the images in FIG. 50, FIG. 51, and FIG. 55 through FIG. 59.

HPLC. The above technique was used to generate the images in FIG. 52, FIG. 53 and FIG. 54.

Example 11. Various Solvent Solubility Systems

The solvent solubility experiment was carried out using various solvents to determine solid formation. A known

TABLE 10

Results and observations from competitive slurry experiments

| Sample | Input Material | Solvent | Volume of Solvent (μL) | Temperature | Observations | XRPD Form |
|---|---|---|---|---|---|---|
| 1 | 1 + 2 + 3 | EtOH | 1000 | Ambient | Yellow slurry | 1 |
| 2 | 1 + 2 + 3 | MEK | 1000 | Ambient | Yellow slurry | 1 with traces of 2 |
| 3 | 1 + 2 + 3 | 2N HCl | 1000 | Ambient | Yellow slurry | 1 |
| 4 | 1 + 2 + 3 | IPA | 1000 | Ambient | Yellow slurry | 1 with traces of 2 |
| 5 | 1 + 2 + 3 | MeCN/water (97:3% v/v) | 1000 | Ambient | Yellow slurry | 1 |
| 6 | 1 + 2 + 3 | Acetone/water (85:15% v/v) | 1000 | Ambient | Yellow slurry | 1 |
| 7 | 1 + 2 + 3 | EtOH | 1000 | 60° C. | Yellow slurry | 1 |
| 8 | 1 + 2 + 3 | MEK | 1000 | 60° C. | Yellow slurry | Mix of 1, 2 and 3 |
| 9 | 1 + 2 + 3 | 2N HCl | 1000 | 60° C. | Yellow slurry | 1 with traces of 2 |
| 10 | 1 + 2 + 3 | IPA | 1000 | 60° C. | Yellow slurry | 1 with traces of 2 |
| 11 | 1 + 2 + 3 | MeCN/water (97:3% v/v) | 1000 | 60° C. | Yellow slurry | 1 |
| 12 | 1 + 2 + 3 | Acetone/water (85:15% v/v) | 1000 | 60° C. | Yellow slurry | 1 |

Example 9. XRPD Analysis after DVS Experiment

XRPD analysis was carried out on a PANalytical X'pert pro, scanning the samples between 3 and 35° 2θ. The material was gently grounded to release any agglomerates and loaded onto a multi-well plate with Kapton or Mylar polymer film to support the sample. The multi-well plate was then placed into the diffractometer and analyzed using Cu K radiation (α1 λ=1.54060 Å; α2 =1.54443 Å; β=1.39225 Å; α1:α2 ratio=0.5) running in transmission mode (step size 0.0130° 2θ) using 40 kV/40 mA generator settings.

The post-DVS samples were analyzed by XRPD. After DVS was performed, samples were analyzed by XRPD to confirm any changes in the material. The above technique was used to generate the images in FIG. 7, FIG. 42 and FIG. 49.

Example 10. Stability Study after 1 Week

Stability study was carried out using ca. 10 mg of material. Samples were prepared in duplicate for XRPD and HPLC analysis. One set of samples were capped and stored under ambient light, temperature and humidity. One set of samples were capped and stored in an oven at 80° C. One set of samples (75%) were uncapped and stored in a desiccator containing sodium chloride solution at 40° C. After 7 days the samples were collected and analyzed by XRPD and volume aliquot (typically 5 volumes) of solvent was added to approximately 10 mg of amorphous Compound 1 as a dihydrochloride. Between each addition, the mixture was checked for dissolution and where no dissolution was apparent, the mixture was heated to ca. 40° C. and checked again. This procedure was continued until dissolution was observed or until 100 volumes of solvent had been added. All observed solids were isolated and analyzed by XRPD.

Examples of solvents include, but are not limited to, 1,4-dioxane, methanol, ethanol, propanol, butanol, butanone, ethoxyethanol, trifluoroethanol, methyl-THF, acetone, acetonitrile, anisole, chlorobenzene, DMSO, DMF, cumene, dichloromethane, ethyl acetate, ethylene glycol, heptane, isopropyl acetate, nitromethane, n-methylpyrrolidone, MIBK, t-BME, tetrahydrofuran, toluene, water and mixtures thereof. The above technique was used to generate the images in FIG. 8, FIG. 9, FIG. 10, FIG. 11, FIG. 12, FIG. 14.

TABLE 11

Approximate solubility results from solvent screen

| Sample | Solvent | Approx. Solubility (mg/mL) |
|---|---|---|
| 1 | 1,4-Dioxane | <5 |
| 2 | 1-Butanol | <5 |
| 3 | 2,2,2-Trifluoroethanol | >200 |

TABLE 11-continued

Approximate solubility results from solvent screen

| Sample | Solvent | Approx. Solubility (mg/mL) |
|---|---|---|
| 4 | 2-Butanone | <5 |
| 5 | 2-Ethoxyethanol | <5 |
| 6 | 2-Methyl THF | <5 |
| 7 | 2-Propanol | ca 5 |
| 8 | Acetone | <5 |
| 9 | Acetonitrile | <5 |
| 10 | Acetonitrile/water (90:10% v/v) | <5 |
| 11 | Anisole | <5 |
| 12 | Chlorobenzene | <5 |
| 13 | DMSO | ca 5 |
| 14 | DMF | <5 |
| 15 | Cumene | ca 5 |
| 16 | Dichloromethane | <5 |
| 17 | Ethanol | ca 5 |
| 18 | Ethanol/water (85:15% v/v) | <5 |
| 19 | Ethyl Acetate | <5 |
| 20 | Ethylene glycol | 50 |
| 21 | Heptane | <5 |
| 22 | Isopropyl acetate | <5 |
| 23 | Methanol | ca 5 |
| 24 | Methanol/water (95:5% v/v) | 20 |
| 25 | Nitromethane | 33 |
| 26 | N-Methylpyrrolidone | <5 |
| 27 | Methyl isobutyl ketone | <5 |
| 28 | t-Butylmethyl ether | <5 |
| 29 | Tetrahydrofuran | <5 |
| 30 | Tetrahydrofuran/water (99:1% v/v) | <5 |
| 31 | Toluene | <5 |
| 32 | Deionized Water | >200 |

TABLE 12

XRPD results from solvent solubility screen

| Sample | Solvent | XRPD |
|---|---|---|
| 1 | 1,4-Dioxane | Pattern 1 |
| 2 | 1-Butanol | Pattern 2 |
| 3 | 2,2,2-Trifluoroethanol | Pattern 3 |
| 4 | 2-Butanone | Pattern 2 |
| 5 | 2-Ethoxyethanol | Pattern 2 |
| 6 | 2-Methyl THF | Pattern 2 |
| 7 | 2-Propanol | Pattern 2 |
| 8 | Acetone | Pattern 5 |
| 9 | Acetonitrile | Pattern 4 |
| 10 | Acetonitrile/water (90:10% v/v) | Pattern 1 |
| 11 | Anisole | Pattern 6 |
| 12 | Chlorobenzene | Amorphous |
| 13 | DMSO | Amorphous |
| 14 | DMF | Amorphous |
| 15 | Cumene | Pattern 2 |
| 16 | Dichloromethane | Pattern 1 |
| 17 | Ethanol | Pattern 1 |
| 18 | Ethanol/water (85:15% v/v) | Pattern 1 |
| 19 | Ethyl Acetate | Pattern 2 |
| 20 | Ethylene glycol | No solid |
| 21 | Heptane | Pattern 3 |
| 22 | Isopropyl acetate | Pattern 2 |
| 23 | Methanol | Pattern 1 |
| 24 | Methanol/water (95:5% v/v) | Pattern 1 |
| 25 | Nitromethane | Pattern 1 |
| 26 | N-Methylpyrrolidone | Pattern 2 |
| 27 | Methyl isobutyl ketone | Pattern 2 |
| 28 | t-Butylmethyl ether | Pattern 5 |
| 29 | Tetrahydrofuran | Pattern 1 |
| 30 | Tetrahydrofuran/water (99:1% v/v) | Pattern 1 |
| 31 | Toluene | Pattern 2 |
| 32 | Water | No solid |

After removing the initial solid, samples in which dissolution was observed were uncapped and allowed to evaporate. This resulted in the diffractograms in FIG. 30 and FIG. 31.

TABLE 13

Observations from the evaporation experiments

| Sample | Solvent System | Observations Post-Evaporation |
|---|---|---|
| 1 | 1,4-Dioxane | No solid |
| 2 | Acetone/water (20:80% v/v) | Yellow solid |
| 3 | 2,2,2-Trifluoroethanol | Yellow solid |
| 4 | 2-Butanone | No solid |
| 5 | 2-Propanol | No solid |
| 6 | Acetone | No solid |
| 7 | Acetonitrile | No solid |
| 8 | Acetonitrile/water (90:10% v/v) | No solid |
| 9 | Dichloromethane | No solid |
| 10 | Ethanol | Small amount of yellow solid |
| 11 | Ethanol/water (85:15% v/v) | Small amount of yellow solid |
| 12 | Ethyl Acetate | No solid |
| 13 | Heptane | No solid |
| 14 | Isopropyl acetate | No solid |
| 15 | Methanol | No solid |
| 16 | Methanol/water (95:5% v/v) | Small amount of yellow solid |
| 17 | 2N HCl | No solid |
| 18 | Methyl isobutyl ketone | No solid |
| 19 | t-Butylmethyl ether | No solid |
| 20 | Tetrahydrofuran | No solid |
| 21 | Toluene | No solid |

Example 12. Anti-Solvent Addition Experiments

The antisolvent addition experiments were carried out using selected anti-solvent (for example t-BME) layered over the material solution in each sample until precipitation was observed or 1 mL of anti-solvent was added. The samples were stored in a fridge at ca. 5° C. to promote precipitation and any observed solids were collected and analyzed by XRFD. Material solution were prepared using solvent systems listed in Example 13. The above technique was used to generate the images in FIG. 32.

TABLE 14

Observations from the anti-solvent addition experiments

| Sample | Solvent System | Anti-Solvent | Volume of Anti-Solvent (µL) | Observations Post AS Addition |
|---|---|---|---|---|
| 1 | 1,4-Dioxane | t-BME | 1000 | Clear colorless solution |
| 2 | Acetone/water (20:80% v/v) | t-BME | 1000 | Clear colorless solution |
| 3 | 2,2,2-Trifluoroethanol | t-BME | 500 | Yellow solid |
| 4 | 2-Butanone | t-BME | 1000 | Clear colorless solution |
| 5 | 2-Ethoxyethanol | t-BME | 1000 | Clear colorless solution |
| 6 | 2-Propanol | t-BME | 1000 | Clear colorless solution |
| 7 | Acetone | t-BME | 1000 | Clear colorless solution |
| 8 | Acetonitrile | t-BME | 1000 | Clear colorless solution |
| 9 | Acetonitrile/water (90:10% v/v) | t-BME | 1000 | Clear colorless solution |
| 10 | Anisole | t-BME | 1000 | Clear colorless solution |
| 11 | Cumene | t-BME | 1000 | Clear colorless solution |
| 12 | Dichloromethane | t-BME | 1000 | Clear colorless solution |
| 13 | Ethanol | t-BME | 1000 | Clear colorless solution |
| 14 | Ethanol/water (85:15% v/v) | t-BME | 1000 | Clear colorless solution |
| 15 | Ethyl Acetate | t-BME | 1000 | Clear colorless solution |
| 16 | Heptane | t-BME | 1000 | Clear colorless solution |

TABLE 14-continued

Observations from the anti-solvent addition experiments

| Sample | Solvent System | Anti-Solvent | Volume of Anti-Solvent (µL) | Observations Post AS Addition |
|---|---|---|---|---|
| 17 | Isopropyl acetate | t-BME | 1000 | Clear colorless solution |
| 18 | Methanol | t-BME | 1000 | Clear colorless solution |
| 19 | Methanol/water (95:5% v/v) | t-BME | 1000 | Clear colorless solution |
| 20 | 2N HCl | t-BME | 1000 | Clear colorless solution |
| 21 | Methyl isobutyl ketone | t-BME | 1000 | Clear colorless solution |
| 22 | t-Butylmethyl ether | Heptane | 1000 | Clear colorless solution |
| 23 | Tetrahydrofuran | t-BME | 1000 | Clear colorless solution |
| 24 | Toluene | t-BME | 1000 | Clear colorless solution |

TABLE 15

Observed solids from the anti-solvent addition experiments

| Sample | Solvent System | Anti-Solvent | XRPD |
|---|---|---|---|
| 1 | 1,4-Dioxane | t-BME | No solid |
| 2 | Acetone/water (20:80% v/v) | t-BME | No solid |
| 3 | 2,2,2-Trifluoroethanol | t-BME | Pattern 3 |
| 4 | 2-Butanone | t-BME | No solid |
| 5 | 2-Ethoxyethanol | t-BME | No solid |
| 6 | 2-Propanol | t-BME | No solid |
| 7 | Acetone | t-BME | No solid |
| 8 | Acetonitrile | t-BME | No solid |
| 9 | Acetonitrile/water (90:10% v/v) | t-BME | No solid |
| 10 | Anisole | t-BME | No solid |
| 11 | Cumene | t-BME | No solid |
| 12 | Dichloromethane | t-BME | No solid |
| 13 | Ethanol | t-BME | No solid |
| 14 | Ethanol/water (85:15% v/v) | t-BME | No solid |
| 15 | Ethyl Acetate | t-BME | No solid |
| 16 | Heptane | t-BME | No solid |
| 17 | Isopropyl acetate | t-BME | No solid |
| 18 | Methanol | t-BME | No solid |
| 19 | Methanol/water (95:5% v/v) | t-BME | No solid |
| 20 | 2N HCl | t-BME | No solid |
| 21 | Methyl isobutyl ketone | t-BME | No solid |
| 22 | t-Butylmethyl ether | Heptane | No solid |
| 23 | Tetrahydrofuran | t-BME | No solid |
| 24 | Toluene | t-BME | No solid |

Example 13. Scale Up of Pattern 2, Pattern 3, and Pattern 5

Pattern 2 was scaled up via the addition of 100 uL aliquots of MEK to approximately 500 mg of amorphous Compound 1 as a di HCl salt until a mobile slurry was formed. The slurry was then temperature cycled between ambient and 40° C. for approximately 72 hours. The sample was collected, and an aliquot of the slurry was analyzed by XRPD. The solid was then isolated and dried under vacuum at 40° C. for approximately 4 hours. The resulting material was a mixture of Pattern 2 and Pattern 6.

Pattern 3 was scaled up via the addition of 100 uL aliquots of ethanol to approximately 500 mg of amorphous Compound 1 as a di HCl salt until a mobile slurry was formed. The slurry was then temperature cycled between ambient and 40° C. for approximately 72 hours. The sample was collected, and an aliquot of the slurry was analyzed by XRPD. The solid was then isolated and dried under vacuum at 40° C. for approximately 4 hours.

Pattern 5 was scaled up via the addition of 100 µL aliquots of ethanol to approximately 500 mg of amorphous Compound 1 as a di HCl salt until a mobile slurry was formed. The slurry was then temperature cycled between ambient and 40° C. for approximately 72 hours. The sample was collected, and an aliquot of the slurry was analyzed by XRPD. The solid was then isolated and dried under vacuum at 40° C. for approximately 4 hours. This resulting material was then slurried in 10 mL of methyl isobutyl ketone for another twenty-four hours. An aliquot of the slurry was analyzed by XRPD. The solid was then isolated and dried under vacuum at 40° C. for approximately four hours. The dried material was analyzed by XRPD.

Example 14. The pH Solubility and pH Solvent Systems

Experiments of pH solubility were carried out on Pattern 7 solids at pH 2 to pH 13. A total of 12 vials contained Pattern 7 (100 mg) and 500 µL of 66% DMSO: 33% THF (% v/v), in order to make a slurry. The starting pH of each slurry was measured using a pH meter. The pH of each vial was adjusted to the required pH using aliquots of acetic acid or 1M sodium hydroxide solution. If dissolution was observed at a selected pH, additional Pattern 7 solid was added to the vial, until a slurry persisted or a maximum of 500 mg had been added. The pH was then readjusted as required. Recovered solids were determined to have high purity (% area), with the majority of the experiments returning values of 99.5 and 99.4%. Purity values did not differ significantly between pH values with the exception of the solid from pH 4, where the % area purity was determined to be 99.9%. Concentration analysis of the filtered mother liquors showed that the concentration values generally decreased (i.e. decreased solubility) as the pH of the system was increased. Sticky, highly viscous slurries were observed at pH 4 and pH 8. The above technique was used to generate the diffractograms in FIG. 67, FIG. 68 and FIG. 69.

Example 15. Crystallization of Set 1

Small scale crystallization trials were carried out on Pattern 7 with Set 1 to determine the effect of altering the starting concentration of Pattern 7 in DMSO/THF solvent systems. Several concentrations of Pattern 7 in DMSO/THF were prepared, with starting concentrations of 100, 150 and 200 mg/mL respectively. Samples were prepared in a volume of 66% DMSO: 33% THF (% v/v) and Pattern 7 (200 mg) was added as the appropriate starting concentration. Acetic acid (100 µL aliquots) was added at ambient temperature to each sample, until dissolution was achieved. At each of the three concentrations, solid was crystallized from solution by using a) a 1:1 equivalent ratio of acetic acid to base (1M sodium hydroxide solution), or b) adjusting the final pH to 12 using 1M sodium hydroxide. The pH of the solution was measured using a pH meter and adjusted to pH 12 using 1M sodium hydroxide solution.

The sample sets were stirred at ambient temperature for ca. 18 hours with agitation provided via a magnetic stirrer plate. After ca. 18 hours, stirring was stopped and the supernatants were filtered using 0.45 μm PVDF needle filters and syringes. The concentration of the supernatants was analyzed by HPLC. The remaining slurries in the vials were each transferred into 0.22 μm nylon filter centrifuge tubes and the solids were isolated by centrifugation, and the recovered solids were analyzed by XRPD, PLM and HPLC for purity. The above technique was used to generate the images in FIG. 70 and FIG. 71.

TABLE 16

Set 1: pH of 12

| Starting free base mass (mg) | Starting volume (DMSO:THF 66/33) mL) | Starting Conc. (mg/mL) | Acetic Acid added (mL) | 1M NaOH solution added (mL) | Final pH |
|---|---|---|---|---|---|
| 200 | 2 | 100 | 2.4 | 39 | 12.26 |
| 200 | 1.3 | 150 | 1.8 | 33.5 | 12.13 |
| 200 | 1 | 200 | 1.2 | 23 | 12.31 |

TABLE 17

Set 1: 1:1 acid to base ratio

| Starting volume (DMSO:THF 66/33) mL | Starting Conc. (mg/mL) | Acetic Acid added (mL) | Acetic Acid Equiv. | 1M NaOH solution added (mL) | Final pH |
|---|---|---|---|---|---|
| 2 | 100 | 2.4 | 94 | 42.1 | 12.42 |
| 1.3 | 150 | 1.8 | 70.5 | 31.6 | 12.22 |
| 1 | 200 | 1.2 | 47 | 21 | 12.02 |

Example 16. Crystallization Set 2

Small scale crystallization trials were carried out on Pattern 7 with Set 2 focusing on the most suitable pH range of Pattern 7. The starting concentration of Set 2 of crystallization experiments was lowered to 44 mg/mL and the final pH was also lowered from 12 to 7, in order to reduce the volume of base required.

Samples (1 and 2) was prepared by adding Pattern 7 (200 mg) with DMSO (3 mL) and THF (1.6 mL) for a slurry to be formed. The resulting slurries were heated to 70° C. using a temperature-controlled block. Acetic acid was added until dissolution was achieved. The experiments were held for 1 hour at 70° C. After 1 hour, Sample 1 was added 1M sodium hydroxide solution in 100 μL aliquots, until the experiment reached pH 7. The experiment was then cooled from 70° C. to 25° C. at a rate of 0.25° C./min. Sample 2 solution was cooled from 70° C. to 25° C. at a rate of 0.25° C./min. Once this experiment reached 25° C., 1M sodium hydroxide solution was added in 100 μL aliquots until the experiment reached pH 7. Both samples were stirred at ambient temperature for ca. 18 hours with agitation provided via a magnetic stirrer plate. After ca. 18 hours, stirring was stopped and the supernatants were filtered using 0.45 μm PVDF needle filters and syringes. The concentration of the supernatants was analyzed by HPLC. The remaining slurries in each sample was each transferred into 0.22 μm nylon filter centrifuge tubes and the solids were isolated by centrifugation. The recovered solids were analyzed by XRPD, PLM and HPLC for purity. The above technique was used to generate the $2^{nd}$ and $3^{rd}$ diffractograms in FIG. 72.

TABLE 18

Set 2

| Vial | Experiment | FB Mass (mg) | Starting Volume (DMSO:THF 66/33) | Starting Conc. (mg/mL) | Acetic Acid Added (mL) | 1M Sodium Hydroxide Solution Added (mL) | Final pH |
|---|---|---|---|---|---|---|---|
| 1 | 1M sodium hydroxide added | 200 | 4.57 | 44 | 2.85 mL | 52.5 | 7.06 |
| 2 | 1M sodium hydroxide added | 200 | 4.57 | 44 | 2.85 mL | 52.5 | 7.38 |

Example 17. Crystallization Set 3

Small scale crystallization trials were carried out on Pattern 7 with Set 3 to determine the effect of seeding, whereby both cooling and isothermal processing was used. Samples (1 and 2) were prepared by adding Pattern 7 (200 mg) and 1 mL of 66% DMSO: 33% THF (% v/v) for a slurry to be formed. Acetic acid was added in 100 μL aliquots at ambient temperature until dissolution was noted. Sodium hydroxide solution (1M) was added in 100 μL aliquots until the pH reached pH 5. The solution was then seeded with 4 mg (2%) of Pattern 7 and the pH was adjusted further with 1M sodium hydroxide solution until pH 7 was achieved. Sample 1 was stirred at ambient temperature for ca. 18 hours with agitation provided via a magnetic stirrer plate. Sample 2 was cooled at 5° C. at 0.1° C./min and stirred for approximately 18 hours. After ca. 18 hours, stirring was stopped and the supernatants of each sample were filtered using 0.45 μm PVDF needle filters and syringes. The concentration of the supernatants was analyzed by HPLC. The remaining slurries from each sample were each transferred into 0.22 μm nylon filter centrifuge tubes and the solids were isolated by centrifugation. The recovered solid was analyzed by XRPD, PLM and HPLC for purity. The above technique was used to generate the 3rd and 4th diffractograms in FIG. 72.

TABLE 19

| | | | | 1M Sodium Hydroxide Solution Added to reach pH 5 | | 1M Sodium Hydroxide Solution Added to reach pH 7 | |
|---|---|---|---|---|---|---|---|
| Vial | Experiment | Starting Conc. (mg/mL) | Acetic Acid Added (mL) | (mL) | pH | (mL) | Final pH |
| 1 | Ambient agitation | 200 | 1.3 | 18 | 5.07 | 5.7 | 7.18 |
| 2 | Cooling with agitation | 200 | 1.3 | 18 | 5.09 | 5.5 | 7.04 |

Example 18. Crystallization Set 4

Small-scale crystallizations were carried out on Pattern 7 with Set 4 using higher concentrations (5M and 10M) of sodium hydroxide solution, in order to decrease the volume required to reach the desired pH. Samples were prepared by adding Pattern 7 (200 mg) and added 1 mL of 66% DMSO: 33% THF (% v/v) at ambient temperature for a slurry to be formed. Acetic acid was added in 100 µL aliquots at ambient temperature until dissolution was noted. Sodium hydroxide solution (5M) was then added in 100 µL aliquots, until the pH of the system reached pH 5. The solution was then seeded with Pattern 7 (4 mg or 2%) and the pH of the samples was adjusted to pH 7 by the addition of sodium hydroxide solution (NaOH); whereby Vial 1 contained 5M NaOH and Vial 2 contained 10M NaOH. Samples were stirred at ambient temperature for ca. 18 hours with agitation provided via a magnetic stirrer plate. After ca. 18 hours, stirring was stopped and the formation of any solid was isolated by vacuum filtration, using a Büchner funnel and Whatman grade 1 filter paper. The recovered solid was analyzed by XRPD, PLM and HPLC for purity, and the concentration of the supernatants was analyzed by HPLC. The above technique was used to generate the diffractograms in FIG. 73.

TABLE 20

| | | | | Sodium Hydroxide Solution Added to reach pH 5 | | Sodium Hydroxide Solution Added to reach pH 7 | |
|---|---|---|---|---|---|---|---|
| Vial | Experiment | Starting Conc. (mg/mL) | Acetic Acid Added (mL) | (mL) | pH | (mL) | Final pH |
| 1 | 5M sodium hydroxide | 200 | 1.3 | 1.45 | 5 | 3.1 | 7.05 |
| 2 | 10M sodium hydroxide | 200 | 1.3 | 0.51 | 5 | 1.6 | 7.02 |

Example 19. Maturation Experimentation

100 µL aliquots of selected solvents were added to 40 mg of amorphous Pattern 1 until a mobile slurry was formed. The slurries were temperature cycled between ambient temperature and 40° C. for 72 hours. The samples were then collected, and the observed solids were isolated and then analyzed by XRPD.

The samples were then dried and reanalyzed by XRPD. To conduct the drying the XRPD plate was placed in an oven at 40° C. and allowed to dry for ca. 4 hours, after which the dried samples were analyzed by RFD. The above technique was used to generate the diffractograms in FIG. 16, FIG. 17, FIG. 18, FIG. 19, FIG. 20, FIG. 21, FIG. 22, FIG. 23, FIG. 24, FIG. 25, FIG. 26, FIG. 27, FIG. 28, and FIG. 29.

TABLE 21

Observations from maturation experiments

| Sample | Solvent System | Volume of Solvent (µL) | Initial Observations | Observations Post-Maturation |
|---|---|---|---|---|
| 1 | 1,4-Dioxane | 1000 | Yellow slurry | Pale yellow slurry |
| 2 | Acetone/water (20:80% v/v) | 500 | Yellow slurry | Yellow slurry |
| 3 | 2,2,2-Trifluoroethanol | 200 | Yellow slurry | Yellow solution |
| 4 | 2-Butanone | 1000 | Yellow slurry | Yellow slurry |
| 5 | 2-Ethoxyethanol | 1000 | Pale yellow slurry | Yellow slurry |
| 6 | 2-Propanol | 1000 | Yellow slurry | Pale yellow slurry |
| 7 | Acetone | 1300 | Yellow slurry | Pale yellow slurry |
| 8 | Acetonitrile | 1300 | Yellow slurry | Pale yellow slurry |
| 9 | Acetonitrile/water (90:10% v/v) | 1000 | Yellow slurry | Yellow slurry |
| 10 | Anisole | 1200 | Yellow slurry | Yellow slurry |
| 11 | Cumene | 1200 | Yellow slurry | Yellow slurry |

TABLE 21-continued

Observations from maturation experiments

| Sample | Solvent System | Volume of Solvent (μL) | Initial Observations | Observations Post-Maturation |
|---|---|---|---|---|
| 12 | Dichloromethane | 700 | Yellow slurry | Pale yellow slurry |
| 13 | Ethanol | 700 | Yellow slurry | Yellow slurry |
| 14 | Ethanol/water (85:15% v/v) | 1300 | Pale yellow slurry | Yellow slurry |
| 15 | Ethyl Acetate | 1500 | Pale yellow slurry | Yellow slurry |
| 16 | Heptane | 1500 | Yellow slurry | Yellow slurry |
| 17 | Isopropyl acetate | 400 | Yellow slurry | Yellow slurry |
| 18 | Methanol | 300 | Pale yellow slurry | Yellow slurry |
| 19 | Methanol/water (95:5% v/v) | 400 | Pale yellow slurry | Yellow slurry |
| 20 | 2N HCl | 1500 | Pale yellow slurry | Yellow slurry |
| 21 | Methyl isobutyl ketone | 1500 | Yellow slurry | Yellow slurry |
| 22 | t-Butylmethyl ether | 1500 | Yellow slurry | Yellow slurry |
| 23 | Tetrahydrofuran | 1500 | Yellow slurry | Yellow slurry |
| 24 | Toluene | 1500 | Yellow slurry | Pale yellow slurry |

TABLE 22

XRPD results after maturation experiments

| Sample | Solvent System | XRPD Post-Maturation | XRPD Post-Drying |
|---|---|---|---|
| 1 | 1,4-Dioxane | Converting to 2 | Converting to 2 |
| 2 | Acetone/water (20:80% v/v) | Insufficient solid | Insufficient solid |
| 3 | 2,2,2-Trifluoroethanol | No solid | No solid |
| 4 | 2-Butanone | Pattern 2 | Pattern 2 |
| 5 | 2-Ethoxyethanol | Pattern 2 | Pattern 2 |
| 6 | 2-Propanol | Pattern 3 | Pattern 3 |
| 7 | Acetone | Pattern 2 | Pattern 2 |
| 8 | Acetonitrile | Pattern 4 | Pattern 2 |
| 9 | Acetonitrile/water (90:10% v/v) | Pattern 1 | Pattern 1 |
| 10 | Anisole | Weak Pattern | 5 with extra peak |
| 11 | Cumene | Weak Pattern | 5 with extra peak |
| 12 | Dichloromethane | Pattern 2 | Pattern 2 |
| 13 | Ethanol | Pattern 3 (amorphous halo) | Pattern 3 |
| 14 | Ethanol/water (85:15% v/v) | Pattern 1 (Highly crystalline) | Pattern 1 (Highly crystalline) |
| 15 | Ethyl Acetate | Pattern 2 (amorphous halo) | Pattern 5 |
| 16 | Heptane | Weak Pattern | Pattern 3 and Pattern 6 |
| 17 | Isopropyl acetate | Pattern 2 | Pattern 2 |
| 18 | Methanol | Pattern 1 (Highly crystalline) | Pattern 1 (Highly crystalline) |
| 19 | Methanol/water (95:5% v/v) | Pattern 1 | Pattern 1 |
| 20 | 2N HCl | Pattern 1 | Pattern 1 |
| 21 | Methyl isobutyl ketone | Pattern 5 | Pattern 5 |
| 22 | t-Butylmethyl ether | Weak Pattern | Weak Pattern |
| 23 | Tetrahydrofuran | Pattern 2 | Pattern 2 |
| 24 | Toluene | Weak Pattern | Pattern 5 |

Example 20. Thermodynamic Solubility

Thermodynamic solubility was carried out for Pattern 1, Pattern 2/6 mixture, Pattern 3, amorphous di-HCl salts and Pattern 7 in water at pH 4.2. All samples were prepared at 30 mg/mL. Initial observations were made. The samples were agitated at ambient temperature for ca. 24 hours. The samples were collected and observations made. Observed solids were isolated via centrifugation. The mother liquor from the filtered sample was analyzed by HPLC. The pH 4.3 solution was prepared by diluting glacial acetic acid (11.6 mL) to 100 mL in deionized water, then adding sodium acetate (1.07 g) and acetic acid solution (5.9 mL) preparing up to 500 mL with deionized water; then the pH was adjusted to 4.2. The above technique was used to generate the images in FIG. 60.

TABLE 23

Observations and results from thermodynamic solubility experiments

| Sample | Form | Observations at T = 0 hours | Observations at T = 24 hours |
|---|---|---|---|
| 1 | Pattern 1 | Yellow slurry | Yellow solution |
| 2 | Pattern 2/6 | Yellow solution (dissolved upon addition) | Yellow solution |
| 3 | Pattern 3 | Yellow solution (dissolved upon addition) | Yellow solution |
| 4 | Amorphous Di-HCl | Yellow solution (dissolved upon addition) | Yellow solution |
| 5 | Pattern 7 | Off-white slurry | Off-white slurry |

Example 21. Summary of Crystallization Experiments on Compound 1 Free Base Material The experiments from Examples 17, 18, 19, and 20 are summarized below.

TABLE 24

Summary of crystallization conditions

| Set | Exp. | Starting conc. | Base used | Target pH for precipitation | Experimental Summary |
|---|---|---|---|---|---|
| 1 | 1 | 100 | 1M | 12 | Sodium hydroxide added to pH 12 |
|  | 2 | 100 | 1M | 12 | 1:1 ratio acid to base |
|  | 3 | 150 | 1M | 12 | Sodium hydroxide added to pH 12 |
|  | 4 | 150 | 1M | 12 | 1:1 ratio acid to base |
|  | 5 | 200 | 1M | 12 | Sodium hydroxide added to pH 12 |
|  | 6 | 200 | 1M | 12 | 1:1 ratio acid to base |
| 2 | 7 | 44 mg/mL | 1M | 7 | Experiment heated to 70° C. after DMSO/THF addition. Base added after cooling to 25° C. |
|  | 8 | 44 mg/mL | 1M | 7 | Experiment heated to 70° C. after DMSO/THF addition. Base added after cooling to 25° C. |
| 3 | 9 | 200 mg/mL | 1M | 7 | Experiment seeded at pH 5 (2%). Ambient agitation post-seed. |
|  | 10 | 200 mg/mL | 1M | 7 | Experiment seeded at pH 5 (2%). Cooled to 5° C. post-seed. |
| 4 | 11 | 200 mg/mL | 5M | 7 | Experiment seeded at pH 5 (2%). Ambient agitation post-seed. |
|  | 12 | 200 mg/mL | 10M | 7 | Experiment seeded at pH 5 (2%). Ambient agitation post-seed. |

Example 22. Formation of Pattern 11

A saturated solution of Compound 1 di-HCl was prepared in N,N'-dimethylacetamide at ambient temperature and the solution was then cooled from 60° C. to 25° C. at 0.1° C. per minute. The sample was left at ambient temperature until large crystals were obtained (roughly two weeks). During an attempt to carry out polarized light microscopy, the crystals re-dissolved upon agitation of the solution. The solution was placed in the fridge for one week to encourage crystal growth, but no crystals appeared. Finally, ca. 10 drops of acetone were added as anti-solvent and crystals were yielded.

Example 23. Single Crystal X-Ray Analysis of Pattern 11

A suitable crystal of Pattern 11 was selected and mounted in a loop using paratone oil. Data were collected using a Bruker D8Venture diffractometer equipped with a Photon III detector operating in shutterless mode at 100(2) K with Cu-Kα radiation (1.54178 Å). The structure was solved in the Olex2 software package with the She1XT (intrinsic phasing) structure solution program and refined with the She1XL3 refinement package using Least Squares minimization. Data were collected, solved and refined in the triclinic space-group P-1.

All non-hydrogen atoms were located in the Fourier map and their positions refined prior to describing the thermal movement of all non-hydrogen atoms anisotropically. Within the structure, two complete G1T28 dihydrochloride formula units were refined. All fully occupied hydrogen atoms were placed in calculated positions using a riding model with fixed Uiso at 1.2 times for all CH, $CH_2$ and NH groups and 1.5 times for all $CH_3$ groups. All partially occupied hydroxyl hydrogen atoms were located in the Fourier map and their positions and occupancy refined.

The highest residual Fourier peak was found to be 0.54 e·Å$^{-3}$ approx. 1.19 Å from C(1) and the deepest Fourier hole was found to be −0.29 e·Å$^{-3}$ approx. 0.63 Å from C1(2).

Crystal Data $C_{24}H_{33}C_{12}N_8O_{1.5}$ (M=528.48 g/mol): triclinic, space group P-1 (no. 2), a=12.2824(2) Å, b=14.5593(3) Å, c=15.9459(3) Å, α=72.0580(10)°, β=85.7150(10)°, γ=74.6560(10)°, V=2616.05(9) Å3, Z=4, T=100.0 K, μt(CuKα)=2.523 mm-1, Dcalc=1.342 g/cm$^3$, 77718 reflections measured (6.598°≤2Θ≤149.518°), 10714 unique ($R_{int}$=0.0685, $R_{sigma}$=0.0357) which were used in all calculations. The final $R_1$ was 0.0461 (I>2σ(I)) and $wR_2$ was 0.1363 (all data).

TABLE 25

Crystallographic parameters to refine Pattern 11
Pattern 11 (di-HCl semihydrate)

| | |
|---|---|
| Empirical formula | $C_{24}H_{33}Cl_2N_8O_{1.5}$ |
| Formula weight | 528.48 |
| Temperature/K | 100 |
| Crystal system | triclinic |
| Space group | P-1 |
| a/Å | 12.2824(2) |
| b/Å | 14.5593(3) |
| c/Å | 15.9459(3) |
| α/° | 72.0580(10) |
| β/° | 85.7150(10) |
| γ/° | 74.6560(10) |
| Volume/Å$^3$ | 2616.05(9) |
| Z | 4 |
| ρcalc g/cm$^3$ | 1.342 |
| μ/mm$^{-1}$ | 2.523 |
| F(000) | 1116 |
| Crystal size/mm$^3$ | 0.18 × 0.08 × 0.02 |
| Radiation | CuKα (λ = 1.54178) |

TABLE 25-continued

Crystallographic parameters to refine Pattern 11
Pattern 11 (di-HCl semihydrate)

| | |
|---|---|
| 2Θ range for data collection/° | 6.598 to 149.518 |
| Index ranges | −15 ≤ h ≤ 15, −18 ≤ k ≤ 18, −19 ≤ l ≤ 19 |
| Reflections collected | 77718 |
| Independent reflections | 10714 [$R_{int}$ = 0.0685, $R_{sigma}$ = 0.0357] |
| Data/restraints/parameters | 10714/0/633 |
| Goodness-of-fit on F$^2$ | 1.038 |
| Final R indexes [I >= 2σ (I)] | R1 = 0.0461, wR2 = 0.1260 |
| Final R indexes [all data] | R1 = 0.0613, wR2 = 0.1363 |
| Largest diff. peak/hole/e Å$^{-3}$ | 0.54/−0.29 |

Example 24. Single Crystal Determination Results for Pattern 11

The hemihydrate of Compound 1 as a dihydrochloride was found to be extremely crystalline and possess unit cell dimensions as follows:

| | |
|---|---|
| Triclinic P-1 | |
| a = 12.2824(2) A | a = 72.0580(10)° |
| b = 14.5593(3) A | b = 85.7150(10)° |
| c = 15.9459(3) A | a = 74.6560(10)° |
| Volume = 2,616.05 (9) A$^3$ | |
| Z = 4, Z' = 2 | |

This asymmetric unit contains two complete Compound 1 formula units and two chloride anions. The solvent mask was calculated and 91.1 electrons were found within a volume of 341.0 Å$_3$ in a void in the unit cell. This corresponds to 45.5 electrons per asymmetric unit and 22.75 electrons per G1T28 formula unit. This is consistent with the presence of one additional chloride anion and a water molecule at 50% occupancy per G1T28 molecule, totaling 44 electrons per asymmetric unit. The solvent mask was removed in order to determine the location of the disordered chlorides which were found within channels intersecting the unit cell at the cell origins.

The final refinement parameters were as follows:
$R_1$[I>2σ(I)]=4.61%
GooF (Goodness of fit)=1.038
$wR_2$ (all data)=13.63%
$R_{int}$=6.85%

Packing within the structure was shown to be efficient whereby a moderate density of 1.342 g/cm$^3$ was noted. A solvent mask was applied to a channel along the a-axis which contained the disordered solvent and counterion.

A discrete hydrogen bonding motif was noted in the asymmetric unit, as shown in FIG. 90. The hydrogen bonding association between the protonated piperazine (H(29) or H29)') and chloride counterion (Cl(1) or Cl(2)), and between the amide hydrogen (H(3) or H(3)') and chloride counterion (Cl(1) or Cl(2)), with H(29) . . . Cl(1)/H(29)' . . . Cl(2) and Cl(1) . . . H(3)'/Cl(2) . . . H(3) measuring 2.08(3)/2.10(3) and 2.40(3)/2.36(3) Å, respectively.

In addition to the discrete cage-like hydrogen bonding association noted, the pyrimidine and bridging amines appeared to show a clear association. This interaction was found to be of moderate strength, measuring 2.15(2) Å between N(9) and H(19), forming a R22(8) motif. There was no evidence of π-π interactions, the primary drive to crystallization was via hydrogen bond formation, as described above. The remaining interactions between molecules in the structure were made up of van de Waal's interactions. A simulated XRPD diffractogram of has been calculated and compared to an experimental diffractogram of Pattern 1 (FIG. 96). The diffractograms are not consistent with each other.

TABLE 26

XRPD simulated peak list for Pattern 11

| No. | Pos. [°2θ] | d-spacing [Å] | Height [cts] | Rel Int. [%] |
|---|---|---|---|---|
| 1 | 5.8209 | 15.17080 | 2075.83 | 20.53 |
| 2 | 6.5936 | 13.39452 | 10112.42 | 100 |
| 3 | 7.3734 | 11.97972 | 7190.89 | 71.11 |
| 4 | 9.2538 | 9.54913 | 52.20 | 0.52 |
| 5 | 10.0260 | 8.81529 | 3409.28 | 33.71 |
| 6 | 11.1511 | 7.92828 | 189.13 | 1.87 |
| 7 | 11.6573 | 7.58514 | 3732.39 | 36.91 |
| 8 | 12.7374 | 6.94428 | 1333.24 | 13.18 |
| 9 | 13.9012 | 6.36539 | 99.45 | 0.98 |
| 10 | 14.7220 | 6.01229 | 1164.27 | 11.51 |
| 11 | 15.0305 | 5.88958 | 2108.97 | 20.86 |
| 12 | 15.1432 | 5.84602 | 1602.37 | 15.85 |
| 13 | 15.9841 | 5.54030 | 3119.67 | 30.85 |
| 14 | 16.5233 | 5.36071 | 1270.96 | 12.57 |
| 15 | 16.7700 | 5.28239 | 445.67 | 4.41 |
| 16 | 17.5939 | 5.03682 | 326.19 | 3.23 |
| 17 | 17.8378 | 4.96850 | 2822.86 | 27.91 |
| 18 | 18.5352 | 4.78310 | 994.29 | 9.83 |
| 19 | 18.9219 | 4.68623 | 1632.15 | 16.14 |
| 20 | 19.0676 | 4.65074 | 3212.03 | 31.76 |
| 21 | 19.4254 | 4.56589 | 860.64 | 8.51 |
| 22 | 19.9606 | 4.44465 | 2694.80 | 26.65 |
| 23 | 20.5317 | 4.32229 | 179.94 | 1.78 |
| 24 | 20.8288 | 4.26130 | 750.55 | 7.42 |
| 25 | 21.4583 | 4.13769 | 905.33 | 8.95 |
| 26 | 21.6452 | 4.10237 | 471.94 | 4.67 |
| 27 | 22.0978 | 4.01937 | 297.14 | 2.94 |
| 28 | 22.4959 | 3.94913 | 6503.85 | 64.32 |
| 29 | 23.1964 | 3.83144 | 1588.05 | 15.70 |
| 30 | 23.9311 | 3.71545 | 236.96 | 2.34 |
| 31 | 24.1998 | 3.67479 | 1260.44 | 12.46 |
| 32 | 24.3822 | 3.64771 | 524.70 | 5.19 |
| 33 | 25.0249 | 3.55548 | 711.00 | 7.03 |
| 34 | 25.6050 | 3.47621 | 114.77 | 1.13 |
| 35 | 26.2507 | 3.39216 | 712.98 | 7.05 |
| 36 | 26.5654 | 3.35268 | 1069.11 | 10.57 |
| 37 | 27.1874 | 3.27737 | 990.66 | 9.80 |
| 38 | 27.3587 | 3.25725 | 428.86 | 4.24 |
| 39 | 28.0072 | 3.18327 | 272.76 | 2.70 |
| 40 | 28.3983 | 3.14033 | 132.18 | 1.31 |
| 41 | 28.6382 | 3.11455 | 569.96 | 5.64 |
| 42 | 28.7733 | 3.10024 | 600.54 | 5.94 |
| 43 | 29.3735 | 3.03825 | 603.26 | 5.97 |
| 44 | 30.1575 | 2.96103 | 250.17 | 2.47 |
| 45 | 30.6752 | 2.91221 | 206.57 | 2.04 |
| 46 | 30.8126 | 2.89955 | 297.80 | 2.94 |
| 47 | 31.0668 | 2.87640 | 306.34 | 3.03 |
| 48 | 31.5495 | 2.83348 | 181.12 | 1.79 |
| 49 | 31.7273 | 2.81801 | 153.60 | 1.52 |
| 50 | 32.3419 | 2.76584 | 316.57 | 3.13 |
| 51 | 32.6990 | 2.73645 | 406.20 | 4.02 |
| 52 | 32.9597 | 2.71539 | 220.82 | 2.18 |
| 53 | 33.2544 | 2.69201 | 443.02 | 4.38 |
| 54 | 33.5207 | 2.67123 | 254.44 | 2.52 |
| 55 | 34.0803 | 2.62863 | 397.79 | 3.93 |
| 56 | 34.2787 | 2.61387 | 121.68 | 1.20 |
| 57 | 34.6959 | 2.58339 | 141.94 | 1.40 |
| 58 | 34.9584 | 2.56459 | 81.57 | 0.81 |

TABLE 27

Highest intensity simulated XRPD diffractogram peaks for Pattern 11

| No. | Pos. [°2θ] | d-spacing [Å] | Height | Rel. Int. [%] |
|---|---|---|---|---|
| 1 | 5.8209 | 15.17080 | 2075.83 | 20.53 |
| 2 | 6.5936 | 13.39452 | 10112.42 | 100 |
| 3 | 7.3734 | 11.97972 | 7190.89 | 71.11 |
| 4 | 10.0260 | 8.81529 | 3409.28 | 33.71 |
| 5 | 11.6573 | 7.58514 | 3732.39 | 36.91 |
| 6 | 12.7374 | 6.94428 | 1333.24 | 13.18 |
| 7 | 14.7220 | 6.01229 | 1164.27 | 11.51 |
| 8 | 15.0305 | 5.88958 | 2108.97 | 20.86 |
| 9 | 15.1432 | 5.84602 | 1602.37 | 15.85 |
| 10 | 15.9841 | 5.54030 | 3119.67 | 30.85 |
| 11 | 16.5233 | 5.36071 | 1270.96 | 12.57 |
| 12 | 17.8378 | 4.96850 | 2822.86 | 27.91 |
| 13 | 18.5352 | 4.78310 | 994.29 | 9.83 |
| 14 | 18.9219 | 4.68623 | 1632.15 | 16.14 |
| 15 | 19.0676 | 4.65074 | 3212.03 | 31.76 |
| 16 | 19.9606 | 4.44465 | 2694.80 | 26.65 |
| 17 | 22.4959 | 3.94913 | 6503.85 | 64.32 |
| 18 | 23.1964 | 3.83144 | 1588.05 | 15.70 |
| 19 | 24.1998 | 3.67479 | 1260.44 | 12.46 |
| 20 | 26.5654 | 3.35268 | 1069.11 | 10.57 |

Example 24. Single Crystal Solution of Pattern 11

The coordinates and solved parameters of the single crystal solution for Pattern 11 are provided below:

TABLE 28

Atom coordinates for Pattern 11

| Atom | x | y | z | U(eq) |
|---|---|---|---|---|
| Cl1 | 5968.1(4) | 7961.9(3) | 4715.8(3) | 27.07(11) |
| C1 | 1379.6(14) | 3923.2(13) | 3199.1(11) | 19.8(3) |
| C2 | 1218.2(16) | 3038.6(14) | 3983.3(12) | 26.1(4) |
| N3 | 774.0(15) | 2331.4(13) | 3714.7(12) | 31.5(4) |
| O4 | 971.0(13) | 1287.2(11) | 2877.5(10) | 34.9(3) |
| C4 | 1166.4(16) | 2015.1(14) | 3018.8(13) | 27.5(4) |
| C5 | 1874.1(16) | 2601.6(14) | 2413.9(13) | 26.2(4) |
| C6 | 2426.2(17) | 2431.5(14) | 1680.0(13) | 26.9(4) |
| C7 | 2955.6(15) | 3223.7(13) | 1311.4(12) | 22.5(4) |
| C8 | 3664.2(15) | 3494.8(13) | 608.8(12) | 23.1(4) |
| N9 | 4016.6(12) | 4321.3(11) | 440.4(10) | 21.1(3) |
| N29 | 4003.8(12) | 9560.7(12) | 3720.1(10) | 21.3(3) |
| C10 | 3637.3(14) | 4904.4(13) | 979.8(11) | 18.7(3) |
| N11 | 2977.4(12) | 4724.2(11) | 1682.7(10) | 20.4(3) |
| C12 | 2670.0(14) | 3867.6(13) | 1847.7(12) | 20.4(3) |
| N13 | 2042.9(13) | 3467.9(11) | 2543.4(10) | 22.4(3) |
| C14 | 2044.9(15) | 4496.8(14) | 3537.7(12) | 24.5(4) |
| C15 | 1312.3(17) | 5098.3(15) | 4115.2(13) | 28.9(4) |
| C16 | 251.5(18) | 5779.1(15) | 3624.6(14) | 34.5(5) |
| C17 | −434.0(17) | 5198.0(17) | 3339.0(14) | 34.7(5) |
| C18 | 273.0(16) | 4603.2(15) | 2759.6(13) | 28.2(4) |
| N19 | 4016.4(13) | 5755.4(11) | 750.7(10) | 21.2(3) |
| C20 | 3786.8(15) | 6505.3(13) | 1157.8(11) | 19.8(3) |
| N21 | 4545.5(12) | 7047.4(11) | 996.8(10) | 20.1(3) |
| C22 | 4444.0(15) | 7740.1(12) | 1413.9(11) | 19.8(3) |
| C23 | 3596.1(14) | 7936.8(12) | 2007.6(12) | 19.6(3) |
| C24 | 2757.8(15) | 7413.6(14) | 2111.0(13) | 24.8(4) |
| C25 | 2842.4(15) | 6706.2(14) | 1684.8(13) | 24.1(4) |
| N26 | 3518.6(12) | 8641.4(11) | 2473.3(10) | 20.6(3) |
| C27 | 4464.3(17) | 9099.2(15) | 2348.5(13) | 27.6(4) |
| C28 | 4219.2(19) | 9942.0(15) | 2762.0(13) | 31.3(4) |
| C29 | 3811.0(17) | 10355.8(15 | 4159.4(15) | 30.6(4) |
| C30 | 3039.5(16) | 9086.1(15) | 3850.9(14) | 28.1(4) |
| C31 | 3300.8(16) | 8258.1(14) | 3421.1(12) | 24.6(4) |
| Cl2 | −741.1(4) | 1809.4(4) | 5414.3(3) | 27.98(12) |
| N29 | 1143.4(13) | 213.1(12) | 6499.5(11) | 24.6(3) |
| C1' | 3792.0(14) | 5843.2(13) | 6922.0(11) | 19.3(3) |
| C2' | 4910.9(15) | 6136.6(14) | 6681.8(13) | 24.4(4) |
| N3' | 4798.2(14) | 7190.1(13) | 6583.2(11) | 27.5(3) |
| O4' | 4185.4(12) | 8516.1(10) | 7119.1(10) | 31.8(3) |

TABLE 28-continued

Atom coordinates for Pattern 11

| Atom | x | y | z | U(eq) |
|---|---|---|---|---|
| C4' | 4219.5(15 | 7648.1(14 | 7149.6(13) | 24.5(4) |
| C5' | 3557.2(15 | 7054.1(13 | 7803.5(12) | 22.6(4) |
| C6' | 2966.3(16 | 7280.4(14 | 8502.0(12) | 24.5(4) |
| C7' | 2371.0(15 | 6530.8(13 | 8862.6(12) | 21.6(4) |
| C8' | 1584.2(16 | 6339.9(14 | 9522.5(13) | 23.2(4) |
| N9' | 1139.3(13 | 5562.6(11 | 9667.3(10) | 22.0(3) |
| C10' | 1494.7(14 | 4960.0(13 | 9141.7(11) | 18.9(3) |
| N11' | 2217.1(12 | 5071.8(11 | 8477.9(10) | 19.3(3) |
| C12' | 2644.0(14 | 5861.3(13 | 8350.9(11) | 19.2(3) |
| N13' | 3390.2(12 | 6168.8(11 | 7711.9(10) | 19.8(3) |
| C14' | 2901.2(15 | 6362.3(13 | 6191.8(12) | 22.5(4) |
| C15' | 3229.4(16 | 6008.9(14 | 5374.4(12) | 26.4(4) |
| C16' | 3477.5(16 | 4872.2(14 | 5606.1(13) | 27.0(4) |
| C17' | 4368.2(16 | 4352.5(14 | 6324.6(12) | 25.1(4) |
| C18' | 4018.2(15 | 4703.1(13 | 7141.7(12) | 23.5(4) |
| N19' | 1005.7(13 | 4170.4(11 | 9346.8(10) | 21.2(3) |
| C20' | 1207.6(14 | 3410.0(13 | 8956.3(11) | 19.2(3) |
| N21' | 342.1(12) | 3005.5(11 | 8986.5(10) | 21.6(3) |
| C22' | 455.3(15) | 2284.2(13 | 8601.9(12) | 21.2(3) |
| C23' | 1418.4(14 | 1932.0(13 | 8165.0(11) | 19.8(3) |
| C24' | 2339.9(15 | 2319.0(13 | 8190.6(13) | 23.3(4) |
| C25' | 2250.1(14 | 3050.6(13 | 8589.9(12) | 22.2(4) |
| N26' | 1524.6(12 | 1195.2(11 | 7724.3(10) | 20.4(3) |
| C27' | 1809.5(16 | 1545.0(14 | 6785.6(13) | 25.9(4) |
| C28' | 2109.2(16 | 684.7(15) | 6391.2(14) | 27.4(4) |
| C29' | 1380.1(18 | −613.6(16) | 6098.7(16) | 34.2(5) |
| C30' | 843.8(17) | −116.7(14) | 7447.6(13) | 27.6(4) |
| C31' | 562.4(15) | 759.4(13) | 7821.8(12) | 22.9(4) |

TABLE 29

Anisotropic displacement parameters ($A^2 \times 10^3$) for Pattern 11. The anisotropic displacement factor exponent takes the form: $-2\pi^2[h^2a^{*2}U_{11} + 2hka^*b^*U_{12} + \ldots]$

| Atom | U11 | U22 | U33 | U23 | U13 | U12 |
|---|---|---|---|---|---|---|
| Cl1 | 25.4(2) | 33.0(2) | 23.3(2) | −7.14(18) | 3.64(1 | — |
| C1 | 19.5(8) | 25.8(9) | 18.1(8) | −10.7(7) | 6.5(6) | −9.4(7) |
| C2 | 27.7(9) | 30.7(10) | 22.5(9) | −8.0(8) | 4.1(7) | −12.7(8) |
| N3 | 39.1(9) | 33.2(9) | 30.5(9) | −12.5(7) | 15.3(8 | −23.6(8) |
| O4 | 47.7(8) | 31.1(7) | 35.6(8) | −13.6(6) | 13.9(7 | −25.9(7) |
| C4 | 31.5(9) | 25.7(9) | 29.3(10) | −8.5(8) | 6.8(8) | −15.9(8) |
| C5 | 30.5(9) | 24.9(9) | 29.0(10) | −11.1(8) | 8.6(8) | −14.2(8) |
| C6 | 34.9(10 | 22.6(9) | 28.8(10) | −12.0(8) | 9.5(8) | −14.1(8) |
| C7 | 27.4(9) | 21.4(8) | 22.6(9) | −10.7(7) | 5.6(7) | −9.7(7) |
| C8 | 29.8(9) | 22.5(8) | 22.0(9) | −12.2(7) | 6.5(7) | −10.3(7) |
| N9 | 25.9(7) | 23.0(7) | 19.7(7) | −10.7(6) | 6.3(6) | −11.4(6) |
| N29 | 19.9(7) | 26.2(8) | 23.9(8) | −14.1(6) | 3.9(6) | −9.1(6) |
| C10 | 21.3(8) | 20.2(8) | 17.7(8) | −7.7(7) | 3.2(6) | −9.1(6) |
| N11 | 23.5(7) | 24.1(7) | 18.8(7) | −10.1(6) | 6.7(6) | −12.2(6) |
| C12 | 21.6(8) | 22.8(8) | 19.8(8) | −7.9(7) | 5.3(7) | −10.0(7) |
| N13 | 26.1(7) | 23.7(7) | 23.2(8) | −11.7(6) | 9.5(6) | −13.1(6) |
| C14 | 23.0(8) | 32.9(10) | 21.9(9) | −10.7(8) | 4.2(7) | −12.7(7) |
| C15 | 34.5(10 | 34.7(10) | 23.6(9) | −14.1(8) | 8.0(8) | −14.8(8) |
| C16 | 41.6(11 | 30.6(10) | 28.1(10) | −9.8(8) | 10.7(9 | −5.4(9) |
| C17 | 25.1(9) | 41.3(12) | 31.9(11) | −11.0(9) | 0.8(8) | 1.2(8) |
| C18 | 23.7(9) | 35.8(10) | 23.6(9) | −8.4(8) | 0.5(7) | −6.1(8) |
| N19 | 25.9(7) | 22.4(7) | 20.9(8) | −11.2(6) | 8.8(6) | −12.8(6) |
| C20 | 23.2(8) | 19.7(8) | 18.4(8) | −6.6(7) | 1.1(7) | −7.9(6) |
| N21 | 25.4(7) | 20.8(7) | 17.2(7) | −7.2(6) | 4.0(6) | −10.4(6) |
| C22 | 23.8(8) | 19.0(8) | 19.5(8) | −5.8(7) | 2.3(7) | −10.9(7) |
| C23 | 21.3(8) | 16.4(8) | 23.1(9) | −7.6(7) | −1.6(7) | −5.7(6) |
| C24 | 18.4(8) | 27.9(9) | 33.6(10) | −16.7(8) | 6.5(7) | −8.0(7) |
| C25 | 19.5(8) | 25.9(9) | 33.5(10) | −15.9(8) | 4.7(7) | −10.0(7) |
| N26 | 22.2(7) | 21.3(7) | 23.0(8) | −11.0(6) | 3.3(6) | −9.1(6) |
| C27 | 38.0(10 | 34.2(10) | 23.2(9) | −16.2(8) | 13.2(8 | −24.8(9) |
| C28 | 47.0(12 | 30.7(10) | 25.4(10) | −11.4(8) | 6.1(9) | −23.3(9) |
| C29 | 28.6(9) | 33.6(10) | 40.5(12) | −25.3(9) | 3.8(8) | −10.2(8) |
| C30 | 23.2(9) | 37.1(10) | 36.1(11) | −23.9(9) | 11.8(8 | −15.7(8) |
| C31 | 28.1(9) | 27.4(9) | 26.2(10) | −15.4(8) | 12.2(7 | −15.0(7) |
| Cl2 | 22.4(2) | 37.4(2) | 24.8(2) | −8.01(18) | 4.76(1 | — |
| N29' | 21.3(7) | 30.2(8) | 29.1(9) | −18.4(7) | 4.1(6) | −8.0(6) |
| C1' | 19.7(8) | 23.0(8) | 17.2(8) | −8.3(7) | 5.1(6) | −7.5(6) |
| C2' | 19.5(8) | 30.7(9) | 26.3(9) | −11.8(8) | 5.0(7) | −9.2(7) |
| N3' | 29.1(8) | 32.1(9) | 26.8(8) | −9.8(7) | 9.6(7) | −18.6(7) |
| O4' | 35.6(7) | 28.4(7) | 36.3(8) | −10.6(6) | 8.4(6) | −17.8(6) |
| C4' | 24.0(8) | 26.7(9) | 26.0(9) | −7.5(7) | 2.1(7) | −12.6(7) |
| C5' | 23.8(8) | 24.0(9) | 24.3(9) | −9.5(7) | 3.8(7) | −11.7(7) |
| C6' | 29.4(9) | 25.7(9) | 24.5(9) | −11.0(7) | 5.3(7) | −14.4(7) |
| C7' | 25.7(8) | 23.0(8) | 20.9(9) | −10.8(7) | 3.5(7) | −10.4(7) |
| C8' | 29.4(9) | 25.6(9) | 22.2(9) | −14.2(7) | 7.0(7) | −13.1(7) |
| N9' | 26.2(7) | 24.2(7) | 20.9(8) | −11.2(6) | 7.5(6) | −12.0(6) |
| C10' | 20.4(8) | 20.5(8) | 18.1(8) | −8.0(7) | 2.0(6) | −7.2(6) |
| N11' | 20.0(7) | 23.2(7) | 18.5(7) | −9.3(6) | 3.5(6) | −9.0(6) |
| C12' | 17.8(7) | 23.5(8) | 18.6(8) | −8.1(7) | 2.8(6) | −7.9(6) |
| N13' | 21.0(7) | 22.8(7) | 19.6(7) | −9.6(6) | 5.3(6) | −9.7(6) |
| C14' | 21.7(8) | 24.7(9) | 23.1(9) | −9.5(7) | 2.6(7) | −7.2(7) |

TABLE 29-continued

Anisotropic displacement parameters ($Å^2 \times 10^3$) for Pattern 11. The anisotropic displacement factor exponent takes the form: $-2\pi^2[h^2a^{*2}U_{11} + 2hka^*b^*U_{12} + \ldots]$

| Atom | U11 | U22 | U33 | U23 | U13 | U12 |
|---|---|---|---|---|---|---|
| C15' | 30.3(9) | 28.7(9) | 20.1(9) | −6.9(7) | 1.2(7) | −8.1(8) |
| C16' | 29.4(9) | 30.1(10) | 25.7(10) | −13.5(8) | 8.3(8) | −10.8(8) |
| C17' | 28.1(9) | 23.0(9) | 25.5(9) | −10.2(7) | 11.0(7 | −8.0(7) |
| C18' | 25.7(9) | 20.6(8) | 22.4(9) | −6.3(7) | 5.9(7) | −4.7(7) |
| N19' | 23.2(7) | 24.9(7) | 22.2(8) | −13.0(6) | 9.7(6) | −12.8(6) |
| C20' | 22.4(8) | 20.4(8) | 17.1(8) | −6.8(6) | 3.3(6) | −8.9(6) |
| N21' | 24.6(7) | 24.1(7) | 21.1(7) | −10.9(6) | 8.0(6) | −11.9(6) |
| C22' | 24.7(8) | 23.8(8) | 20.7(9) | −9.5(7) | 5.6(7) | −13.3(7) |
| C23' | 23.2(8) | 19.2(8) | 19.3(8) | −7.6(7) | 2.0(7) | −7.7(7) |
| C24' | 18.5(8) | 24.4(9) | 29.3(10) | −13.0(7) | 4.3(7) | −4.4(7) |
| C25' | 19.2(8) | 23.9(9) | 28.2(9) | −12.1(7) | 1.9(7) | −8.7(7) |
| N26' | 21.8(7) | 22.6(7) | 21.7(8) | −11.9(6) | 3.8(6) | −8.7(6) |
| C27' | 29.5(9) | 28.7(9) | 26.4(10) | −15.3(8) | 11.6(7 | −14.0(8) |
| C28' | 24.4(9) | 34.7(10) | 32.7(10) | −20.9(9) | 9.1(8) | −13.1(8) |
| C29' | 31.5(10 | 39.1(11) | 47.3(13) | −32.2(10) | 6.9(9) | −13.6(9) |
| C30' | 32.9(10 | 25.5(9) | 30.7(10) | −13.7(8) | 5.3(8) | −13.4(8) |
| C31' | 26.5(9) | 24.7(9) | 24.1(9) | −12.4(7) | 5.8(7) | −13.1(7) |
| N29' | 21.3(7) | 30.2(8) | 29.1(9) | −18.4(7) | 4.1(6) | −8.0(6) |
| C1' | 19.7(8) | 23.0(8) | 17.2(8) | −8.3(7) | 5.1(6) | −7.5(6) |
| C2' | 19.5(8) | 30.7(9) | 26.3(9) | −11.8(8) | 5.0(7) | −9.2(7) |
| N3' | 29.1(8) | 32.1(9) | 26.8(8) | −9.8(7) | 9.6(7) | −18.6(7) |
| O4' | 35.6(7) | 28.4(7) | 36.3(8) | −10.6(6) | 8.4(6) | −17.8(6) |
| C4' | 24.0(8) | 26.7(9) | 26.0(9) | −7.5(7) | 2.1(7) | −12.6(7) |
| C5' | 23.8(8) | 24.0(9) | 24.3(9) | −9.5(7) | 3.8(7) | −11.7(7) |
| C6' | 29.4(9) | 25.7(9) | 24.5(9) | −11.0(7) | 5.3(7) | −14.4(7) |
| C7' | 25.7(8) | 23.0(8) | 20.9(9) | −10.8(7) | 3.5(7) | −10.4(7) |
| C8' | 29.4(9) | 25.6(9) | 22.2(9) | −14.2(7) | 7.0(7) | −13.1(7) |
| N9' | 26.2(7) | 24.2(7) | 20.9(8) | −11.2(6) | 7.5(6) | −12.0(6) |
| C10' | 20.4(8) | 20.5(8) | 18.1(8) | −8.0(7) | 2.0(6) | −7.2(6) |
| N11' | 20.0(7) | 23.2(7) | 18.5(7) | −9.3(6) | 3.5(6) | −9.0(6) |
| C12' | 17.8(7) | 23.5(8) | 18.6(8) | −8.1(7) | 2.8(6) | −7.9(6) |
| N13' | 21.0(7) | 22.8(7) | 19.6(7) | −9.6(6) | 5.3(6) | −9.7(6) |
| C14' | 21.7(8) | 24.7(9) | 23.1(9) | −9.5(7) | 2.6(7) | −7.2(7) |
| C15' | 30.3(9) | 28.7(9) | 20.1(9) | −6.9(7) | 1.2(7) | −8.1(8) |
| C16' | 29.4(9) | 30.1(10) | 25.7(10) | −13.5(8) | 8.3(8) | −10.8(8) |
| C17' | 28.1(9) | 23.0(9) | 25.5(9) | −10.2(7) | 11.0(7 | −8.0(7) |
| C18' | 25.7(9) | 20.6(8) | 22.4(9) | −6.3(7) | 5.9(7) | −4.7(7) |
| N19' | 23.2(7) | 24.9(7) | 22.2(8) | −13.0(6) | 9.7(6) | −12.8(6) |
| C20' | 22.4(8) | 20.4(8) | 17.1(8) | −6.8(6) | 3.3(6) | −8.9(6) |
| N21' | 24.6(7) | 24.1(7) | 21.1(7) | −10.9(6) | 8.0(6) | −11.9(6) |
| C22' | 24.7(8) | 23.8(8) | 20.7(9) | −9.5(7) | 5.6(7) | −13.3(7) |
| C23' | 23.2(8) | 19.2(8) | 19.3(8) | −7.6(7) | 2.0(7) | −7.7(7) |
| C24' | 18.5(8) | 24.4(9) | 29.3(10) | −13.0(7) | 4.3(7) | −4.4(7) |
| C25' | 19.2(8) | 23.9(9) | 28.2(9) | −12.1(7) | 1.9(7) | −8.7(7) |
| N26' | 21.8(7) | 22.6(7) | 21.7(8) | −11.9(6) | 3.8(6) | −8.7(6) |
| C27' | 29.5(9) | 28.7(9) | 26.4(10) | −15.3(8) | 11.6(7 | −14.0(8) |
| C28' | 24.4(9) | 34.7(10) | 32.7(10) | −20.9(9) | 9.1(8) | −13.1(8) |
| C29' | 31.5(10 | 39.1(11) | 47.3(13) | −32.2(10) | 6.9(9) | −13.6(9) |
| C30' | 32.9(10 | 25.5(9) | 30.7(10) | −13.7(8) | 5.3(8) | −13.4(8) |
| C31' | 26.5(9) | 24.7(9) | 24.1(9) | −12.4(7) | 58(7) | −13.1(7) |

TABLE 30

Bond lengths for Pattern 11

| Atom | Atom | Length/Å |
|---|---|---|
| C1 | C2 | 1.539(2) |
| C1 | N13 | 1.487(2) |
| C1 | C14 | 1.537(2) |
| C1 | C18 | 1.524(3) |
| C2 | N3 | 1.465(2) |
| N3 | C4 | 1.339(3) |
| O4 | C4 | 1.233(2) |
| C4 | C5 | 1.475(2) |
| C5 | C6 | 1.364(3) |
| C5 | N13 | 1.408(3) |
| C6 | C7 | 1.421(2) |
| C7 | C8 | 1.390(2) |
| C7 | C12 | 1.417(2) |
| C8 | N9 | 1.329(2) |
| N9 | C10 | 1.363(2) |
| N29 | C28 | 1.486(2) |
| N29 | C29 | 1.489(2) |
| N29 | C30 | 1.494(2) |
| C10 | N11 | 1.333(2) |
| C10 | N19 | 1.373(2) |
| N11 | C12 | 1.341(2) |
| C12 | N13 | 1.369(2) |
| C14 | C15 | 1.543(2) |
| C15 | C16 | 1.511(3) |
| C16 | C17 | 1.518(3) |
| C17 | C18 | 1.527(3) |
| N19 | C20 | 1.393(2) |
| C20 | N21 | 1.336(2) |
| C20 | C25 | 1.401(2) |
| N21 | C22 | 1.345(2) |

TABLE 30-continued

Bond lengths for Pattern 11

| Atom | Atom | Length/Å |
|---|---|---|
| C22 | C23 | 1.387(2) |
| C23 | C24 | 1.407(2) |
| C23 | N26 | 1.421(2) |
| C24 | C25 | 1.377(2) |
| N26 | C27 | 1.458(2) |
| N26 | C31 | 1.472(2) |
| C27 | C28 | 1.518(3) |
| C30 | C31 | 1.516(2) |
| N29' | C28' | 1.495(2) |
| N29' | C29' | 1.484(2) |
| N29' | C30' | 1.488(2) |
| C1' | C2' | 1.533(2) |
| C1' | N13' | 1.485(2) |
| C1' | C14' | 1.528(2) |
| C1' | C18' | 1.539(2) |
| C2' | N3' | 1.463(2) |
| N3' | C4' | 1.338(2) |
| O4' | C4' | 1.239(2) |
| C4' | C5' | 1.479(2) |
| C5' | C6' | 1.362(3) |
| C5' | N13' | 1.409(2) |
| C6' | C7' | 1.424(2) |
| C7' | C8' | 1.389(2) |
| C7' | C12' | 1.416(2) |
| C8' | N9' | 1.334(2) |
| N9' | C10' | 1.363(2) |
| C10' | N11' | 1.328(2) |
| C10' | N19' | 1.376(2) |
| N11' | C12' | 1.340(2) |
| C12' | N13' | 1.369(2) |
| C14' | C15' | 1.533(2) |
| C15' | C16' | 1.530(3) |
| C16' | C17' | 1.516(3) |
| C17' | C18' | 1.534(2) |
| N19' | C20' | 1.390(2) |
| C20' | N21' | 1.336(2) |
| C20' | C25' | 1.406(2) |
| N21' | C22' | 1.344(2) |
| C22' | C23' | 1.387(2) |
| C23' | C24' | 1.399(2) |
| C23' | N26' | 1.428(2) |
| C24' | C25' | 1.377(2) |
| N26' | C27' | 1.473(2) |
| N26' | C31' | 1.460(2) |
| C27' | C28' | 1.519(2) |
| C30' | C31' | 1.519(2) |

TABLE 31

Bond angles for Pattern 11

| Atom | Atom | Atom | Angle/° |
|---|---|---|---|
| N13 | C1 | C2 | 105.39(14) |
| N13 | C1 | C14 | 111.19(13) |
| N13 | C1 | C18 | 107.77(14) |
| C14 | C1 | C2 | 107.44(15) |
| C18 | C1 | C2 | 113.32(15) |
| C18 | C1 | C14 | 111.60(15) |
| N3 | C2 | C1 | 112.63(15) |
| C4 | N3 | C2 | 122.86(16) |
| N3 | C4 | C5 | 115.08(16) |
| O4 | C4 | N3 | 123.95(17) |
| O4 | C4 | C5 | 120.96(18) |
| C6 | C5 | C4 | 128.19(17) |
| C6 | C5 | N13 | 110.69(15) |
| N13 | C5 | C4 | 121.11(16) |
| C5 | C6 | C7 | 106.47(16) |
| C8 | C7 | C6 | 137.25(17) |
| C8 | C7 | C12 | 115.52(15) |
| C12 | C7 | C6 | 107.21(15) |
| N9 | C8 | C7 | 121.79(16) |
| C8 | N9 | C10 | 117.04(15) |

TABLE 31-continued

Bond angles for Pattern 11

| Atom | Atom | Atom | Angle/° |
|---|---|---|---|
| C28 | N2 | C29 | 111.98(15) |
| C28 | N2 | C30 | 109.42(15) |
| C29 | N2 | C30 | 112.00(14) |
| N9 | C1 | N19 | 113.54(15) |
| N11 | C1 | N9 | 127.31(15) |
| N11 | C1 | N19 | 119.14(15) |
| C10 | N1 | C12 | 113.82(14) |
| N11 | C1 | C7 | 124.37(16) |
| N11 | C1 | N13 | 126.83(14) |
| N13 | C1 | C7 | 108.80(14) |
| C5 | N1 | C1 | 121.69(14) |
| C12 | N1 | C1 | 129.83(14) |
| C12 | N1 | C5 | 106.71(14) |
| C1 | C1 | C15 | 111.95(14) |
| C29' | N29' | C28' | 111.90(14) |
| C29' | N29' | C30' | 112.09(16) |
| C30' | N29' | C28' | 109.99(15) |
| C2' | C1' | C18' | 108.89(14) |
| N13' | C1' | C2' | 104.98(13) |
| N13' | C1' | C14' | 109.06(14) |
| N13' | C1' | C18' | 110.78(14) |
| C14' | C1' | C2' | 112.98(14) |
| C14' | C1' | C18' | 110.05(14) |
| N3' | C2' | C1' | 112.38(15) |
| C4' | N3' | C2' | 122.79(16) |
| N3' | C4' | C5' | 114.67(16) |
| O4' | C4' | N3' | 123.90(17) |
| O4' | C4' | C5' | 121.36(17) |
| C6' | C5' | C4' | 128.25(17) |
| C6' | C5' | N13' | 110.60(15) |
| N13' | C5' | C4' | 120.95(16) |
| C5' | C6' | C7' | 106.45(16) |
| C8' | C7' | C6' | 136.96(17) |
| C8' | C7' | C12' | 115.55(15) |
| C12' | C7' | C6' | 107.36(15) |
| N9' | C8' | C7' | 121.54(16) |
| C8' | N9' | C10' | 117.10(15) |
| N9' | C10' | N19' | 113.09(15) |
| N11' | C10' | N9' | 127.35(15) |
| N11' | C10' | N19' | 119.56(15) |
| C10' | N11' | C12' | 113.82(14) |
| N11' | C12' | C7' | 124.61(15) |
| N11' | C12' | N13' | 126.81(15) |
| N13' | C12' | C7' | 108.58(14) |
| C5' | N13' | C1' | 121.28(14) |
| C12' | N13' | C1' | 130.41(14) |
| C12' | N13' | C5' | 106.96(14) |
| C1' | C14' | C15' | 111.80(15) |

TABLE 32

Bond angles for Pattern 11 continued

| Atom | Atom | Atom | Angle/° |
|---|---|---|---|
| C16 | C15 | C14 | 110.47(16) |
| C15 | C16 | C17 | 111.59(17) |
| C16 | C17 | C18 | 110.50(17) |
| C1 | C18 | C17 | 112.70(16) |
| C10 | N19 | C20 | 128.14(15) |
| N19 | C20 | C25 | 124.39(15) |
| N21 | C20 | N19 | 114.26(15) |
| N21 | C20 | C25 | 121.34(16) |
| C20 | N21 | C22 | 118.67(15) |
| N21 | C22 | C23 | 124.36(15) |
| C22 | C23 | C24 | 115.77(15) |
| C22 | C23 | N26 | 124.13(15) |
| C24 | C23 | N26 | 120.06(15) |
| C25 | C24 | C23 | 120.58(16) |
| C24 | C25 | C20 | 118.84(16) |
| C23 | N26 | C27 | 115.10(14) |
| C23 | N26 | C31 | 113.71(14) |
| C27 | N26 | C31 | 109.67(14) |

TABLE 32-continued

Bond angles for Pattern 11 continued

| Atom | Atom | Atom | Angle/° |
|---|---|---|---|
| N26 | C27 | C28 | 110.71(15) |
| N29 | C28 | C27 | 110.27(15) |
| N29 | C30 | C31 | 109.70(14) |
| N26 | C31 | C30 | 111.14(15) |
| C16' | C15' | C14' | 111.55(15) |
| C17' | C16' | C15' | 111.64(16) |
| C16' | C17' | C18' | 110.55(15) |
| C17' | C18' | C1' | 111.87(15) |
| C10' | N19' | C20' | 127.48(15) |
| N19' | C20' | C25' | 123.57(15) |
| N21' | C20' | N19' | 114.77(15) |
| N21' | C20' | C25' | 121.60(16) |
| C20' | N21' | C22' | 118.62(15) |
| N21' | C22' | C23' | 124.05(15) |
| C22' | C23' | C24' | 116.36(15) |
| C22' | C23' | N26' | 124.19(15) |
| C24' | C23' | N26' | 119.43(15) |
| C25' | C24' | C23' | 120.60(16) |
| C24' | C25' | C20' | 118.47(16) |
| C23' | N26' | C27' | 112.98(14) |
| C23' | N26' | C31' | 114.98(14) |
| C31' | N26' | C27' | 109.96(14) |
| N26' | C27' | C28' | 110.61(15) |
| N29' | C28' | C27' | 109.76(14) |
| N29' | C30' | C31' | 110.37(15) |
| N26' | C31' | C30' | 110.07(14) |

TABLE 33

Hydrogen positions for Pattern 11

| Ato | x | y | z | U(eq |
|---|---|---|---|---|
| H2 | 1952.82 | 2684.00 | 4287.21 | 31 |
| H2 | 692.24 | 3296.46 | 4408.15 | 31 |
| H3 | 290(20) | 2055(18) | 4088(17) | 38 |
| H6 | 2451.78 | 1890.37 | 1458.87 | 32 |
| H8 | 3903.14 | 3078.05 | 238.95 | 28 |
| H29 | 4630(19 | 9044(17) | 3990(15) | 26 |
| H14 | 2330.99 | 4958.46 | 3028.79 | 29 |
| H14 | 2703.91 | 4017.82 | 3886.35 | 29 |
| H15 | 1107.50 | 4633.61 | 4664.44 | 35 |
| H15 | 1748.76 | 5501.07 | 4278.38 | 35 |
| H16 | 458.50 | 6273.83 | 3098.44 | 41 |
| H16 | −214.76 | 6147.55 | 4009.52 | 41 |
| H17 | — | 5666.28 | 3006.91 | 42 |
| H17 | −689.43 | 4736.56 | 3865.85 | 42 |
| H18 | −171.39 | 4192.92 | 2617.73 | 34 |
| H18 | 440.12 | 5073.20 | 2198.81 | 34 |
| H19 | 4530(20 | 5778(16) | 399(15) | 25 |
| H22 | 4989.26 | 8119.89 | 1293.93 | 24 |
| H24 | 2127.98 | 7549.40 | 2477.86 | 30 |
| H25 | 2270.39 | 6360.61 | 1747.02 | 29 |
| H27 | 4603.62 | 9362.95 | 1710.35 | 33 |
| H27 | 5153.40 | 8588.81 | 2620.46 | 33 |
| H28 | 4870.71 | 10241.40 | 2673.81 | 38 |
| H28 | 3550.90 | 10467.89 | 2471.64 | 38 |
| H29 | 3108.17 | 10859.93 | 3935.86 | 46 |
| H29 | 4443.11 | 10670.00 | 4033.98 | 46 |
| H29 | 3754.81 | 10060.90 | 4797.45 | 46 |
| H30 | 2344.25 | 9593.22 | 3586.92 | 34 |
| H30 | 2910.10 | 8809.41 | 4488.97 | 34 |
| H31 | 3971.22 | 7734.39 | 3710.35 | 30 |
| H31 | 2655.36 | 7951.83 | 3502.74 | 30 |
| H29 | 560(20) | 692(18) | 6199(16) | 29 |
| H2' | 5477.81 | 5719.97 | 7147.31 | 29 |
| H2' | 5189.48 | 5999.15 | 6122.69 | 29 |
| H3' | 5130(20 | 7539(18 | 6144(16) | 33 |
| H6' | 2953.53 | 7829.77 | 8708.09 | 29 |
| H8' | 1357.40 | 6772.85 | 9879.05 | 28 |
| H14 | 2805.30 | 7092.82 | 6025.24 | 27 |
| H14 | 2169.10 | 6223.95 | 6415.63 | 27 |
| H15 | 2606.17 | 6321.08 | 4936.54 | 32 |

TABLE 33-continued

Hydrogen positions for Pattern 11

| Ato | x | y | z | U(eq |
|---|---|---|---|---|
| H15 | 3906.18 | 6227.17 | 5103.58 | 32 |
| H16 | 2773.98 | 4662.18 | 5805.18 | 32 |
| H16 | 3740.12 | 4667.85 | 5072.76 | 32 |
| H17 | 5097.07 | 4500.45 | 6103.61 | 30 |
| H17 | 4471.84 | 3621.32 | 6485.66 | 30 |
| H18 | 4624.61 | 4376.30 | 7592.81 | 28 |
| H18 | 3327.54 | 4497.13 | 7393.07 | 28 |
| H19 | 410(20) | 4234(16 | 9628(15) | 25 |
| H22 | −162.62 | 1997.61 | 8631.02 | 25 |
| H24 | 3033.65 | 2074.81 | 7930.26 | 28 |
| H25 | 2878.04 | 3306.40 | 8617.03 | 27 |
| H27 | 2456.74 | 1846.14 | 6723.87 | 31 |
| H27 | 1158.30 | 2064.81 | 6461.48 | 31 |
| H28 | 2280.62 | 933.41 | 5757.37 | 33 |
| H28 | 2788.87 | 182.57 | 6690.01 | 33 |
| H29 | 2084.80 | — | 6345.00 | 51 |
| H29 | 1453.35 | −345.66 | 5459.06 | 51 |
| H29 | 758.50 | −940.55 | 6227.50 | 51 |
| H30 | 1485.34 | −641.08 | 7780.47 | 33 |
| H30 | 185.78 | −404.85 | 7512.32 | 33 |
| H31 | −101.53 | 1270.66 | 7507.69 | 27 |
| H31 | 370.70 | 530.13 | 8453.40 | 27 |

Example 25. Single Crystal X-Ray Crystallization Experiment Conditions Used on Pattern 1

Diffraction data were collected on XRD1 beamline (Lausi, et al, 2015), in its standard single crystal configuration. The experimental setup consists in a Huber goniometer with κ geometry, fully controllable from remote. Samples diffraction properties were characterized at 100K (nitrogen stream supplied through an Oxford Cryostream 700—Oxford Cryosystems Ltd., Oxford, United Kingdom) through the rotating crystal method.

Data were acquired using a monochromatic wavelength of 0.6199 Å, on a Pilatus 6M hybrid-pixel area detector (DECTRIS Ltd., Baden-Daettwil, Switzerland). Crystals were dipped in NHV oil (Jena Bioscience, Jena, Germany), mounted at RT on kapton loops (MiTeGen, Ithaca, USA) and flash frozen in liquid nitrogen. Diffraction properties of 15 different crystals have been assessed—all of them appear as thin yellow needles less than 50-80 mm in the longest direction. Most of specimens diffracted around ~0.9-1 Å, but few of them diffracted up to ~0.7-0.8 Å. Standard "Omega-scan" XRD data have been collected on the best diffracting ones, till radiation damage started degrading the data quality significantly. An oscillation range of 0.5° has been chosen for optimal Bragg peaks separation. The same crystalline form has been found in crystals from all the three batches supplied.

The structure was solved using direct methods by SHELXT-2014/7 (Sheldrick, G. M., 2015a) and refined by least-square full matrix refinement using SHELXL-2014/7 (Sheldrick, G. M., 2015b). All H-atoms, except for those linked to N or O atoms, were included from the geometry. In the final cycles of refinement, the large peak ~2 e/Å3 was found nearby ClB atom. This was interpreted as partial disorder of this atom. The refinement revealed that disorder can be established as ~0.9 and ~0.1. This disorder affects the water molecule (O1W); therefore, to keep the model intact H1W1 was kept with AFIX card (AFIX 1) and thermal parameter at 150% of neighboring O atom.

The HR-XRPD data were collected on D8 Advance diffractometer using Cu Kα1 radiation (1.54056 Å) with germanium monochromator at RT. Diffraction data were collected in the 2θ range 2-41.5°. Detector scan on solid state LynxEye detector was performed using 0.016° per step with 5 sec/step scan speed. The samples were measured in 8 mm long glass capillary with 0.3 mm outer diameter.

The first step of calculation was taken by finding unit cell parameters using LSI-Index (Coelho, 2003; Coelho & Kern, 2005) indexing program. The space group was selected on reflections condition and knowledge of the compound. The cell parameters, purity as well as instrument parameters were refined using Whole Powder Pattern Decomposition method (Pawley, 1981).

For Rietveld calculation the cell parameters were taken from the RT measurement while the atom positions and their thermal parameters from single crystal measurement file (cif) at 100K. During the refinement the following parameters were refined:
cell constants;
background;
instrument geometry;
zero shift;
absorption.

No atom positions nor thermal motion parameters were refined during whole process. The following criteria of fit were used:

$Y_{o,m}$ and $Y_{c,m}$ are the observed and calculated data, respectively at data point m, M the number of data points, P the number of parameters, $w_m$ the weighting given to data point m which for counting statistics is given by $wm=1/\sigma(Y_{o,m})^2$ where $\sigma(Y_{o,m})$ is the error in $Y_{o,m}$;

$$R_{exp} = \sqrt{\frac{M-P}{\sum w_m Y_{o,m}^2}} \; ; \; R_{wp} = \sqrt{\frac{\sum w_m (T_{o,m} - T_{c,m})^2}{\sum w_m Y_{o,m}^2}} \; ;$$

$$R_p = \sqrt{\frac{\sum |Y_{o,m} - Y_{c,m}|}{\sum Y_{o,m}}}$$

$$GOF = chi^2 = \frac{R_{wp}}{R_{exp}} = \sqrt{\frac{\sum w_m (Y_{o,m} - Y_{c,m})^2}{M-P}}$$

The resulting crystal structure is displayed in FIG. 97 and FIG. 98 as well as a simulation comparison in FIG. 99 which shows close agreement between the predicted and experimental diffractograms.

Example 26. Pattern 1 Single Crystal Description

Compound 1 dihydrochloride crystallizes as yellow columnar crystals in the monoclinic centrosymmetric space group P21/c. In the asymmetric unit, one dicationic API2+, two chloride anions and two water molecules were found (overall ratio 1:2:2).

As it can be seen in FIG. 97, the molecule is charged on the most basic amine N atom (N2) as well as on the pyridine N atom (N10). The molecule adopts an extended (unfolded) conformation.

The crystal is held by intermolecular H-bond interactions (see FIG. 98). One of the chloride anions (ClA) interacts directly with the positively-charged N atom (N2). The second chloride anion (ClB) acts as a bridge between the two water molecules (see FIG. 97).

However, this ClB interacts also through H-bond with another amine N atom (N14). In the crystal, all water molecules act as donors as well as acceptors of H-bonds, while N atoms act preferably as donors only. The only acceptor of H-bond is N16 atom and in this case this interaction is intramolecular.

The intermolecular H-bond network is extended in all three dimensions and therefore, it produces 3D structure. The HR-XRPD data and Rietveld analyses performed on starting material delivered by G1 Therapeutics allowed to obtain cell parameters at RT and revealed that bulk material consists of a pure form without any detectable crystalline impurities. Pattern 1 crystallizes in centrosymmetric space group P21/c as a dication associated with two chloride anions. Two water molecules were also found in the asymmetric unit. The results are tabulated below.

TABLE 34

Single crystal data for Pattern 1

| Pattern 1 Single Crystal | |
|---|---|
| Empirical formula | [(C$_{24}$H$_{32}$N$_8$O)Cl$_2$•2H$_2$O] |
| Formula weight | 555.51 |
| T [K] | 100(2) K |
| λ [Å] | 0.61993 Å |
| Crystal system | Monoclinic |
| Space group | P21/c |
| Unit cell dimensions | |
| a [Å] | 22.118(4) [22.2447(9)] |
| b [Å] | 6.9060(14) [6.9472(4)] |
| c [Å] | 18.431(4) [18.5906(8)] |
| β [°] | 109.58(3) [109.407(2)] |
| V[Å$^3$] | 2652.5(10) [2709.7(4)] |
| Z | 4 |
| Dc [g/cm$^3$] | 1.391 |
| [mm$^{-1}$] | 0.199 |
| F(000) | 1176 |
| Crystal size [mm$^3$] | 0.07 × 0.02 × 0.01 |
| θ range for data collection [°] | 1.9-27.6. |
| Reflections collected | 45308 |
| Independent reflections | 9184 [R$_{int}$ = 0.1141] |
| Completeness to θ = 25.242° [%] | 99.8 |
| Absorption correction | None |
| Max. and min. transmission | 0.992 and 0.978 |
| Data/restraints/parameters | 9183/0/367 |
| Goodness-of-fit on F$^2$ | 1.019 |
| Final R indices [I > 2(I)] | R1 = 0.0609, wR2 = 0.1271 |
| R indices (all data) | R1 = 0.1366, wR2 = 0.1603 |
| Absolute configuration | |
| Extinction coefficient | n/a |
| Largest diff. peak and hole [e/Å$^3$] | 0.355 and −0.471 |

TABLE 35

Hydrogen bonds from Pattern 1 single crystal structure

| D-H...A | D-H [Å] | H...A [Å] | D...A [Å] | D-H...A [°] |
|---|---|---|---|---|
| O(1W)—H(1W2)...ClA$^i$ | 1.08 | 2.20 | 3.246(3) | 162 |
| O(1W)—H(1W1)...ClB | 1.16(5) | 1.92(6) | 3.064(3) | 168(4) |
| O(2W)—H(2W1)...O(1W) | 0.86(2) | 1.90(2) | 2.752(4) | 167(2) |
| O(2W)—H(2W2)...ClB$^{ii}$ | 0.88(3) | 2.20(3) | 3.075(3) | 170(2) |
| N(2)—H(2)...ClA | 0.94(3) | 2.13(3) | 3.044(2) | 163(3) |
| N(10)—H(10)...O(2W) | 0.95(4) | 2.08(4) | 2.827(3) | 135(3) |
| N(10)—H(10)...N(16) | 0.95(4) | 2.05(4) | 2.713(3) | 125(3) |
| N(14)—H(14)...ClB$^{iii}$ | 0.78(2) | 2.45(2) | 3.218(2) | 171(3) |
| N(23)—H(23)...O(22)$^{IV}$ | 0.87(3) | 1.95(3) | 2.814(3) | 176(2) |

TABLE 36

Final Rietveld parameters for Pattern 1

| | |
|---|---|
| 2theta range (°) | 2-41.5 |
| $R_{exp}$ | 1.94 |
| $R_{wp}$ | 3.05 |
| $R_p$ | 2.36 |
| GOF | 1.57 |
| $R_{Bragg}$ | 1.29 |
| Impurities, other forms [%] | below detection limit |

Example 27. X-Ray Powder Diffraction (XRPD)

XRPD analysis was carried out on a PANalytical X'pert pro, scanning the free base samples between 3 and 35° 2θ. The material was gently grounded to release any agglomerates and loaded onto a multi-well plate with Kapton or Mylar polymer film to support the sample. The multi-well plate was then placed into the diffractometer and analyzed using Cu K radiation (α1 λ=1.54060 Å; α2=1.54443 Å; β=1.39225 Å; α1:α2 ratio=0.5) running in transmission mode (step size 0.0130°2θ) using 40 kV/40 mA generator settings.

TABLE 37

XRPD Peak List for Pattern 7.

| Pos. [°2θ] | Height [cts] | FWHM Left [°2θ] | d-spacing [Å] | Rel. Int. [%] |
|---|---|---|---|---|
| 5.8473 | 7100.68 | 0.0768 | 15.11477 | 100.00 |
| 7.5415 | 466.35 | 0.0768 | 11.72267 | 6.57 |
| 10.8993 | 2345.84 | 0.1023 | 8.11763 | 33.04 |
| 11.7793 | 2076.64 | 0.1279 | 7.51310 | 29.25 |
| 14.3833 | 227.29 | 0.1023 | 6.15820 | 3.20 |
| 15.2147 | 884.88 | 0.0895 | 5.82352 | 12.46 |
| 15.6354 | 1009.60 | 0.0895 | 5.66775 | 14.22 |
| 15.9906 | 516.06 | 0.1151 | 5.54265 | 7.27 |
| 16.6298 | 252.87 | 0.1023 | 5.33102 | 3.56 |
| 17.5834 | 825.28 | 0.0895 | 5.04399 | 11.62 |
| 18.0629 | 1476.22 | 0.1279 | 4.91116 | 20.79 |
| 18.2780 | 645.99 | 0.0895 | 4.85384 | 9.10 |
| 18.6556 | 1724.82 | 0.1407 | 4.75644 | 24.29 |
| 19.2537 | 4278.41 | 0.1151 | 4.61001 | 60.25 |
| 19.9143 | 184.16 | 0.1279 | 4.45855 | 2.59 |
| 21.0463 | 515.45 | 0.0768 | 4.22124 | 7.26 |
| 21.6098 | 3110.68 | 0.1407 | 4.11243 | 43.81 |
| 22.1211 | 283.04 | 0.1023 | 4.01851 | 3.99 |
| 22.7282 | 1065.70 | 0.0895 | 3.91254 | 15.01 |
| 23.3148 | 2921.40 | 0.1407 | 3.81540 | 41.14 |
| 23.6006 | 520.09 | 0.0768 | 3.76984 | 7.32 |
| 24.0363 | 142.34 | 0.1535 | 3.70249 | 2.00 |
| 24.5873 | 908.96 | 0.1535 | 3.62075 | 12.80 |
| 24.8731 | 374.85 | 0.1279 | 3.57978 | 5.28 |
| 25.1286 | 307.79 | 0.1023 | 3.54397 | 4.33 |
| 27.1701 | 678.40 | 0.2047 | 3.28213 | 9.55 |
| 29.1007 | 332.84 | 0.1791 | 3.06864 | 4.69 |
| 29.6940 | 173.72 | 0.2558 | 3.00867 | 2.45 |
| 30.2169 | 163.05 | 0.1279 | 2.95779 | 2.30 |
| 31.4442 | 135.77 | 0.2558 | 2.84508 | 1.91 |
| 33.2805 | 241.46 | 0.1791 | 2.69218 | 3.40 |
| 33.9789 | 188.22 | 0.3070 | 2.63843 | 2.65 |

In certain embodiments, the morphic form is Pattern 7 and is characterized by an XRPD pattern comprising at least 2 peaks selected from 5.8±0.2°, 10.9±0.2°, 11.8±0.2°, 15.2±0.2°, 15.6±0.2°, 17.6±0.2°, 18.1±0.2°, 18.7±0.2°, 19.3±0.2°, 21.6±0.2°, 22.7±0.2°, 23.3±0.2°, and 24.6±0.2°.

In certain embodiments, the morphic form is Pattern 7 and is characterized by an XRPD pattern comprising at least 3 peaks selected from 5.8±0.2°, 10.9±0.2°, 11.8±0.2°, 15.2±0.2°, 15.6±0.2°, 17.6±0.2°, 18.1±0.2°, 18.7±0.2°, 19.3±0.2°, 21.6±0.2°, 22.7±0.2°, 23.3±0.2°, and 24.6±0.2°.

In certain embodiments, the morphic form is Pattern 7 and is characterized by an XRPD pattern comprising at least 4 peaks selected from 5.8±0.2°, 10.9±0.2°, 11.8±0.2°, 15.2±0.2°, 15.6±0.2°, 17.6±0.2°, 18.1±0.2°, 18.7±0.2°, 19.3±0.2°, 21.6±0.2°, 22.7±0.2°, 23.3±0.2°, and 24.6±0.2°.

In certain embodiments, the morphic form is Pattern 7 and is characterized by an XRPD pattern comprising at least 5 peaks selected from 5.8±0.2°, 10.9±0.2°, 11.8±0.2°, 15.2±0.2°, 15.6±0.2°, 17.6±0.2°, 18.1±0.2°, 18.7±0.2°, 19.3±0.2°, 21.6±0.2°, 22.7±0.2°, 23.3±0.2°, and 24.6±0.2°.

In certain embodiments, the morphic form is Pattern 7 and is characterized by an XRPD pattern comprising at least 6 peaks selected from 5.8±0.2°, 10.9±0.2°, 11.8±0.2°, 15.2±0.2°, 15.6±0.2°, 17.6±0.2°, 18.1±0.2°, 18.7±0.2°, 19.3±0.2°, 21.6±0.2°, 22.7±0.2°, 23.3±0.2°, and 24.6±0.2°.

In certain embodiments, the morphic form is Pattern 7 and is characterized by an XRPD pattern comprising at least 7 peaks selected from 5.8±0.2°, 10.9±0.2°, 11.8±0.2°, 15.2±0.2°, 15.6±0.2°, 17.6±0.2°, 18.1±0.2°, 18.7±0.2°, 19.3±0.2°, 21.6±0.2°, 22.7±0.2°, 23.3±0.2°, and 24.6±0.2°.

In certain embodiments, the morphic form is Pattern 7 and is characterized by an XRPD pattern comprising at least 8 peaks selected from 5.8±0.2°, 10.9±0.2°, 11.8±0.2°, 15.2±0.2°, 15.6±0.2°, 17.6±0.2°, 18.1±0.2°, 18.7±0.2°, 19.3±0.2°, 21.6±0.2°, 22.7±0.2°, 23.3±0.2°, and 24.6±0.2°.

In certain embodiments, the morphic form is Pattern 7 and is characterized by an XRPD pattern comprising at least 9 peaks selected from 5.8±0.2°, 10.9±0.2°, 11.8±0.2°, 15.2±0.2°, 15.6±0.2°, 17.6±0.2°, 18.1±0.2°, 18.7±0.2°, 19.3±0.2°, 21.6±0.2°, 22.7±0.2°, 23.3±0.2°, and 24.6±0.2°.

In certain embodiments, the morphic form is Pattern 7 and is characterized by an XRPD pattern comprising at least 10 peaks selected from 5.8±0.2°, 10.9±0.2°, 11.8±0.2°, 15.2±0.2°, 15.6±0.2°, 17.6±0.2°, 18.1±0.2°, 18.7±0.2°, 19.3±0.2°, 21.6±0.2°, 22.7±0.2°, 23.3±0.2°, and 24.6±0.2°.

In certain embodiments, the morphic form is Pattern 7 and is characterized by an XRPD pattern comprising at least 11 peaks selected from 5.8±0.2°, 10.9±0.2°, 11.8±0.2°, 15.2±0.2°, 15.6±0.2°, 17.6±0.2°, 18.1±0.2°, 18.7±0.2°, 19.3±0.2°, 21.6±0.2°, 22.7±0.2°, 23.3±0.2°, and 24.6±0.2°.

In certain embodiments, the morphic form is Pattern 7 and is characterized by an XRPD pattern comprising at least 12 peaks selected from 5.8±0.2°, 10.9±0.2°, 11.8±0.2°, 15.2±0.2°, 15.6±0.2°, 17.6±0.2°, 18.1±0.2°, 18.7±0.2°, 19.3±0.2°, 21.6±0.2°, 22.7±0.2°, 23.3±0.2°, and 24.6±0.2°.

In certain embodiments, the morphic form is Pattern 7 and is characterized by an XRPD pattern comprising the 2theta values selected from 5.8±0.2°, 10.9±0.2°, 11.8±0.2°, 18.1±0.2°, 18.7±0.2°, 19.3±0.2°, 21.6±0.2°, 23.3±0.2°, and 25.6±0.2°.

TABLE 38

XRPD Peak List for Pattern 8.

| Pos. [°2θ] | Height [cts] | FWHM Left [°2θ] | d-spacing [Å] | Rel. Int. [%] |
|---|---|---|---|---|
| 4.0480 | 347.38 | 0.0768 | 21.82815 | 11.93 |
| 7.4108 | 547.85 | 0.0640 | 11.92907 | 18.82 |
| 8.1013 | 187.49 | 0.0512 | 10.91390 | 6.44 |
| 9.3731 | 222.58 | 0.0640 | 9.43567 | 7.65 |
| 10.7926 | 549.61 | 0.0768 | 8.19763 | 18.88 |
| 15.2279 | 177.64 | 0.1023 | 5.81849 | 6.10 |
| 15.7970 | 398.88 | 0.1279 | 5.61015 | 13.70 |
| 16.4382 | 1158.24 | 0.0895 | 5.39272 | 39.79 |
| 17.2971 | 593.58 | 0.1023 | 5.12682 | 20.39 |

TABLE 38-continued

XRPD Peak List for Pattern 8.

| Pos. [°2θ] | Height [cts] | FWHM Left [°2θ] | d-spacing [Å] | Rel. Int. [%] |
|---|---|---|---|---|
| 18.4863 | 2910.63 | 0.1151 | 4.79963 | 100.00 |
| 18.7442 | 1043.18 | 0.1151 | 4.73417 | 35.84 |
| 19.3171 | 921.07 | 0.1407 | 4.59503 | 31.64 |
| 19.5765 | 482.48 | 0.1151 | 4.53473 | 16.58 |
| 20.0240 | 820.68 | 0.1023 | 4.43439 | 28.20 |
| 20.9059 | 353.65 | 0.1791 | 4.24928 | 12.15 |
| 21.6070 | 931.36 | 0.1023 | 4.11294 | 32.00 |
| 21.8743 | 671.04 | 0.1279 | 4.06328 | 23.05 |
| 23.0044 | 345.45 | 0.1023 | 3.86617 | 11.87 |
| 23.4827 | 2080.97 | 0.2047 | 3.78850 | 71.50 |
| 23.8209 | 1125.13 | 0.1151 | 3.73548 | 38.66 |
| 24.1806 | 1401.67 | 0.0640 | 3.68072 | 48.16 |
| 25.5457 | 846.89 | 0.1151 | 3.48704 | 29.10 |
| 26.3518 | 179.23 | 0.1279 | 3.38217 | 6.16 |
| 29.5376 | 209.55 | 0.2303 | 3.02424 | 7.20 |
| 29.9908 | 375.55 | 0.1791 | 2.97957 | 12.90 |
| 31.0626 | 118.34 | 0.1535 | 2.87915 | 4.07 |
| 32.4502 | 89.31 | 0.2047 | 2.75914 | 3.07 |
| 33.1940 | 118.10 | 0.1535 | 2.69900 | 4.06 |
| 33.9568 | 101.24 | 0.1535 | 2.64010 | 3.48 |

In certain embodiments, the morphic form is Pattern 8 and is characterized by an XRPD pattern comprising at least 2 peaks selected from 4.0±0.2°, 7.4±0.2°, 10.8±0.2°, 15.8±0.2°, 16.4±0.2°, 17.3±0.2°, 18.5±0.2°, 18.7±0.2°, 19.3±0.2°, 19.6±0.2°, 20.0±0.2°, 20.9±0.2°, 21.6±0.2°, 21.9±0.2°, 23.0±0.2°, 23.5±0.2°, 23.8±0.2°, 24.2±0.2°, 25.±0.2°, and 29.9±0.2°.

In certain embodiments, the morphic form is Pattern 8 and is characterized by an XRPD pattern comprising at least 3 peaks selected from 4.0±0.2°, 7.4±0.2°, 10.8±0.2°, 15.8±0.2°, 16.4±0.2°, 17.3±0.2°, 18.5±0.2°, 18.7±0.2°, 19.3±0.2°, 19.6±0.2°, 20.0±0.2°, 20.9±0.2°, 21.6±0.2°, 21.9±0.2°, 23.0±0.2°, 23.5±0.2°, 23.8±0.2°, 24.2±0.2°, 25.±0.2°, and 29.9±0.2°.

In certain embodiments, the morphic form is Pattern 8 and is characterized by an XRPD pattern comprising at least 5 peaks selected from 4.0±0.2°, 7.4±0.2°, 10.8±0.2°, 15.8±0.2°, 16.4±0.2°, 17.3±0.2°, 18.5±0.2°, 18.7±0.2°, 19.3±0.2°, 19.6±0.2°, 20.0±0.2°, 20.9±0.2°, 21.6±0.2°, 21.9±0.2°, 23.0±0.2°, 23.5±0.2°, 23.8±0.2°, 24.2±0.2°, 25.±0.2°, and 29.9±0.2°.

In certain embodiments, the morphic form is Pattern 8 and is characterized by an XRPD pattern comprising at least 7 peaks selected from 4.0±0.2°, 7.4±0.2°, 10.8±0.2°, 15.8±0.2°, 16.4±0.2°, 17.3±0.2°, 18.5±0.2°, 18.7±0.2°, 19.3±0.2°, 19.6±0.2°, 20.0±0.2°, 20.9±0.2°, 21.6±0.2°, 21.9±0.2°, 23.0±0.2°, 23.5±0.2°, 23.8±0.2°, 24.2±0.2°, 25.±0.2°, and 29.9±0.2°.

In certain embodiments, the morphic form is Pattern 8 and is characterized by an XRPD pattern comprising at least 9 peaks selected from 4.0±0.2°, 7.4±0.2°, 10.8±0.2°, 15.8±0.2°, 16.4±0.2°, 17.3±0.2°, 18.5±0.2°, 18.7±0.2°, 19.3±0.2°, 19.6±0.2°, 20.0±0.2°, 20.9±0.2°, 21.6±0.2°, 21.9±0.2°, 23.0±0.2°, 23.5±0.2°, 23.8±0.2°, 24.2±0.2°, 25.±0.2°, and 29.9±0.2°.

In certain embodiments, the morphic form is Pattern 8 and is characterized by an XRPD pattern comprising at least 11 peaks selected from 4.0±0.2°, 7.4±0.2°, 10.8±0.2°, 15.8±0.220 , 16.4±0.2°, 17.3±0.2°, 18.5±0.2°, 18.7±0.2°, 19.3±0.2°, 19.6±0.2°, 20.0±0.2°, 20.9±0.2°, 21.6±0.2°, 21.9±0.2°, 23.0±0.2°, 23.5±0.2°, 23.8±0.2°, 24.2±0.2°, 25.±0.2°, and 29.9±0.2°.

In certain embodiments, the morphic form is Pattern 8 and is characterized by an XRPD pattern comprising at least 13 peaks selected from 4.0±0.2°, 7.4±0.2°, 10.8±0.2°, 15.8±0.2°, 16.4±0.2°, 17.3±0.2°, 18.5±0.2°, 18.7±0.2°, 19.3±0.2°, 19.6±0.2°, 20.0±0.2°, 20.9±0.2°, 21.6±0.2°, 21.9±0.2°, 23.0±0.2°, 23.5±0.2°, 23.8±0.2°, 24.2±0.2°, 25.±0.2°, and 29.9±0.2°.

In certain embodiments, the morphic form is Pattern 8 and is characterized by an XRPD pattern comprising at least 15 peaks selected from 4.0±0.2°, 7.4±0.2°, 10.8±0.2°, 15.8±0.2°, 16.4±0.2°, 17.3±0.2°, 18.5±0.2°, 18.7±0.2°, 19.3±0.2°, 19.6±0.2°, 20.0±0.2°, 20.9±0.2°, 21.6±0.2°, 21.9±0.2°, 23.0±0.2°, 23.5±0.2°, 23.8±0.2°, 24.2±0.2°, 25.±0.2°, and 29.9±0.2°.

In certain embodiments, the morphic form is Pattern 8 and is characterized by an XRPD pattern comprising at least 17 peaks selected from 4.0±0.2°, 7.4±0.2°, 10.8±0.2°, 15.8±0.2°, 16.4±0.2°, 17.3±0.2°, 18.5±0.2°, 18.7±0.2°, 19.3±0.2°, 19.6±0.2°, 20.0±0.2°, 20.9±0.2°, 21.6±0.2°, 21.9±0.2°, 23.0±0.2°, 23.5±0.2°, 23.8±0.2°, 24.2±0.2°, 25.±0.2°, and 29.9±0.2°.

In certain embodiments, the morphic form is Pattern 8 and is characterized by an XRPD pattern comprising at least 19 peaks selected from 4.0±0.2°, 7.4±0.2°, 10.8±0.2°, 15.8±0.2°, 16.4±0.2°, 17.3±0.2°, 18.5±0.2°, 18.7±0.2°, 19.3±0.2°, 19.6±0.2°, 20.0±0.2°, 20.9±0.2°, 21.6±0.2°, 21.9±0.2°, 23.0±0.2°, 23.5±0.2°, 23.8±0.2°, 24.2±0.2°, 25.±0.2°, and 29.9±0.2°.

In certain embodiments, the morphic form is Pattern 8 and is characterized by an XRPD pattern comprising the 2theta values selected from 4.0±0.2°, 7.4±0.2°, 10.8±0.2°, 15.8±0.2°, 16.4±0.2°, 17.3±0.2°, 18.5±0.2°, 18.7±0.2°, 19.3±0.2°, 19.6±0.2°, 20.0±0.2°, 20.9±0.2°, 21.6±0.2°, 21.9±0.2°, 23.0±0.2°, 23.5±0.2°, 23.8±0.2°, 24.2±0.2°, 25.±0.2°, and 29.9±0.2°.

TABLE 39

XRPD Peak List for Pattern 9.

| Pos. [°2θ] | Height [cts] | FWHM Left [°2θ] | d-spacing [Å] | Rel. Int. [%] |
|---|---|---|---|---|
| 3.3241 | 66.84 | 0.6140 | 26.58015 | 1.22 |
| 5.8249 | 435.60 | 0.0768 | 15.17296 | 7.95 |
| 10.8757 | 163.63 | 0.0768 | 8.13513 | 2.98 |
| 11.2250 | 455.75 | 0.0384 | 7.88278 | 8.31 |
| 11.3768 | 2582.29 | 0.0256 | 7.77792 | 47.10 |
| 11.4550 | 3239.65 | 0.0512 | 7.72505 | 59.09 |
| 11.7506 | 125.87 | 0.1023 | 7.53135 | 2.30 |
| 12.7555 | 911.61 | 0.0768 | 6.94019 | 16.63 |
| 16.2943 | 579.18 | 0.0640 | 5.44001 | 10.56 |
| 16.9724 | 5482.56 | 0.0640 | 5.22416 | 100.00 |
| 18.3347 | 317.87 | 0.0768 | 4.83897 | 5.80 |
| 19.0290 | 1955.36 | 0.0512 | 4.66393 | 35.67 |
| 21.6233 | 209.25 | 0.1023 | 4.10989 | 3.82 |
| 22.5372 | 3327.96 | 0.0640 | 3.94525 | 60.70 |
| 23.0204 | 228.23 | 0.0895 | 3.86352 | 4.16 |
| 23.3310 | 202.17 | 0.1023 | 3.81279 | 3.69 |
| 24.0081 | 1586.58 | 0.0768 | 3.70676 | 28.94 |
| 24.7459 | 1138.05 | 0.0512 | 3.59790 | 20.76 |
| 25.0321 | 671.51 | 0.0512 | 3.55741 | 12.25 |
| 25.1807 | 628.82 | 0.0384 | 3.53675 | 11.47 |
| 25.6410 | 589.48 | 0.0512 | 3.47430 | 10.75 |
| 26.8890 | 774.68 | 0.0384 | 3.31581 | 14.13 |
| 27.3292 | 336.97 | 0.1535 | 3.26339 | 6.15 |
| 28.1945 | 1400.08 | 0.0768 | 3.16518 | 25.54 |
| 29.2218 | 587.48 | 0.0768 | 3.05620 | 10.72 |
| 29.5880 | 578.30 | 0.0468 | 3.01670 | 10.55 |
| 29.6825 | 2105.96 | 0.0624 | 3.00731 | 38.41 |
| 29.7556 | 2789.47 | 0.0512 | 3.00258 | 50.88 |
| 30.8547 | 227.32 | 0.0768 | 2.89808 | 4.15 |
| 31.3680 | 103.61 | 0.1791 | 2.85182 | 1.89 |

TABLE 39-continued

XRPD Peak List for Pattern 9.

| Pos. [°2θ] | Height [cts] | FWHM Left [°2θ] | d-spacing [Å] | Rel. Int. [%] |
| --- | --- | --- | --- | --- |
| 32.5428 | 1281.07 | 0.0624 | 2.74922 | 23.37 |
| 32.6311 | 1246.75 | 0.0468 | 2.74880 | 22.74 |
| 33.0463 | 389.09 | 0.0468 | 2.70848 | 7.10 |
| 33.1273 | 426.22 | 0.0468 | 2.70204 | 7.77 |
| 33.6270 | 830.91 | 0.0624 | 2.66302 | 15.16 |
| 34.2293 | 196.40 | 0.1248 | 2.61753 | 3.58 |
| 34.4200 | 366.04 | 0.0468 | 2.60346 | 6.68 |
| 34.5206 | 224.05 | 0.0468 | 2.60256 | 4.09 |

In certain embodiments, the morphic form is Pattern 9 and is characterized by an XRPD pattern comprising at least 2 peaks selected from 11.4±0.2°, 11.5±0.2°, 12.8±0.2°, 16.3±0.2°, 16.9±0.2°, 19.0±0.2°, 22.5±0.2°, 24.0±0.2°, 24.7±0.2°, 25.0±0.2°, 25.2±0.2°, 25.6±0.2°, 26.9±0.2°, 28.2±0.2°, 29.2±0.2°, 29.6±0.2°, 29.7±0.2°, 29.8±0.2°, 32.5±0.2°, 32.6±0.2°, and 33.6±0.2°.

In certain embodiments, the morphic form is Pattern 9 and is characterized by an XRPD pattern comprising at least 3 peaks selected from 11.4±0.2°, 11.5±0.2°, 12.8±0.2°, 16.3±0.2°, 16.9±0.2°, 19.0±0.2°, 22.5±0.2°, 24.0±0.2°, 24.7±0.2°, 25.0±0.2°, 25.2±0.2°, 25.6±0.2°, 26.9±0.2°, 28.2±0.2°, 29.2±0.2°, 29.6±0.2°, 29.7±0.2°, 29.8±0.2°, 32.5±0.2°, 32.6±0.2°, and 33.6±0.2°.

In certain embodiments, the morphic form is Pattern 9 and is characterized by an XRPD pattern comprising at least 5 peaks selected from 11.4±0.2°, 11.5±0.2°, 12.8±0.2°, 16.3±0.2°, 16.9±0.2°, 19.0±0.2°, 22.5±0.2°, 24.0±0.2°, 24.7±0.2°, 25.0±0.2°, 25.2±0.2°, 25.6±0.2°, 26.9±0.2°, 28.2±0.2°, 29.2±0.2°, 29.6±0.2°, 29.7±0.2°, 29.8±0.2°, 32.5±0.2°, 32.6±0.2°, and 33.6±0.2°.

In certain embodiments, the morphic form is Pattern 9 and is characterized by an XRPD pattern comprising at least 7 peaks selected from 11.4±0.2°, 11.5±0.2°, 12.8±0.2°, 16.3±0.2°, 16.9±0.2°, 19.0±0.2°, 22.5±0.2°, 24.0±0.2°, 24.7±0.2°, 25.0±0.2°, 25.2±0.2°, 25.6±0.2°, 26.9±0.2°, 28.2±0.2°, 29.2±0.2°, 29.6±0.2°, 29.7±0.2°, 29.8±0.2°, 32.5±0.2°, 32.6±0.2°, and 33.6±0.2°.

In certain embodiments, the morphic form is Pattern 9 and is characterized by an XRPD pattern comprising at least 9 peaks selected from 11.4±0.2°, 11.5±0.2°, 12.8±0.2°, 16.3±0.2°, 16.9±0.2°, 19.0±0.2°, 22.5±0.2°, 24.0±0.2°, 24.7±0.2°, 25.0±0.2°, 25.2±0.2°, 25.6±0.2°, 26.9±0.2°, 28.2±0.2°, 29.2±0.2°, 29.6±0.2°, 29.7±0.2°, 29.8±0.2°, 32.5±0.2°, 32.6±0.2°, and 33.6±0.2°.

In certain embodiments, the morphic form is Pattern 9 and is characterized by an XRPD pattern comprising at least 11 peaks selected from 11.4±0.2°, 11.5±0.2°, 12.8±0.2°, 16.3±0.2°, 16.9±0.2°, 19.0±0.2°, 22.5±0.2°, 24.0±0.2°, 24.7±0.2°, 25.0±0.2°, 25.2±0.2°, 25.6±0.2°, 26.9±0.2°, 28.2±0.2°, 29.2±0.2°, 29.6±0.2°, 29.7±0.2°, 29.8±0.2°, 32.5±0.2°, 32.6±0.2°, and 33.6±0.2°.

In certain embodiments, the morphic form is Pattern 9 and is characterized by an XRPD pattern comprising at least 13 peaks selected from 11.4±0.2°, 11.5±0.2°, 12.8±0.2°, 16.3±0.2°, 16.9±0.2°, 19.0±0.2°, 22.5±0.2°, 24.0±0.2°, 24.7±0.2°, 25.0±0.2°, 25.2±0.2°, 25.6±0.2°, 26.9±0.2°, 28.2±0.2°, 29.2±0.2°, 29.6±0.2°, 29.7±0.2°, 29.8±0.2°, 32.5±0.2°, 32.6±0.2°, and 33.6±0.2°.

In certain embodiments, the morphic form is Pattern 9 and is characterized by an XRPD pattern comprising at least 15 peaks selected from 11.4±0.2°, 11.5±0.2°, 12.8±0.2°, 16.3±0.2°, 16.9±0.2°, 19.0±0.2°, 22.5±0.2°, 24.0±0.2°, 24.7±0.2°, 25.0±0.2°, 25.2±0.2°, 25.6±0.2°, 26.9±0.2°, 28.2±0.2°, 29.2±0.2°, 29.6±0.2°, 29.7±0.2°, 29.8±0.2°, 32.5±0.2°, 32.6±0.2°, and 33.6±0.2°.

In certain embodiments, the morphic form is Pattern 9 and is characterized by an XRPD pattern comprising at least 17 peaks selected from 11.4±0.2°, 11.5±0.2°, 12.8±0.2°, 16.3±0.2°, 16.9±0.2°, 19.0±0.2°, 22.5±0.2°, 24.0±0.2°, 24.7±0.2°, 25.0±0.2°, 25.2±0.2°, 25.6±0.2°, 26.9±0.2°, 28.2±0.2°, 29.2±0.2°, 29.6±0.2°, 29.7±0.2°, 29.8±0.2°, 32.5±0.2°, 32.6±0.2°, and 33.6±0.2°.

In certain embodiments, the morphic form is Pattern 9 and is characterized by an XRPD pattern comprising at least 19 peaks selected from 11.4±0.2°, 11.5±0.2°, 12.8±0.2°, 16.3±0.2°, 16.9±0.2°, 19.0±0.2°, 22.5±0.2°, 24.0±0.2°, 24.7±0.2°, 25.0±0.2°, 25.2±0.2°, 25.6±0.2°, 26.9±0.2°, 28.2±0.2°, 29.2±0.2°, 29.6±0.2°, 29.7±0.2°, 29.8±0.2°, 32.5±0.2°, 32.6±0.2°, and 33.6±0.2°.

In certain embodiments, the morphic form is Pattern 9 and is characterized by an XRPD pattern comprising the 2theta values selected from 11.4±0.2°, 11.5±0.2°, 12.8±0.2°, 16.3±0.2°, 16.9±0.2°, 19.0±0.2°, 22.5±0.2°, 24.0±0.2°, 24.7±0.2°, 25.0±0.2°, 25.2±0.2°, 25.6±0.2°, 26.9±0.2°, 28.2±0.2°, 29.2±0.2°, 29.6±0.2°, 29.7±0.2°, 29.8±0.2°, 32.5±0.2°, 32.6±0.2°, and 33.6±0.2°.

TABLE 40

XRPD Peak List for Pattern 10.

| Pos. [°2θ] | Height [cts] | FWHM Left [°2θ] | d-spacing [Å] | Rel. Int. [%] |
| --- | --- | --- | --- | --- |
| 5.8105 | 111.76 | 0.1023 | 15.21055 | 3.02 |
| 8.4576 | 348.24 | 0.0512 | 10.45487 | 9.42 |
| 8.6052 | 938.19 | 0.0384 | 10.27586 | 25.37 |
| 8.8323 | 3698.48 | 0.0895 | 10.01221 | 100.00 |
| 10.8959 | 47.29 | 0.1535 | 8.12011 | 1.28 |
| 11.7796 | 49.97 | 0.2047 | 7.51285 | 1.35 |
| 17.7257 | 115.24 | 0.2047 | 5.00383 | 3.12 |
| 18.7729 | 461.23 | 0.0768 | 4.72700 | 12.47 |
| 19.2217 | 201.82 | 0.1279 | 4.61762 | 5.46 |
| 19.8311 | 260.56 | 0.1023 | 4.47708 | 7.04 |
| 21.6431 | 180.47 | 0.1279 | 4.10617 | 4.88 |
| 22.7827 | 1974.03 | 0.1023 | 3.90330 | 53.37 |
| 23.3096 | 166.09 | 0.1535 | 3.81624 | 4.49 |
| 24.3184 | 133.94 | 0.1279 | 3.66017 | 3.62 |
| 26.3881 | 331.12 | 0.1023 | 3.37760 | 8.95 |
| 26.7437 | 104.59 | 0.1535 | 3.33350 | 2.83 |
| 27.6105 | 180.69 | 0.1535 | 3.23079 | 4.89 |
| 28.3607 | 1012.39 | 0.0895 | 3.14701 | 27.37 |
| 30.0318 | 3097.78 | 0.1279 | 2.97559 | 83.76 |
| 30.4202 | 255.52 | 0.0768 | 2.93848 | 6.91 |
| 30.6379 | 1479.82 | 0.0468 | 2.91568 | 40.01 |
| 30.7217 | 2244.78 | 0.0512 | 2.91033 | 60.69 |
| 31.1380 | 428.31 | 0.0895 | 2.87236 | 11.58 |
| 31.3221 | 416.14 | 0.1279 | 2.85589 | 11.25 |
| 31.9484 | 263.81 | 0.0512 | 2.80132 | 7.13 |
| 32.4521 | 119.39 | 0.1279 | 2.75899 | 3.23 |
| 33.1508 | 177.25 | 0.0768 | 2.70241 | 4.79 |
| 33.4324 | 1032.02 | 0.1151 | 2.68030 | 27.90 |
| 34.3039 | 136.16 | 0.1535 | 2.61417 | 3.68 |
| 34.6150 | 319.87 | 0.2047 | 2.59138 | 8.65 |

In certain embodiments, the morphic form is Pattern 10 and is characterized by an XRPD pattern comprising at least 2 peaks selected from 8.6±0.2°, 8.8±0.2°, 18.8±0.2°, 22.8±0.2°, 28.4±0.2°, 30.0±0.2°, 30.6±0.2°, 30.7±0.2°, 31.1±0.2°, 31.3±0.2°, and 33.4±0.2°.

In certain embodiments, the morphic form is Pattern 10 and is characterized by an XRPD pattern comprising at least 3 peaks selected from 8.6±0.2°, 8.8±0.2°, 18.8±0.2°, 22.8±0.2°, 28.4±0.2°, 30.0±0.2°, 30.6±0.2°, 30.7±0.2°, 31.1±0.2°, 31.3±0.2°, and 33.4±0.2°.

In certain embodiments, the morphic form is Pattern 10 and is characterized by an XRPD pattern comprising at least 5 peaks selected from 8.6±0.2°, 8.8±0.2°, 18.8±0.2°, 22.8±0.2°, 28.4±0.2°, 30.0±0.2°, 30.6±0.2°, 30.7±0.2°, 31.1±0.2°, 31.3±0.2°, and 33.4±0.2°.

In certain embodiments, the morphic form is Pattern 10 and is characterized by an XRPD pattern comprising at least 7 peaks selected from 8.6±0.2°, 8.8±0.2°, 18.8±0.2°, 22.8±0.2°, 28.4±0.2°, 30.0±0.2°, 30.6±0.2°, 30.7±0.2°, 31.1±0.2°, 31.3±0.2°, and 33.4±0.2°.

In certain embodiments, the morphic form is Pattern 10 and is characterized by an XRPD pattern comprising at least 9 peaks selected from 8.6±0.2°, 8.8±0.2°, 18.8±0.2°, 22.8±0.2°, 28.4±0.2°, 30.0±0.2°, 30.6±0.2°, 30.7±0.2°, 31.1±0.2°, 31.3±0.2°, and 33.4±0.2°.

In certain embodiments, the morphic form is Pattern 10 and is characterized by an XRPD pattern comprising the 2theta values selected from 8.6±0.2°, 8.8±0.2°, 18.8±0.2°, 22.8±0.2°, 28.4±0.2°, 30.0±0.2°, 30.6±0.2°, 30.7±0.2°, 31.1±0.2°, 31.3±0.2°, and 33.4±0.2°.

This specification has been described with reference to embodiments of the invention. However, one of ordinary sill in the art appreciates that various modifications and changes can be made without departing from the scope of the invention as set forth in the claims below. Accordingly, the specification is to be regarded in an illustrative rather than a restrictive sense, and all such modifications are intended to be included within the scope of invention.

We claim:

1. A crystalline compound of structure:

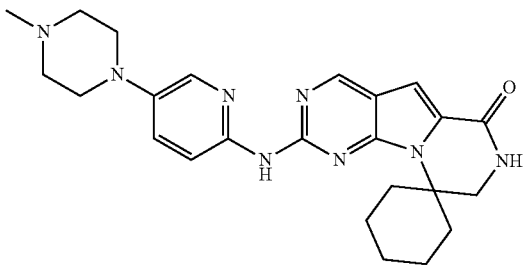 [SMILES: CN1CCN(c2ccc(Nc3ncc4cc5n(c4n3)C3(CCCCC3)CNC5=O)nc2)CC1]

which is a dihydrochloride.

2. The crystalline compound of claim 1 characterized by an X-ray powder diffraction (XRPD) pattern comprising at least three 2theta values selected from 9.6±0.2°, 21.3±0.2°, 19.8±0.2°, 12.2±0.2°, 24.0±0.2°, 26.1±0.2°, 19.3±0.2°, 17.6±0.2°, and 28.6±0.2°.

3. The crystalline compound of claim 2, wherein the XRPD pattern comprises at least four 2theta values selected from 9.6±0.2°, 21.3±0.2°, 19.8±0.2°, 12.2±0.2°, 24.0±0.2°, 26.1±0.2°, 19.3±0.2°, 17.6±0.2°, and 28.6±0.2°.

4. The crystalline compound of claim 2, wherein the XRPD pattern comprises at least five 2theta values selected from 9.6±0.2°, 21.3±0.2°, 19.8±0.2°, 12.2±0.2°, 24.0±0.2°, 26.1±0.2°, 19.3±0.2°, 17.6±0.2°, and 28.6±0.2°.

5. The crystalline compound of claim 2, wherein the XRPD pattern comprises at least six 2theta values selected from 9.6±0.2°, 21.3±0.2°, 19.8±0.2°, 12.2±0.2°, 24.0±0.2°, 26.1±0.2°, 19.3±0.2°, 17.6±0.2°, and 28.6±0.2°.

6. The crystalline compound of claim 2, wherein the XRPD pattern comprises at least the 2theta value of 9.6±0.2°.

7. The crystalline compound of claim 2, wherein the XRPD pattern comprises at least the 2theta values of 9.6±0.2°, 19.8±0.2°, and 21.3±0.2°.

8. A composition comprising the crystalline compound of claim 1, mannitol and citric acid.

9. A pharmaceutical composition comprising the crystalline compound of claim 1 and a pharmaceutically acceptable excipient.

10. The pharmaceutical composition of claim 9, wherein the pharmaceutically acceptable excipient comprises mannitol.

11. The pharmaceutical composition of claim 9, wherein the pharmaceutically acceptable excipient comprises citric acid.

12. The pharmaceutical composition of claim 9, wherein the pharmaceutically acceptable excipient comprises mannitol and citric acid.

13. The pharmaceutical composition of claim 9 comprising about 200-600 milligrams of the crystalline compound.

14. The pharmaceutical composition of claim 9 comprising about 300 milligrams of the crystalline compound.

15. The pharmaceutical composition of claim 9 comprising about 349 milligrams of the crystalline compound.

16. The pharmaceutical composition of claim 10 comprising about 250-350 mg of mannitol.

17. The pharmaceutical composition of claim 10 comprising about 300 mg of mannitol.

18. The pharmaceutical composition of claim 11 comprising about 50-100 mg of citric acid.

19. The pharmaceutical composition of claim 11 comprising about 76 mg of citric acid.

20. The pharmaceutical composition of claim 12 comprising about 250-350 mg of mannitol.

21. The pharmaceutical composition of claim 12 comprising about 300 mg of mannitol.

22. The pharmaceutical composition of claim 12 comprising about 50-100 mg of citric acid.

23. The pharmaceutical composition of claim 12 comprising about 76 mg of citric acid.

24. The pharmaceutical composition of claim 12 comprising about 300 mg of mannitol and about 76 mg of citric acid.

25. The pharmaceutical composition of claim 24 comprising about 300 milligrams of the crystalline compound.

26. The pharmaceutical composition of claim 12 comprising a dose of about 150 mg/m$^2$ to about 350 mg/m$^2$ of the crystalline compound.

27. The pharmaceutical composition of claim 12 comprising a dose of about 240 mg/m$^2$ of the crystalline compound.

* * * * *